(12) United States Patent
Vernejoul et al.

(10) Patent No.: US 9,458,184 B2
(45) Date of Patent: Oct. 4, 2016

(54) COMPOSITIONS OF TLR7 AND/OR TLR8 AGONISTS CONJUGATED TO LIPIDS

(71) Applicant: CAYLA, Toulouse (FR)

(72) Inventors: Fabienne Vernejoul, Toulouse (FR); Arnaud Debin, Escalquens (FR); Daniel Drocourt, Saint Orens de Gameville (FR); Eric Perouzel, Toulouse (FR); Gerard Tiraby, Toulouse (FR); Thierry Lioux, Balma (FR)

(73) Assignee: INVIVOGEN, Toulouse (FR)

( * ) Notice: Subject to any disclaimer, the term of this patent is extended or adjusted under 35 U.S.C. 154(b) by 544 days.

(21) Appl. No.: 13/832,477

(22) Filed: Mar. 15, 2013

(65) Prior Publication Data

US 2013/0336996 A1   Dec. 19, 2013

Related U.S. Application Data

(60) Provisional application No. 61/660,140, filed on Jun. 15, 2012.

(30) Foreign Application Priority Data

Jun. 15, 2012   (EP) .................................... 12305685

(51) Int. Cl.
| | |
|---|---|
| *A61K 31/52* | (2006.01) |
| *C07F 9/6512* | (2006.01) |
| *A61K 47/48* | (2006.01) |
| *C07D 471/04* | (2006.01) |
| *C07F 9/6506* | (2006.01) |
| *C07J 43/00* | (2006.01) |

(52) U.S. Cl.
CPC ....... *C07F 9/6512* (2013.01); *A61K 47/48046* (2013.01); *A61K 47/48053* (2013.01); *A61K 47/48123* (2013.01); *C07D 471/04* (2013.01); *C07F 9/65068* (2013.01); *C07J 43/003* (2013.01)

(58) Field of Classification Search
CPC ....................................................... A61K 31/52
See application file for complete search history.

(56) References Cited

FOREIGN PATENT DOCUMENTS

| WO | 2010/048520 | 4/2010 |
|---|---|---|
| WO | 2011/017611 | 2/2011 |
| WO | 2011/134669 | 11/2011 |
| WO | 2011/139348 | 11/2011 |

OTHER PUBLICATIONS

Vippagunta et al. ("Crystalline Solids"; Advanced Drug Delivery Reviews (2001); 48:3-26).*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
International Search Report dated Oct. 15, 2012, corresponding to the Foreign Priority Application No. 12 30 5685.

* cited by examiner

*Primary Examiner* — Jeffrey S Lundgren
*Assistant Examiner* — Chris Simmons
(74) *Attorney, Agent, or Firm* — Young & Thompson

(57) ABSTRACT

A conjugated compound of formula Q-Z—$R^4$ wherein Q is a TLR7 and/or TLR8 agonist and Z—$R^4$ is a lipid covalently linked to an amino acid or peptide coupled to a polyamine group, and a process for the manufacture of the conjugated compound, as well as a complex formed between the conjugated compound and a polyanionic molecule and a pharmaceutical composition containing the conjugated compound or complex. Also described is the use of the conjugated compound or complex in the treatment of infection, cancer or immune disorders or for use in vaccines.

7 Claims, 6 Drawing Sheets

COMPOSITIONS OF TLR7 AND/OR TLR8 AGONISTS CONJUGATED TO LIPIDS

FIELD OF INVENTION

Figure 1A:
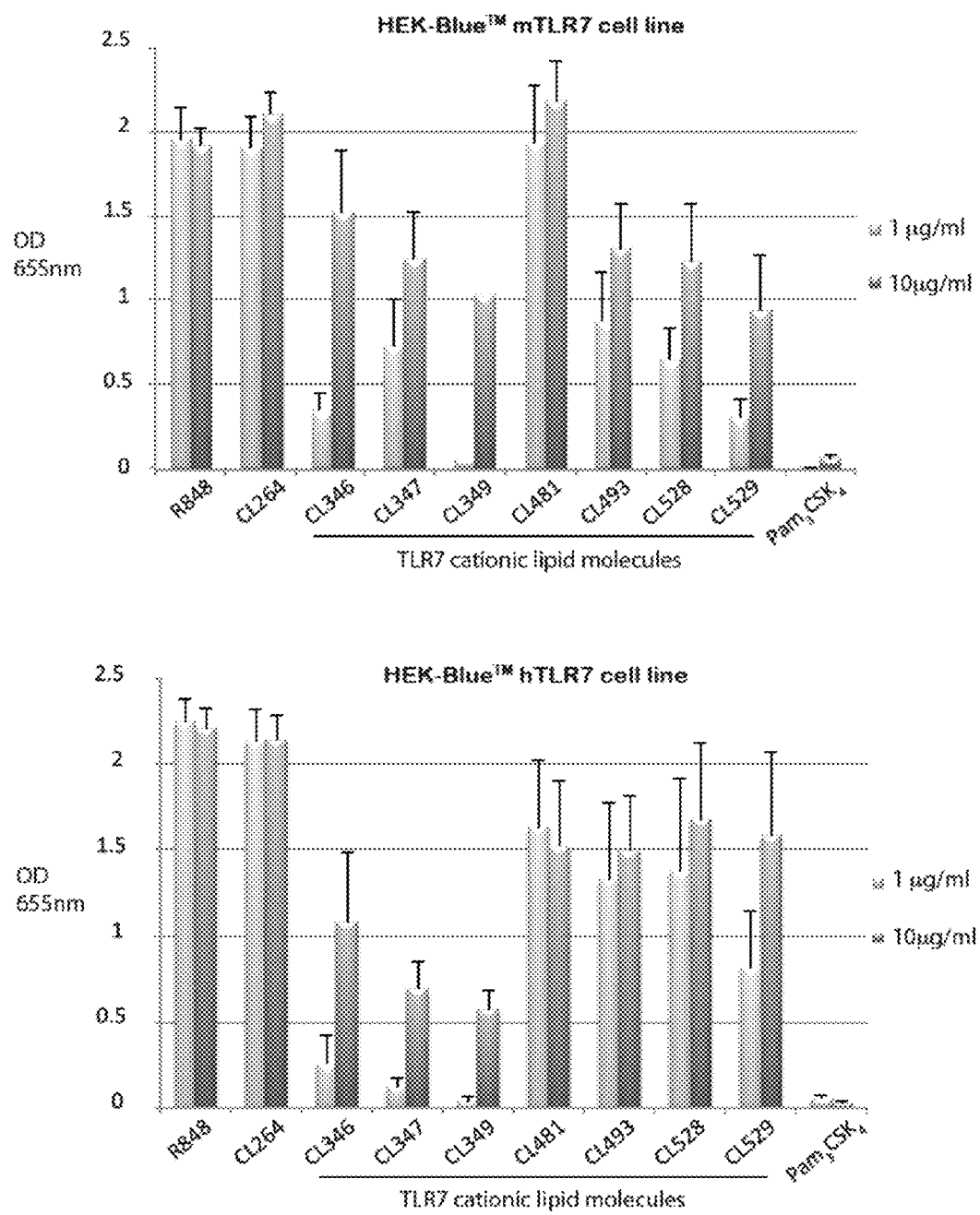

The present invention relates to immunogenic molecule compositions and methods for the modulation of toll-like receptor TLR7 and/or TLR8, and cytosolic nucleic acid sensors, and more particularly to agonists of TLR7 and/or TLR8 and cationic lipids for introducing nucleic acids into cells.

BACKGROUND OF INVENTION

The earliest event upon microbial invasion is the recognition of the pathogen at the plasma membrane. Recognition of microbial pathogens is evolutionary conserved in all classes of plants and animals, mediated by a range of pattern recognition receptors (PRRs) of the innate immune system. The innate immune response is distinguished as the first line of defence that precedes the highly specialized adaptive immune response, which confers long lasting immunity and immunological memory (Janeway and Medzhitov 2002). PRRs sense highly conserved molecular structures across a wide range of pathogens. Such structures exclusively from bacteria, fungi, parasites and viruses with the capacity to stimulate the innate immune system are referred to as pathogen associated molecular patterns (PAMPs). Examples of PAMPs include lipid-based bacterial cell wall components such as lipoproteins and lipopolysaccharides, microbial protein components such as flagellin, and foreign nucleic acids such as single stranded or double stranded DNA and RNA. The innate immune system includes cells and responses that defend the host from infection by pathogens in a non-specific manner. Cells of the innate immune system produce proinflammatory cytokines and chemokines that are involved in clearing the pathogens and also help shape the downstream adaptive immune response. A number of therapeutic strategies have been taken to exploit the human innate immune system as a tool to recognize and eliminate cancer cells, which is the premise of cancer immunotherapy.

The signaling PRRs include large families of membrane bound Toll like receptors (TLRs) and cytosolic PRRs. TLRs are the best-studied class of receptors that are essential players in the detection of a range of lipid-, protein-, nucleic acid-based PAMPs (Beutler 2009; Kawai and Akira 2011). Cytosolic DNA and RNA sensors on the other hand, have more recently been identified to play major roles in the recognition of nucleic acid PAMPs and in triggering innate immune responses (Keating et al. 2011). Several approaches have been attempted to design small molecules to activate TLRs to mount an innate immune response for use in treating infections, immune disorders, cancer, and as vaccine adjuvants. Local in vivo delivery methods of TLR ligands include topically applied antivirals or anti-tumor agents, intramuscular injections, and intranasal and mucosal administration of immune adjuvants (Hemmi et al. 2002; Ambach et al., 2004). However, the promising therapeutic potential of TLR agonists has been limited by drug delivery issues and by unwanted immune side effects. In terms of drug delivery, challenges remains to systemically target and efficiently release TLR agonists. Furthermore TLR ligands as anti-cancer agents face the challenge of the tumor microenvironment, which tends to suppress anti-cancer agent potential by preventing the agent to penetrate. This invention provides novel compounds that are TLR7 and/or TLR8 agonists conjugated to lipids which become cationic at physiological pH. They can aid cellular uptake, and when complexed to DNA, they are able to concomitantly introduce therapeutic genes into cells and trigger a strong innate immune response by stimulating multiple pathways of the innate immune system.

SUMMARY OF THE INVENTION

Provided herein are molecule compositions and methods involved in modulating the innate immune system as well as a means for gene therapy. The aim of the inventors was to efficiently combine the action of TLR7 and/or TLR8 and cytosolic nucleic acid sensors to mount a robust innate immune response that subsequently triggers an adaptive immune response.

Indeed, the compounds of the invention are polycations at physiological pH. By virtue of being polycationic, the compounds of the invention have the ability to form a complex with polyanionic molecules such as nucleic acids, more particularly linear or circular plasmid DNA, which when introduced into cells appropriately trigger interferon (IFN) production by the innate immune system.

Due to their ability to complex with nucleic acids, these molecules induce an immune response via cytosolic nucleic sensors pathways, in addition TLR7 and/or TLR8 pathways.

The ability of the compounds of the invention to form a complex with polyanionic molecules avoids the use of additional liposomes.

One application of the molecules of the invention is to be used as anti-cancer agents to effectively eliminate tumors by efficiently priming tumor antigen-specific CD4+ and CD8+ T cells. This invention provides conjugated compounds wherein novel TLR7 and/or TLR8 agonists are conjugated to lipid molecules, as well as complexes formed between the cationic form of such conjugated compounds and polyanionic molecules, such as nucleic acids, more particularly linear or circular plasmid DNA, which when introduced into cells appropriately trigger interferon (IFN) production by the innate immune system.

Furthermore, the compounds of the invention can be used as nucleic acid transfection agent to introduce a gene of interest into cells when complexed with a plasmid DNA encoding a gene. In this regard, the molecules of the invention may be used for gene therapy.

Thus, in addition to introducing a gene of interest to cells, the primary innate immunostimulation induced by the molecules of the invention and compositions thereof, trigger a secondary immune response of the adaptive immune system to obtain immunological memory. Such would be of interest for instance to induce antitumor immunity to prevent tumor metastases and relapse.

Toll-Like Receptors 7 and 8

Ten TLR isoforms have been identified in humans. TLRs are type I membrane proteins show distinct cellular expression patterns and sub-cellular localization. TLR7 and 8 reside in endosomal compartments along with TLR3 and 9, in contrast to TLR1, 2, 5 and 6, which are localized to the plasma membrane, and TLR4, which shuttles between the plasma membrane and endosomes. The cellular response to TLR activation, following engagement with specific ligands, involves activation of transcription factors such as nuclear factor (NF)-κB, activating protein-1 (AP-1) and interferon regulatory factors (IRFs) leading to the production and secretion of cytokines such as interferons (IFNs), TNF-α and interleukins, and co-stimulatory molecules that contribute to the death and clearance of the pathogenic invasion.

Since activation of the adaptive arm of the immune system in vertebrates depends on the amplitude of the innate immune response, activation through TLRs is an effective way to prime the immune system to elicit strong adaptive immune responses and the development of antigen-specific memory.

TLR7 is expressed predominantly in plasmacytoid dendritic cells (pDCs), macrophages and B cells, whereas TLR8 is expressed predominantly in myeloid dendritic cells (mDCs) and monocytes. Dendritic cells play an important role in bridging innate and adaptive immunity. Their main function is to process antigen material and display a fragment on the surface, bound to a class II MHC molecule, to be recognized by other cells of the immune system. TLR7 and TLR8 evolved to recognize single stranded RNA PAMPs and play a major role in the anti-viral response during viral infection. Several low molecular weight activators of TLR7 have been identified, including imidazoquinolines, and purine-like molecules (Hemmi et al. 2002; Lee et al. 2003). Among the latter, 8-hydroxyadenines, such as 9-benzyl-8-hydroxy-2-(2-methoxyethoxy) adenine (SM-360320), has been identified as a potent and specific TLR7 agonist (Kurimoto et al. 2004). The compound CL264 (InvivoGen) is derived from SM-360320 and synthesized by incorporating an acid. Additional derivatives include those with of an amine functional group on the benzyl moiety, such as 3-deazapurine derivatives (WO Pat. No. 2007/093901 Jones et al. (Pfizer)). The other class of TLR7 and or TLR8 compounds that have received a considerable attention are imidazoquinoline derivatives, 1H-imidazo[4,5-c]quinolones (described in U.S. Pat. No. 4,689,338 Gerster et al.—Riker). Imiquimod (3M-Aldara™, R-837, S-26308), the prototypical member of this class, was found to be effective against basal cell carcinoma, actinic keratosis and genital papilloma virus infections when applied topically in cream form (Garland 2003). The other members of TLR7 ligands are Resiquimod (R-848, S-28609), Gardiquimod, and CL097 (InvivoGen), which in contrast to imiquimod are also ligands for the TLR8 receptor. TLR7/8 agonists have proven to induce apoptosis in a number of tested cancer cells of skin and bladder.

Induced apoptosis further recruits cytotoxic T lymphocytes (CTLs) to induce death of tumor cells. TLR7/8 agonists have also been demonstrated to induce local cytokine production altering the tumor microenvironment to make it more conducive for the action of anti-tumoral agents. A variety of different small molecule compounds that are TLR7 modulators, either purine or imidazoquinoline derivatives, have been reported for the treatment of diseases and infections (Wu et al. US Pat. No. 2011/0053893 (Novartis); Isobe et al. U.S. Pat. No. 8,044,056 (Sumitomo); Fink et al. U.S. Pat. No. 7,485,432 (3M); Gorden et al US Pat. No. 2011/0070575 (Coley); Johnson US Pat. No. 2011/0282061 (Glaxo); Biggadike et al. US Pat. No. 2011/0229500 (Glaxo); Cook et al. US Pat. No. 2010/0240623 (AstraZeneca); Carson et al. US Pat. No. 2010/0210598).

Due to their localization in endosomal compartments, strategies that would increase the penetration of the TLR7 and/or TLR8 ligands into macrophages, DCs and other immune cells could enhance TLR activation and vaccine efficacy as well as ameliorate toxic effects. The present invention provides synthetic immunogenic lipid molecules comprising TLR7 and/or TLR8 agonists, which are cationic in a medium having a physiological pH, methods for their synthesis and methods for their use in the generation of primary innate and secondary adaptive immune responses. More particularly, the invention provides cationic lipids conjugated to TLR7 and/or TLR8 agonists for effective delivery into cells. The cationic lipid element allows the molecules of the invention to serve as transfection agents. Compositions of the molecules of the invention include complexing with nucleic acids to deliver coding or non-coding DNA, or RNA, to cells as well as retaining TLR7 and/or TLR8 activity.

The synthetic immunogenic lipid molecules of the present invention include compounds of Formula (I'):

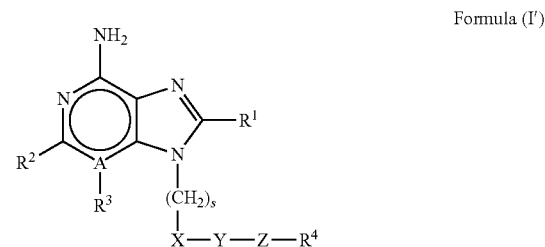

Formula (I')

wherein A, $R^1$, $R^2$, $R^3$, X, Y, Z and $R^4$ are as defined hereafter.

Purine, imidazoquinoline or 3-deazapurine derivatives described herein disclose modulators of TLR7 and/or TLR8 and can be used as nucleic acid transfection agents.

Cationic Lipids

The invention also relates to a complex formed between the cationic form of the molecules of the invention such as defined hereinabove and a nucleic acid of interest. Cationic lipids of the invention can form complexes with polyanionic molecules including double-stranded DNA, single-stranded DNA, double-stranded RNA, single-stranded RNA and oligodeoxynucleotides. Cationic lipid complexes are presently the most effective means of introducing nucleic acids into cells. Plasmids, which are small circular sequences of DNA, are used for gene transfer. However, most plasmids do not possess the attributes required for intracellular delivery and therefore sophisticated delivery systems are required. Most reported examples of gene transfer have been performed in vitro. Gene transfer in vivo requires correct targeting and a reasonably high frequency of transformation to achieve sufficient expression to compensate for a defective endogenous gene. However in vivo gene transfer is complicated by serum interactions, immune clearance, and enzymatic degradation of the genes, toxicity and bio-distribution. The methods of in vivo gene transfer under study in the clinic consist almost entirely of viral vectors. Although viral vectors are effective having the inherent ability to transport nucleic acids across cell membranes, their use poses significant risks. Viruses could present a variety of problems to the patient of toxicity, inflammatory responses and the risk that the viral vector may revert to a pathogenic genotype. In view of the limitations and risks, alternative non-viral-based gene transfer methods have been developed such as the use of cationic lipids nanoparticles, which show reduced cytotoxicity properties. (Jackson et al. US Pat. No. US 2010/0310595 A1; Johnson et al. US Pat. No. 2011/0282061 A1 (Glaxo)).

Accordingly, the novel cationic lipid molecules according to the invention can be used as transfection agents to deliver coding or non-coding DNA, or RNA of interest into cells while concomitantly eliciting responses by activating TLR7, TLR7/8 and intracellular nucleic acid sensors.

Innate Immune Sensors of Nucleic Acids

Recent advances indicate a prominent role of nucleic acid sensors in the detection of foreign or synthetic cytosolic DNA or RNA, and in triggering an innate immune response (Takeshita and Ishii 2008; Barber 2011a). A number of sensors of double-stranded DNA, single-stranded DNA, double-stranded RNA, single-stranded RNA and oligodeoxynucleotides are involved in the proinflammatory response, in particular in the induction of type I IFN, production of pro-inflammatory cytokines and caspase-1-mediated processing of IL-1β (Keating et al. 2011). Single-stranded CpG-rich DNA is recognized by TLR9, whereas double-stranded and specific motifs in single-stranded RNA are recognized by TLR3 and TLR7/TLR8, respectively. In addition to the TLRs, increasing evidence has highlighted the importance of a number of cytosolic nucleic acids sensors.

The first identified cytosolic DNA sensor, named DNA-dependent activator of IFN-regulatory factors (DAI), binds cytosolic double stranded DNA and leads to the production of type I IFNs through the Interferon Regulatory Factor 3 (IRF3) pathway (Takaoka et al. 2007; Wang et al. 2008). DAI and other DNA sensors such as IFI16 and DDX41 act through the endoplasmic reticulum (ER)-resident transmembrane protein stimulator of IFN genes (STING), an essential signaling adaptor activating IRF3 to trigger transcriptional induction of type I IFN genes and interferon inducible proteins (Barber 2011b; Burdette et al. 2011). Recently, a number of cyclic nucleotides that act as second messengers and their analogs have been demonstrated to activate STING, which in turn activates the type I IFN pathway (Burdette et al 2011; Wu et al. 2013; Sun et al. 2013). Another double-stranded DNA sensor Leucine-rich repeat in flightless I-interacting protein-1 (LRRFIP1) can recognize AT-rich B-forms as well as GC-rich Z-forms of double-stranded DNA (Yang et al. 2010). LRRFIP1 triggers the production of IFN-β in a β-catenin-dependent manner. Another DNA sensing pathway leads to the activation of the multi-protein scaffold inflammasome that contains Absent In Melanoma 2 (AIM2), which functions to process proinflammatory cytokines IL-1β and IL-18 to active forms via cleavage by caspase-1 (Muruve et al. 2008).

Cytosolic RNA sensors comprise the retinoic acid-inducible gene (RIG-I)-like receptors (RLRs), which include RIG-I and the melanoma differentiation associated gene 5 protein (MDA-5). RIG-I and MDA-5 signal through TKK-binding kinase (TBK1) upon recognition of foreign cytosolic double-stranded RNA, leading to the activation of transcription factors such as IRF3 to control the transcription of genes encoding interferons and other cytokines (Takeuchi and Akira 2009). Another RNA sensor, the protein laboratory of genetics and physiology 2 (LGP2) has recently been described to facilitate RNA recognition by RIG-I and MDA-5 (Satoh et al. 2010). These RNA sensors can also be activated indirectly upon the introduction of foreign DNA into the cytosol following infection with DNA viruses or bacteria, which are able to be converted to a double stranded 5' triphosphate RNA species in the cytosol by RNA polymerase III (Chiu et al. 2009; Caviar et al. 2012). In summary, coding or non-coding DNA, or RNA, which when complexed with molecules of the invention and consequently delivered into cells, act as immunomodulatory molecules.

In one embodiment, administering a TLR7 and/or TLR8 agonist conjugated to a cationic lipid molecule and compositions of cells, activates multiple receptors giving rise to an effective and amplified immune response implicating both the innate and adaptive arms of the immune system. In one embodiment, molecules of the invention in complex with nucleic acids mediate the synergistic activation of TLR 7/8 and cytosolic nucleic acid sensors to induce a strong interferon response. In one embodiment, molecules of the invention are transfection agents to complex with plasmid DNA for gene transfer.

DETAILED DESCRIPTION OF THE INVENTION

The present invention provides a novel low molecular weight conjugated compound comprising a TLR7 and/or TLR8 agonist conjugated to a lipid, and compositions thereof, that induce innate immune responses. The compounds of the invention are therefore interferon inducers, anti-cancer agents, anti-infectious agents, therapeutic agents for immunological diseases and vaccine adjuvants. More particularly, the molecules of the invention comprise heterocyclic compounds that are TLR7 and/or TLR8 agonists of Formula (I') as defined below, or pharmaceutically acceptable salt thereof. Furthermore, the present invention relates to a process for preparing heterocyclic compounds of the Formula (I'), or pharmaceutically acceptable salts thereof.

Unless stated otherwise, the following terms used in the specification and claims have the meanings indicated below.

$C_i$-$C_j$alkyl means a linear or branched alkyl group comprising from i to j carbon atoms. Alkyl groups include for instance methyl, ethyl, n-propyl, isopropyl, n-butyl, isobutyl, pentyl, and hexyl.

$C_i$-$C_j$alkylamino means a $C_i$-$C_j$alkyl-NH— group wherein $C_i$-$C_j$ alkyl is defined as above. Alkylamino groups include for instance methylamino, ethylamino, n-propylamino, or n-butylamino.

Di($C_i$-$C_j$alkyl)amino means a ($C_i$-$C_j$alkyl)$_2$N— group wherein $C_i$-$C_j$ alkyl is as defined above. Dialkylamino groups include for instance di methylamino or diethylamino.

$C_i$-$C_j$alkoxy means a $C_i$-$C_j$ alkyl-O— group wherein $C_i$-$C_j$ alkyl is defined as above. Alkoxy groups include for instance methoxy or ethoxy.

$C_i$-$C_j$cycloalkyl means a non-aromatic saturated carbocyclic radical, consisting of one or several rings, comprising from i to j carbon atoms. Cycloalkyl groups include for instance cyclopropyl, cyclobutyl, cyclopentyl, cyclohexyl, cycloheptyl, decahydronaphthalene, or octahydro-1H-indene.

$C_i$-$C_j$ carbocyclic means a non-aromatic saturated carbocyclic ring comprising from i to j carbon atoms. Carbocyclic groups include for instance cyclopropyl, cyclobutyl, cyclopentyl, cyclohexyl, cycloheptyl.

$C_i$-$C_j$cycloalkyl-$C_m$-$C_n$alkyl means a $C_i$-$C_j$cycloalkyl-R— group wherein R is a linear or branched alkyl group comprising from m to n carbon atoms. $C_3$-$C_6$cycloalkyl-$C_1$-$C_6$alkyl groups include for instance ethylcyclopentyl, propylcyclopentyl, ethylcyclohexyl, or propylcyclohexyl.

$C_i$-$C_j$cycloalkyl-$C_m$-$C_n$alkylamino means a $C_i$-$C_j$cycloalkyl-R—NH— group wherein R is a linear or branched alkyl group comprising from m to n carbon atoms. $C_3$-$C_6$cycloalkyl-$C_1$-$C_6$alkylamino groups include for instance cyclopentylmethanamino, 2-cyclopentylethanamino, cyclohexylmethanamino, or 2-cyclohexylethanamino.

$C_i$-$C_j$alkoxy$C_m$-$C_n$alkylamino means a $C_i$-$C_j$alkoxy-R—NH— group wherein R is a linear or branched alkyl group comprising from m to n carbon atoms. $C_1$-$C_{10}$alkoxy$C_1$-$C_{10}$alkylamino groups include for instance 2-ethoxyethanamino, 2-propoxyethanamino, 3-ethoxypropan-1-amino, 3-propoxypropan-1-amino.

$C_i$-$C_j$alkoxy$C_m$-$C_n$alkoxy means a $C_i$-$C_j$alkoxy-R— group wherein R is a $C_m$-$C_n$alkoxy group as defined above. $C_1$-$C_{10}$alkoxy$C_1$-$C_{10}$alkoxy groups include for instance 2-ethoxyethoxy, 2-propoxyethoxy, 3-ethoxypropoxy, or 3-propoxypropoxy.

$C_i$-$C_j$aryl means an aromatic carbocyclic radical consisting of one or several rings, containing from i to j carbon atoms. Aryl groups include for instance phenyl.

$C_i$-$C_j$heterocyclyl and $C_i$-$C_j$heterocycle respectively means a non-aromatic saturated cyclic radical and cycle consisting of one or several rings, comprising from i to j atoms including one or several heteroatoms chosen among N, O and S. Heterocyclyl groups include for instance tetrahydrofuranyl, tetrahydropyranyl, tetrahydrothioaziridinyl, N-pyrrolidinyl, N-piperidinyl, or N-morpholinyl.

$C_i$-$C_j$alkoxycarbonyl means a $C_i$-$C_j$alkoxy-CO— group wherein the $C_i$-$C_j$alkoxy group is as defined above.

$C_i$-$C_j$alkanoyl means a $C_i$-$C_j$alkyl-CO— group wherein the $C_i$-$C_j$alkyl group is as defined above.

The suffix "ene" means that the radical is divalent. For instance, $C_1$-$C_6$alkylene means a linear or branched divalent hydrocarbon chain comprising from 1 to 6 carbon atoms, or $C_6$-$C_{20}$arylene means an aromatic carbocyclic divalent radical consisting of one or several rings, containing from 6 to 20 carbon atoms.

The "specific side chain of an amino acid" means the R group of an amino acid having the generic formula $H_2$NCHRCOOH Amino acids include for instance the L or D isomers of alanine, valine, leucine, isoleucine, phenylalanine, tryptophan, methionine, glycine, serine, threonine, cysteine, tyrosine, asparagine, glutamine, aspartic acid, glutamic acid, lysine, arginine, proline and histidine.

"Complex" means the chemical entity formed by the association of two or more compounds.

A "receptor agonist" as used herein refers to the native ligand of that receptor, to analogues thereof or other ligands that similarly "activate" the receptor, and/or to a positive modulator of the receptor.

"TLR7 and/or TLR8" agonist refers to a molecule that is an agonist of TLR7 only, TLR8 only or both TLR7 and TLR8. TLR7 and/or TLR8 agonists are well known in the art. Examples of TLR7 agonists are purine or purine like molecules such as 8-hydroxyadenine, 3-deazapurine, imidazoquinoline and its derivatives such as imiquimod, and pyridinomidazol. Examples of TLR8 agonists are resiquimod and 3M-002. Some molecules are both TLR7 and TLR8 agonists such as Resiquimod, Gardiquimod and CL097 (InvivoGen).

"Treatment or treating" refers to both curative treatment and prophylactic or preventive measures, wherein the object is to prevent or slow down the targeted pathologic condition or disorder. Those in need of treatment include those already with the disorder as well as those prone to have the disorder or those in whom the disorder is to be prevented. Hence, the subject to be treated herein may have been diagnosed as having the disorder or may be predisposed or susceptible to the disorder.

"Pharmaceutically acceptable salts" of a compound means salts that are pharmaceutically acceptable and that possess the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

"Solvates" means solvent additions forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

Polymorphs as referred to herein can include crystalline and amorphous forms, which can be further characterised as follows:
i) Crystalline forms have different arrangements and/or conformations of the molecules in the Crystal lattice,
(ii) Amorphous forms consist of disordered arrangements of molecules that do not possess a distinguishable crystal lattice.

A first object of the present invention is a conjugated compound of formula (I):

$$Q-Z-R^4 \quad (I)$$

a pharmaceutically acceptable salt, solvate or polymorph thereof, wherein:
Q is a TLR7 and/or TLR8 agonist, and
Z—$R^4$ is selected from the group consisting of:

Formula II

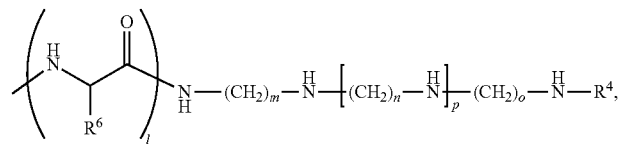

-continued

Formula III
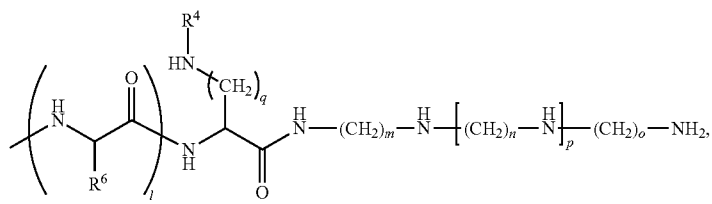

Formula IV
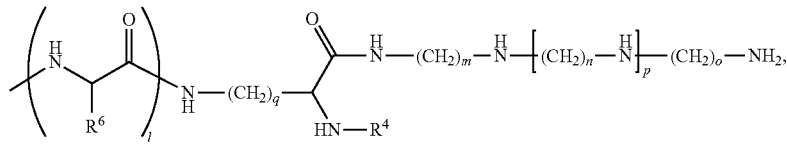

Formula V
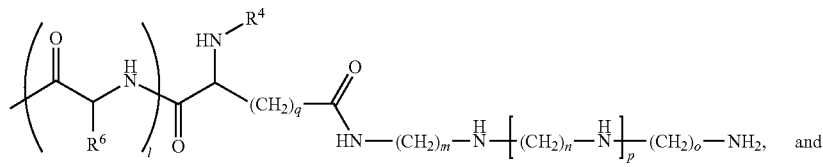

Formula VI
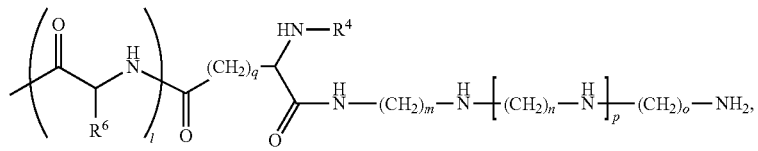

wherein:
$R^6$ is the specific side chain of an amino acid;
l is 0 or 1;
p is integer from 0 to 6;
m, n, o, and q, identical or different, are integers from 1 to 4; and
$R^4$ is a lipid of formula VII or VIII:

Formula VII
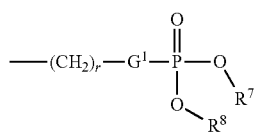

Formula VIII
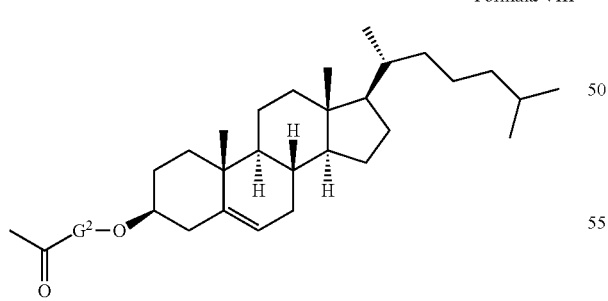

wherein:
$R^7$ and $R^8$ independently of each other are a linear or branched hydrocarbon chain comprising from 10 to 24 carbon atoms, and which optionally contains from 2 to 4 double or triple bonds,
$G^1$ is a single bond, —NH— or —O—,
$G^2$ is a single bond or (—CH$_2$—)$_r$, and
r is an integer from 1 to 6.

Preferably, the compounds of Formula (I) are imidazoline, purine or 3-deazapurine derivatives, i.e. the radical Q of formula (I) contains a moiety which is selected from the group consisting of imidazoquinoline, purine and 3-deazapurine.

Hence, the radical Q may be represented by the following formula:

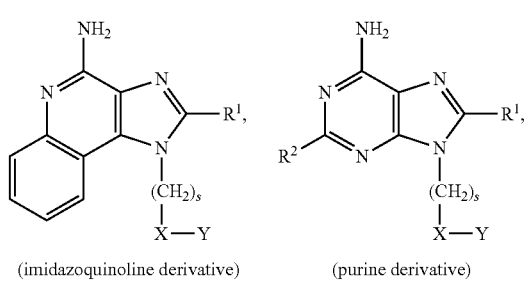

(imidazoquinoline derivative)    (purine derivative)

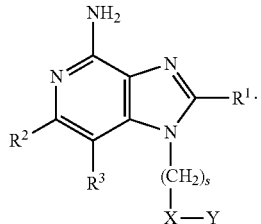

(3-deazapurine derivative)

A preferred class of compounds provided by the present invention comprises those of the general formula (I'):

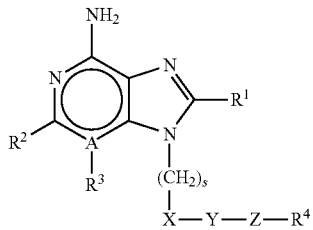

Formula (I')

a tautomer thereof or a pharmaceutically acceptable salt, solvate or polymorph of said compound or tautomer, wherein:

A is a carbon or nitrogen atom;

$R^1$ is —H, —OH, —SH, —NH$_2$, —CF$_3$, halogen, or a group chosen from $C_1$-$C_6$alkyl, $C_1$-$C_6$alkylamino, $C_1$-$C_6$alkoxy, $C_3$-$C_6$cycloalkyl-$C_1$-$C_6$alkyl, $C_3$-$C_6$cycloalkyl-$C_1$-$C_6$alkylamino, $C_3$-$C_6$cycloalkyl, $C_1$-$C_6$alkoxy$C_1$-$C_6$alkylamino, or $C_1$-$C_6$alkoxy$C_1$-$C_6$alkoxy, ($C_1$-$C_6$alkyl)-W—($C_1$-$C_6$alkylene)- wherein W is —O—, —S—, —N(R$^5$)—, —C(O)— or —S(O)$_2$— and $R^5$ is —H, carboxyl, —NH$_2$, $C_1$-$C_6$alkyl, $C_1$-$C_6$alkoxy, $C_1$-$C_6$alkanoyl, $C_6$-$C_{20}$aryl, $C_6$-$C_{20}$ heteroaryl, or $C_1$-$C_6$alkoxycarbonyl, said group being optionally terminally substituted with a hydroxyl, amino, thiol, hydrazino, hydrazido, azido, acetylenyl, carboxyl, or maleimido group;

$R^2$ and $R^3$ independently from each other are H, OH, SH, NH$_2$, CF$_3$, halogen, $C_1$-$C_{10}$alkyl, $C_1$-$C_{10}$alkylamino, $C_1$-$C_{10}$dialkylamino, $C_1$-$C_{10}$alkoxy, $C_1$-$C_{10}$alkoxy-$C_1$-$C_{10}$ alkylamino, $C_1$-$C_{10}$alkoxy-$C_1$-$C_{10}$alkoxy, —NH—SO2-$C_1$-$C_6$alkyl, —C(O)—$C_1$-$C_6$alkyl, —O—C(O)—$C_1$-$C_6$alkyl, —C(O)—$C_1$-$C_{10}$alkylamino, —C(O)—$C_1$-$C_{10}$dialkylamino, $C_5$-$C_{10}$aryl, $C_5$-$C_9$heterocyclyl, $C_3$-$C_9$ carbocyclyl, or when taken together, $R^2$ and $R^3$ form a fused $C_6$-$C_{20}$ aryl $C_6$-$C_{20}$ heteroaryl, $C_5$-$C_7$-carbocycle or a $C_5$-$C_7$heterocycle; where carbocycle, heterocycle, aryl, and heteroaryl are optionally substituted with one or more groups independently selected from F, Cl, Br, I, —CH$_3$, —CH$_2$CH$_3$, CH$_2$CH(CH$_3$)$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CHF$_2$, —CO$_2$H, —COCH$_3$, —CO$_2$CH$_3$, —C(CH$_3$)$_2$CO$_2$CH$_3$, —CO$_2$C(CH$_3$)$_3$, —COCH(OH)CH$_3$, —COCH(CH$_3$)$_2$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —OH, —OCH$_3$, —S(O)$_2$N(CH$_3$)$_2$, —SCH$_3$, —CH$_2$OCH$_3$, —S(O)$_2$CH$_3$, cyclopropyl, oxetanyl, and morpholino;

$R^3$ is absent when A is a nitrogen atom;

s is an integer from 1 to 4;

X is an unbranched —($C_1$-$C_6$ alkylene)-, —($C_6$-$C_{20}$arylene)-, —($C_6$-$C_{20}$heteroarylene)-, —($C_1$-$C_6$ alkylene)-W—($C_1$-$C_6$ alkylene)-, —($C_1$-$C_6$ alkylene)-($C_3$-$C_7$-carbocyclylene)-, —($C_1$-$C_6$ alkylene)-($C_3$-$C_7$-heterocyclylene)-, —($C_1$-$C_6$ alkylene)-($C_6$-$C_{20}$ aryl)-, —($C_1$-$C_6$ alkylene)-($C_6$-$C_{20}$ heteroarylene)-, —($C_1$-$C_6$ alkylene)-W—($C_1$-$C_7$ carbocyclylene)-, —($C_1$-$C_6$ alkylene)-W—($C_3$-$C_7$-heterocyclylene)-, —($C_1$-$C_6$ alkylene)-W—($C_6$-$C_{20}$ arylene)-, —($C_1$-$C_6$ alkylene)-W—($C_6$-$C_{20}$ heteroarylene)-, where alkylene, carbocyclylene, heterocyclylene, arylene, and heteroarylene are optionally substituted with one or more groups independently selected from F, Cl, Br, I, —CH$_3$, —CH$_2$CH$_3$, CH$_2$CH(CH$_3$)$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CHF$_2$, —CO$_2$H, —COCH$_3$, —CO$_2$CH$_3$, —C(CH$_3$)$_2$CO$_2$CH$_3$, —CO$_2$C(CH$_3$)$_3$, —COCH(OH)CH$_3$, —COCH(CH$_3$)$_2$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —OH, —OCH$_3$, —S(O)$_2$N(CH$_3$)$_2$, —SCH$_3$, —CH$_2$OCH$_3$, —S(O)$_2$CH$_3$, cyclopropyl, oxetanyl, and morpholino, and W is as defined above;

Y is a single bond, —O—, —S—, —N(R$^5$)—, —C(O)—, or —S(O)$_2$— and $R^5$ is as defined above; and —Z—$R^4$ is amino acid or peptide linked to polyamine group selected from the group consisting of formulas II to VI:

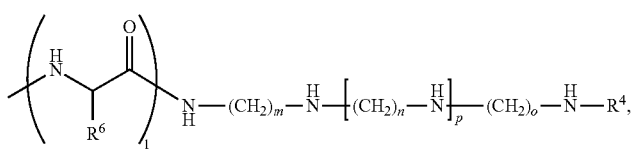

Formula II

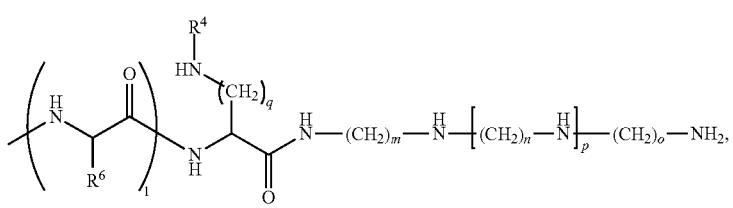

Formula III

-continued

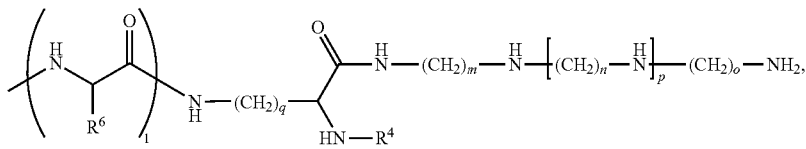

Formula IV

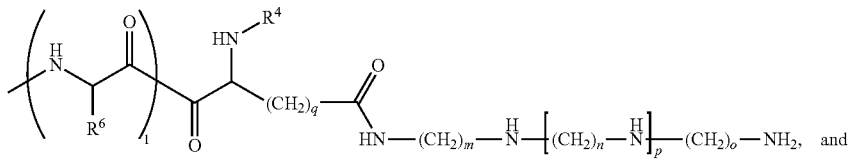

Formula V

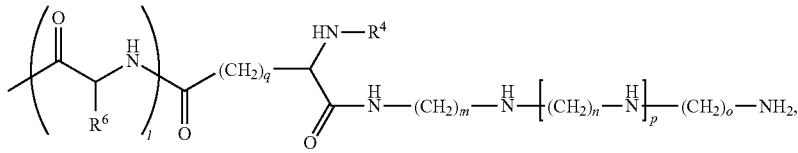

Formula VI wherein:
R$^6$ is the specific side chain of an amino acid;
l is 0 or 1;
p is integer from 0 to 6;
m, n, o, and q, identical or different, are integers from 1 to 4;
R$^4$ is a lipid of formula VII or VIII:

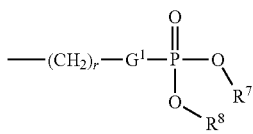

Formula VII

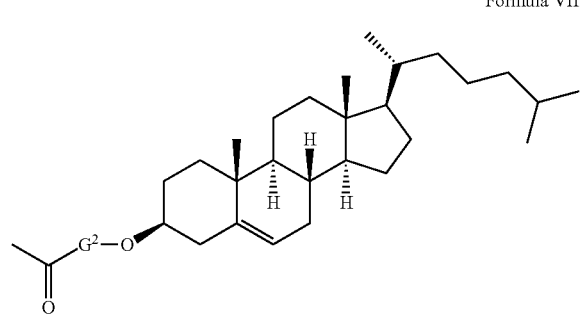

Formula VIII wherein:
R$^7$ and R$^8$ independently of each other are a linear or branched hydrocarbon chain comprising from 10 to 24 carbon atoms, and which optionally contains from 2 to 4 double or triple bonds,
G$^1$ is a single bond, —NH— or —O—,
G$^2$ is a single bond or (—CH$_2$—)$_r$,
r is an integer from 1 to 6.

In one embodiment, the compounds of the invention are chosen among purine derivatives wherein:
A is a nitrogen atom, R$^3$ is absent and R$^2$ is H, OH, SH, NH$_2$, CF$_3$, halogen, C$_1$-C$_{10}$alkyl, C$_1$-C$_{10}$alkylamino, C$_1$-C$_{10}$dialkylamino, C$_1$-C$_{10}$alkoxy, C$_1$-C$_{10}$alkoxy-C$_1$-C$_{10}$ alkylamino, C$_1$-C$_{10}$alkoxy-C$_1$-C$_{10}$alkoxy, C$_1$-C$_{10}$alkoxy-C$_5$-C$_7$heterocycle, C$_1$-C$_{10}$alkyamino-C$_5$-C$_7$heterocycle, —NH—SO$_2$—C$_1$-C$_6$alkyl, —C(O)—C$_1$-C$_6$alkyl, —O—C(O)—C$_1$-C$_6$alkyl, —C(O)—C$_1$-C$_{10}$alkylamino, —C(O)—C$_1$-C$_{10}$dialkylamino, C$_5$-C$_{10}$aryl, C$_5$-C$_9$heterocyclyl, C$_3$-C$_9$ carbocyclyl, C$_1$-C$_{10}$alkylamino-C$_2$-C$_7$heterocycle, (C$_1$-C$_6$alkoxy)-E-(C$_1$-C$_6$alkylene) and preferably R$^1$ is —H, —OH, —SH, —NH$_2$, C$_1$-C$_6$alkyl, such as methyl, ethyl, propyl or butyl, C$_1$-C$_6$alkylamino such as methylamino, ethylamino, propylamino or butylamino, C$_1$-C$_6$alkoxy such as methoxy, ethoxy, propoxy or butoxy, (C$_1$-C$_6$alkyl)-E-(C$_1$-C$_6$alkylene), wherein E is —O— or —NH—, such as —CH$_2$—NH—C$_2$H$_5$, —CH$_2$—O—C$_2$H$_5$, —(CH$_2$)$_2$—NH—CH$_3$, or —(CH$_2$)$_2$—O—CH$_3$, more preferably R$^1$ is —OH.

In other embodiment, the compounds of the invention are chosen among imidazoquinoline derivatives wherein:
A is a carbon atom and R$^2$ and R$^3$ form together a fused phenyl optionally substituted with one or more groups independently selected from F, Cl, Br, I, —CH$_3$, —CH$_2$CH$_3$, CH$_2$CH(CH$_3$)$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CHF$_2$, —CO$_2$H, —COCH$_3$, —CO$_2$CH$_3$, —C(CH$_3$)$_2$CO$_2$CH$_3$, —CO$_2$C(CH$_3$)$_3$, —COCH(OH) CH$_3$, —COCH(CH$_3$)$_2$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$) COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —OH, —OCH$_3$, —S(O)$_2$N(CH$_3$)$_2$, —SCH$_3$, —CH$_2$OCH$_3$, —S(O)$_2$CH$_3$, cyclopropyl, oxetanyl, and morpholino, and preferably R$^1$ is —H, —OH, —SH, —NH$_2$, C$_1$-C$_6$alkyl, such as methyl, ethyl, propyl or butyl, C$_1$-C$_6$alkylamino such as methylamino, ethylamino, propylamino or butylamino, C$_1$-C$_6$alkoxy such as methoxy, ethoxy, propoxy or butoxy, (C$_1$-C$_6$alkyl)-E-(C$_1$-C$_6$alkylene), wherein E is —O— or —NH—, such as —CH$_2$—NH—C$_2$H$_5$, —CH$_2$—O—C$_2$H$_5$, —(CH$_2$)$_2$—NH—CH$_3$, or —(CH$_2$)$_2$—O—CH$_3$.

In another embodiment, the compounds of the invention are chosen among 3-deazapurine derivatives wherein:
A is a carbon atom and R$^2$ and R$^3$ independently from each other are H, OH, SH, NH$_2$, CF$_3$, halogen, $C_1$-$C_{10}$alkyl, $C_1$-$C_{10}$alkylamino, $C_1$-$C_{10}$dialkylamino, $C_1$-$C_{10}$alkoxy, $C_1$-$C_{10}$alkoxy-$C_1$-$C_{10}$ alkylamino, $C_1$-$C_{10}$alkoxy-$C_1$-$C_{10}$alkoxy, $C_1$-$C_{10}$alkoxy-$C_5$-$C_7$heterocycle, $C_1$-$C_{10}$alkyamino-$C_5$-$C_7$heterocycle, —NH—$SO_2$—$C_1$-$C_6$alkyl, —C(O)—$C_1$-$C_6$alkyl, —O—C(O)—$C_1$-$C_6$alkyl, —C(O)—$C_1$-$C_{10}$alkylamino, —C(O)—$C_1$-$C_{10}$dialkylamino, $C_5$-$C_{10}$aryl, $C_5$-$C_9$heterocyclyl, $C_3$-$C_9$ carbocyclyl, $C_1$-$C_{10}$alkylamino-$C_2$-$C_7$heterocycle, ($C_1$-$C_6$alkoxy)-E-($C_1$-$C_6$alkylene) and preferably $R^1$ is —H, —OH, —SH, —$NH_2$, $C_1$-$C_6$alkyl, such as methyl, ethyl, propyl or butyl, $C_1$-$C_6$alkylamino such as methylamino, ethylamino, propylamino or butylamino, $C_1$-$C_6$alkoxy such as methoxy, ethoxy, propoxy or butoxy, ($C_1$-$C_6$alkyl)-E-($C_1$-$C_6$alkylene), wherein E is —O— or —NH—, such as —$CH_2$—NH—$C_2H_5$, —$CH_2$—O—$C_2H_5$, —$(CH_2)_2$—NH—$CH_3$, or —$(CH_2)_2$—O—$CH_3$, more preferably $R^1$ is —OH.

A preferred class of compounds of formula (I) or formula (I') comprises those where $R^4$ is of formula (VII):

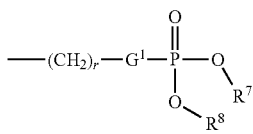

(VII)

wherein:
r is an integer from 1 to 4, preferably 3,
$G^1$ is a single bond,
$R^7$ and $R^8$, identical or different, preferably identical, are selected from the group consisting of tetradecyl, hexadecyl, octadecyl, oleyl, phytanyl, C18:2 alkenyl, C18:3 alkenyl or C18:1 alkenyl,
or, where $R^4$ is of formula (VIII):

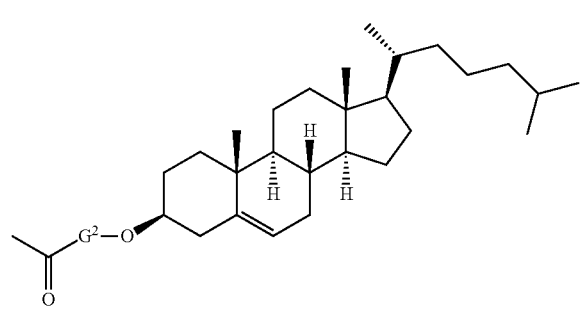

Formula VIII wherein $G^2$ is a single bond or (—$CH_2$—)$_r$, wherein r is an integer from 1 to 6.

When combined with a group that is cationic at physiological pH, such as described below (spermine, spermidine, polyamines), the lipid moiety of Formula VII and Formula VIII provides conjugated molecules of Formula (I) with the ability of transfecting cells with nucleic acids of interest. The nature of the cationic form of the lipophilic conjugated compounds of Formula (I) according to the invention is likely to promote the destabilization of endosomal vesicles in the cytoplasm following cellular osmosis, due to their impact on endosomal proton pumps. Endosomal disruption enhances the delivery of DNA to the cytosol of the cell.

According to a preferred embodiment of lipid of Formula VII, the groups $R^7$ and $R^8$ are, independently of one another, chosen from:
Tetradecyl group,
Hexadecyl group,
Octadecyl group,
Oleyl group,
Phytanyl group
groups polyalkenyl $C_{18:2}$ and $C_{18:3}$ where the first number represents the number of carbon atoms in the alkenyl chain and the second number represents the number of double bonds in the alkenyl chain, and
Group monoalkenyl $C_{18:1}$ where the first number represents the number of carbon atoms in the alkenyl chain and the second number represents the number of double bonds in the alkenyl chain.

According to another preferred embodiment of lipid of Formula VII, $R^7$ and $R^8$ groups are identical.

A specific class of compounds of formula (I) or formula (I') comprises those where Y is a single bond or —CO—, —N($R^5$)—, —O—, —S— or —S(O)$_2$—, wherein $R^5$ is —H, carboxyl, —$NH_2$ or a radical chosen from $C_1$-$C_6$alkyl, $C_1$-$C_6$alkoxy, $C_1$-$C_6$alkanoyl, $C_6$-$C_{20}$aryl, $C_6$-$C_{20}$ heteroaryl, or $C_1$-$C_6$alkoxycarbonyl.

A specific class of compounds of formula (I) or formula (I') comprises those where X is a —($C_6$-$C_{20}$arylene) (preferably a phenylene), a —($C_1$-$C_6$ alkylene)- (preferably an ethylene), a —($C_6$-$C_{20}$heteroarylene)- (preferably a pyridinylene), a —($C_1$-$C_6$ alkylene)-W—($C_1$-$C_6$ alkylene)- (preferably an ethylene-W-ethylene) wherein W is —O— or —NH—.

A specific class of compounds of formula (I) or formula (I') comprises those where s is 1.

A specific class of compounds of formula (I) or formula (I') comprises those where $R^1$ is —H, —OH, $C_1$-$C_6$alkyl, or ($C_1$-$C_6$alkyl)-W—($C_1$-$C_6$alkylene), wherein W is —O— or —NH—.

A specific class of compounds of formula (I) or formula (I') comprises those where A is a nitrogen atom.

Preferably, A is a nitrogen atom and $R^2$ is a $C_1$-$C_6$alkylamino or $C_1$-$C_{10}$alkoxy-$C_1$-$C_{10}$alkoxy, and $R^3$ is absent, or $R^2$ and $R^3$ form a fused $C_6$-$C_{20}$ aryl, preferably a phenyl.

A specific class of compounds of formula (I) or formula (I') comprises those where —Z— is selected from the group consisting of:

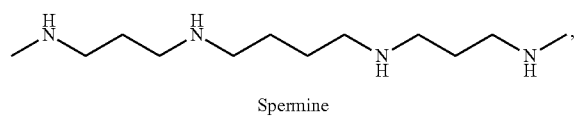

Spermine

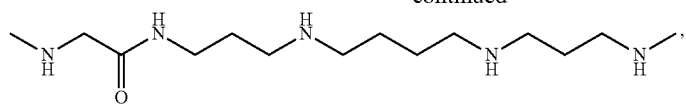
Glycinyl-spermine
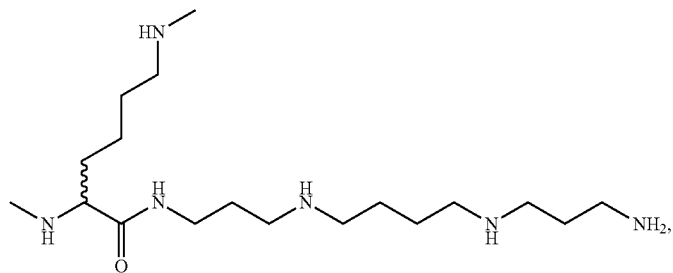
(L or D)-Lysinyl-α-spermine
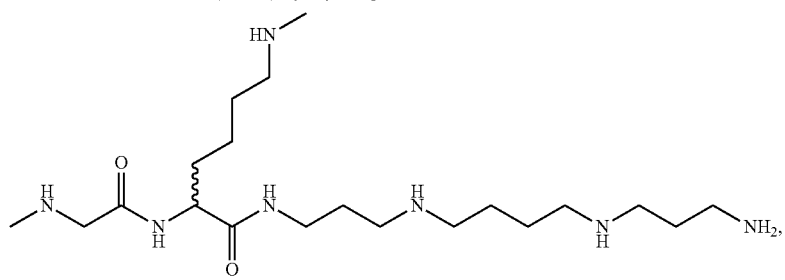
Glycinyl-α-(L or D)-lysinyl-α-spermine
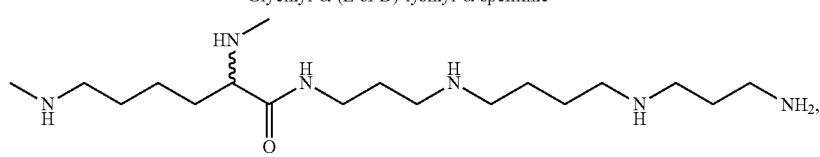
ε-(L or D)-Lysinyl-α-spermine
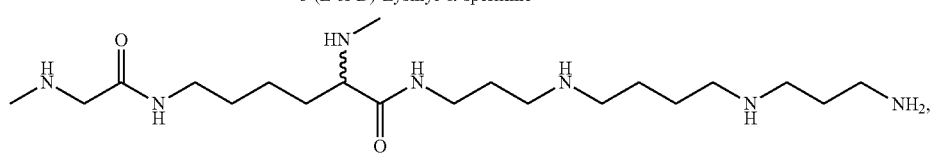
Glycinyl-ε-(L or D)-Lysinyl-α-spermine
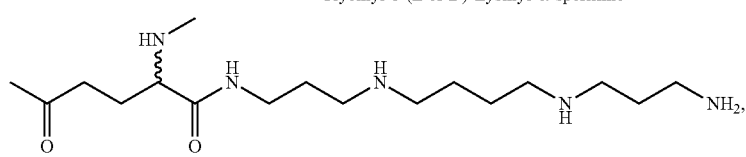
(L or D)-Glutamyl-α-spermine
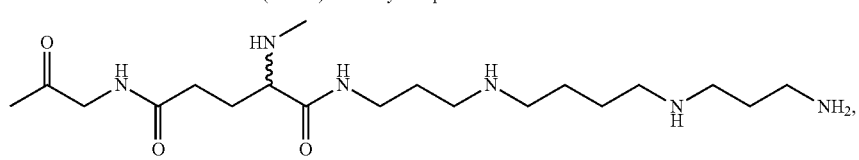
Glycinyl-γ-(L or D)-Glutamyl-α-spermine
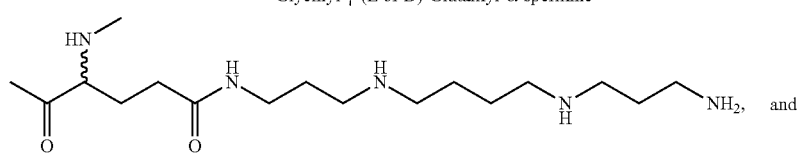
and
(L or D)-Glutamyl-γ-spermine

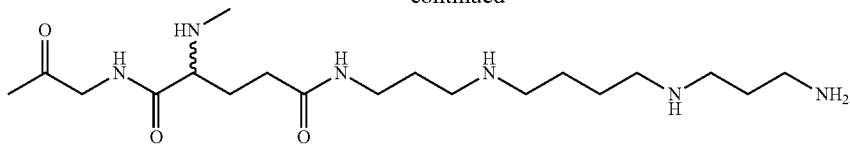

Glycinyl-α-(L or D)-glutamyl-γ-spermine

Another preferred embodiment of the compounds according to the present invention relates to compounds of Formula (I) selected from:

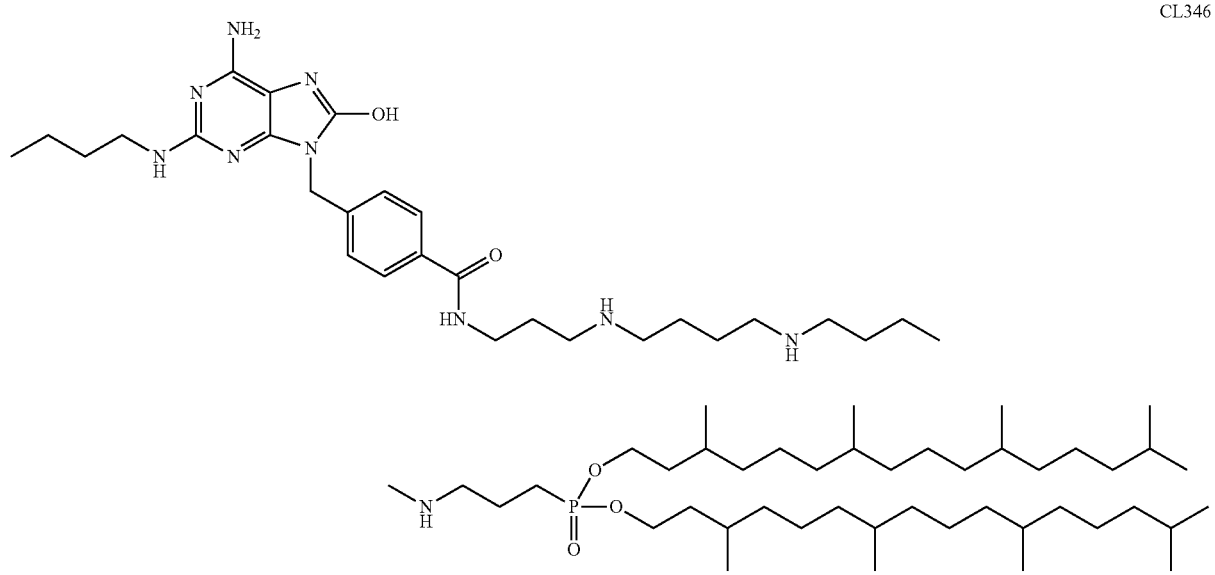

bis(3,7,11,15-tetramethylhexadecyl) 1-(4-((6-amino-2-(butylamino)-8-hydroxy-9H-purin-9-yl)methyl)phenyl)-1-oxo-2,6,11,15-tetraazaoctadecan-18-ylphosphonate bis(3,7,11,15-tetramethylhexadecyl) 1-(4-((6-amino-2-(butylamino)-8-hydroxy-9H-purin-9-yl)methyl)phenyl)-1,4-dioxo-2,5,9,14,18-pentaazahenicosan-21-ylphosphonate

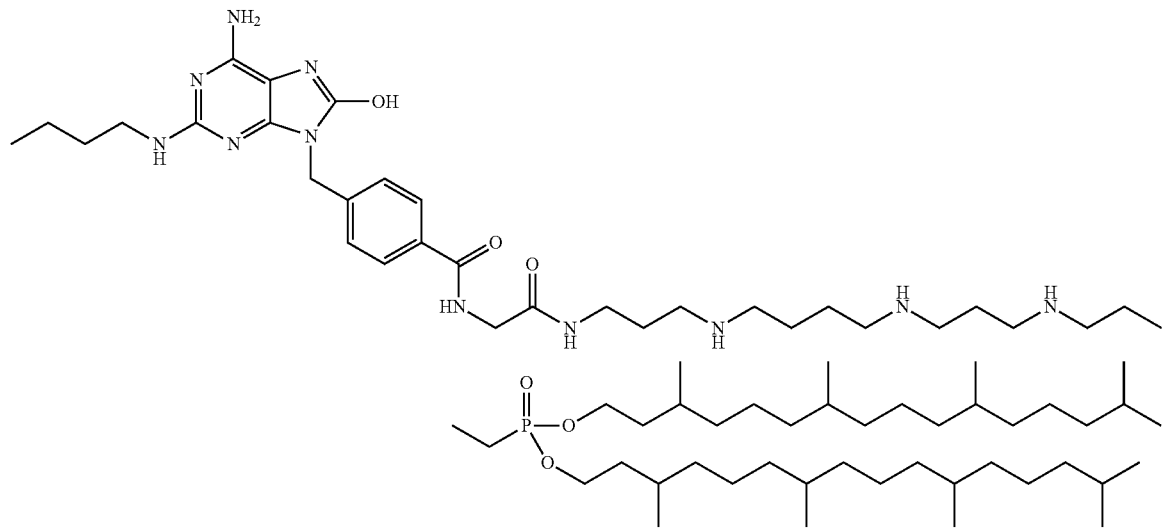

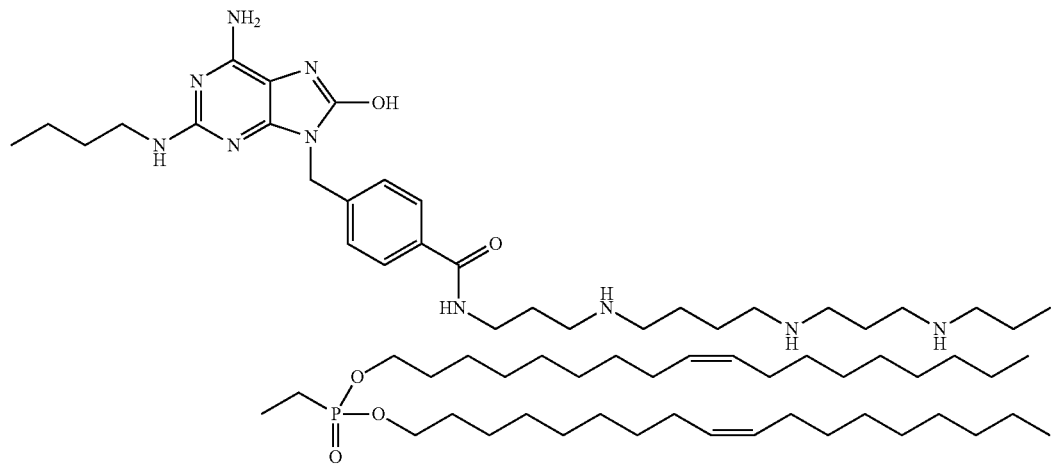
CL348
di(Z)-octadec-9-enyl 1-(4-(((6-amino-2-(butylamino)-8-hydroxy-9H-purin-9-yl)methyl)phenyl)-1-oxo-2,6,11,15-tetraazaoctadecan-18-ylphosphonate
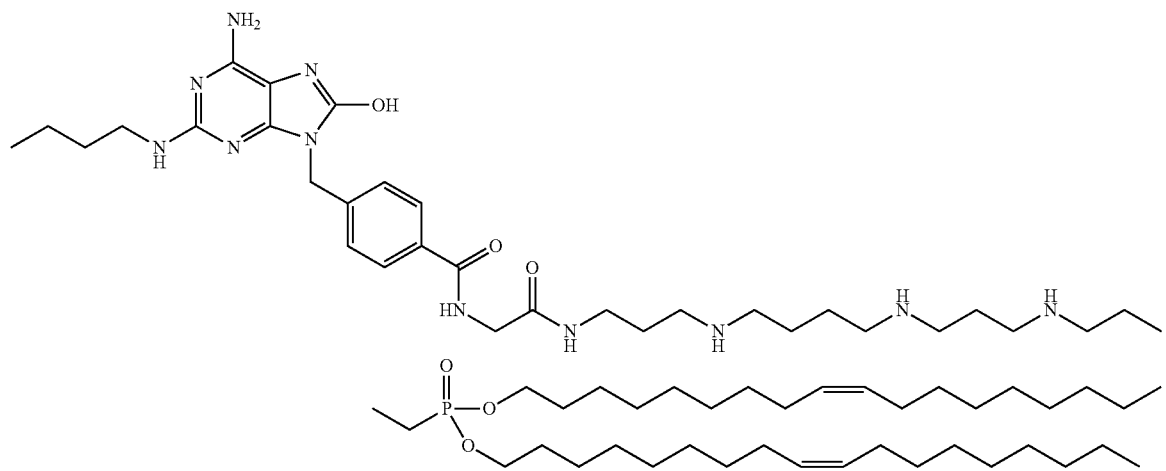
CL349
di(Z)-octadec-9-enyl 1-(4-(((6-amino-2-(butylamino)-8-hydroxy-9H-purin-9-yl)methyl)phenyl)-1,4-dioxo-2,5,9,14,18-pentaazahenicosan-21-ylphosphonate
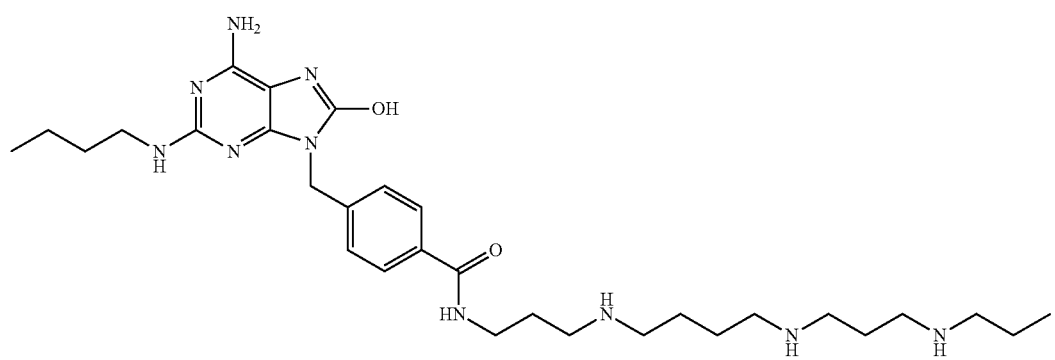
CL540

-continued
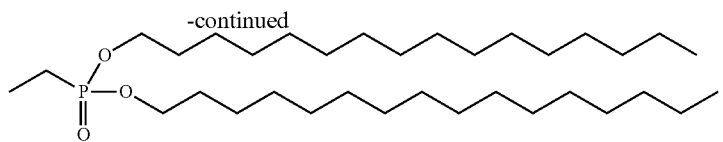
dihexadecyl 1-(4-(((6-amino-2-(butylamino)-8-hydroxy-9H-purin-9-yl)methyl)phenyl)-1-oxo-2,6,11,15-tetraazaoctadecan-18-ylphosphonate
CL548
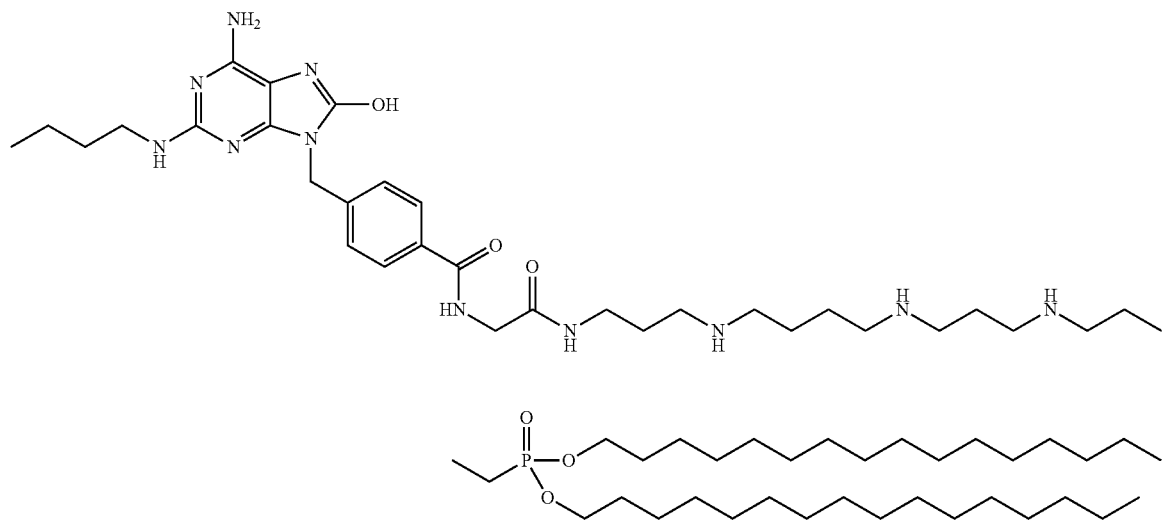
dihexadecyl 1-(4-(((6-amino-2-(butylamino)-8-hydroxy-9H-purin-9-yl)methyl)phenyl)-1,4-dioxo-2,5,9,14,18-pentaazahenicosan-21-ylphosphonate
CL481
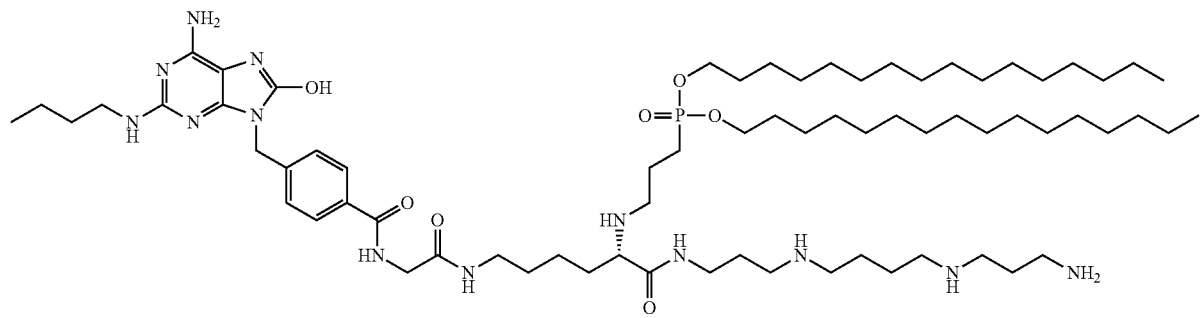
(S)-dihexadecyl 19-amino-5-(4-(2-(4-((6-amino-2-(butylamino)-8-hydroxy-9H-purin-9-yl)methyl)benzamido)acetamido)butyl)-6-oxo-4,7,11,16-tetraazanonadecylphosphonate

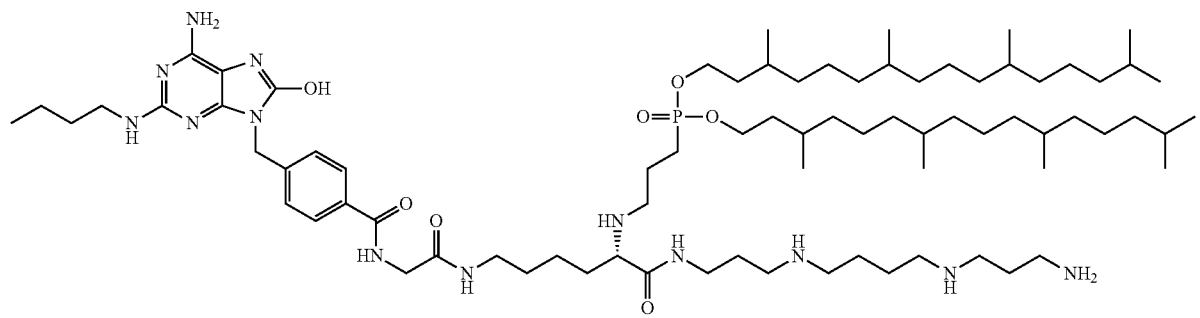

CL493

(S)-bis(3,7,11,15-tetramethylhexadecyl)-19-amino-5-(4-(2-(4-((6-amino-2-(butylamino)-8-hydroxy-9H-purin-9-yl)methyl)benzamido)acetamido)butyl)-6-oxo-4,7,11,16-tetraazanonadecylphosphonate

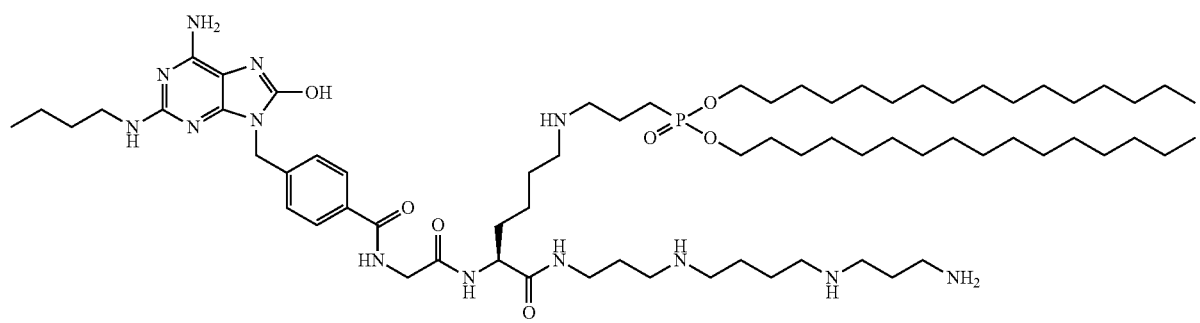

CL489

(S)-Dihexadecyl-1-amino-15-(2-(4-((6-amino-2-(butylamino)-8-hydroxy-9H-purin-9-yl)methyl)benzamido)acetamido)-14-oxo-4,9,13,20-tetraazatricosan-23-ylphosphonate

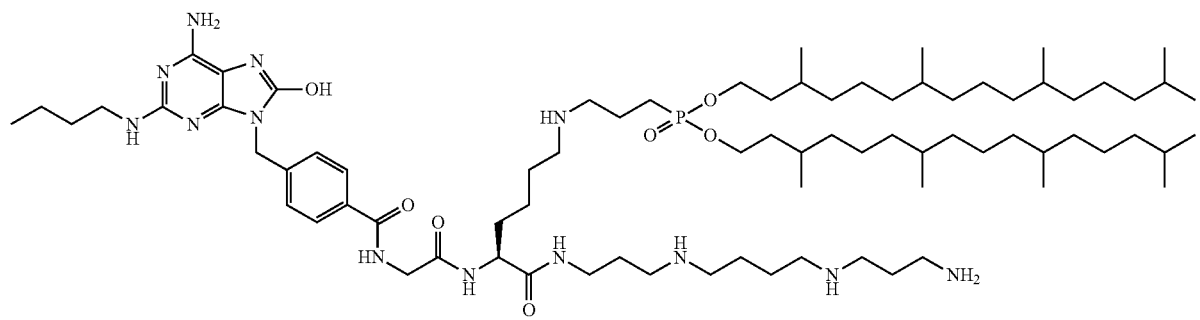

CL495

(S)-bis(3,7,11,15-tetramethylhexadecyl)-1-amino-15-(2-(4-((6-amino-2-(butylamino)-8-hydroxy-9H-purin-9-yl)methyl)benzamido)acetamido)-14-oxo-4,9,13,20-tetraazatricosan-23-ylphosphonate

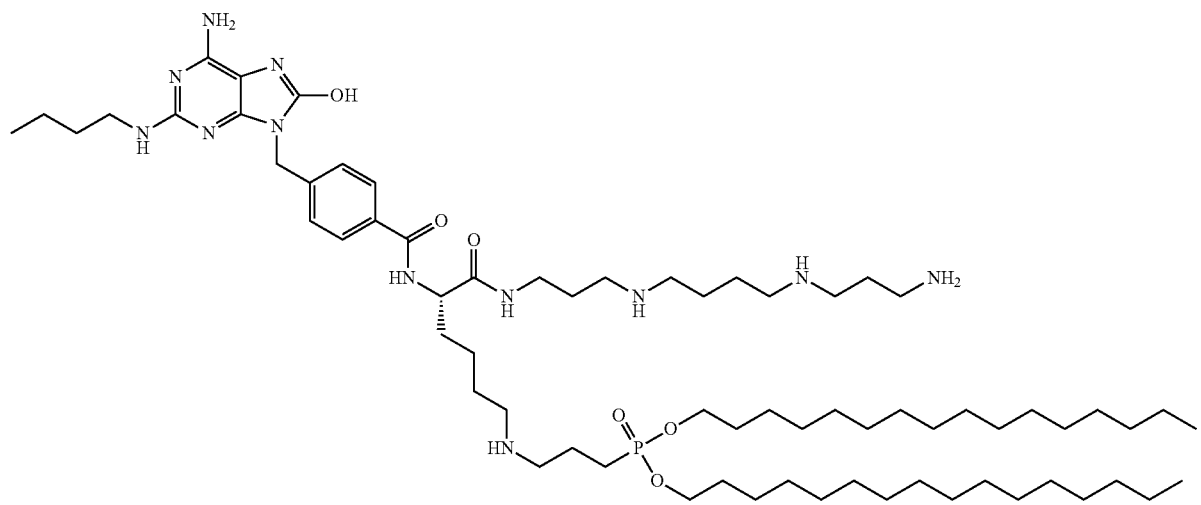
CL488
(S)-Dihexadecyl-1-amino-15-(4-((6-amino-2-(butylamino)-8-hydroxy-9H-purin-9-yl)methyl)benzamido)-14-oxo-4,9,13,20-tetraazatricosan-23-ylphosphonate
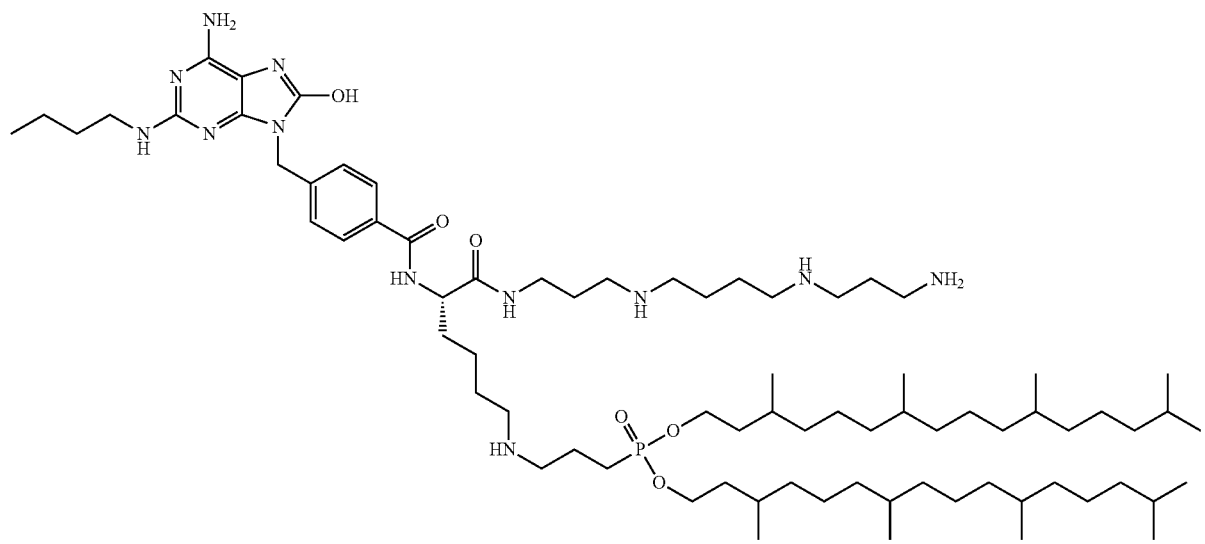
CL494
(S)-bis(3,7,11,15-tetramethylhexadecyl)-1-amino-15-(4-((6-amino-2-(butylamino)-8-hydroxy-9H-purin-9-yl)methyl)benzamido)-14-oxo-4,9,13,20-tetraazatricosan-23-ylphosphonate

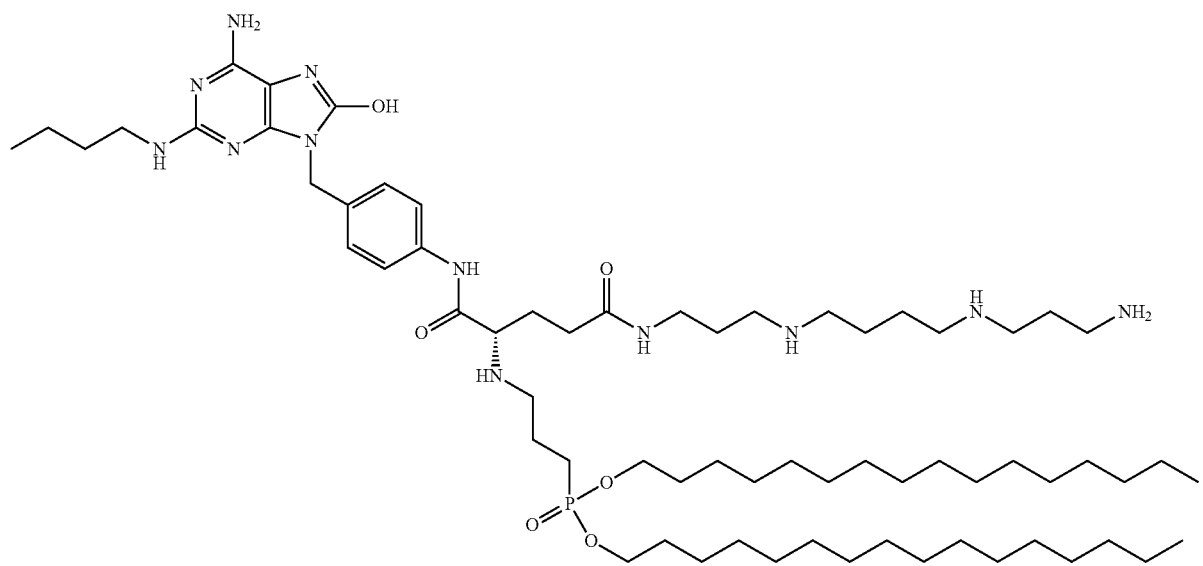
(S)-dihexadecyl-21-amino-5-(4-((6-amino-2-(butylamino)-8-hydroxy-9H-purin-9-yl)methyl)phenylcarbamoyl)-8-oxo-4,9,13,18-tetraazahenicosylphosphonate
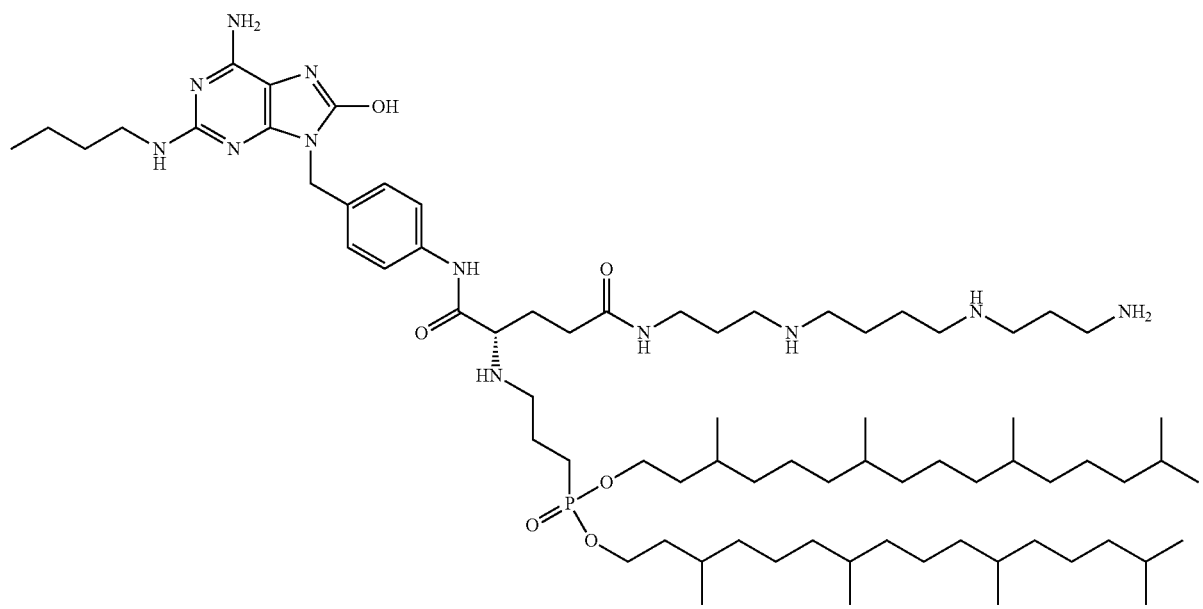
bis(3,7,11,15-tetramethylhexadecyl)-(S)-21-amino-5-(4-((6-amino-2-(butylamino)-8-hydroxy-9H-purin-9-yl)methyl)phenylcarbamoyl)-8-oxo-4,9,13,18-tetraazahenicosylphosphonate

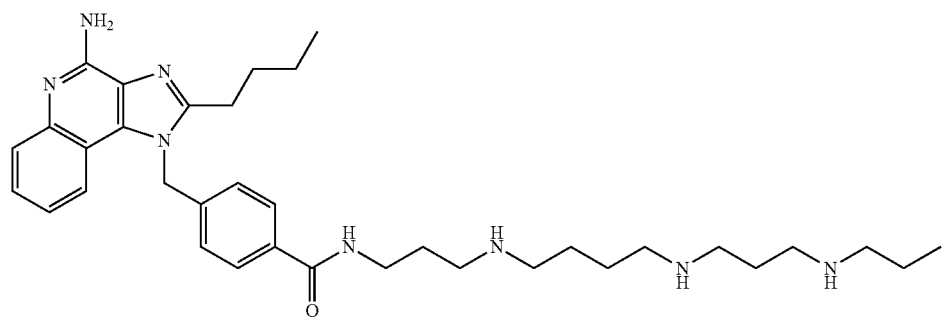
CL397
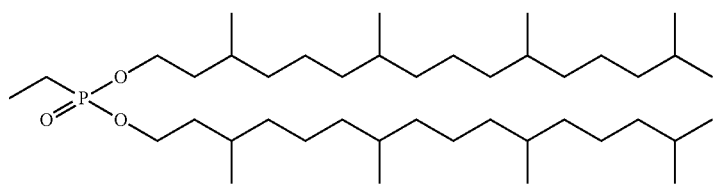
bis(3,7,11,15-tetramethylhexadecyl)-1-(4-((4-amino-2-butyl-1H-imidazo[4,5-c]quinolin-1-yl)methyl)phenyl)-1-oxo-2,6,11,15-tetraazaoctadecan-18-ylphosphonate
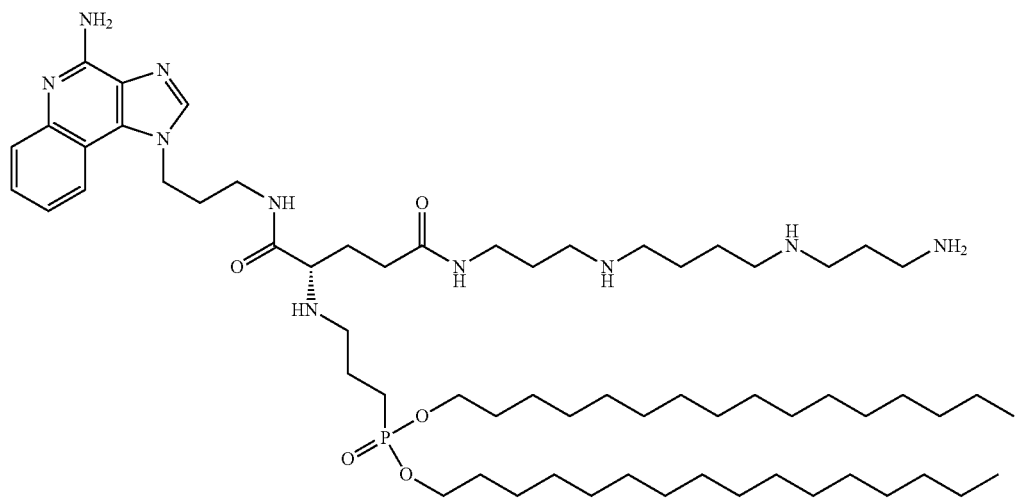
CL545
(S)-dihexadecyl-21-amino-5-(3-(4-amino-2-(ethoxymethyl)-1H-imidazo[4,5-c]quinolin-1-yl)propylcarbamoyl)-8-oxo-4,9,13,18-tetraazahenicosylphosphonate

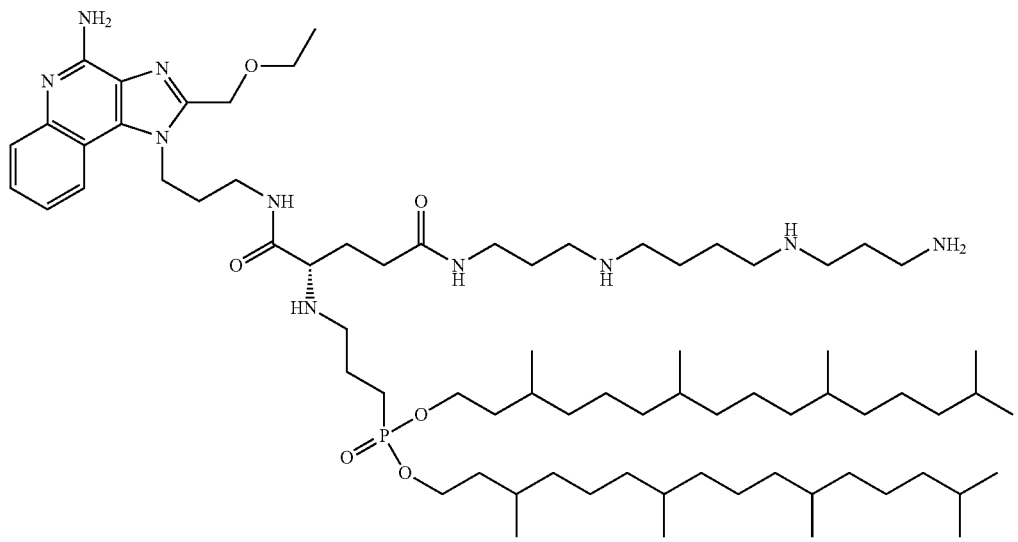
CL546
bis(3,7,11,15-tetramethylhexadecyl)-(S)-21-amino-5-(3-(4-amino-2-(ethoxymethyl)-1H-imidazo[4,5-c]quinolin-1-yl)propylcarbamoyl)-8-oxo-4,9,13,18-tetraazahenicosyl-phosphonate
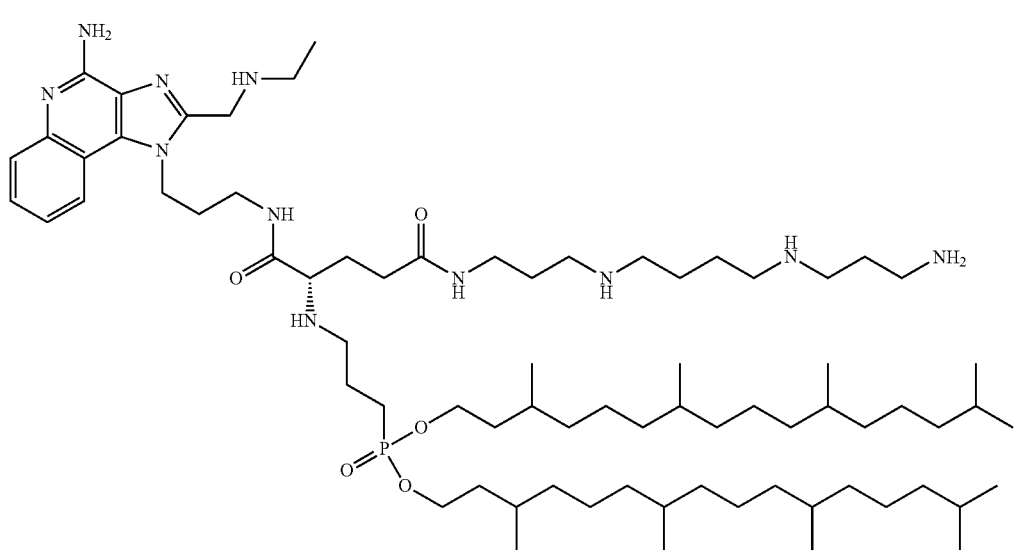
CL547
bis(3,7,11,15-tetramethylhexadecyl)-(S)-21-amino-5-(3-(4-amino-2-((ethylamino)methyl)-1H-imidazo[4,5-c]quinolin-1-yl)propylcarbamoyl)-8-oxo-4,9,13,18-tetraazaheni-cosylphosphonate, and

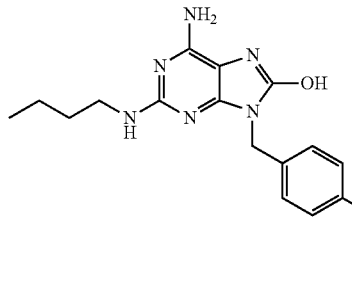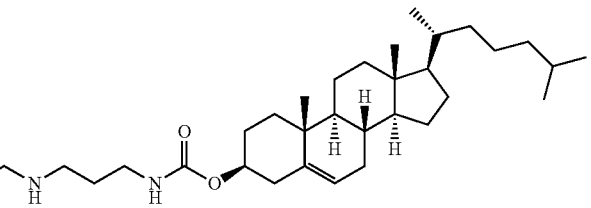

(3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(4-(3-(4-((6-amino-2-(butylamino)-8-hydroxy-9H-purin-9-yl)methyl)benzamido)propylamino)butylamino)propylcarbamate, a tautomer thereof or a pharmaceutically acceptable salt, solvate or polymorph of said compound or tautomer.

The compounds of Formula (I') containing one or more asymmetric carbon atoms can exist as two or more stereoisomers. Where a compound of Formula (I') contains an alkenyl or alkenylene group, geometric cis/trans (or Z/E) isomers are possible. Where structural isomers are interconvertible via a low energy barrier, tautomeric isomerism ('tautomerism') can occur. The invention includes the use of conjugates of TLR7 and/or TLR8 agonists and a lipid gene delivery agent that is cationic at physiological pH. The conjugates may include lipophosphonate linked to a TLR7 and/or TLR8 agonist via a linker (the polyamine).

The lipid molecules of the invention and their cationic form may exist unsolvated and in solvated forms of pharmaceutically acceptable salts. The compounds of Formula I and their pharmaceutically acceptable salts, solvates and polymorphs are useful because they have pharmacological activity in animals, including humans. More particularly, they are useful in the immune modulation for the treatment of a disease. In one aspect, the compounds of the invention are useful in the treatment of a viral, bacterial, fungal, and protozoal infections, tumors or cancer, or immunological diseases. In yet another aspect, the compounds of the invention are useful as vaccine adjuvants. Accordingly the invention provides a compound of Formula I or a pharmaceutically acceptable salt, solvate or derivative thereof for use as a medicament, in immune modulation for the treatment of a disease.

At physiological pH, the conjugated compound of the invention is positively charged on its Z moiety, thereby being able to form a complex with a polyanionic molecule, such as a nucleic molecule.

The cationic lipid molecules of the invention are typically provided in aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of compound of Formula I under sterile conditions, for example, by lyophilisation, may readily be accomplished using standard pharmaceutical techniques well known to those skilled in the art. Due to the lipid moiety $R^4$ of formula VII or VIII, the compounds of the invention may form liposomes in aqueous solution.

Another object of the present invention is a complex formed between a polyanionic molecule and the conjugated compound of formula (I) as defined above in a medium having a physiological pH, i.e. a pH comprised between 4 and 8. In this range of pH, the conjugated compound of formula (I) is in cationic form and is capable of forming a complex with a nucleic acid. Preferably, a complex formed between a polyanionic molecule and the compound of formula (I') as defined above, or its preferred embodiments as defined above.

Preferably, the polyanionic molecule, e.g., pDNA, mRNA, polynucleotide or nucleic acid oligomer can be solubilized in any of various buffers prior to mixing or complexing with the conjugated compound of formula (I) in cationic form. Suitable buffers include phosphate buffered saline (PBS), normal saline, carbohydrates buffer such as Glucose 5% or Bionolyte G5, Tris buffer, and sodium phosphate. Insoluble polynucleotides can be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art.

According to the present disclosure, the polyanionic molecule can be complexed with the conjugated compound of the present disclosure in cationic form by any means known in the art, e.g., by mixing a pDNA solution and a solution of cationic lipid (I) liposomes. In one embodiment, the concentration of each of the constituent solutions is adjusted prior to mixing such that the desired final pDNA/cationic lipid ratio and the desired pDNA final concentration is obtained upon mixing the two solutions. For example, if the desired final solution is to be physiological saline (Bionolyte G5), a nonionic surfactant, such as Pluronic® F-68, can be used to stabilize the complex. Both pDNA and cationic lipid liposomes are prepared in Bionolyte G5 with PF-68 (2%) and then simply mixed to produce the desired complex. The cationic lipid liposomes can be prepared by any means known in the art.

Preferably, the polyanionic molecule is a nucleic acid, such as a coding or non-coding plasmid DNA, a double-stranded DNA, a single-stranded DNA, a double-stranded RNA, a single-stranded RNA, an oligodeoxynucleotide, a cyclic dinucleotide or a mixture thereof.

Since nucleic acids, due to the phosphate groups within the backbone of nucleic acids, are net negatively charged molecules, they are bound by the positively charged groups of the molecules of the present invention, via electrostatic interaction, to form a stable complex.

According to the invention, a complex between a cationic lipid molecule and a nucleic acid suggests that the nucleic acid is linked to a cationic lipid molecule by non-covalent bonds, because of the ability of nucleic acids, both RNAs and DNAs, to interact with positively charged substances.

Hence, a cationic lipid molecule according to the invention is a compound comprising:
- at least one lipophilic hydrocarbon chain and
- at least one chemical group that is positively charged at physiological pH, said compound being capable of forming a complex with a nucleic acid.

This composition forms a lipophilic complex with nucleic acids of interest, which include non-coding or coding DNA.

According to the present invention, a gene of interest can be complexed with the compounds of the invention by mixing a pDNA (plasmid DNA) solution. The concentration of each of the constituent solutions is adjusted prior to mixing such that the desired final pDNA/cationic lipid ratio and the desired pDNA final concentration is obtained upon mixing the two solutions. Complexes of the compounds of the invention with pDNA provide further immunogenic compositions of the present disclosure.

Compounds of the invention complexed with pDNA may be administered alone or in combination with one or more other drugs (or as any combination thereof). The compounds of the invention complexed with a pDNA of interest may be administered directly into the site of disease. In one aspect, immunogenic compositions of the compounds of the invention may be administered intratumorally. Suitable devices for intratumoral administration include needle (including microneedle) injectors, needle-free injectors and infusion techniques. The preparation of intratumoral formulations under sterile conditions may readily be accomplished using standard pharmaceutical techniques well known to those skilled in the art.

Another object of the present invention is a pharmaceutical composition comprising the conjugated compound as defined previously or the complex as defined above and a pharmaceutically acceptable excipient or carrier.

A pharmaceutically acceptable excipient or carrier means an excipient or carrier that is useful in preparing a pharmaceutical composition that is safe, non-toxic and neither biologically nor otherwise undesirable, and includes an excipient that is acceptable for human use as well as veterinary use.

Another object the invention is a vaccine comprising the conjugated compound as defined previously or the complex as defined above.

Another object of the present invention is a conjugated compound as defined previously or a complex as defined above, for use in a therapeutic treatment in human or animals.

Another object of the present invention is a conjugated compound as defined previously or a complex as defined previously, for use in the treatment of a pathology selected from the group consisting of an infection, a cancer and an immune disorder.

Another object of the present invention is a conjugated compound as defined previously or complex as defined previously, for use in the treatment of a pathology which may be alleviated by the induction of an immune response via TLR7 and/or TLR8 pathway(s).

The compounds of formula (I) and their pharmaceutically acceptable salts, solvates and polymorphs are useful because they have pharmacological activity in animals, including humans. More particularly, they are useful in the treatment of a disorder in which the modulation, especially agonism, of TLR7 is implicated. In one aspect, the compounds of the invention are useful in the treatment of infections caused by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, or respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), a retrovirus (e.g., a lentivirus such as HIV) or a filovirus (e.g., Ebola virus or Marburg virus).

In another aspect, the compounds of the invention are useful to treat tumors or cancers including but not limited to carcinomas, sarcomas, and leukemias, e.g. squamous cell carcinoma, pancreatic carcinoma, hepatocarcimona, renal cell carcinoma, Kaposi's sarcoma, melanoma, renal cell carcinoma, myelogeous leukemia, chronic lymphocytic leukemia, multiple myeloma, or non-Hodgkin's lymphoma.

In yet another aspect, the compounds of the invention are useful to treat bacterial, fungal, and protozoal infections including but not limited to infections caused by bacteria of the genus *Escherichia, Enterobacter, Salmonella, Staphylococcus, Klebsiella, Proteus, Pseudomonas, Streptococcus, Chlamydia*; or fungal infections such as candidiasis, aspergillosis, histoplasmosis, or cryptococcal meningitis.

In yet another aspect, the compounds of the invention are useful to treat Th2-mediated diseases (see e.g. Dabbagh et al., Curr Opin Infect Dis 2003, 16: 199-204, incorporated herein by reference), including but not limited to atopic diseases, such as atopic dermatitis or eczema, eosinophilia, asthma, allergy, or allergic rhinitis.

In yet another aspect, the compounds of the invention are useful in the treatment of autoimmune diseases.

Another object of the present invention is a method for treating pathology selected from the group consisting of an infection, a cancer and an immune disorder in a subject in need thereof comprising administering to said subject a therapeutically effective amount of the conjugated compound as defined previously or of the complex as defined previously.

Another object of the present invention is a method for inducing an immune response via TLR7 and/or TLR8 pathway(s) in a patient, comprising administering to said patient a therapeutically effective amount of the conjugated compound as defined previously or of the complex as defined previously.

Another object of the present invention is a method for inducing an immune response via TLR7 and/or TLR8 pathway(s) and/or cytosolic nucleic acids sensors pathway(s) in a patient, comprising administering to said patient a therapeutically effective amount of the complex as defined previously, in particular in the form of complex with a polyanionic molecule.

Another object of the present invention is the use of a conjugated compound of formula (I) as defined above or a complex as defined above for the preparation of a medicament for the treatment of an infection, a cancer or an immune disorder.

The therapeutically effective amount of the conjugated compound as defined above or of the complex may be administered directly into the blood stream, into muscle, into tumor, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for administration include needle (including microneedle) injectors, needle-free injectors and infusion techniques.

The therapeutically effective amount of the conjugated compound as defined above or of the complex may also be administered topically to the subject.

The dosage can vary within wide limits and will, of course, be fitted to the individual requirements in each particular case. In general, in the case of administration to adults a convenient daily dosage of the conjugated compound of the invention should be about 1 µg to about 500 mg, preferably about 100 µg to about 1 mg. The daily dosage may be administered as a single dose or in divided doses and, in addition, the upper dosage limit referred to earlier may be exceeded when this is found to be indicated.

Chemistry

The compounds of the present invention can be synthesized by an appropriate combination of generally well known synthetic methods. Techniques employed in synthesizing the compounds of the disclosure are both readily apparent and accessible to those of skill in the relevant art. The discussion below is offered to illustrate a number of the diverse methods available for use in assembling the compounds of the disclosure. However, the discussion is not intended to define the scope of reactions or reaction sequences that are useful in preparing the compounds of the present disclosure. The compounds of this disclosure may be made by the procedures and techniques disclosed in the Examples section below, as well as by known organic synthesis techniques.

The compounds of the present disclosure may be synthesized using one or more protecting groups generally known in the art of chemical synthesis. The term "protecting group" refers to chemical moieties that block some or all reactive moieties of a compound and prevent such moieties from participating in chemical reactions until the protective group is removed. Examples of the moieties listed are described in 'Protective Groups in Organic Synthesis' by Green and Wuts, third edition, (John Wiley and Sons, 1999). Where different protecting groups were employed, each (different) protective group was removable by a different means. Protective groups that were cleaved under totally disparate reaction conditions allowed for differential removal of such protecting groups. For example, protective groups can be removed by acid, base, and hydrogenolysis.

An object of the present invention is a process for the manufacture of the compounds of formula (I') as defined previously, which process comprises reacting a compound of formula (XII):

wherein $R^1$, $R^2$, $R^3$, A, s, X and Y are as defined previously, with a compound of formula (XIII):

H—Z—R⁴ (XIII)

wherein Z and $R^4$ are as defined previously, or reacting a compound of formula (XIV):

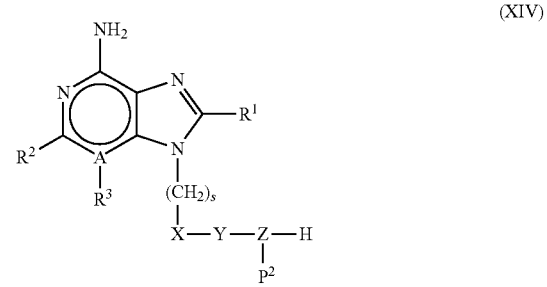

wherein $R^1$, $R^2$, $R^3$, A, s, X, Y and Z are as defined in claim 3, and $P^2$ is a protecting group, with a compound of formula (XV):

L-R⁴ (XV)

wherein $R^4$ is as defined in claim 3, and L is a leaving group.

A general scheme of synthesis is illustrated below. The TLR7 and/or TLR8 agonists that are purine, imidazoquinoline or deazapurine derivatives, can be synthesized from 2-chloroadenine, 4-hydroxyquinoline or from malonic dichloride, respectively, with acid or amine function linked to the imidazole group. The functional acid or amino on the exocyclic moiety enabled us to couple the agonist to many different auxiliary chemical entities, including lipids or phospholipids through a linker molecule that contained a polyamino group.

Scheme 1

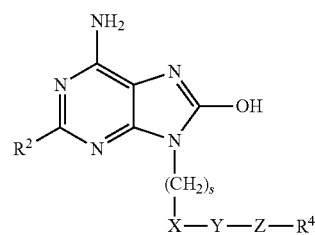

Formula X

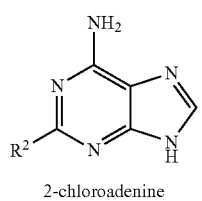

2-chloroadenine

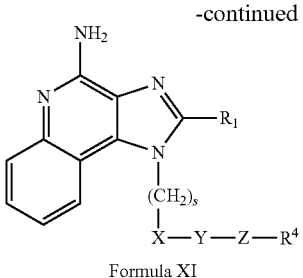

Formula XI

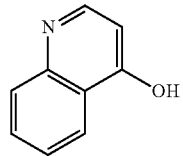

4-hydroxyquinoline

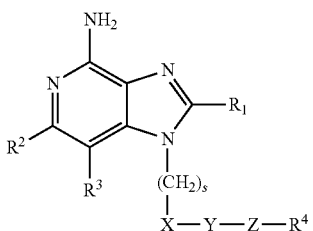

Formula XII

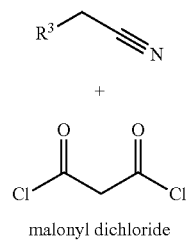

malonyl dichloride

The compounds of Formula (I') containing one or more asymmetric carbon atoms can exist as two or more stereoisomers. Where a compound of Formula (I') contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula (I') containing, for example, an imino, keto, or oxime group, or so-called valence tautomerism in compounds which contain an aromatic moiety. It follows that a single compound may exhibit more than one type of isomerism.

In particular, a compound of Formula $X_A$ is the tautomer of the compound of Formula $X_B$:

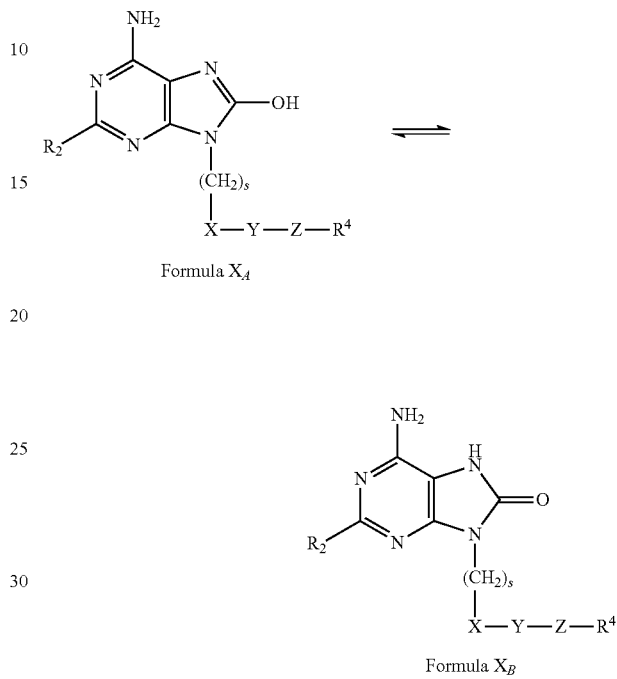

It will be appreciated by those skilled in the art that certain of the procedures described in the schemes for the preparation of compounds of Formula (I') or intermediates thereof may not be applicable to some of the possible substituents. It will be further appreciated by those skilled in the art that it may be necessary or desirable to carry out the transformations described in the schemes in a different order from that described, or to modify one or more of the transformations, to provide the desired compound of Formula (I').

It will be still further appreciated by those skilled in the art that it may be necessary or desirable at any stage in the synthesis of compounds of Formula (I') to protect one or more sensitive groups in the molecule so as to prevent undesirable side reactions. In particular, it may be necessary or desirable to protect amino groups. The protecting groups used in the preparation of compounds of Formula (I') may be used in conventional manner. See, for example, those described in 'Protective Groups in Organic Synthesis' by Green and Wuts, third edition, (John Wiley and Sons, 1999), in particular chapter 7, pages 494-653 ("Protection for the Amino Group"), incorporated herein by reference, which also describes methods for the removal of such groups.

The purine derivatives of Formula X can be prepared by the following methods. The starting compounds not disclosed below can be prepared by a similar method to the following method or by a known method and similar methods to that.

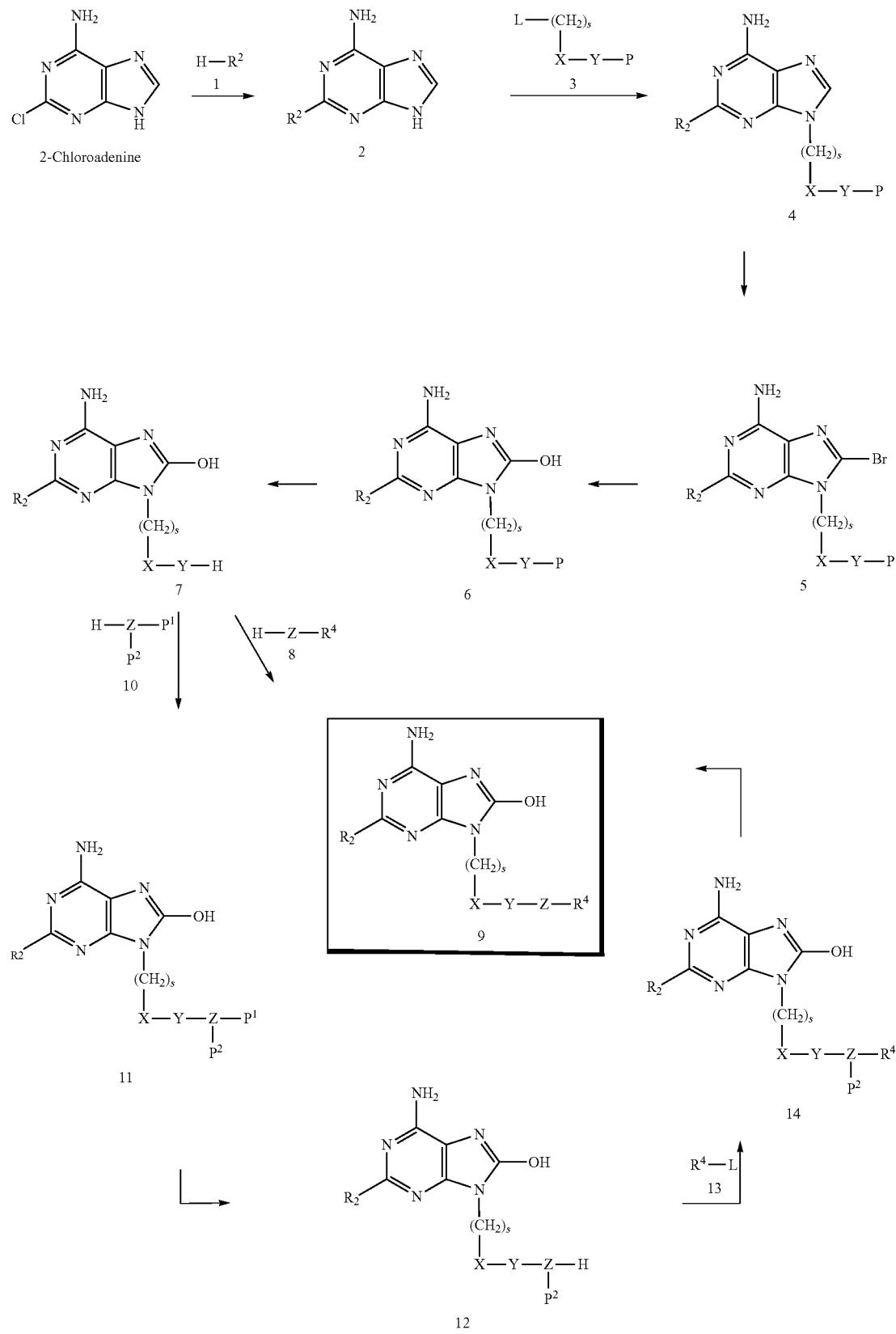

In the above formulas, L is a leaving group, P, P¹ and P² are different protecting groups R², s, X, Y, Z and R⁴ are same as defined above.

Commercially available 2-Chloroadenine can be reacted with compound 1 in an organic solvent. When compound 1 is an amine, the reaction is preferably carried out in the amine as solvent. Reaction vessels such as an autoclave etc. may be used in the reaction, if necessary. When compound is alcohol or thioalcohol, the reaction is preferably carried out in the presence of a base. The bases are alkali metals, such as sodium or potassium, alkali metal hydrides, such as sodium hydride or potassium hydride, organometalic compounds, such as methyl lithium, butyl lithium or lithium diisopropylamide. The base is preferably used about equimolar to compound 1. The organic solvents are aprotic solvents, such as dimethylformamide, acetonitrile or hexamethylphosphoroustriamide, or ethers such as diethyl ether, tetrahydrofuran or 1,4-dioxane or diglyme. The reaction temperature is selected from the range between about room temperature and around the boiling point of the solvent.

The chlorine atom of 2-chloroadenine can be also coupled under a variety of conditions in which a reactive organometallic reagent can be treated with 2-chloroadenine in the presence of a transition metal catalyst, for example a stannane, zincate or boronic acid in the presence of a palladium catalyst, to give the 2-substituted adenine 2.

Compound 2 and compound 3 can react in the presence of a base in an organic solvent. Compound 3 can be used about equal molar or several molars to compound 2. Bases are inorganic bases such as alkali metal carbonates (e.g. sodium carbonate, potassium carbonate, cesium carbonate), or organic bases, such as tertiary amines (e.g. triethylamine, diisopropylethylamine) or pyridines (e.g. 4-dimethylaminopyridine, pyridine). The base is preferably used about equimolar to compound 3. The organic solvents are halogenated hydrocarbons such as tetrachloromethane, chloroform or methylene chloride, ethers such as diethyl ether, tetrahydrofuran or 1,4-dioxane, or aprotic solvents, such as dimethylformamide, dimethyl sulfoxide, acetonitrile or hexamethylphosphoroustriamide. The reaction temperature is selected from the range between about 0° C. and around the boiling point of the solvent.

Compound 4 can react with a brominating reagent such as bromine, hydrobromic acid perbromide, N-bromo succinimide, etc. in an organic solvent. A reaction promoter such as sodium acetate may be added to the reaction mixture. The brominating reagent is used from equimolar to several moles of compound 4, preferably from equimolar to one and one-half moles. The organic solvents are halogenated hydrocarbons, such as tetrachloromethane, chloroform or methylene chloride, ethers such as diethyl ether, acetic acid, or carbon disulfide. The reaction temperature is selected from the range between about 0° C. and around boiling point of the solvent.

Compound 5 can react with an alcohol such as methanol in the presence of a base in an organic solvent. The bases are alkali metals, such as sodium or potassium, alkali metal hydrides, such as sodium hydride or potassium hydride, organometallic compounds, such as methyl lithium, butyl lithium or lithium diisopropylamide. The base is preferably used from about equal molar to about two times as much to compound 5. The organic solvents are ethers, such as diethyl ether, tetrahydrofuran or 1,4-dioxane, or aprotic solvents, such as dimethylformamide, dimethyl sulfoxide, acetonitrile or hexamethylphosphoroustriamide. The alcohol as the reagent, such as methanol, ethanol, propanol or butanol may serve as a solvent. The reaction temperature is selected from the range between about room temperature and around boiling point of the solvent. This intermediate can be hydrolysed under either acidic or basic conditions, typically with an acid in water or a mixture of water and an organic solvent. The acids are inorganic acids, such as hydrochloric acid or hydrobromic acid, or organic acids such as trifluoroacetic acid. The organic solvents are ethers, such as diethyl ether or tetrahydrofuran, aprotic solvents such as dimethylformamide, alcohols, such as methanol, ethanol or propanol, or acetic acid. The reaction temperature is selected from the range between about room temperature and around boiling point of the solvent.

The protection on compound 6 can be removed by acid, base or hydrogenolysis.

The compounds 9 and 11 are prepared from respectively compounds 8 and 10 by any well known peptide synthesis procedure in the art. The most commonly employed methods for peptide bond formation in solution include: the carbodiimide method (DCC, DIC), symmetric or mixed anhydrides, active esters (OPfp, Odhbt, OSu), phosphonium salts (BOP, PyBOP, AOP, PyAOP) and uronium/guanidinium-mediated salt built around processes using HOBt and HAOt (HBTU, HATU, HBPyU, COMU etc). HATU reacts exclusively with carboxylate salts (R—COO—); mixtures of HATU and a carboxylic acid (R—COOH) remain stable. This procedure eliminates the requirement for a separate neutralization step saving time and minimizing diketopiperazine formation. Three equivalents of base (DIEA or NMM) are necessary to neutralize the carboxylic acid, the amine salt, and the acidic hydroxybenzotriazole. When using HATU, the reaction mixture has to be kept near basic pH in order to ensure a fast coupling. Under such conditions, the coupling rate is so high that racemization is negligible using urethane-protected amino acid couplings and fairly low in segment coupling. The excess of acid and "onium" salt (HATU) is typically 1.1 molar equivalent in solution synthesis. This reaction is preferably carried out in a solvent such as methylene chloride, chloroform, tetrahydrofuran, dioxane, ethyl acetate, or the like under ice-cooling to at ambient temperature and the reaction in the presence of an inert gas is usually carried out in an anhydrous, but not critical, conditions. The reaction temperature is selected from the range between about room temperature and around boiling point of the solvent.

The protection on compound 11 can be removed by acid, base or hydrogenolysis.

Compound 12 and compound 13 can react in the presence of a base in an organic solvent. Compound 13 can be used about equal molar or several molars to compound 12. Bases are inorganic bases such as alkali metal carbonates (e.g. sodium carbonate, potassium carbonate, cesium carbonate), or organic bases, such as tertiary amines (e.g. triethylamine, diisopropylethylamine) or pyridines (e.g. 4-dimethylaminopyridine, pyridine). The base is preferably used about equimolar to compound 3. The organic solvents are halogenated hydrocarbons such as tetrachloromethane, chloroform or methylene chloride, ethers such as diethyl ether, tetrahydrofuran or 1,4-dioxane, or aprotic solvents, such as dimethylformamide, dimethyl sulfoxide, acetonitrile or hexamethylphosphoroustriamide. The reaction temperature is selected from the range between about 0° C. and around the boiling point of the solvent.

The protection on compound 14 can be removed by acid, base or hydrogenolysis.

Imidazoquinolines derivatives of Formula XI of the invention can be prepared according to reaction Scheme 5:

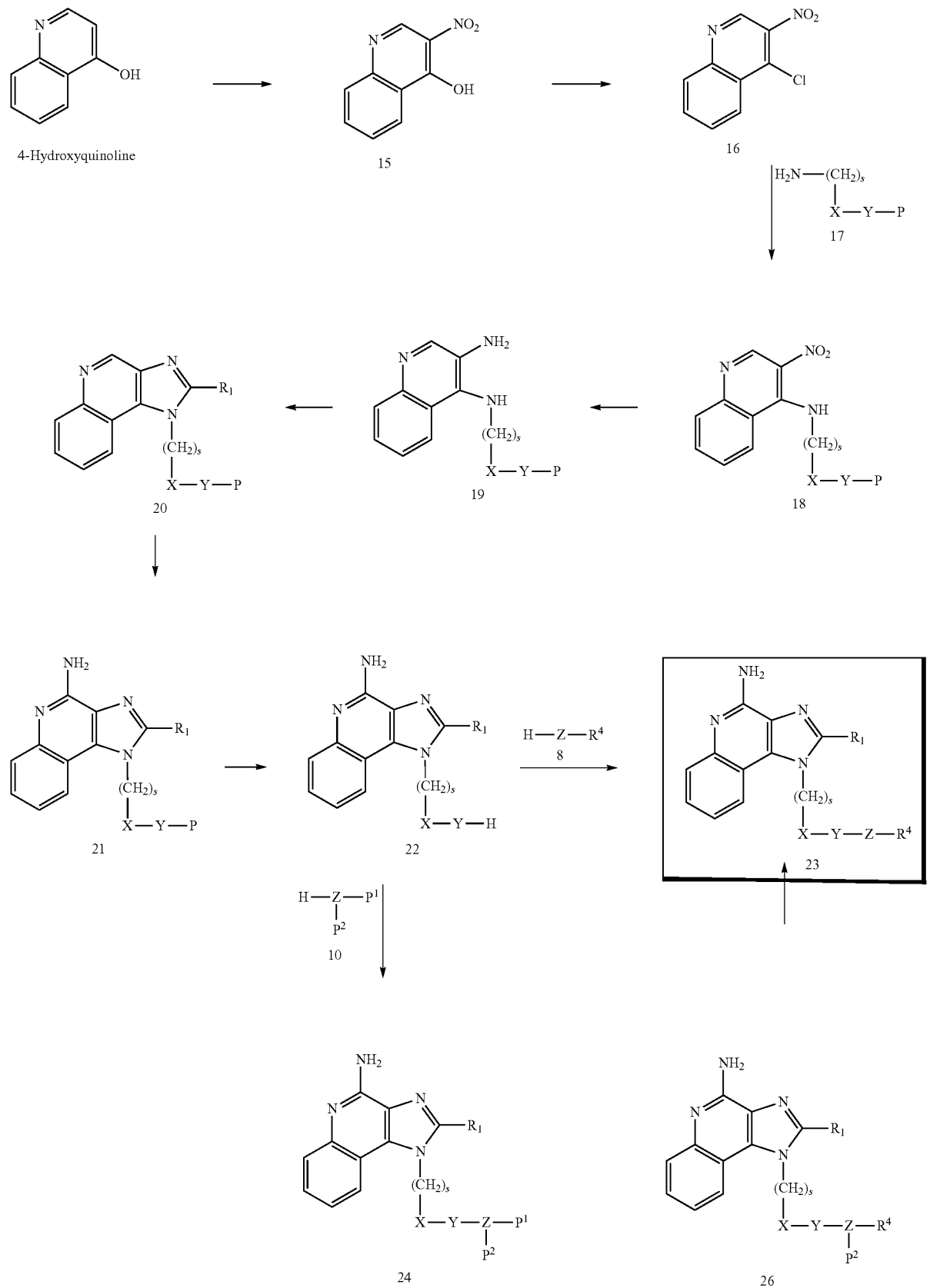
Scheme 5

-continued

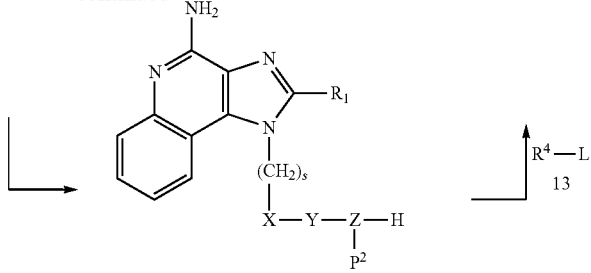

In the above formulas P, P¹, P², L, R¹ R², R⁴, s, X, Y, and Z are same as defined above.

The Reaction Scheme begins with a commercially available 4-hydroxyquinoline. The nitration of a 4-hydroxyquinoline provide the 3-nitro-4-hydroxyquinoline compound 15. Conventional conditions for such reactions are well known. Preferred conditions in the instance afford a product of Formula 15 in superior yield compared with conditions used in the prior art, involve heating at about 125° C.-130° C. in propionic acid in the presence of nitric acid.

Compound 15 is chlorinated at the 4-position to provide a 3-nitro-4-chloroquinoline compound 16. Preferred conditions involve chlorination in methylene chloride with a Vilsmeier reagent prepared from thionyl chloride and N,N-dimethylformamide. In such a reaction, the compound of Formula 15 is suspended in methylene chloride, and a slight molar excess of thionyl chloride and N,N-dimethylformamide is added to the suspension. Heating to reflux facilitates the chlorination.

Compound 16 is reacted with an amine of Formula 17. The reaction can be carried out by adding amine to a solution of a compound of compound 16 in a suitable solvent such as chloroform or dichloromethane in presence of base such as triéthylamine or diisopropyl-ethylamine and optionally heating.

Compound 18 is reduced to provide a quinoline-3,4-diamine compound 19. Compound 18 may then be reduced under any of the conditions known in the literature to reduce a nitro aromatic compound to an amine using for example iron or tin in HCl, hydrogenation in the presence of a transition metal catalyst such as palladium, platinum or nickel or a chemical reductant such as lithium aluminium hydride to give 19. Preferably, the reduction is carried out using a conventional heterogeneous hydrogentation catalyst such as platinum on carbon or palladium on carbon. The reaction can conveniently be carried out in a suitable solvent such as ethanol, isopropyl alcohol or toluene.

Compound 19 is reacted with a carboxylic acid or an equivalent thereof to provide a 1H-imidazo[4,5-c]quinoline compound 20. Suitable equivalents to carboxylic acid include acid halides, orthoesters, and 1,1-dialkoxyalkyl alkanoates. The carboxylic acid or equivalent is selected such that it will provide the desired R¹ substituent in a compound 20. For example, triethyl orthoformate will provide a compound where R¹ is hydrogen and triethyl orthoacetate will provide a compound where R¹ is methyl. The reaction can be run in the absence of solvent or in an inert solvent such as toluene. The reaction is run with sufficient heating to drive off any alcohol or water formed as a byproduct of the reaction.

Compound 20 is oxidized to provide a 1H-imidazo[4,5-c]quinoline-5N-oxide using a conventional oxidizing agent that is capable of forming N-oxides. Preferred reaction conditions involve by reacting a solution of a compound 20 in chloroform with 3-chloroperoxybenzoic acid at ambient conditions. The intermediate 1H-imidazo[4,5-c]quinoline-5N-oxide is then directly aminated to provide a 1H-imidazo[4,5-c]quinolin-4-amine compound 21. In this step the N-oxide compound is reacted with an acylating agent such as: alkyl- or arylsulfonyl chlorides (e.g., benezenesulfonyl chloride, methanesulfonyl chloride, p-toluenesulfonyl chloride). Arylsulfonyl chlorides are preferred. Para-toluenesulfonyl chloride is most preferred. The product obtained is mixed with an excess of an aminating agent. Suitable aminating agents include ammonia (e.g., in the form of ammonium hydroxide) and ammonium salts (e.g., ammonium carbonate, ammonium bicarbonate, ammonium phosphate) Ammonium hydroxide is preferred. The reaction is preferably carried out by dissolving the N-oxide compound in an inert solvent such as dichloromethane, adding the aminating agent to the solution, and then slowly adding the acylating agent. The product or a pharmaceutically acceptable salt thereof can be isolated using conventional methods.

The protection on compound 21 can be removed by acid, base or hydrogenolysis to provide compound 22.

The compounds 23 and 24 are prepared from compound 22 with respectively compounds 8 and 10 by any well-known peptide synthesis procedure in the art as described above for compound 9 and 11.

The protection on compound 24 can be removed by acid, base or hydrogenolysis to provide compound 25.

Compound 25 and compound 13 can react in the presence of a base in an organic solvent as described below for compound 12 to give compound 26.

The protection on compound 26 can be removed by acid, base or hydrogenolysis to provide compound 23.

3-deazapurine derivatives of formula 38 of the invention can be prepared according to reaction Scheme 6:

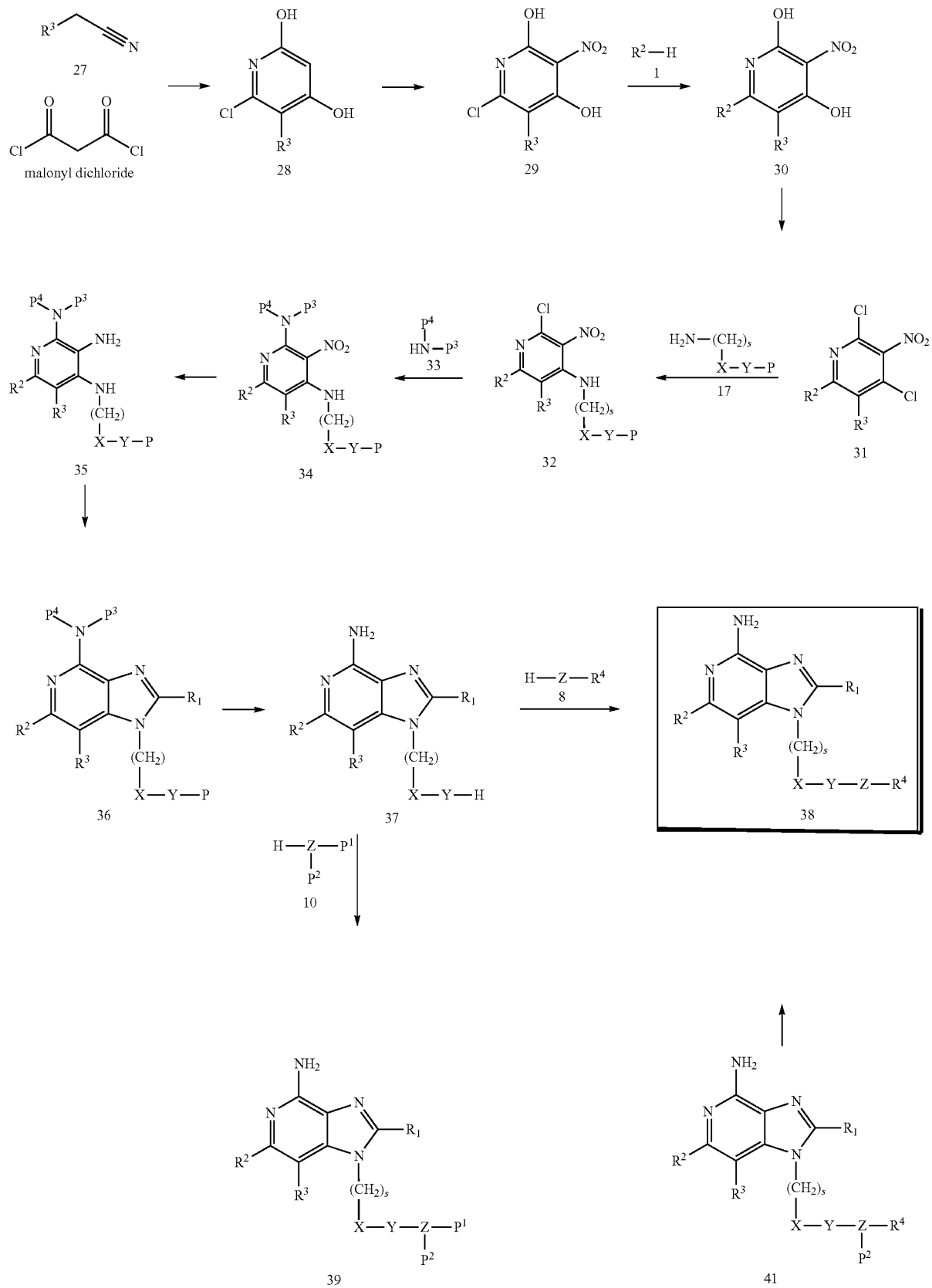

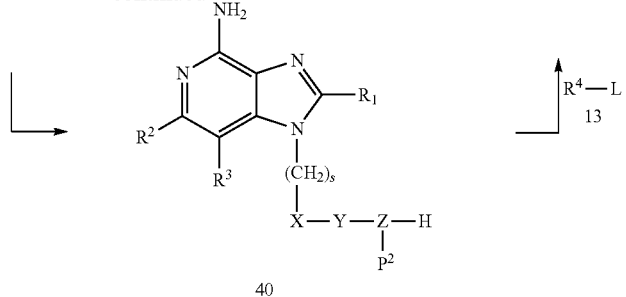

In the above formulas, $P^3$ and $P^4$ are different protecting groups, P, $P^1$, $P^2$, L, $R^1$ $R^2$, $R^3$, $R^4$, s, X, Y, and Z are same as defined above.

A commercially available nitrile 27 which possesses a methylene group adjacent to the nitrile function is reacted with malonyl dichloride to provide the pyridines 28. (Synthesis, 1984, 765-766).

The pyridines 28 is then nitrated using method described above for the 4-hydroxyquinoline.

The chlorine atom of compound 29 is then reacted as described above for 2-chloroadenine.

Compound 30 is chlorinated using a variety of conditions which convert hydroxyl groups to chlorines, such as thionyl chloride or phosphorus oxychloride to give 31. Preferred condition is described above for the preparation of compound 16.

Compound 31 is reacted with an amine of general formula 17, as described above for the preparation of compound 18. This amine preferentially reacts at the 4-chloro group to give 32. Some displacement of both chlorine groups or a minor amount of displacement at the 2-chloro group can occur, but does not detract from the ability to secure predominantly compound 32.

Compound 32 is then reacted with ammonia $P^3$=$P^4$=H in methanol at 150° C. under pressure to give compound 34. Alternatively, compound 32 can be reacted with a protected form of ammonia 33, in which $P^3$ and $P^4$ protecting group which can be later removed under mild conditions, such as dibenzylamine or diallylamine.

The compound 34 is then reduced under conditions as described above for compound 18 to give compound 35.

Compound 35 is then reacted with a source of C=O such as 1,1-carbonyldiimidazole or phosgene. Alternatively, compound 35 can be reacted with a carboxylic acid or an equivalent, as described for compound 19, to provide a 1H-imidazo[4,5-c]pyridine compound 36.

The protection on compound 36 can be removed by acid, base or hydrogenolysis to provide compound 37.

The compounds 38 and 39 are prepared from compound 37 with respectively compounds 8 and 10 by any well-known peptide synthesis procedure in the art as described above for compound 9 and 11.

The protection on compound 39 can be removed by acid, base or hydrogenolysis to provide compound 40.

Compound 40 and compound 13 can react in the presence of a base in an organic solvent as described below for compound 12 to give compound 41.

The protection on compound 41 can be removed by acid, base or hydrogenolysis to provide compound 38.

The invention will be further illustrated by the following figures and examples. However, these examples and figures should not be interpreted in any way as limiting the scope of the present invention.

FIGURES

Figure 1B:
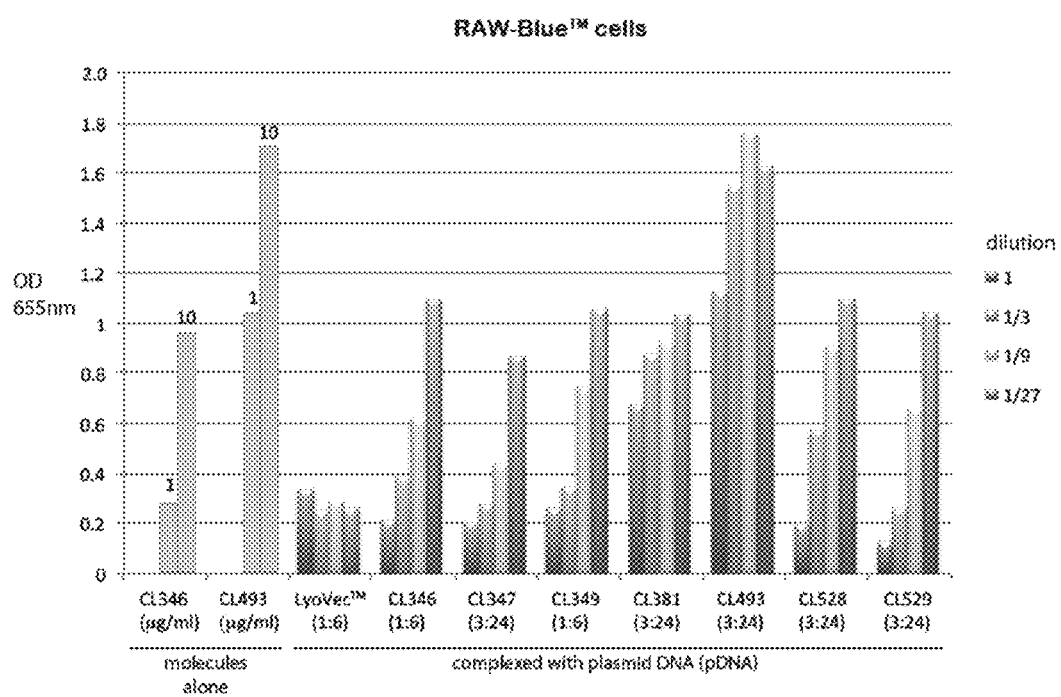

FIG. 1 demonstrates the ability of TLR7-cationic lipid molecules of the invention to activate TLR7 receptors compared to positive controls, TLR7 activators R848 and CL264 and the negative control, TLR2 agonist Pam3CSK4. In FIG. 1A, graphs show the effect of molecules alone on HEK Blue™ mTLR7 or hTLR7 reporter cell lines. In FIG. 1B graphs show the effect of molecules complexed with plasmid DNA (pBsr2 pCpGLacZh plasmid) on stimulating TLR7-induced NF-κB activity using the RAW Blue™ reporter cell line. LyoVec™ cationic lipid transfection agent is used a positive control for cell transfection and negative control for TLR7-induced activity.

Figures 2A, 2B:
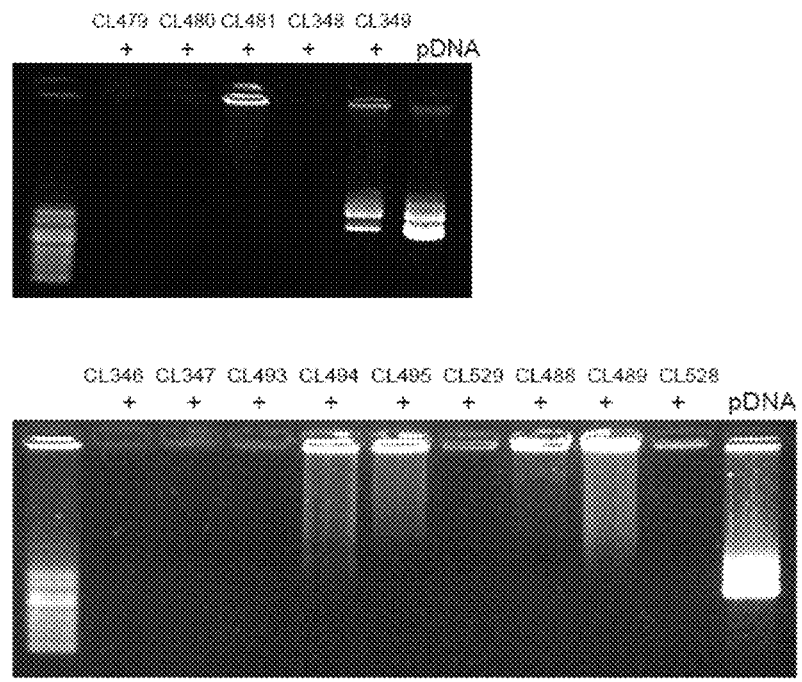

FIG. 2 demonstrates the physio-chemical characterization of TLR7-cationic lipid molecules complexed with plasmid DNA. In FIG. 2A, the gel shift assays indicate the ability of the TLR7-cationic lipid molecules to complex with plasmid DNA as assessed by retardation of mobility through a gel compared to plasmid DNA alone. The table in FIG. 2B illustrates the size dimensions and conformity (ability to form uniform complexes) of the TLR7-cationic lipid molecules complexed with plasmid DNA.

Figure 3:
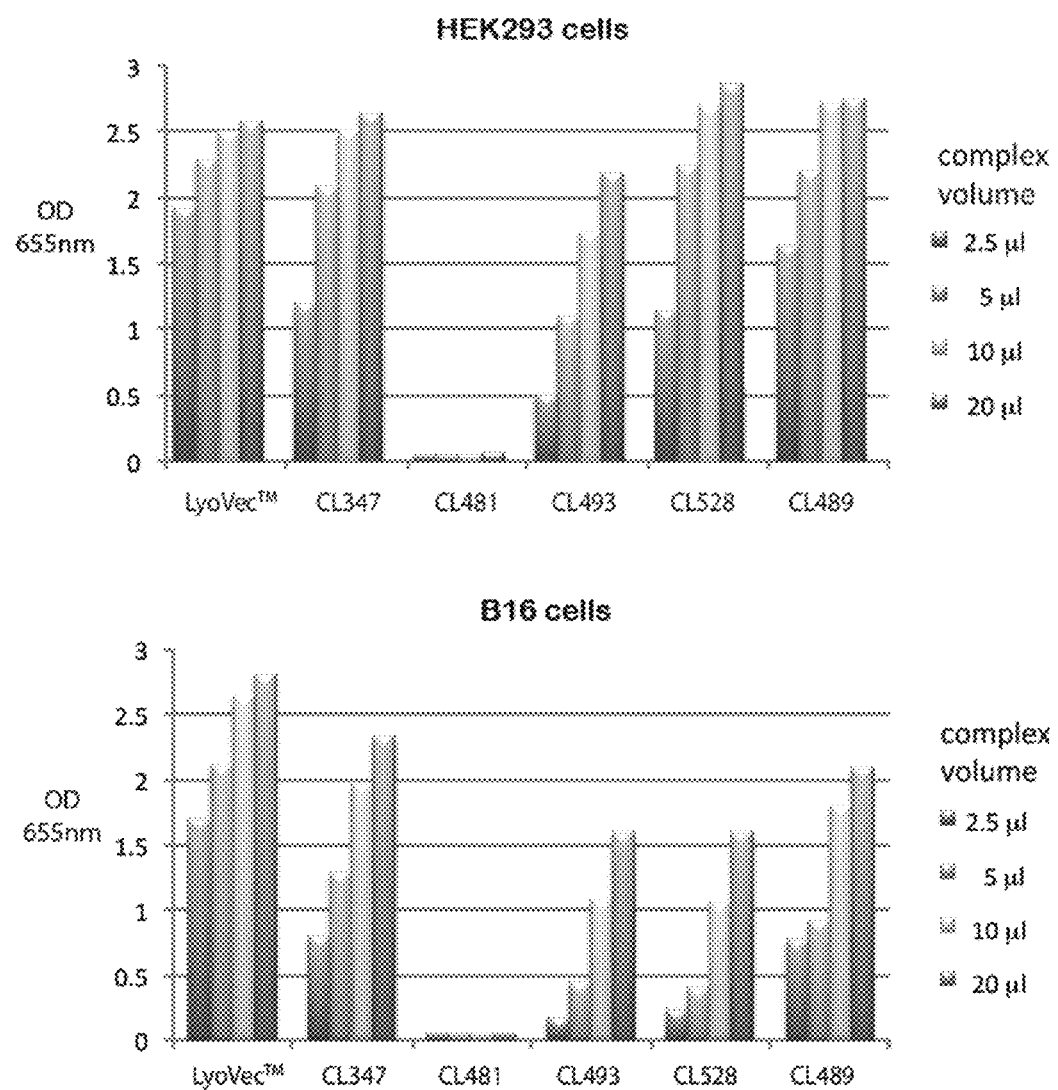

FIG. 3 demonstrates the ability of TLR7-cationic lipid molecules to transfect B 16 mouse melanoma cell line and human HEK293 cell line compared to the positive control for transfection LyoVec™ (InvivoGen), a cationic lipid transfection agent. The graph shows expression of the SEAP reporter gene contained in the plasmid DNA construct that is complexed with the TLR7-cationic lipid molecules or LyoVec™ upon contacting with cells. Due to the non-conformity of CL481 (FIG. 2) and inability to form complex with plasmid DNA, CL481 is used as a negative control for this experiment.

Figure 4:
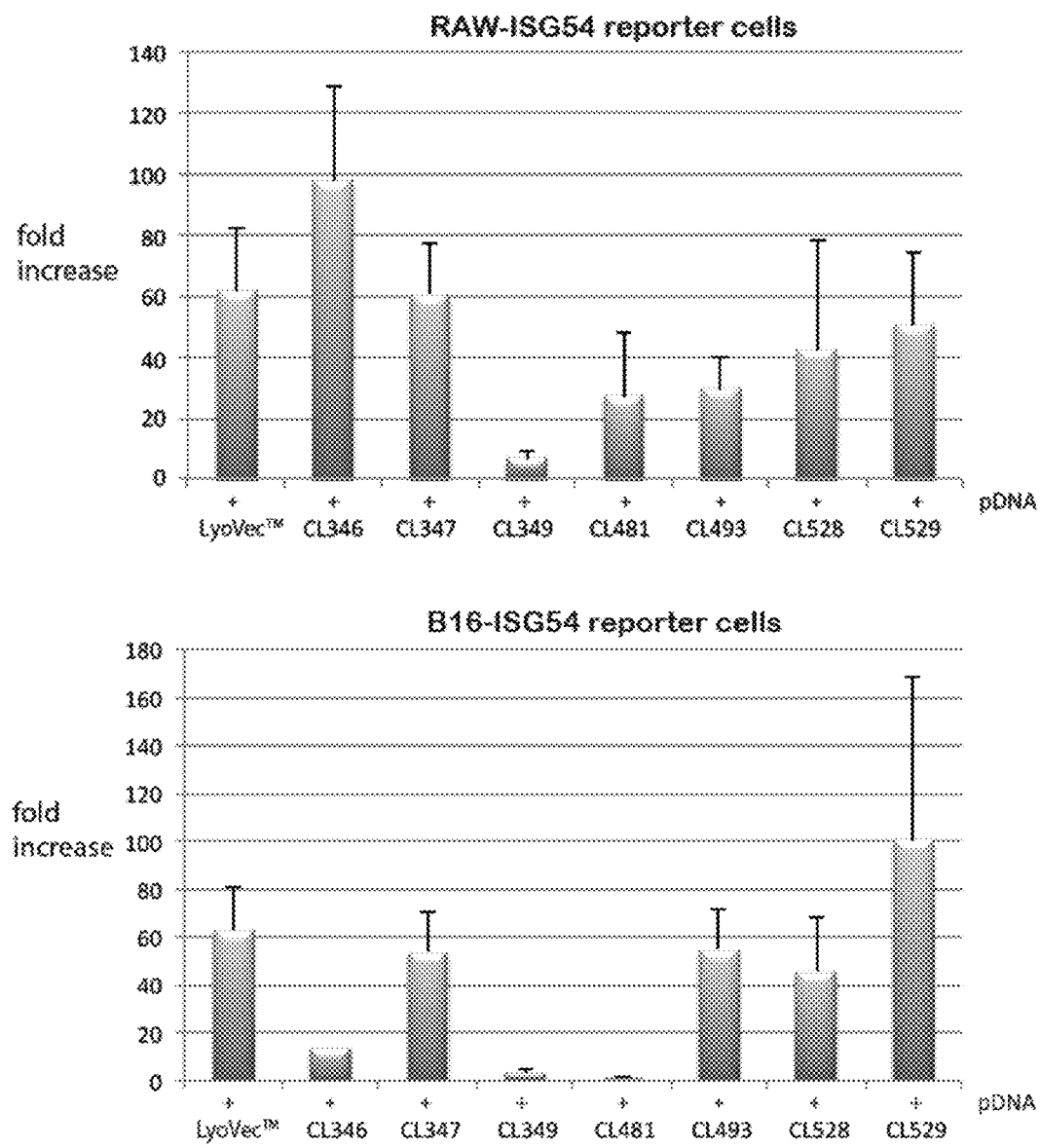

FIG. 4 demonstrates that the plasmid DNA introduced into cells by transfection with TLR7-cationic lipid molecules induce a type I interferon response in B 16 cells and in the mouse leukemic monocyte macrophage RAW cell line. LyoVec™ (InvivoGen) was used as a positive control for transfection. The luciferase activity shown in the graph corresponds to ISG54 promoter activity in the reporter cell lines.

Figure 5A:
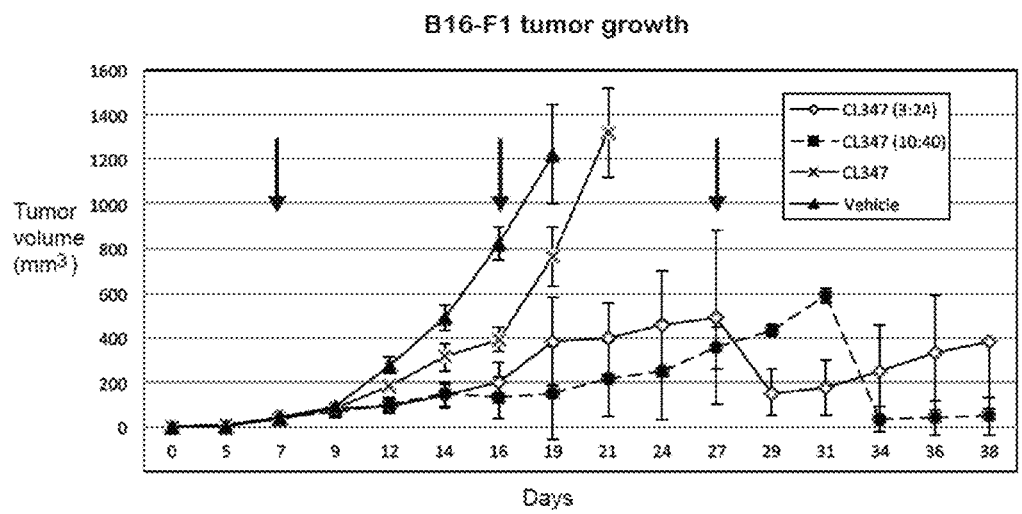
Figure 5B:
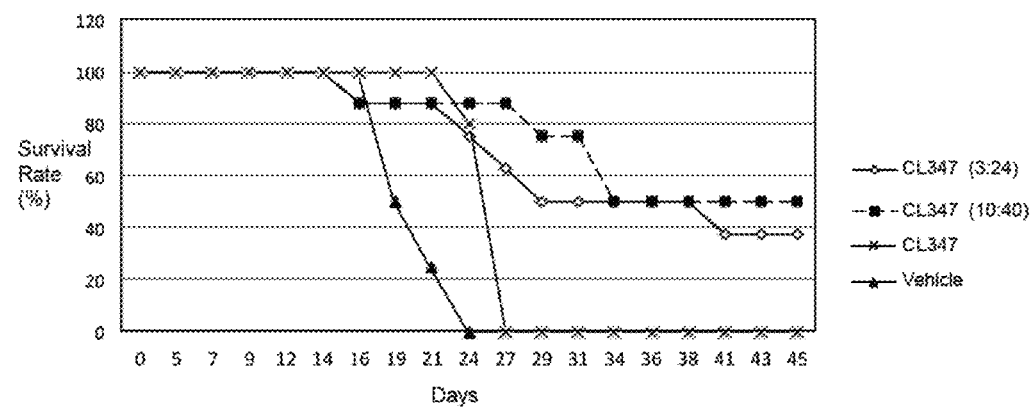

FIG. 5 demonstrates the in vivo results in B 16 allograft tumor mouse model treated with TLR7-cationic lipid molecule CL347 complexed with plasmid DNA. The graph in FIG. 5A shows the tumor volume over time of treated mice compared to control vehicle treated. Arrows indicate timing of intratumoral injections. The graph in FIG. 5B shows the survival curve of the mice compared to control vehicle treated.

EXAMPLES

Methods of Synthesis

The present invention is next described by means of the following examples. However, the use of these and other examples anywhere in the specification is illustrative only, and in no way limits the scope and meaning of the invention or of any exemplified form. Likewise, the invention is not limited to any particular preferred embodiments described herein. Indeed, many modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

Abbreviations

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification:

Bn for benzyl; $C_{14}$ for myristoyl; $CDCl_3$ for deuterated chloroform; $Cs_2CO_3$ for cesium carbonate; $D_2O$ for Deuterium oxide; DCM for dichloromethane; DIAD for diisopropyl azodicarboxylate; DMF for N,N-dimethyl formamide; DMSO-d6 for deuterated dimethylsulfoxide; EDCI or EDC for 1-(3-diethylaminopropyl)-3-ethylcarbodiimide hydrochloride; EtOH for ethanol; $Et_2O$ for diethyl ether; EtOAc for ethyl acetate; ESI for electrospray ionization; g grams; HCl for hydrochloric acid; HPLC for high performance liquid chromatography; hr for hours; Hz for Hertz; mg for milligrams; $MgSO_4$ for magnesium sulfate; MeOH for methanol; mL for milliliters; mM for millimolar; mmol for millimoles; MHz for megahertz; min for minutes; μL for microliters; nM for micromolar; MS for mass spectrometry; $Na_2CO_3$ for sodium carbonate; $Na_2SO_4$ for sodium sulfate; $Na_2S_2O_3$ for sodium thiosulfate; $NaHCO_3$ for sodium hydrogenocarbonate; NH4Cl for ammonium chloride; NMM for N4-methylmorpholine; NMR for nuclear magnetic resonance; OMe for methoxy; $P_2O_5$ for phosphorus pentoxide; Pd/C for Palladium on activated charcoal; PyBOP for Benzotriazole-1-yl-oxy-tris-pyrrolidino-phosphonium hexafluorophosphate; TEA for triethylamine; TFA for trifluoroacetic acid; THF for tetrahydrofuran; TLC for thin layer chromatography; tBOC or Boc for tert-butyloxy carbonyl; and Z for benzyloxy carbonyl;

General Information

Characterization:

1. Analytical HPLC and LC-MS Methods: Unless otherwise indicated, all analytical HPLC analyses were run on an Agilent Model 1290 Infinity system LC coupled to 6130 quadrupole MS using one of the two following Columns: (a) Phenomenex Sernegi (4 micron, C18, 50×2 mm) or (b) a Gemini column (5 micron, C18, 100×2 mm) A typical run through the instrument included: eluting at 0.4 ml/min with a linear gradient of 10% (v/v) to 100% MeCN (0.1% v/v TFA) in water (0.1% TFA) over 10 minutes; conditions may be varied to achieve optimal separation.

2. Preparative HPLC Method: Unless otherwise indicated, the compounds described herein were purified via reverse phase HPLC using one of the following instruments. Shimadzu, varian, Gilson; utilizing one of the following two HPLC columns: (a) a Phenomenex Luna or (b) a Gemini column (5 micron or 10 micron, C18, 150×50 mm) A typical run through the instrument included: eluting at 45 ml/min with a linear gradient of 110% (v/v) to 100% MeCN (0.1% v/v TFA) in water (0.1% TFA) over 10 minutes; conditions can be varied to achieve optimal separations.

3. Proton NMR Spectra: Unless otherwise indicated, all $_1$H NMR spectra were run on a Bruker series 300 MHz instrument. Where so characterized, all observed protons are reported as parts-per-million (ppm) downfield from tetramethylsilane (TMS) or other internal reference in the appropriate solvent indicated. NMR spectra were recorded on a Brucker 300 spectrometer. For 1H (300 MHz) spectra δ values were referenced to $CDCl_3$ (7.26 ppm), CD3OD (3.30 ppm), or DMSO-d 6 (2.50 ppm).

4. Mass Spectra (MS) Unless otherwise indicated, all mass spectral data for starting materials, intermediates and/or exemplary compounds are reported as mass/charge (m/z), having an $(M+H)^+$ molecular ion. The molecular ion reported was obtained by electrospray detection method (commonly referred to as an ESI MS). Compounds having an isotopic atom, such as bromine and the like, are generally reported according to the detected isotopic pattern, as appreciated by those skilled in the art.

5. Particle Size: Particle size was determined using a Malvern Nanosizer (Malvern, Worcestershire, UK) and Malvern ZETASIZER™ (Malvern, Worcestershire, UK).

6. Naming Convention: The compounds disclosed and described herein have been named using the naming convention provided with Chem-Draw Ultra 11.0 software, available in Chem. Office. In some instances, compounds were named with the term "spermine" inserted where appropriate. For example, where the spermine is substituted with Boc, "$N_1,N_5,N_{10}$-TriBoc-spermine" is added to the Chem-Draw nomenclature in the appropriate place. Chem-Draw utilizes the ISIS Draw software compound naming convention, as appreciated by those skilled in the art.

Reagents and Solvents: All commercially available reagents and protected amino acids were purchased and used without further purification. All the solvents used for reactions were distilled over appropriate drying reagents prior to use. Commercially available ACS grade solvents (>99.0% purity) were used for column chromatography without any further purification.

Reactions and Purifications: For all of the following examples, standard work-up and purification methods known to those skilled in the art can be utilized. Unless otherwise indicated, all temperatures are expressed in ° C. (degrees Centigrade). All reactions conducted at room temperature unless otherwise noted. All reactions and fractions from column chromatography were monitored by thin layer chromatography (TLC) using glass plates with a UV fluorescent indicator (normal $SiO_2$, Merck 60 F254). One or more of the following methods were used for visualization: UV absorption by fluorescence quenching; (Ninhydrin/Etha-

Example 1

Molecule CL346

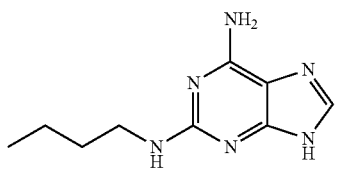

Intermediate 1

6-amino-2-butylamino-9H-purine: 2-Chloroadenine (10.0 g, 59 mmol), butylamine (43 mL, 589 mmol) and water (40 mL) were placed in an autoclave (250 ml), and the content of the autoclave was allowed to react at 18° C. for 18 hours. The reaction solution was concentrated under reduced pressure, and water was poured into the residue to precipitate a solid. The precipitated solid was sequentially washed with water, EtOH and acetone. Thus, 10.39 g of the title compound was obtained as a yellowish orange powdery solid (yield: 86%). Intermediate 1 was characterized by the following spectroscopic data: $^1$H NMR (DMSO-d6, 300 MHz): 11.92 (br. S, 1H), 7.63 (s, 1H), 6.51 (br. s, 2H), 6.04 (s, 1H), 3.19 (q, 2H), 1.51 (m, 2H), 1.33 (m, 2H), 0.92 (t, 3H).

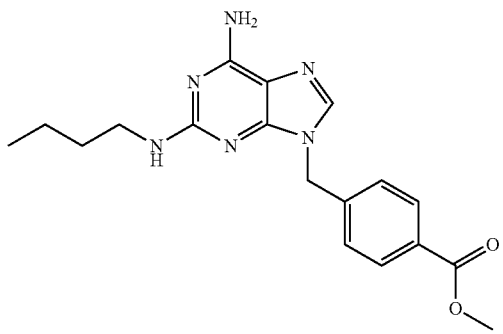

Intermediate 2

Methyl 4-((6-amino-2-(butylamino)-9H-purin-9-yl)methyl)benzoate: 6-amino-2-butylamino-9H-purine (10.39 g, 50.4 mmol) and Cs$_2$CO$_3$ (16.42 g, 50.4 mmol) were suspended in DMF (200 ml). 4-bromomethyl benzoate (13.85 mg, 60.4 mmol) was added thereto and the mixture was stirred at room temperature for 18 hours. After condensing the suspension in vacuo, to the residue was added brine and the mixture was extracted with ethyl acetate. The organic layer was washed the mixture was with brine, dried on MgSO$_4$, filtered and the solvent was evaporated in vacuo. The residue was purified on column of silica gel (5% MeOH/DCM) to give the subject compound (14.67 g, yield 82%). Intermediate 2 was characterized by the following spectroscopic data: $^1$H NMR (DMSO-d6, 300 MHz) δ (ppm) 7.91 (d, 2H), 7.81 (s, 1H), 7.40 (d, 2H), 6.66 (br. s, 2H), 6.22 (t, 1H), 5.27 (s, 2H), 3.83 (s, 1H), 3.19 (q, 2H), 1.44 (m, 2H), 1.26 (m, 2H), 0.85 (t, 3H).

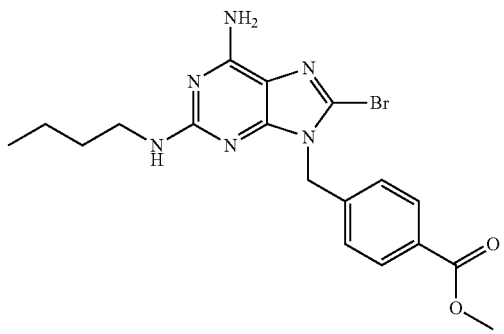

Intermediate 3

Methyl 4-((6-amino-8-bromo-2-(butylamino)-9H-purin-9-yl)methyl)benzoate

Methyl 4-((6-amino-2-(butylamino)-9H-purin-9-yl)methyl)benzoate (14.67 g, 41.9 mmol) and bromine (7.94 mL, 49.7 mmol) were dissolved in 300 ml of CHCl$_3$ and the solution was stirred at room temperature for 18 hours. Aqueous Na$_2$S$_2$O$_3$ was added to the reaction mixture. The precipitate obtained was filtered off and washed with water and DCM. The solid was purified on column of silica gel (3% MeOH/DCM) to give the subject compound (15.41 g, yield 86%). Intermediate 3 was characterized by the following spectroscopic data: $^1$H NMR (DMSO-d6, 300 MHz) δ (ppm) 7.95 (d, 2H), 7.38 (d, 2H), 6.67 (br. s, 2H), 6.24 (t, 1H), 5.30 (s, 2H), 3.84 (s, 1H), 3.28 (q, 2H), 1.45 (m, 2H), 1.25 (m, 2H), 0.85 (t, 3H).

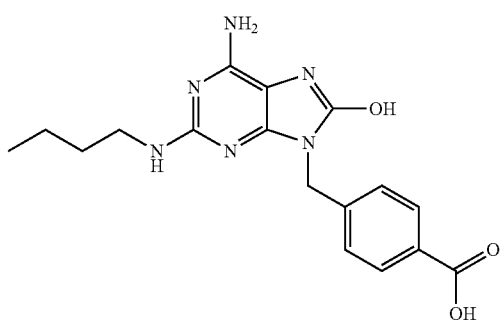

Intermediate 4

4-((6-amino-2-(butylamino)-8-hydroxy-9H-purin-9-yl)methyl)benzoic acid: To Methyl 4-((6-amino-8-bromo-2-(butylamino)-9H-purin-9-yl)methyl)benzoate (15.41 g, 35.6 mmol) in 150 ml of methanol was added 6N aqueous NaOH (150 ml). The mixture was refluxed on heating under stirring for 18 hours. The residue was dissolved in 12N HCl solution and stirred at room temperature for 18 hours. The mixture was concentrated in vacuo and the pH was adjusted to 5 with 2N aqueous NaOH to precipitate a solid. The solid was filtered, washed with water and dried in vacuo in presence of P$_2$O$_5$ to give the subject compound (12.2 g, yield 97%). Intermediate 4 was characterized by the following spectroscopic data: $^1$H NMR (DMSO-d6, 300 MHz) δ (ppm) 11.10 (s, 1H), 8.18 (br. s, 2H), 7.97 (t, 1H), 7.89 (d, 2H), 7.40 (d, 2H), 4.93 (s, 2H), 3.27 (q, 2H), 1.47 (m, 2H), 1.27 (m, 2H), 0.85 (t, 3H).

Intermediate 5

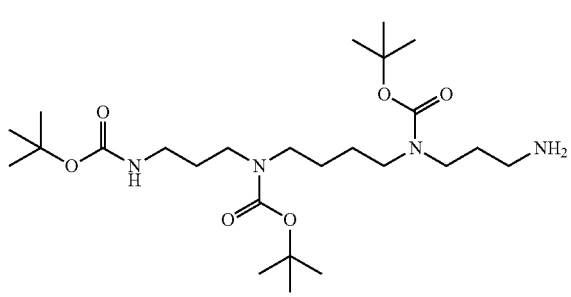

N1,N5,N10-triBoc-spermine: N1,N5,N10-triBoc-spermine was prepared according to the process described in the literature [Blagbrough, I. S.; Geall, A. J. Practical synthesis of unsymmetrical polyamine amides. Tetrahedron Lett. 1998, 39, 439-442. Wellendorph P, Jaroszewski J W, Hansen S H, Franzyk H. A sequential high-yielding large-scale solution-method for synthesis of philanthotoxin analogues. European Journal of Medicinal chemistry 2003, 38, 117-122.1. Intermediate 5 was characterized by the following spectroscopic data: $^1$H NMR (CDCl$_3$-d1, 300 MHz) δ (ppm) 8.49 (sl, 2H), 3.45 (m, 2H), 3.16 (m, 4H), 3.05 (m, 2H), 2.46 (m, 2H), 1.95 (m, 2H), 1.72 (m, 2H), 1.45 (s, 27H).

Intermediate 6

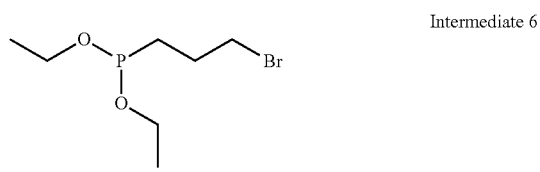

Diethyl 3-bromopropylphosphonite: Triethylphosphite (10 g, 60.2 mmol) was added to 1,3-dibromopropane under inert atmosphere. The mixture was stirred at 90° C. for 18 hr. The solvent was evaporated and the residue was purified through Kugelrohr distillation (90° C./15 mmHg) to obtain the title compound as a colourless liquid (10.5 g, yield 67%). Intermediate 6 was characterized by the following spectroscopic data: $^1$H NMR (CDCl$_3$-d1, 300 MHz) δ (ppm) 4.12 (m, 4H), 3.49 (td., 2H), 2.17 (m, 2H), 1.93 (m, 2H), 1.35 (td, 6H). $^{31}$P NMR (d$_1$-CDCl$_3$, 121.47 MHz) δ (ppm) 30.64.

Intermediate 7

3-bromopropyl dichlorophosphine: To diethyl 3-bromopropylphosphonite (10.5 g, 40.5 mmol) was added PCl5 (21.1 g, 101.3 mmol) at 0° C. under inert atmosphere. When the solid was totally dissolved the reaction mixture was heated at 75° C. under stirring for 18 hr. The mixture was purified through Kugelrohr distillation (90° C./15 mmHg) to obtain the title compound as a colourless liquid (8.12 g, yield 83%). Intermediate 7 was characterized by the following spectroscopic data: $^1$H NMR (CDCl$_3$-d1, 300 MHz) δ (ppm) 3.58 (m, 2H), 2.83 (m, 2H), 2.41 (m, 2H). $^{31}$P NMR (d$_1$-CDCl$_3$, 121.47 MHz) δ (ppm) 48.36.

Intermediate 8

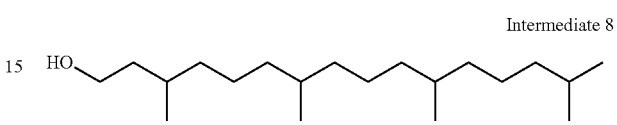

3,7,11,15-tetramethylhexadecan-1-ol: To a solution of phytanol (20 g, 67.45 mmol) in EtOH was added Raney Nickel (3.96, 67.5 mmol), and the reaction mixture was hydrogenated at room temperature under 1 atm of hydrogen for two hours. The reaction mixture was filtered over Celite, and the filtrate was concentrated to give the title compound (19.84 g, yield 98%), which was used in the next step without further purification. Intermediate 8 was characterized by the following spectroscopic data: $^1$H NMR (CDCl$_3$-d1, 300 MHz) δ (ppm) 3.70 (m, 2H), 1.54 (m, 4H), 1.41-1.10 (m, 21H), 0.87 (m, 15H).

Intermediate 9

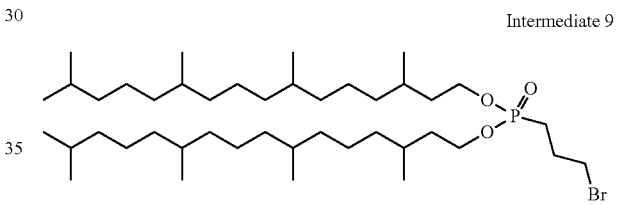

bis(3,7,11,15-tetramethylhexadecyl) 3-bromopropylphosphonate: The 3-bromopropyl dichlorophosphine (5.0 g, 20.8 mmol) was dissolved in dry toluene (50 mL) under argon and ice cooling. DIEA (9.10 mL, 52.1 mmol) was added, followed by oleyl alcohol (12.4 mL, 41.7 mmol). The mixture was stirred at RT for 18 hr. Then, the mixture was filtered under minimal exposure to air, the filter washed with dry Diethyl ether, and the filtrate concentrated in vacuo. The residue was chromatographed on silica gel in a gradient of EtOAc in Cyclohexane rising from 20% to 80%. Fractions containing product were combined, and concentrated in vacuo, to obtain the title compound as an oil (7.76 g, 49%). Intermediate 9 was characterized by the following spectroscopic data: $^1$H NMR (CDCl$_3$-d1, 300 MHz) δ (ppm) 4.21 (m, 4H), 3.49 (m, 2H), 2.18 (m, 2H), 1.93 (m, 2H), 1.70 (m, 4H), 1.41-1.10 (m, 44H), 0.87 (m, 30H).

Intermediate 10

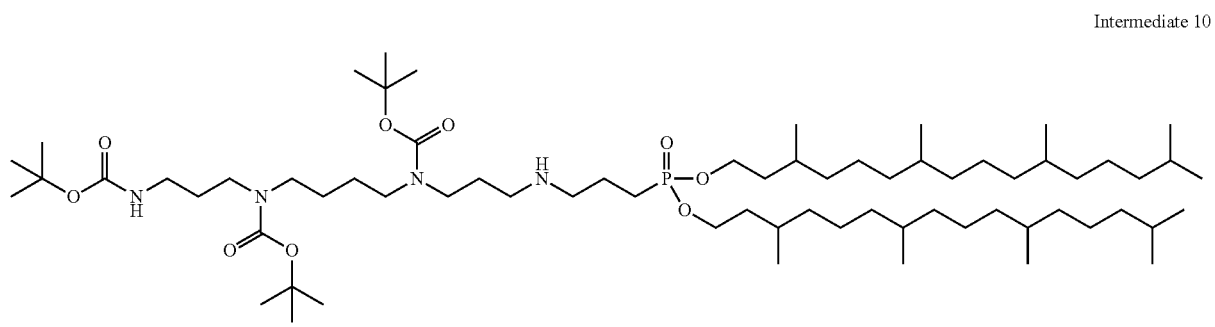 [SMILES: CC(C)CCCC(C)CCCC(C)CCCC(C)CCOP(=O)(CCCNCCCN(CCCCN(CCCNC(=O)OC(C)(C)C)C(=O)OC(C)(C)C)C(=O)OC(C)(C)C)OCCC(C)CCCC(C)CCCC(C)CCCC(C)C]

N1-N5-N10-triBoc-N14-[bis(3,7,11,15-tetramethylhexadecyl)propylphosphonate]spermine: To a solution of bis(3,7,11,15-tetramethylhexadecyl) 3-bromopropylphosphonate 9 (1.2 g, 1.6 mmol) in dry DMF (10 mL) was added Na$_2$CO$_3$ (0.2 g, 1.9 mmol) and a solution of N1,N5,N10-triBoc-spermine (0.79 g, 1.7 mmol) in dry DMF (2 mL). The mixture was stirred at 50° C. for 18H00. The solvent was then removed in vacuo, the residue was dissolved with DCM (20 mL) and was washed with water and brine. The organic layer was dried over MgSO$_4$ and concentrated in vacuo. The crude material was purified on column of silica gel (10% MeOH/DCM) to give the subject compound (0.8 g, yield 43%). Intermediate 10 was characterized by the following spectroscopic data: $^1$H NMR (CDCl$_3$-d1, 300 MHz) δ (ppm) 4.03 (m, 4H), 3.37-3.12 (m, 10H), 2.95 (m, 2H), 2.82 (m, 2H), 2.15-1.76 (m, 12H), 1.75-1.47 (m, 36H), 1.45-1.05 (m, 40H), 0.96-0.86 (m, 30H). $^{31}$P NMR (d$_1$-CDCl$_3$, 121.47 MHz) δ (ppm) 30.75.

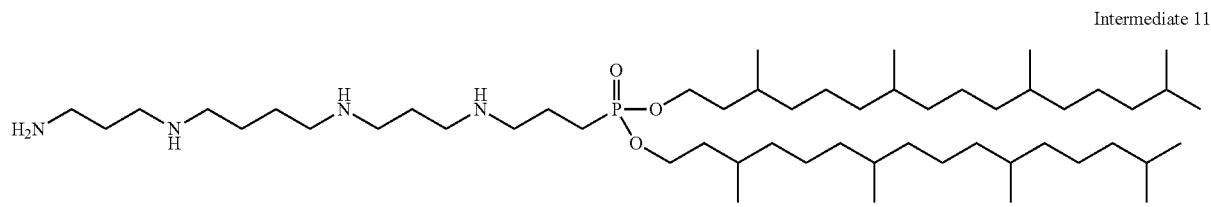 [SMILES: CC(C)CCCC(C)CCCC(C)CCCC(C)CCOP(=O)(CCCNCCCNCCCCNCCCN)OCCC(C)CCCC(C)CCCC(C)CCCC(C)C]

Intermediate 11

N1-[bis(3,7,11,15-tetramethylhexadecyl)propylphosphonate]spermine: To a solution of intermediate 10 (0.8 g, 0.67 mmol) in DCM (10 mL) was added 10 mL of TFA. The mixture was stirred at RT for 1H00. Then the solvent were removed in vacuo, the residue was coevaporated 3 times with toluene. The residue was precipitated in diethyl ether to give the subject compound (0.84 g, yield 93%). Intermediate 11 was characterized by the following spectroscopic data: $^1$H NMR (CDCl$_3$-d1, 300 MHz) δ (ppm) 4.09 (m, 4H), 2.65-2.55 (m, 16H), 2.15 (m, 4H), 1.72-1.62 (m, 16H), 1.52-1.38 (m, 6H), 1.25-1.22 (m, 36H), 0.96-0.91 (m, 30H). $^{31}$P NMR (d$_1$-CDCl$_3$, 121.47 MHz) δ (ppm) 29.75.

Compound 12

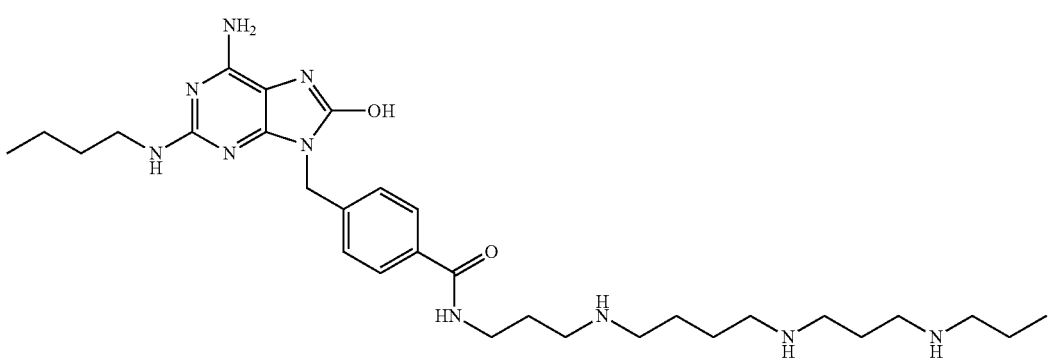

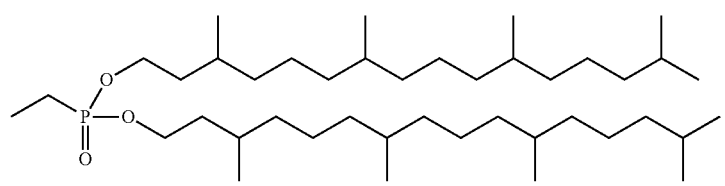

CL346 bis(3,7,11,15-tetramethylhexadecyl) 1-(4-((6-amino-2-(butylamino)-8-hydroxy-9H-purin-9-yl)methyl)phenyl)-1-oxo-2,6,11,15-tetraazaoctadecan-18-ylphosphonate:

To a solution of intermediate 4 (88 mg, 0.25 mmol) in dry DMF (5 mL) was added HATU (104 mg, 0.27 mmol), intermediate 11 (400 mg, 0.29 mmol) and NMM (126 µL, 1.24 mmol). The mixture was stirred at RT overnight. The solvent was removed in vacuo and the residue was directly applied to a column of silica gel (iPrOH/NH$_4$OH/H$_2$O 85/10/5) to give the subject compound (96 mg, yield 32%). Compound 12 was characterized by the following spectroscopic data: $^1$H NMR (DMSO-d6, 300 MHz) δ (ppm) 8.57 (s, 1H), 7.78 (d, 2H), 7.34 (d, 2H), 6.16 (t, 1H), 6.09 (sl, 2H), 4.84 (s, 2H), 3.93 (m, 5H), 3.29 (m, 2H), 3.14 (m, 2H), 2.72-2.68 (m, 1H), 1.55 (m, 18H), 1.11-1.06 (m, 46H), 0.82 (m, 33H). MS (+)–ES [M+H]$^+$1225 m/z.

Example 2

Molecule CL347

Intermediate 13

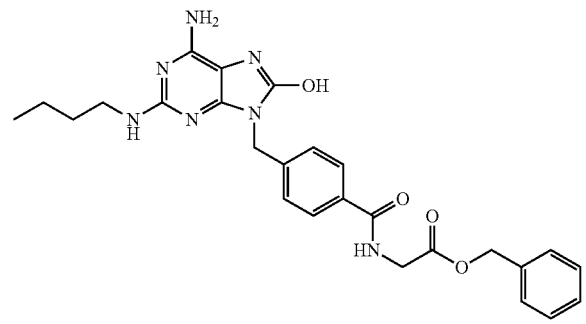

Benzyl 2-(4-((6-amino-2-(butylamino)-8-hydroxy-9H-purin-9-yl)methyl)benzamido)acetate: To a suspension of intermediate 4 (4 g, 11 mmol) in dry DMF (20 mL) was added Glycine benzyl ester hydrochloride (2.7 g, 13 mmol), followed by PyBOP (6.4 g, 12 mmol) and N-methylmorpholine (5.68 g, 56.1 mmol). The mixture was stirred at RT for 18H00. The solvent was then removed in vacuo and the residue was dissolved in EtOAc (50 mL) and was washed with water, saturated solution of NH4Cl and brine. The organic layer was dried over MgSO$_4$, filtered and concentrated in vacuo. The crude material was purified on column of silica gel (5% MeOH/DCM) to give the subject compound (5.65 g, yield 100%). Intermediate 13 was characterized by the following spectroscopic data: $^1$H NMR (DMSO-d6, 300 MHz) δ (ppm) 9.68 (sl, 1H), 8.89 (m, 1H), 7.81 (d, 2H), 7.37 (m, 7H), 6.25 (t, 1H), 6.04 (sl, 2H), 5.15 (s, 2H), 4.86 (s, 2H), 4.06 (d, 2H), 3.15 (m, 2H), 1.49 (m, 2H), 1.33 (m, 2H), 0.86 (t, 3H).

Intermediate 14

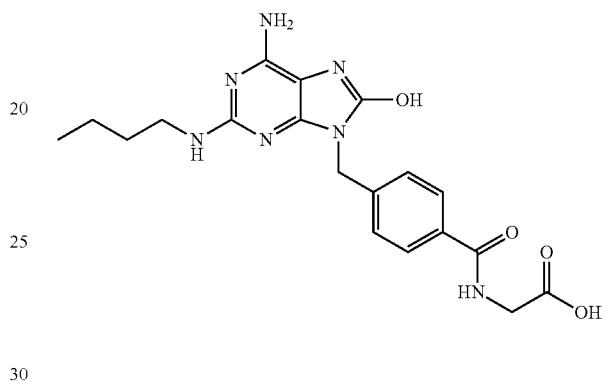

2-(4-((6-amino-2-(butylamino)-8-hydroxy-9H-purin-9-yl)methyl)benzamido)acetic Acid: To a solution of intermediate 13 (5.65 g, 11 mmol) in a mixture of THF/MeOH (1/1) (20 mL) was added palladium on activated carbon 10% (0.05 eq). The reaction mixture was stirred under hydrogen (1 atm) overnight. The palladium was filtered off the filtrate was concentrated in vacuo. The crude mixture was purified on column of silica gel (12% MeOH/DCM) to give the subject compound (3.58 g, yield 77%). Intermediate 14 was characterized by the following spectroscopic data: $^1$H NMR (DMSO-d6, 300 MHz) δ (ppm) 12.3 (sl, 1H), 10.60 (sl, 1H), 8.83 (m, 1H), 7.82 (d, 2H), 7.38 (m, 2H), 4.89 (s, 2H), 3.91 (d, 2H), 3.24 (m, 2H), 1.46 (m, 2H), 1.31 (m, 2H), 0.85 (t, 3H).

Compound 15

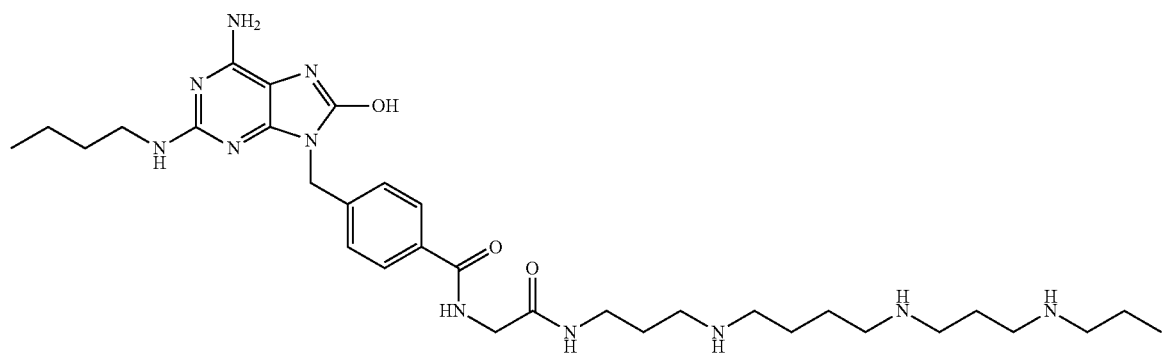

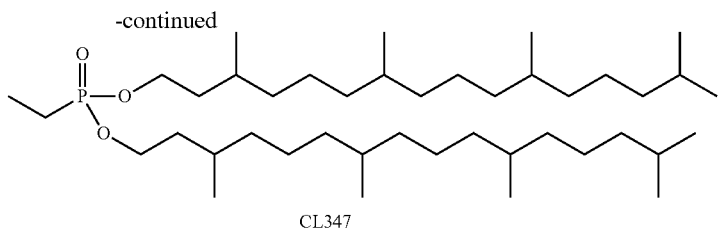

CL347 bis(3,7,11,15-tetramethylhexadecyl) 1-(4-(((6-amino-2-(butylamino)-8-hydroxy-9H-purin-9-yl)methyl)phenyl)-1,4-dioxo-2,5,9,14,18-pentaazahenicosan-21-yl)phosphonate: To a solution of intermediate 14 (109 mg, 0.26 mmol) in dry DMF (5 mL) was added HATU (112 mg, 0.29 mmol), intermediate 11 (428 mg, 0.32 mmol) and NMM (146 μL, 1.33 mmol). The mixture was stirred at RT overnight. The solvent was removed in vacuo and the residue was directly applied to a column of silica gel (iPrOH/NH$_4$OH/H$_2$O 85/10/5) to give the subject compound (49 mg, yield 14%). Compound 15 was characterized by the following spectroscopic data: $^1$H NMR (DMSO-d6, 300 MHz) δ (ppm) 9.15 (m, 3H), 8.88 (m, 2H), 8.15 (m, 1H), 7.86 (d, 2H), 7.39 (d, 2H), 4.91 (s, 2H), 3.97 (m, 4H), 3.83 (m, 3H), 3.28 (m, 4H), 2.72-2.68 (m, 12H), 2.22 (m, 2H), 1.85-1.35 (m, 18H), 1.24-1.07 (m, 46H), 0.83 (m, 33H). MS (+)–ES [M+H]$^+$ 1282 m/z.

Example 3

Molecule CL348

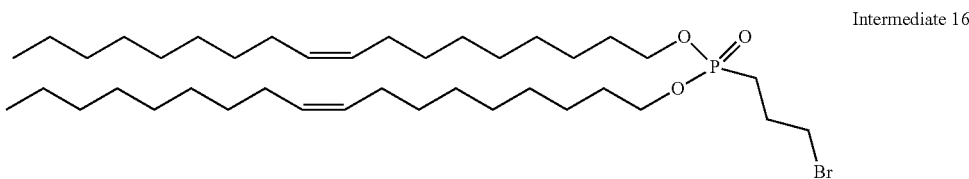 [SMILES: CCCCCCCC/C=C\CCCCCCCCOP(=O)(CCCBr)OCCCCCCCC/C=C\CCCCCCCC]

Intermediate 16 di(Z)-octadec-9-enyl 3-bromopropylphosphonate: The 3-bromopropyl dichlorophosphine (3.0 g, 12.5 mmol) was dissolved in dry toluene (30 mL) under argon and ice cooling. DIEA (5.46 mL, 31.3 mmol) was added, followed by oleyl alcohol (9.29 mL, 25.01 mmol). The mixture was stirred at RT for 18 hr. Then, the mixture was filtered under minimal exposure to air, the filter washed with dry Diethyl ether, and the filtrate concentrated in vacuo. The residue was chromatographed on silica gel in a gradient of EtOAc in Cyclohexane rising from 20% to 80%. Fractions containing product were combined, and concentrated in vacuo, to obtain the title compound as an oil (2.68 g, 54%). Intermediate 16 was characterized by the following spectroscopic data: $^1$H NMR (CDCl$_3$-d1, 300 MHz) δ (ppm) 5.36 (m, 4H), 4.03 (m, 4H), 3.62 (m, 2H), 2.19-1.88 (m, 12H), 1.70-1.63 (m, 8H), 1.31 (m, 44H), 0.86 (t, 6H).

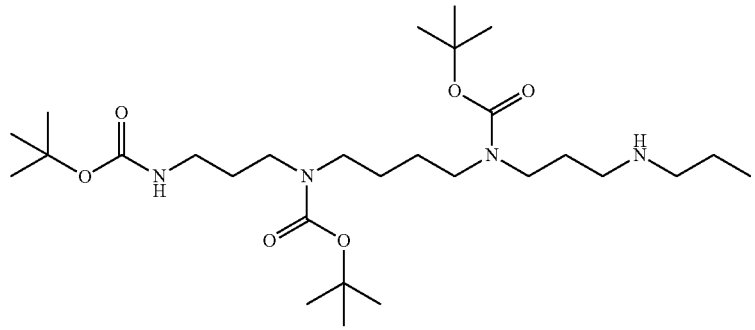

Intermediate 17

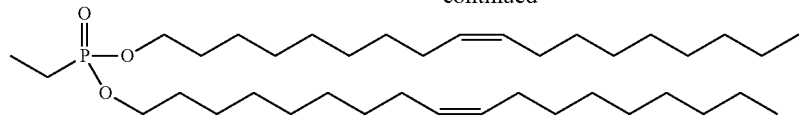

N1-N5-N10-triBoc-N14-(di(Z)-octadec-9-enyl propylphosphonate)spermine: To a solution of di(Z)-octadec-9-enyl 3-bromopropylphosphonate 16 (1.0 g, 1.4 mmol) in dry DMF (10 mL) was added Na$_2$CO$_3$ (0.18 g, 1.7 mmol) and a solution of N1,N5,N10-triBoc-spermine (0.71 g, 1.4 mmol) in dry DMF (2 mL). The mixture was stirred at 50° C. for 18H00. The solvent was then removed in vacuo, the residue was dissolved with DCM (20 mL) and was washed with water and brine. The organic layer was dried over MgSO$_4$ and concentrated in vacuo. The crude material was purified on column of silica gel (12% MeOH/DCM) to give the subject compound (0.7 g, yield 44%). Intermediate 17 was characterized by the following spectroscopic data: $^1$H NMR (CDCl$_3$-d1, 300 MHz) δ (ppm) 5.37 (m, 4H), 4.03 (m, 4H), 3.18 (m, 2H), 3.13 (m, 12H), 2.91 (m, 2H), 2.19-1.88 (m, 14H), 1.78 (m, 16H), 1.68 (m, 7H), 1.48 (m, 14H), 1.28 (m, 44H), 0.91 (t, 6H).

Intermediate 18

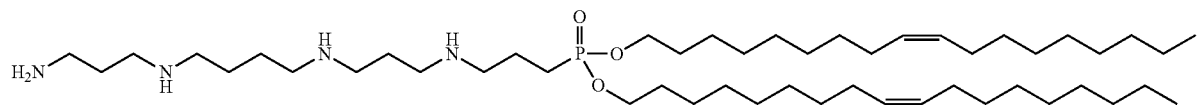

N1-(di(Z)-octadec-9-enyl propylphosphonate)spermine: To a solution of intermediate 17 (0.7 g, 0.62 mmol) in DCM (10 mL) was added 10 mL of TFA. The mixture was stirred at RT for 1H00. Then the solvent were removed in vacuo, the residue was coevaporated 3 times with toluene. The residue was precipitated in diethyl ether to give the subject compound (0.71 g, yield 89%). Intermediate 18 was characterized by the following spectroscopic data: $^1$H NMR (DMSO-d6, 300 MHz) δ (ppm) 4.15 (m, 4H), 3.97 (m, 4H), 3.17 (m, 2H), 2.96 (m, 12H), 2.09-1.75 (m, 8H), 1.63 (m, 12H), 1.18 (m, 46H), 0.91 (t, 6H).

Compound 19

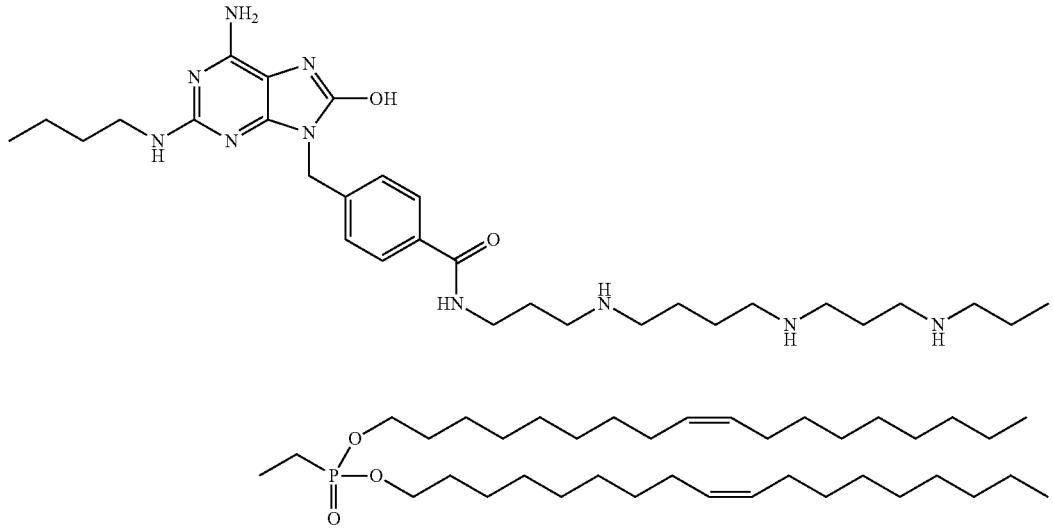

CL348 di(Z)-octadec-9-enyl 1-(4-((6-amino-2-(butylamino)-8-hydroxy-9H-purin-9-yl)methyl) phenyl)-1-oxo-2,6,11,15-tetraazaoctadecan-18-ylphosphonate: To a solution of intermediate 4 (69 mg, 0.19 mmol) in dry DMF (5 mL) was added HATU (81 mg, 0.21 mmol), intermediate 18 (300 mg, 0.23 mmol) and NMM (107 µL, 0.97 mmol). The mixture was stirred at RT overnight. The solvent was removed in vacuo and the residue was directly applied to a column of silica gel (iPrOH/NH$_4$OH/H$_2$O 85/10/5) to give the subject compound (87 mg, yield 38%). Compound 19 was characterized by the following spectroscopic data: $^1$H NMR (DMSO-d6, 300 MHz) δ (ppm) 8.78 (m, 2H), 8.22 (m, 1H), 7.87 (d, 2H), 7.45 (d, 2H), 5.32 (s, 2H), 4.55 (m, 4H), 3.93 (m, 4H), 3.06 (m, 2H), 2.95 (m, 12H), 2.73 (m, 2H), 2.09-1.88 (m, 15H), 1.72 (m, 4H), 1.56 (m, 5H), 1.18 (m, 52H), 0.85 (t, 9H). MS (+)-ES [M+H]$^+$1165 m/z.

Example 4

Molecule CL349

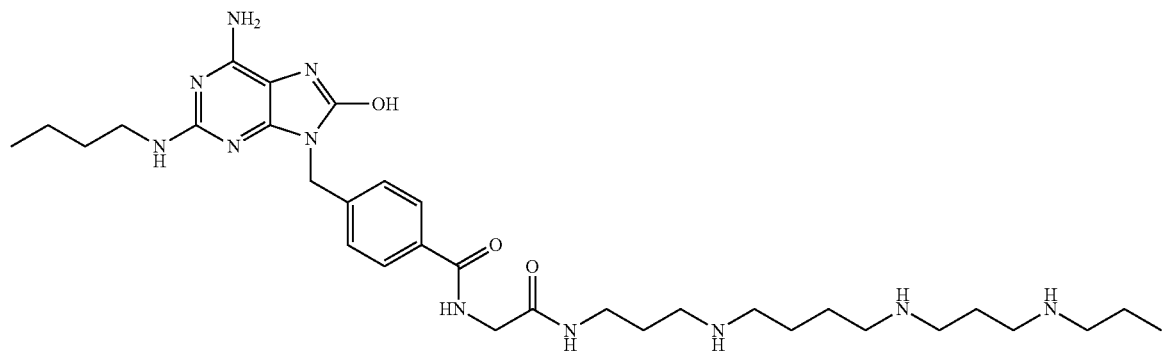

CL349 di(Z)-octadec-9-enyl 1-(4-((6-amino-2-(butylamino)-8-hydroxy-9H-purin-9-yl)methyl) phenyl)-1,4-dioxo-2,5,9,14,18-pentaazahenicosan-21-ylphosphonate: To a solution of intermediate 14 (98 mg, 0.24 mmol) in dry DMF (5 mL) was added HATU (99 mg, 0.26 mmol), intermediate 18 (365 mg, 0.28 mmol) and NMM (130 µL, 1.19 mmol). The mixture was stirred at RT overnight. The solvent was removed in vacuo and the residue was directly applied to a column of silica gel (iPrOH/NH$_4$OH/H$_2$O 85/10/5) to give the subject compound (128 mg, yield 44%). Compound 20 was characterized by the following spectroscopic data: $^1$H NMR (DMSO-d6, 300 MHz) δ (ppm) 8.73 (m, 3H), 8.02 (m, 1H), 7.84 (d, 2H), 7.32 (d, 2H), 5.32 (s, 2H), 3.88 (m, 4H), 3.37 (m, 4H), 3.06-2.95 (m, 15H), 2.75 (m, 2H), 2.09 (m, 6H), 1.78 (m, 4H), 1.56 (m, 8H), 1.18 (m, 55H), 0.83 (t, 9H). MS (+)-ES [M+H]$^+$1165 m/z.

Example 5

Molecule CL540

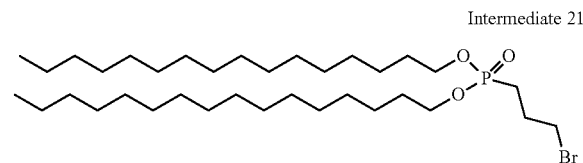 [SMILES: CCCCCCCCCCCCCCCCOP(=O)(CCCBr)OCCCCCCCCCCCCCCCC]

Intermediate 21

Dihexadecyl 3-bromopropylphosphonate: The 3-bromopropyl dichlorophosphine (2.0 g, 8.34 mmol) was dissolved in dry toluene (20 mL) under argon and ice cooling.

Compound 20

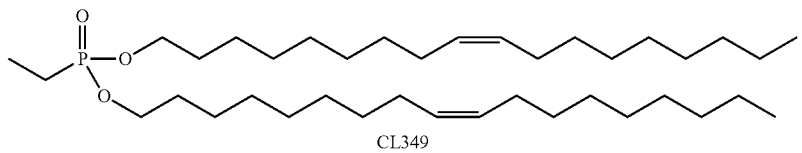

DIEA (3.64 mL, 20.8 mmol) was added, followed by 1-tetradecanol (3.57 g, 16.68 mmol). The mixture was stirred at RT for 18 hr. Then, the mixture was filtered under minimal exposure to air, the filter washed with dry Diethyl ether, and the filtrate concentrated in vacuo. The residue was chromatographed on silica gel in a gradient of EtOAc in Cyclohexane rising from 20% to 80%. Fractions containing product were combined, and concentrated in vacuo, to obtain the title compound as an oil (2.68 g, 54%). Intermediate 21 was characterized by the following spectroscopic data: $^1$H NMR (CDCl$_3$-d1, 400 MHz) δ (ppm) 4.05 (m, 4H), 3.50 (m, 2H), 2.19 (m, 2H), 1.95 (m, 2H), 1.63 (m, 4H), 1.31 (m, 44H), 0.86 (t, 6H).

Intermediate 22

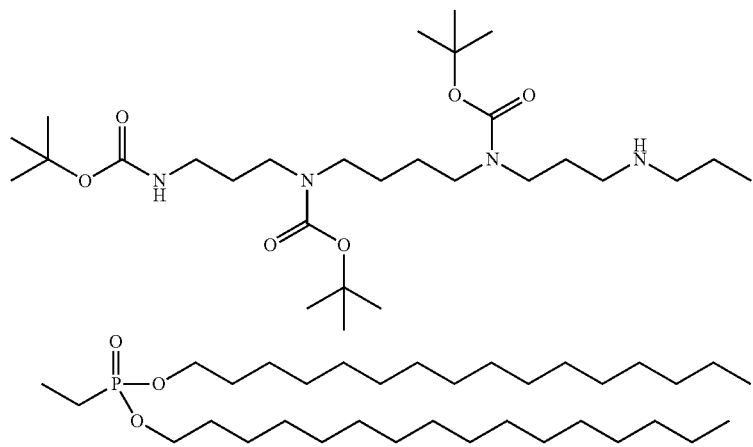

N1-N5-N10-triBoc-N14-(dihexadecyl propylphosphonate)spermine: To a solution of intermediate 21 (1.29 g, 1.98 mmol) in dry DMF (10 mL) was added Na$_2$CO$_3$ (0.25 g, 2.4 mmol) and a solution of N1,N5,N10-triBoc-spermine (1.00 g, 1.98 mmol) in dry DMF (2 mL). The mixture was stirred at 50° C. for 18H00. The solvent was then removed in vacuo, the residue was dissolved with DCM (20 mL) and was washed with water and brine. The organic layer was dried over MgSO$_4$ and concentrated in vacuo. The crude material was purified on column of silica gel (8% MeOH/DCM) to give the subject compound (0.72 g, yield 34%). Intermediate 22 was characterized by the following spectroscopic data: $^1$H NMR (DMSO-d6, 300 MHz) δ (ppm) 3.90 (m, 4H), 3.17 (m, 2H), 2.96 (m, 8H), 2.55 (m, 4H), 1.75 (m, 4H), 1.56 (m, 6H), 1.37 (m, 35H), 1.30-1.23 (m, 52H), 0.82 (t, 6H).

Intermediate 23

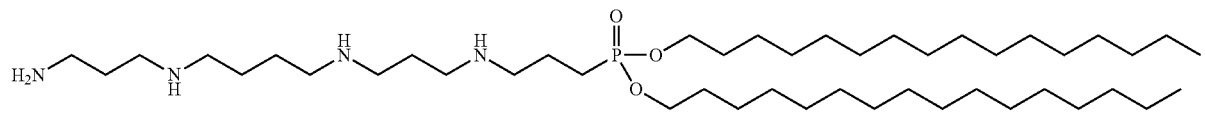

N1-(dihexadecyl propylphosphonate)spermine: To a solution of intermediate 22 (723 mg, 0.67 mmol) in dioxane (5 mL) was added 15 mL of 4M HCl in dioxane. The mixture was stirred at RT overnight. Then the solvent were removed in vacuo and the residue was precipitated in diethyl ether to give the subject compound (593 mg, yield 96%). Intermediate 23 was characterized by the following spectroscopic data: $^1$H NMR (DMSO-d6, 300 MHz) δ (ppm) 3.92 (m, 4H), 3.69 (m, 4H), 3.59 (m, 2H), 2.91 (m, 12H), 2.09-1.65 (m, 10H), 1.43 (m, 12H), 1.23 (m, 47H), 0.85 (t, 6H).

Compound 24

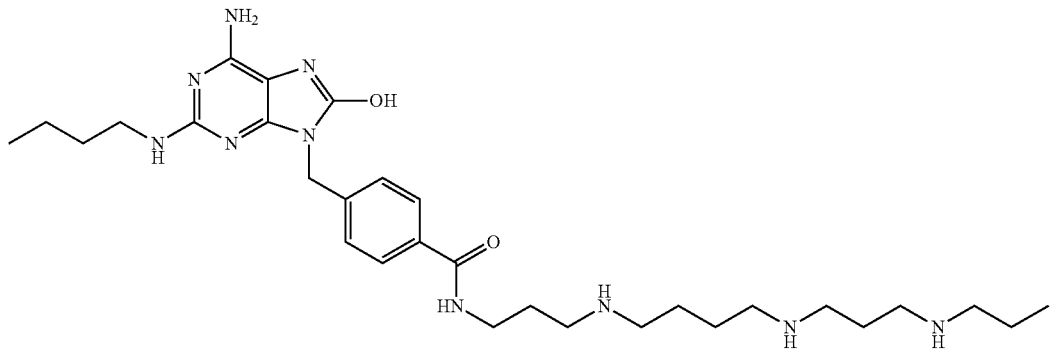

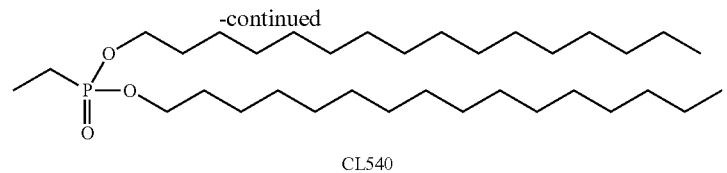

CL540

Dihexadecyl 1-(4-(((6-amino-2-(butylamino)-8-hydroxy-9H-purin-9-yl)methyl)phenyl)-1-oxo-2,6,11,15-tetraazaoctadecan-18-yl)phosphonate: To a solution of intermediate 4 (100 mg, 0.28 mmol) in dry DMF (5 mL) were added N-hydroxysuccinimide (35 mg, 0.30 mmol), EDCI (64 mg, 0.33 mmol) and DMAP (40 mg, 0.33 mmol). The mixture was stirred at RT overnight. Then the solvent was removed in vacuo and the residue was triturated with water. The precipitate was filtered, washed with water EtOH and Et₂O and dried. The resulting solid was dissolved in dry DMF (3 mL) and were added intermediate 23 (216 mg, 0.28 mmol) and DIEA (538 μL, 3.3 mmol). The mixture was stirred at RT overnight. The solvent was removed in vacuo and the residue was directly applied to a column of silica gel (iPrOH/NH₄OH/H₂O 85/10/5) to give the subject compound (93 mg, yield 30%). Compound 24 was characterized by the following spectroscopic data: $^1$H NMR (DMSO-d6, 300 MHz) δ (ppm) 10.20 (m, 3H), 8.71 (m, 1H), 7.81 (d, 2H), 7.34 (d, 2H), 6.22-6.18 (m, 3H), 4.84 (s, 2H), 3.92 (m, 4H), 3.16 (m, 4H), 3.06-2.95 (m, 8H), 1.86 (m, 4H), 1.69 (m, 4H), 1.55 (m, 4H), 1.43 (m, 14H), 1.23 (m, 48H), 1.02 (m, 2H), 0.85 (t, 9H). MS (+)–ES [M+H]⁺ 1113 m/z.

Dihexadecyl 1-(4-(((6-amino-2-(butylamino)-8-hydroxy-9H-purin-9-yl)methyl)phenyl)-1,4-dioxo-2,5,9,14,18-pentaazahenicosan-21-yl)phosphonate: To a solution of intermediate 14 (150 mg, 0.36 mmol) in dry DMF (5 mL) were added N-hydroxysuccinimide (50 mg, 0.43 mmol), EDCI (82 mg, 0.43 mmol) and DMAP (52 mg, 0.43 mmol). The mixture was stirred at RT overnight. Then the solvent was removed in vacuo and the residue was triturated with water. The precipitate was filtered, washed with water EtOH and Et₂O and dried. The resulting solid was dissolved in dry DMF (3 mL) and were added intermediate 23 (278 mg, 0.36 mmol) and DIEA (587 μL, 3.6 mmol). The mixture was stirred at RT overnight. The solvent was removed in vacuo and the residue was directly applied to a column of silica gel (iPrOH/NH₄OH/H₂O 85/10/5) to give the subject compound (105 mg, yield 25%). Compound 25 was characterized by the following spectroscopic data: $^1$H NMR (DMSO-d6, 300 MHz) δ (ppm) 10.20 (m, 3H), 8.71 (m, 1H), 7.81 (d, 2H), 7.34 (d, 2H), 6.22-6.18 (m, 3H), 4.84 (s, 2H), 3.92 (m, 4H), 3.16 (m, 4H), 3.06-2.95 (m, 8H), 1.86 (m, 4H), 1.69 (m, 4H), 1.55 (m, 4H), 1.43 (m, 14H), 1.23 (m, 48H), 1.02 (m, 2H), 0.85 (t, 9H). MS (+)–ES [M+H]⁺ 1168 m/z.

Example 6

Molecule CL548

Compound 25

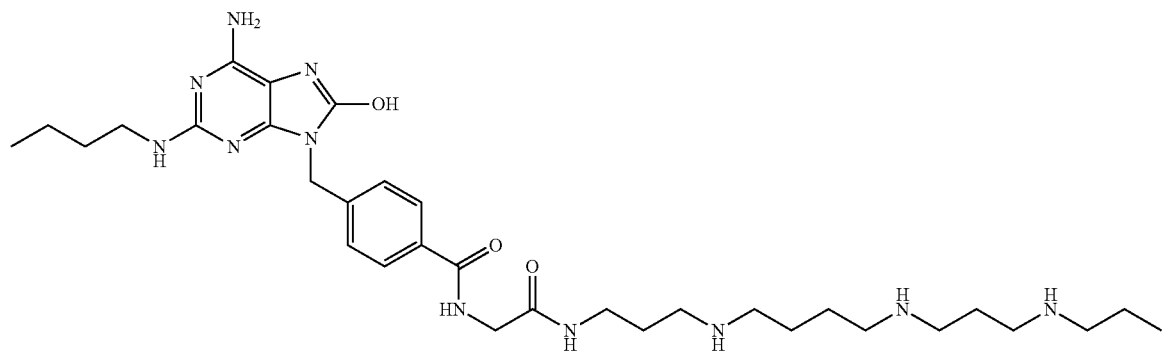

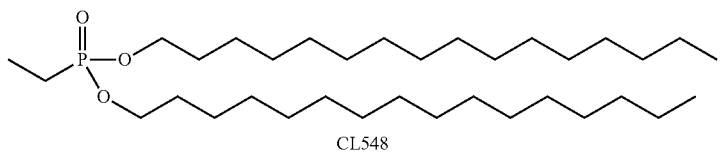

CL548

Example 7

Molecule CL481

Intermediate 26

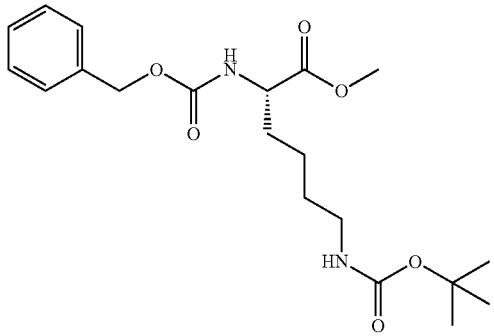

(S)-Methyl 2-(benzyloxycarbonylamino)-6-(tert-butoxycarbonylamino)hexanoate:

To a solution of Z-L-Lys(Boc)OH (5.00 g, 13.1 mmol) in dry DMF (100 mL) was added CsCO₃ (2.36 g, 0.26 mmol). The mixture was stirred at RT for 2H00. To the reaction mixture was then added dropwise methyl iodide (980 µL, 15.77 mmol) and the mixture was stirred at RT overnight. The solvent was removed in vacuo and the residue was dissolved in EtOAc (100 mL) and washed with saturated NaHCO₃ solution water and brine. The organic layer was dried over MgSO₄, filtered and concentrated in vacuo. The crude compound was purified on column of silica gel (2% MeOH/DCM) to give the subject compound (5.00 g, yield 96%). Intermediate 26 was characterized by the following spectroscopic data: ¹H NMR (DMSO-d6, 300 MHz) δ (ppm) 7.47 (m, 5H), 6.76 (t, 1H), 5.09 (s, 2H), 4.51 (m, 1H), 3.68 (s, 3H), 3.18 (m, 2H), 1.90 (m, 2H), 1.55 (m, 2H), 1.38 (s, 9H), 1.25 (m, 2H).

Intermediate 27

(S)-Methyl 6-amino-2-(benzyloxycarbonylamino) hexanoate: To a solution of Z-L-Lys(Boc)OMe 26 (5.00 g, 12.6 mmol) in DCM (100 mL) was added 100 mL of TFA. The mixture was stirred at RT for 1H00. Then the solvent were removed in vacuo, the residue was coevaporated 3 times with toluene. The residue was precipitated in diethyl ether to give the subject compound (5.08 g, yield 98%). Intermediate 27 was characterized by the following spectroscopic data: ¹H NMR (DMSO-d6, 300 MHz) δ (ppm) 8.45 (sl, 2H), 7.33 (m, 5H), 7.31 (t, 1H), 5.01 (s, 2H), 3.96 (m, 1H), 3.75 (s, 3H), 3.02 (m, 2H), 1.78 (m, 2H), 1.44 (m, 4H).

Intermediate 28

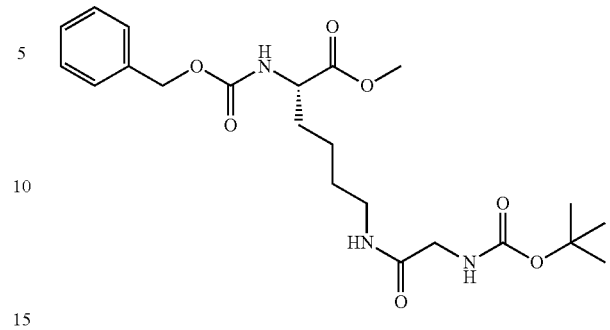

(S)-Methyl 2-(benzyloxycarbonylamino)-6-(2-(tert-butoxycarbonylamino)acetamido) hexanoate: To a solution of Z-L-LysOMe 27 (2.20 g, 5.39 mmol) in dry DMF (100 mL) was added Boc-GlyOH (0.90 g, 5.14 mmol), HATU (2.15 g, 5.65 mmol), and DIEA (4.47 mL, 25.7 mmol). The mixture was stirred at RT overnight. The solvent was then removed in vacuo and the residue was dissolved in EtOAc (100 mL) and washed with saturated NaHCO₃ solution water and brine. The organic layer was dried over MgSO₄, filtered and concentrated in vacuo. The crude compound was purified on column of silica gel (2% MeOH/DCM) to give the subject compound (2.22 g, yield 95%). Compound 28 was characterized by the following spectroscopic data: ¹H NMR (DMSO-d6, 300 MHz) δ (ppm) 8.10 (t, 1H), 7.95 (t, 1H), 7.47-7.38 (m, 5H), 6.95 (t, 1H), 5.11 (s, 2H), 4.55 (m, 1H), 3.95 (d, 2H), 3.70 (s, 3H), 3.02 (m, 2H), 1.90 (m, 2H), 1.55 (m, 2H), 1.38 (s, 9H), 1.25 (m, 2H).

Intermediate 29

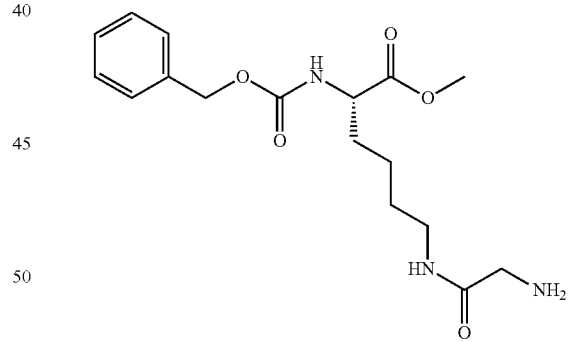

(S)-Methyl 6-(2-aminoacetamido)-2-(benzyloxycarbonylamino)hexanoate: To a solution of dipeptide Z-L-Lys(Boc-Gly)OMe 28 (2.20 g, 4.9 mmol) in DCM (100 mL) was added 100 mL of TFA. The mixture was stirred at RT for 1H00. Then the solvent were removed in vacuo, the residue was coevaporated 3 times with toluene. The residue was precipitated in diethyl ether to give the subject compound (2.28 g, yield 100%). Intermediate 29 was characterized by the following spectroscopic data: ¹H NMR (DMSO-d6, 300 MHz) δ (ppm) 8.35 (sl, 2H), 8.05 (t, 1H), 7.47-7.38 (m, 5H), 7.05 (t, 1H), 5.09 (s, 2H), 4.51 (m, 1H), 3.80 (d, 2H), 3.69 (s, 3H), 3.15 (m, 2H), 1.98 (m, 2H), 1.56-1.44 (m, 4H).

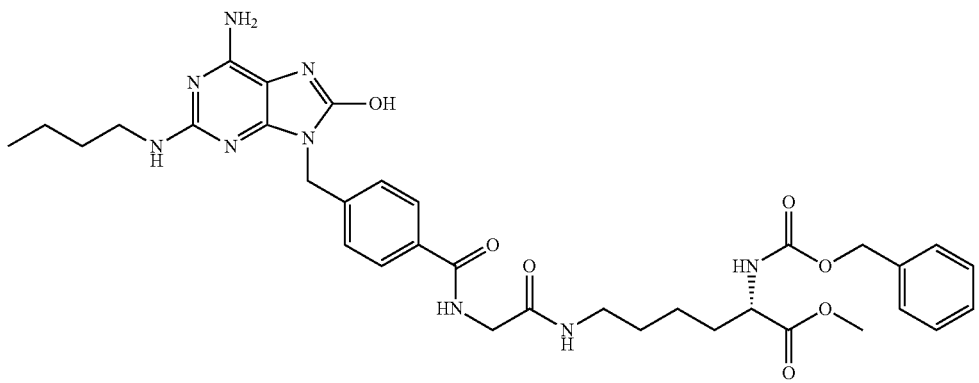

Intermediate 30

(S)-Methyl 6-(2-(4-((6-amino-2-(butylamino)-8-hydroxy-9H-purin-9-yl)methyl)benzamido)acetamido)-2-(benzyloxycarbonylamino)hexanoate: To a solution of Z-L-Lys(Gly)OMe 29 (718 mg, 1.54 mmol) in dry DMF (10 mL) was added intermediate 4 (500 mg, 1.4 mmol), HATU (586 mg, 1.54 mmol), and DIEA (1.22 mL, 7.1 mmol). The mixture was stirred at RT overnight. The solvent was then removed in vacuo and the residue was dissolved in EtOAc (30 mL) and washed with saturated $NaHCO_3$ solution water and brine. The organic layer was dried over $MgSO_4$, filtered and concentrated in vacuo. The crude compound was purified on column of silica gel (3% MeOH/DCM) to give the subject compound (950 mg, yield 98%). Intermediate 30 was characterized by the following spectroscopic data: $^1$H NMR (DMSO-d6, 300 MHz) δ (ppm) 10.20 (s, 1H), 8.68 (t, 1H), 8.33 (d, 1H), 7.36 (d, 2H), 7.32-7.24 (m, 9H), 6.28 (sl, 2H), 6.14 (t, 1H), 4.85 (s, 2H), 4.24 (s, 2H), 4.25 (m, 1H), 3.92 (d, 2H), 3.62 (s, 3H), 3.15 (m, 2H), 2.90 (m, 2H), 1.68-1.61 (m, 2H), 1.46-1.24 (m, 8H), 0.85 (t, 3H).

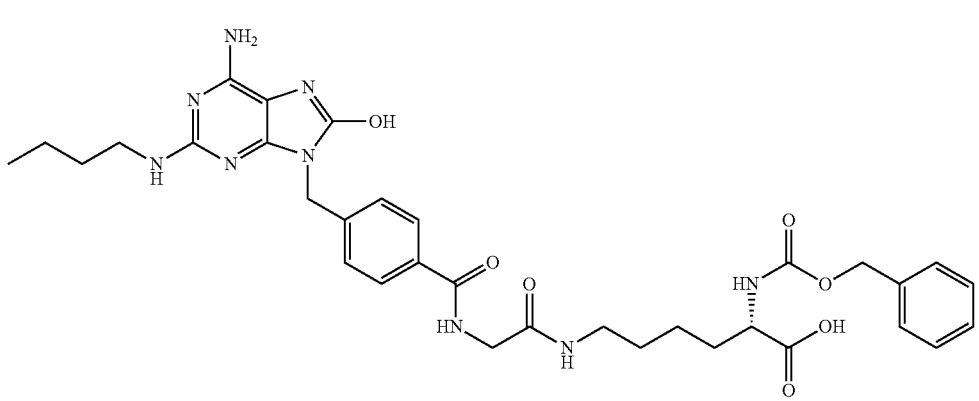

Intermediate 31

(S)-6-(2-(4-((6-amino-2-(butylamino)-8-hydroxy-9H-purin-9-yl)methyl)benzamido) acetamido)-2-(benzyloxycarbonylamino)hexanoic acid: To a solution of intermediate 30 (950 mg, 1.37 mmol) in dioxane (30 mL) was added 1N LiOH solution until pH=10. The mixture was stirred at RT overnight. The mixture was neutralized with 1M HCl solution (pH 6). The precipitate was filtered off, washed with water, EtOH and $Et_2O$ to give the subject compound (825 mg, yield 88%) which was used for the next step without any further purification.

Intermediate 32

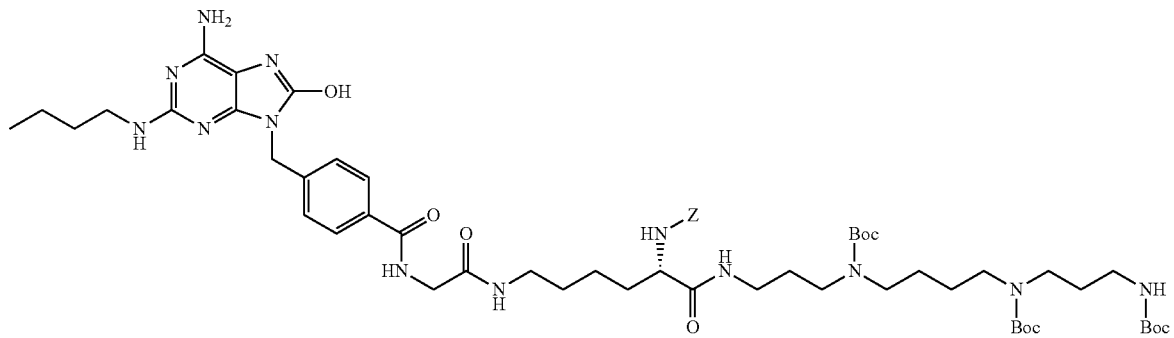

N1,N5,N10-triBoc-spermine (S)-6-(2-(4-((6-amino-2-(butylamino)-8-hydroxy-9H-purin-9-yl)methyl)benzamido)acetamido)-2-(benzyloxycarbonylamino)hexanamide: To a solution of intermediate 31 (825 mg, 1.22 mmol) in dry DMF (20 mL) was added intermediate 5 (675 mg, 1.34 mmol), HATU (510 mg, 1.34 mmol), and DIEA (1.06 mL, 6.1 mmol). The mixture was stirred at RT overnight. The solvent was then removed in vacuo and the residue was dissolved in EtOAc (30 mL) and washed with saturated NaHCO$_3$ solution water and brine. The organic layer was dried over MgSO$_4$, filtered and concentrated in vacuo. The crude compound was purified on column of silica gel (3% MeOH/DCM) to give the subject compound (911 mg, yield 64%). Intermediate 32 was characterized by the following spectroscopic data: $^1$H NMR (DMSO-d6, 300 MHz) δ (ppm) 9.69 (s, 1H), 8.71 (t, 1H), 8.03 (d, 1H), 7.86 (d, 2H), 7.36-7.32 (m, 7H), 7.20 (t, 1H), 6.72 (t, 1H), 6.17 (t, 1H), 6.03 (sl, 2H), 4.89 (s, 2H), 4.86 (s, 2H), 4.16 (m, 1H), 3.88 (d, 2H), 3.15 (m, 2H), 3.16-2.85 (m, 16H), 1.68-1.52 (m, 6H), 1.48-1.20 (m, 37H), 0.83 (t, 3H).

Intermediate 33

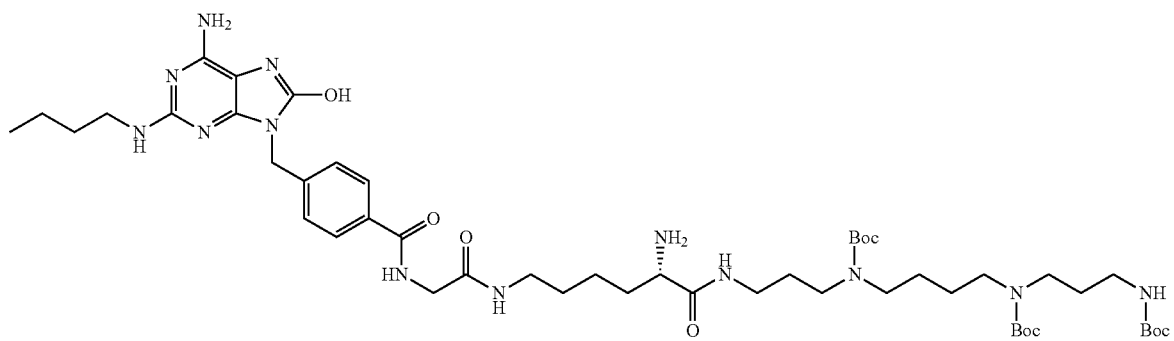

N1,N5,N10-triBoc-spermine (S)-6-(2-(4-((6-amino-2-(butylamino)-8-hydroxy-9H-purin-9-yl) methyl)benzamido)acetamido) hexanamide: To a solution of intermediate 32 (911 mg, 0.78 mmol) in a mixture of THF/MeOH (1/1) (30 mL) was added palladium on activated carbon 10% (1/1) (0.05 eq). hydrogen gas was introduced via a balloon; the reaction mixture was stirred overnight at RT. The mixture was filtered through Celite and was washed with MeOH, the filtrate was concentrated in vacuo. The resulting solid was used for the next step without any further purification.

Intermediate 34

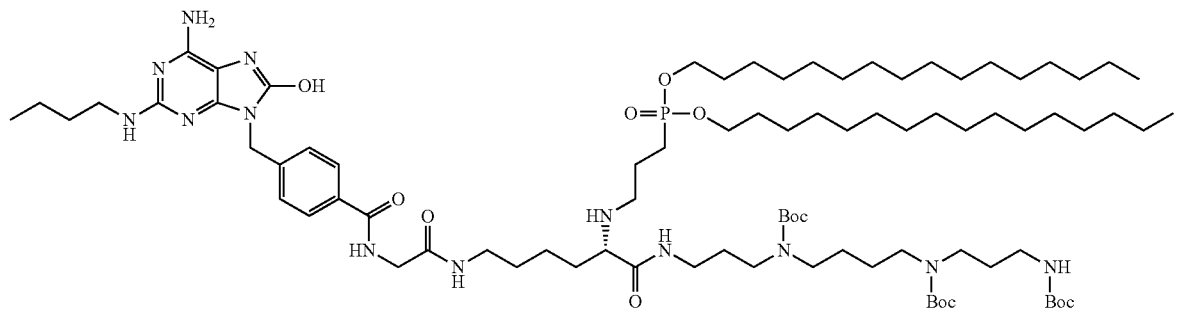

N1,N5,N10-triBoc-spermine (S)-6-(2-(4-((6-amino-2-(butylamino)-8-hydroxy-9H-purin-9-yl)methyl)benzamido) acetamido)-2-(1-aminopropyl-3-dihexadecylphosphonate) hexanamide: To a solution of intermediate 33 (100 mg, 0.097 mmol) in absolute EtOH (10 mL) was added $Na_2CO_3$ (12 mg, 0.12 mmol) and intermediate 21 (63 mg, 0.097 mmol). The mixture was stirred under reflux for 18H00.

The solvent was then removed in vacuo, the residue was dissolved with DCM (20 mL) and was washed with water and brine. The organic layer was dried over $MgSO_4$ and concentrated in vacuo. The crude material was purified on column of silica gel (2% MeOH/DCM) to give the subject compound (140 mg, yield 90%). Intermediate 34 was characterized by the following spectroscopic data: $^1$H NMR NMR (DMSO-d6, 300 MHz) δ (ppm) 8.73 (s, 1H), 8.25 (t, 1H), 7.81 (d, 1H), 7.79 (d, 2H), 7.34 (d, 2H), 7.20 (t, 1H), 6.73 (t, 1H), 6.20 (t, 1H), 6.03 (sl, 2H), 4.85 (s, 2H), 4.16 (m, 1H), 3.87 (m, 6H), 3.20-2.88 (m, 22H), 1.65-1.55 (m, 14H), 1.36 (m, 45H), 1.23 (m, 43H), 0.85 (m, 9H).

Compound 35

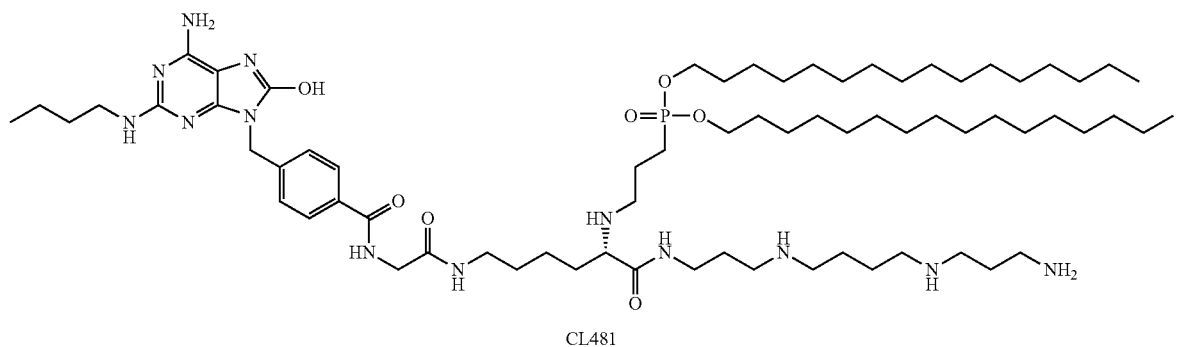

CL481

(S)-dihexadecyl 19-amino-5-(4-(2-(4-((6-amino-2-(butylamino)-8-hydroxy-9H-purin-9-yl) methyl)benzamido)acetamido)butyl)-6-oxo-4,7,11,16-tetraazanonadecylphosphonate: To a solution of intermediate 34 (140 mg, 0.087 mmol) in dioxane (5 mL) was added 4N HCl solution in dioxane (15 mL). The mixture was stirred at RT overnight. Then the solvent were removed in vacuo, the residue was coevaporated 3 times with toluene. The residue was purified by flash chromatography on an ARMEN® system with C18 column eluting with a gradient of 0-10% MeCN in $NH_4OAc$ (10 mM) solution (pH 9) to give the subject compound (73 mg, yield 52%). Compound 35 was characterized by the following spectroscopic data: $^1$H NMR (DMSO-d6, 300 MHz) δ (ppm) 10.37 (s, 1H), 9.25 (m, 1H), 9.24 (m, 1H), 9.05 (m, 2H), 8.89 (m, 1H), 8.21 (m, 4H), 8.04 (m, 1H), 7.86 (d, 2H), 7.34 (d, 2H), 6.44 (m, 2H), 6.25 (m, 1H), 4.86 (s, 2H), 4.14 (m, 4H), 3.92 (m, 2H), 3.80 (m, 2H), 3.78 (m, 2H), 3.69 (m, 2H), 3.16-2.85 (m, 26H), 2.02 (m, 2H), 1.98-1.77 (m, 8H), 1.69 (m, 4H), 1.55 (m, 2H), 1.43-1.22 (m, 48H), 0.85 (m, 9H). MS (+)-ES [M+H]$^+$ 1297 m/z.

Example 8

Molecule CL493

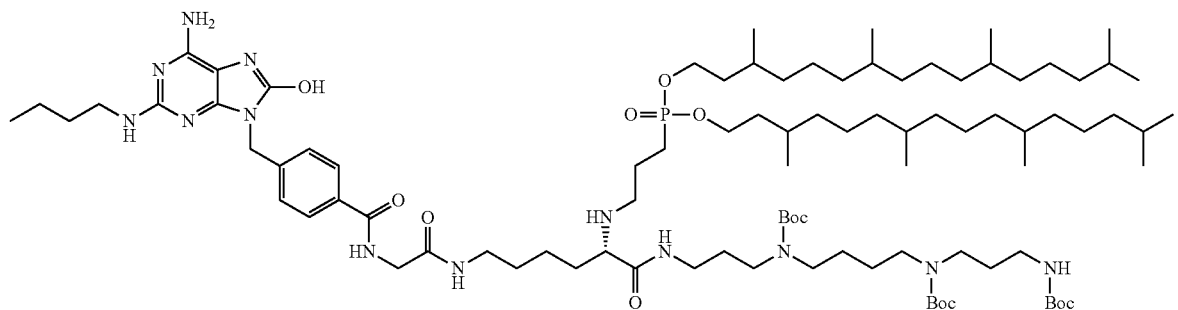

Intermediate 36

N1,N5,N10-triBoc-spermine (S)-6-(2-(4-(((6-amino-2-(butylamino)-8-hydroxy-9H-purin-9-yl) methyl)benzamido)acetamido)-2-(1-aminopropyl bis(3,7,11,15-tetramethylhexadecyl) 3-phosphonate)hexanamide: To a solution of intermediate 33 (134 mg, 0.13 mmol) in absolute EtOH (10 mL) was added $Na_2CO_3$ (16 mg, 0.16 mmol) and intermediate 9 (100 mg, 0.13 mmol). The mixture was stirred under reflux for 18H00. The solvent was then removed in vacuo, the residue was dissolved with DCM (20 mL) and was washed with water and brine. The organic layer was dried over $MgSO_4$ and concentrated in vacuo. The crude material was purified on column of silica gel (2% MeOH/DCM) to give the subject compound (220 mg, yield 98%). Intermediate 36 was characterized by the following spectroscopic data: $^1$H NMR (DMSO-d6, 300 MHz) δ (ppm) 8.73 (s, 1H), 8.06 (m, 1H), 7.89 (m, 1H), 7.81 (d, 2H), 7.35 (d, 2H), 6.75 (m, 1H), 6.19 (m, 1H), 6.02 (sl, 2H), 4.85 (s, 2H), 4.18 (m, 2H), 3.90 (m, 12H), 3.10-2.88 (m, 14H), 2.87 (m, 4H), 2.72 (m, 2H), 1.94 (m, 4H), 1.65-1.05 (m, 86H), 0.78 (m, 33H).

(S)-bis(3,7,11,15-tetramethylhexadecyl) 19-amino-5-(4-(2-(4-(((6-amino-2-(butylamino)-8-hydroxy-9H-purin-9-yl) methyl)benzamido)acetamido)butyl)-6-oxo-4,7,11,16-tetraazanonadecylphosphonate: To a solution of intermediate 36 (220 mg, 0.12 mmol) in dioxane (5 mL) was added 4N HCl solution in dioxane (15 mL). The mixture was stirred at RT overnight. Then the solvent were removed in vacuo, the residue was coevaporated 3 times with toluene. The residue was purified by flash chromatography on an ARMEN® system with C18 column eluting with a gradient of 0-10% MeCN in $NH_4OAc$ (10 mM) solution (pH 9) to give the subject compound (153 mg, yield 77%). Compound 35 was characterized by the following spectroscopic data: $^1$H NMR (DMSO-d6, 300 MHz) δ (ppm) 9.19 (m, 2H), 8.94 (m, 2H), 8.15 (m, 4H), 7.96 (m, 1H), 7.86 (d, 2H), 7.37 (d, 2H), 4.89 (s, 2H), 4.15 (m, 2H), 3.92 (m, 6H), 3.77 (m, 4H), 3.07 (m, 6H), 2.55 (m, 10H), 1.98-1.23 (m, 68H), 0.78 (m, 33H). MS (+)–ES $[M+H]^+$ 1409 m/z.

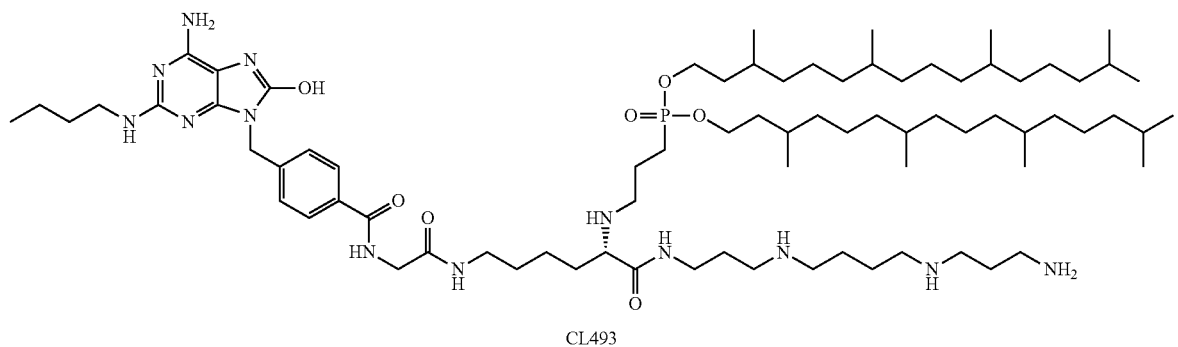

Compound 37

CL493

Example 9

Molecule CL489

Intermediate 38

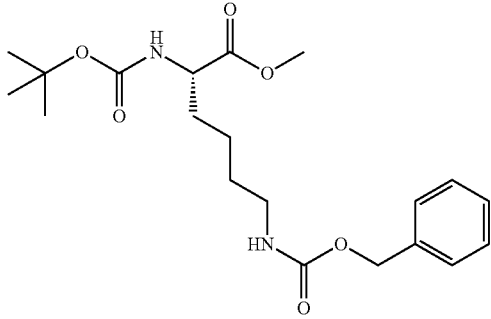

(S)-Methyl 6-(benzyloxycarbonylamino)-2-(tert-butoxycarbonylamino)hexanoate:

To a solution of Boc-L-Lys(Z)OH (2.00 g, 5.25 mmol) in dry DMF (50 mL) was added CsCO$_3$ (1.71 g, 5.26 mmol). The mixture was stirred at RT for 2H00. To the reaction mixture was then added dropwise methyl iodide (392 µL, 6.3 mmol) and the mixture was stirred at RT overnight. The solvent was removed in vacuo and the residue was dissolved in EtOAc (100 mL) and washed with saturated NaHCO$_3$ solution water and brine. The organic layer was dried over MgSO$_4$, filtered and concentrated in vacuo. The crude compound was purified on column of silica gel (2% MeOH/DCM) to give the subject compound (2.00 g, yield 97%). Intermediate 38 was characterized by the following spectroscopic data: $^1$H NMR (DMSO-d6, 300 MHz) δ (ppm) 7.34 (m, 5H), 7.23 (t, 1H), 4.99 (s, 2H), 3.91 (m, 1H), 3.60 (s, 3H), 3.34 (s, 2H), 2.96 (m, 2H), 1.56 (m, 2H), 1.37 (m, 11H), 1.32 (m, 2H).

Intermediate 39

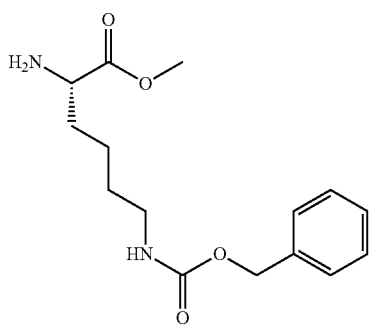

(S)-Methyl 2-amino-6-(benzyloxycarbonylamino)hexanoate: To a solution of Boc-L-Lys(Z)OMe 38 (2.00 g, 12.6 mmol) in DCM (30 mL) was added 30 mL of TFA. The mixture was stirred at RT for 1H00. Then the solvent were removed in vacuo, the residue was coevaporated 3 times with toluene. The residue was precipitated in diethyl ether to give the subject compound (2.1 g, yield 100%). Intermediate 39 was characterized by the following spectroscopic data: $^1$H NMR (DMSO-d6, 300 MHz) δ (ppm) 8.45 (sl, 2H), 7.33 (m, 5H), 7.31 (t, 1H), 5.00 (s, 2H), 4.03 (m, 1H), 3.74 (s, 3H), 2.97 (m, 2H), 1.75 (m, 2H), 1.39 (m, 4H).

Intermediate 40

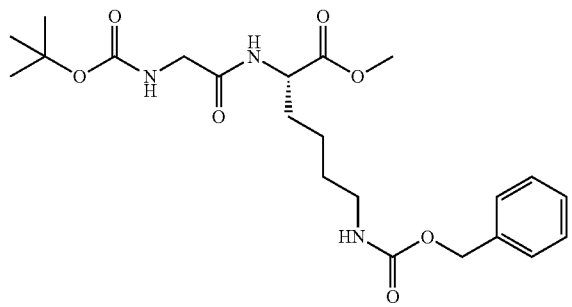

(S)-Methyl 16,16-dimethyl-3,11,14-trioxo-1-phenyl-2,15-dioxa-4,10,13-triazaheptadecane-9-carboxylate: To a solution of L-Lys(Z)OMe 39 (1.05 g, 2.57 mmol) in dry DMF (40 mL) was added Boc-GlyOH (0.494 g, 2.82 mmol), HATU (0.977 g, 2.57 mmol), and DIEA (2.03 mL, 11.7 mmol). The mixture was stirred at RT overnight. The solvent was then removed in vacuo and the residue was dissolved in EtOAc (100 mL) and washed with saturated NaHCO$_3$ solution water and brine. The organic layer was dried over MgSO$_4$, filtered and concentrated in vacuo. The crude compound was purified on column of silica gel (2% MeOH/DCM) to give the subject compound (0.960 g, yield 90%). Compound 40 was characterized by the following spectroscopic data: $^1$H NMR (DMSO-d6, 300 MHz) δ (ppm) 8.12 (t, 1H), 7.98 (t, 1H), 7.47-7.38 (m, 5H), 6.98 (t, 1H), 5.13 (s, 2H), 4.56 (m, 1H), 4.05 (d, 2H), 3.65 (s, 3H), 3.02 (m, 2H), 1.90 (m, 2H), 1.55 (m, 2H), 1.38 (s, 9H), 1.25 (m, 2H).

Intermediate 41

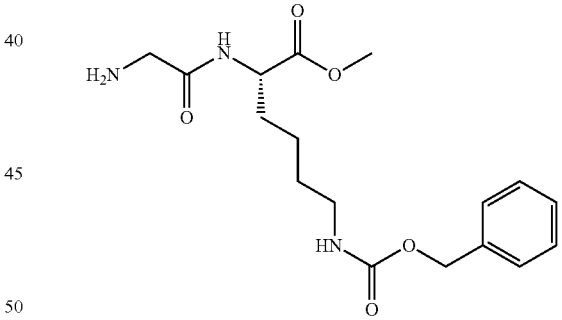

(S)-Methyl 2-(2-aminoacetamido)-6-(benzyloxycarbonylamino)hexanoate: To a solution of dipeptide Boc-Gly-L-Lys(Z)OMe 40 (0.960 g, 2.13 mmol) in DCM (10 mL) was added 10 mL of TFA. The mixture was stirred at RT for 1H00. Then the solvent were removed in vacuo, the residue was coevaporated 3 times with toluene. The residue was precipitated in diethyl ether to give the subject compound (0.99 g, yield 100%). Intermediate 41 was characterized by the following spectroscopic data: $^1$H NMR (DMSO-d6, 300 MHz) δ (ppm) 8.76 (d, 1H), 8.05 (sl, 2H), 7.34-7.29 (m, 6H), 4.99 (s, 2H), 4.28 (m, 1H), 3.64 (s, 3H), 2.88 (m, 2H), 1.65 (m, 2H), 1.39-1.28 (m, 4H).

Intermediate 42

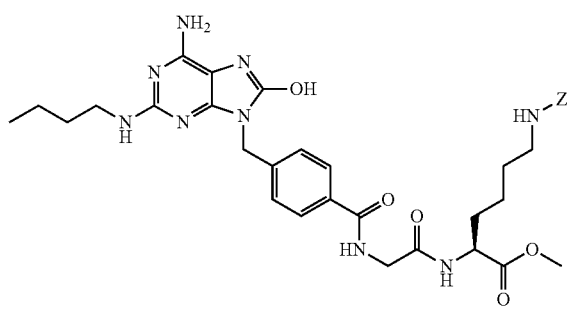

(DMSO-d6, 300 MHz) δ (ppm) 9.88 (s, 1H), 8.68 (t, 1H), 8.31 (d, 1H), 7.82 (d, 2H), 7.34 (m, 9H), 6.19 (t, 1H), 6.13 (sl, 2H), 4.99 (s, 2H), 4.85 (s, 2H), 4.23 (m, 1H), 3.91 (d, 2H), 3.61 (s, 3H), 3.15 (m, 2H), 2.96 (m, 2H), 1.64 (m, 2H), 1.41 (m, 4H), 1.28 (m, 4H), 0.85 (t, 3H).

Intermediate 43

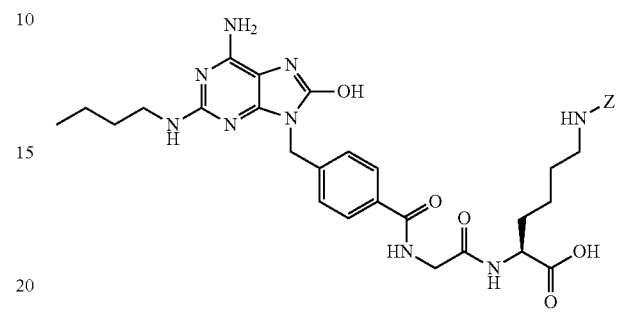

(S)-Methyl 2-(2-(4-((6-amino-2-(butylamino)-8-hydroxy-9H-purin-9-yl)methyl)benzamido)acetamido)-6-(benzyloxycarbonylamino)hexanoate: To a solution of Gly-L-Lys(Z)OMe 41 (990 mg, 2.13 mmol) in dry DMF (20 mL) was added intermediate 4 (722 mg, 2.03 mmol), HATU (847 mg, 2.23 mmol), and DIEA (1.76 mL, 10.1 mmol). The mixture was stirred at RT overnight. The solvent was then removed in vacuo and the residue was dissolved in EtOAc (50 mL) and washed with saturated NaHCO₃ solution water and brine. The organic layer was dried over MgSO₄, filtered and concentrated in vacuo. The crude compound was purified on column of silica gel (3% MeOH/DCM) to give the subject compound (1.20 g, yield 86%). Intermediate 42 was characterized by the following spectroscopic data: ¹H NMR (S)-2-(2-(4-((6-amino-2-(butylamino)-8-hydroxy-9H-purin-9-yl)methyl)benzamido) acetamido)-6-(benzyloxycarbonylamino)hexanoic acid: To a solution of intermediate 42 (1.2 g, 1.74 mmol) in dioxane (20 mL) was added 1N LiOH solution until pH 10. The mixture was stirred at RT overnight. The mixture was neutralized with 1M HCl solution (pH 6). The precipitate was filtered off, washed with water, EtOH and Et₂O to give the subject compound (1.05 g, yield 89%) which was used for the next step without any further purification.

Intermediate 44

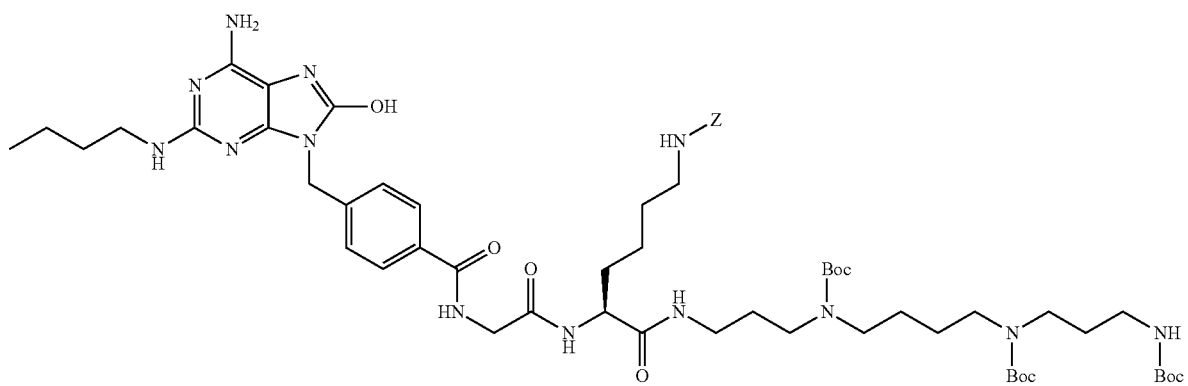

N1,N5,N10-triBoc-spermine (S)-2-(2-(4-((6-amino-2-(butylamino)-8-hydroxy-9H-purin-9-yl) methyl)benzamido)acetamido)-6-(benzyloxycarbonylamino) hexanamide: To a solution of intermediate 43 (1.05 mg, 1.55 mmol) in dry DMF (20 mL) was added intermediate 5 (859 mg, 1.71 mmol), HATU (649 mg, 1.71 mmol), and DIEA (1.35 mL, 7.8 mmol). The mixture was stirred at RT overnight. The solvent was then removed in vacuo and the residue was dissolved in EtOAc (30 mL) and washed with saturated NaHCO$_3$ solution water and brine. The organic layer was dried over MgSO$_4$, filtered and concentrated in vacuo. The crude compound was purified on column of silica gel (3% MeOH/DCM) to give the subject compound (1.7 g, yield 94%). Intermediate 44 was characterized by the following spectroscopic data: $^1$H NMR (DMSO-d6, 300 MHz) δ (ppm) 9.70 (s, 1H), 8.73 (t, 1H), 8.04 (d, 1H), 7.87 (m, 1H), 7.80 (d, 2H), 7.32 (m, 7H), 7.22 (t, 1H), 6.76 (t, 1H), 6.20 (t, 1H), 6.04 (sl, 2H), 4.99 (s, 2H), 4.85 (s, 2H), 4.16 (m, 1H), 3.87 (d, 2H), 3.07-2.86 (m, 18H), 1.68-1.52 (m, 6H), 1.48-1.20 (m, 37H), 0.83 (t, 3H).

Intermediate 45

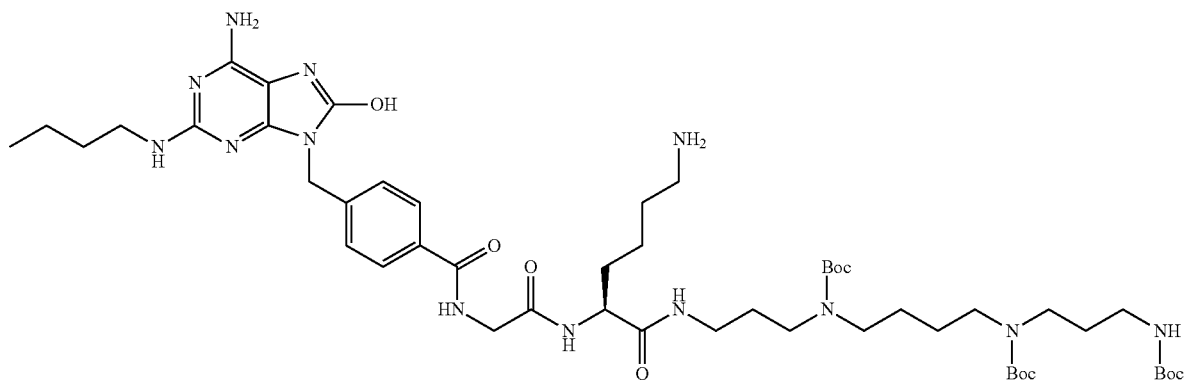

N1,N5,N10-triBoc-spermine (S)-2-(2-(4-((6-amino-2-(butylamino)-8-hydroxy-9H-purin-9-yl) methyl)benzamido)acetamido)-6-amino-hexanamide: To a solution of intermediate 44 (1.7 g, 1.5 mmol) in a mixture of THF/MeOH (1/1) (30 mL) was added palladium on activated carbon 10% (0.05 eq). hydrogen gas was introduced via a balloon; the reaction mixture was stirred overnight at RT. The mixture was filtered through Celite and was washed with MeOH, the filtrate was concentrated in vacuo. The resulting solid was used for the next step without any further purification.

Intermediate 46

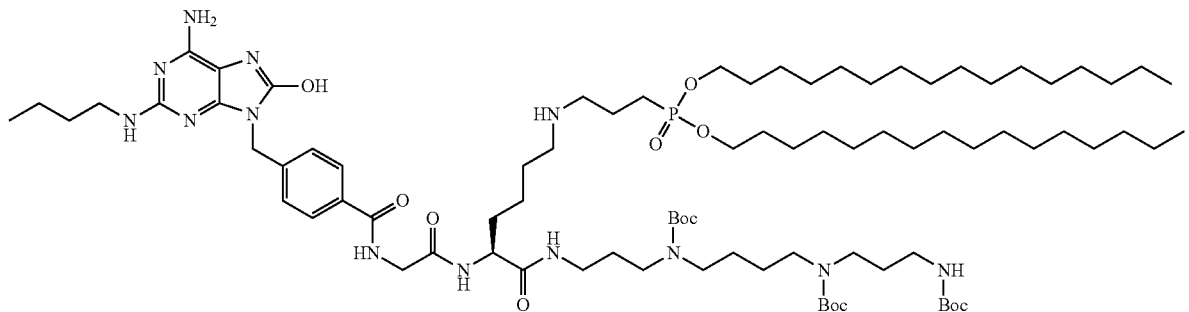

N1,N5,N10-triBoc-spermine (S)-2-(2-(4-((6-amino-2-(butylamino)-8-hydroxy-9H-purin-9-yl)methyl)benzamido)acetamido)-6-(1-aminopropyl-3-dihexadecylphosphonate)-hexanamide: To a solution of intermediate 45 (100 mg, 0.097 mmol) in absolute EtOH (10 mL) was added Na$_2$CO$_3$ (12 mg, 0.117 mmol) and intermediate 21 (63 mg, 0.097 mmol). The mixture was stirred under reflux for 24H00. The solvent was then removed in vacuo; the residue was dissolved with DCM (20 mL) and was washed with water and brine. The organic layer was dried over MgSO$_4$ and concentrated in vacuo. The crude material was purified on column of silica gel (2% MeOH/DCM) to give the subject compound (150 mg, yield 97%). Intermediate 46 was characterized by the following spectroscopic data: $^1$H NMR (DMSO-d6, 300 MHz) δ (ppm) 8.82 (s, 1H), 8.13 (d, 1H), 7.94 (m, 1H), 7.82 (d, 2H), 7.34 (d, 2H), 6.76 (m, 1H), 6.25 (sl, 2H), 6.16 (t, 1H), 4.85 (s, 2H), 4.17 (m, 1H), 3.87 (m, 4H), 3.08-2.88 (m, 8H), 2.86 (m, 4H), 1.65-1.55 (m, 12H), 1.36 (m, 50H), 1.23 (m, 44H), 0.85 (m, 9H).

Compound 47

CL489

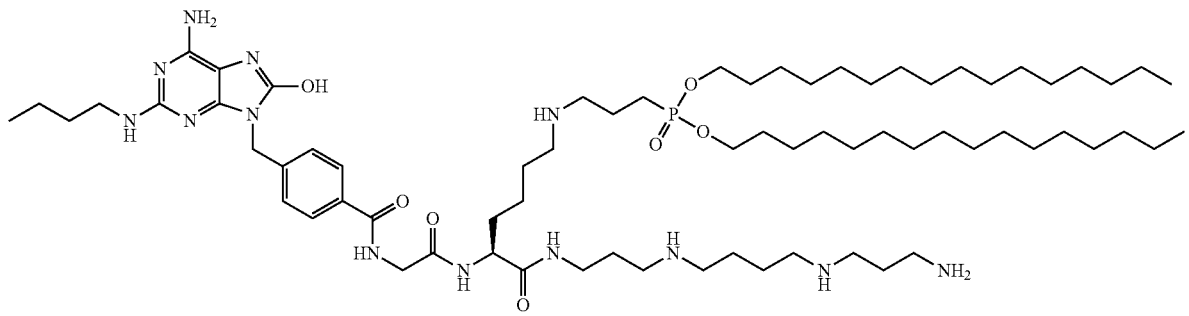

(S)-Dihexadecyl-1-amino-15-(2-(4-((6-amino-2-(butylamino)-8-hydroxy-9H-purin-9-yl) methyl)benzamido)acetamido)-14-oxo-4,9,13,20-tetraazatricosan-23-ylphosphonate: To a solution of intermediate 46 (150 mg, 0.090 mmol) in dioxane (5 mL) was added 4N HCl solution in dioxane (15 mL). The mixture was stirred at RT overnight. Then the solvent were removed in vacuo, the residue was coevaporated 3 times with toluene. The residue was purified by flash chromatography on an ARMEN® system with C18 column eluting with a gradient of 0-10% MeCN in NH$_4$OAc (10 mM) solution (pH 9) to give the subject compound (120 mg, yield 88%). Compound 47 was characterized by the following spectroscopic data: $^1$H NMR (DMSO-d6, 300 MHz) δ (ppm) 10.28 (s, 1H), 9.11 (m, 1H), 8.92 (m, 1H), 8.24 (m, 4H), 7.86 (d, 2H), 7.34 (d, 2H), 7.22 (m, 2H), 7.17 (m, 2H), 6.38 (m, 2H), 6.14 (m, 1H), 4.86 (s, 2H), 4.68 (m, 1H), 4.5 (m, 1H), 4.16 (m, 2H), 3.80 (m, 2H), 3.78 (m, 2H), 3.69 (m, 2H), 3.15-2.85 (m, 26H), 2.01 (m, 2H), 1.98-1.77 (m, 8H), 1.69 (m, 4H), 1.55 (m, 2H), 1.43-1.22 (m, 48H), 0.85 (m, 9H). MS (+)–ES [M+H]$^+$ 1297 m/z.

Example 10

Molecule CL495

Intermediate 48

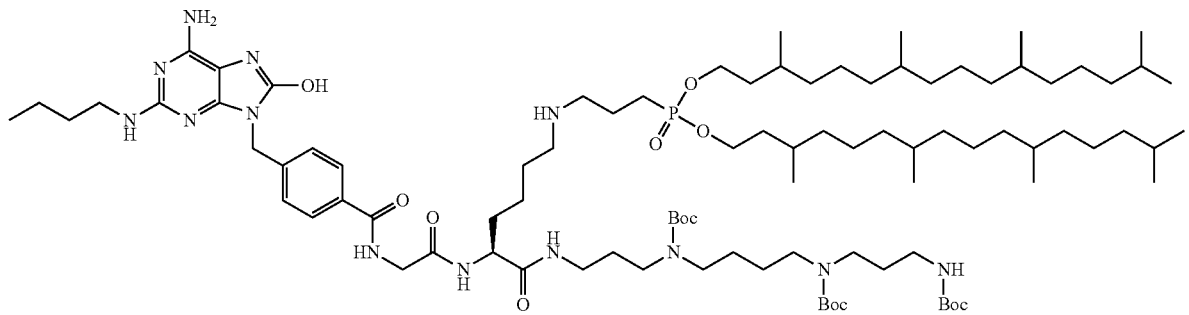

N1,N5,N10-triBoc-spermine (S)-2-(2-(4-((6-amino-2-(butylamino)-8-hydroxy-9H-purin-9-yl)methyl)benzamido)acetamido)-6-(1-aminopropylbis(3,7,11,15-tetramethyl hexadecyl)-3-phosphonate)-hexanamide: To a solution of intermediate 45 (100 mg, 0.097 mmol) in absolute EtOH (10 mL) was added Na$_2$CO$_3$ (12 mg, 0.12 mmol) and intermediate 9 (74 mg, 0.097 mmol). The mixture was stirred under reflux for 18H00. The solvent was then removed in vacuo, the residue was dissolved with DCM (20 mL) and was washed with water and brine. The organic layer was dried over MgSO$_4$ and concentrated in vacuo. The crude material was purified on column of silica gel (2% MeOH/DCM) to give the subject compound (160 mg, yield 96%). Intermediate 48 was characterized by the following spectroscopic data: $^1$H NMR (DMSO-d6, 300 MHz) δ (ppm) 8.78 (s, 1H), 8.09 (m, 1H), 7.96 (m, 1H), 7.82 (d, 2H), 7.35 (m, 2H), 6.75 (m, 1H), 6.19 (m, 1H), 6.03 (sl, 2H), 4.85 (s, 2H), 4.17 (m, 1H), 3.89 (m, 4H), 3.16-2.90 (m, 16H), 2.88 (m, 6H), 1.94-1.05 (m, 93H), 0.78 (m, 33H).

Example 11

Molecule CL488

Intermediate 50

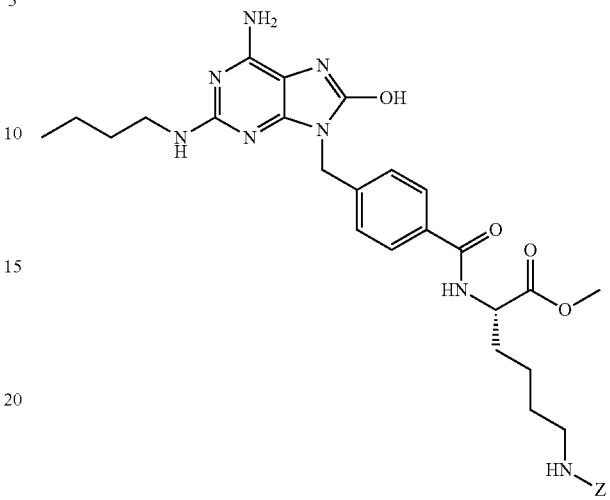

Compound 49

CL495

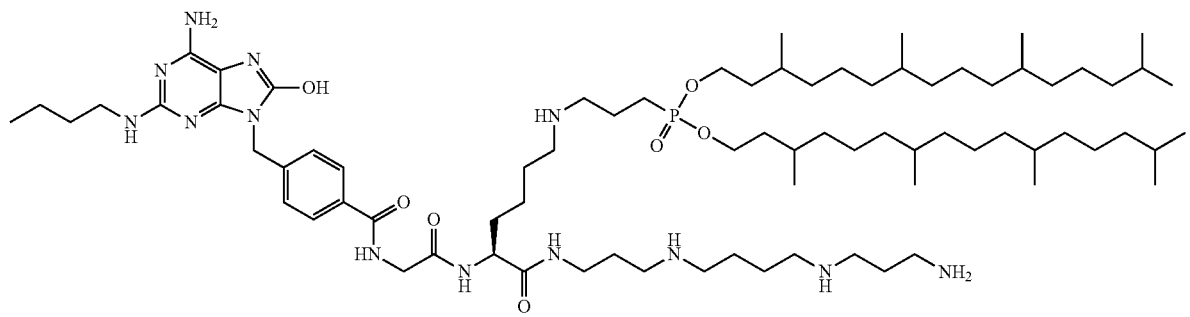

(S)-bis(3,7,11,15-tetramethylhexadecyl)-1-amino-15-(2-(4-((6-amino-2-(butylamino)-8-hydroxy-9H-purin-9-yl)methyl)benzamido)acetamido)-14-oxo-4,9,13,20-tetraazatricosan-23-ylphosphonate: To a solution of intermediate 48 (160 mg, 0.097 mmol) in dioxane (5 mL) was added 4N HCl solution in dioxane (15 mL). The mixture was stirred at RT overnight. Then the solvent were removed in vacuo, the residue was coevaporated 3 times with toluene. The residue was purified by flash chromatography on an ARMEN® system with C18 column eluting with a gradient of 0-10% MeCN in NH$_4$OAc (10 mM) solution (pH 9) to give the subject compound (111 mg, yield 74%). Compound 49 was characterized by the following spectroscopic data: $^1$H NMR (DMSO-d6, 300 MHz) δ (ppm) 10.26 (s, 1H), 9.65 (m, 2H), 8.88 (m, 2H), 8.54 (m, 4H), 8.28-8.19 (m, 4H), 7.85 (d, 2H), 7.36 (d, 2H), 6.34 (sl, 2H), 6.19 (m, 1H), 4.86 (s, 2H), 4.33 (m, 1H), 3.98 (m, 2H), 3.73 (m, 4H), 3.67 (m, 2H), 3.14 (m, 6H), 3.06 (m, 2H), 2.55 (m, 10H), 2.15 (m, 4H), 2.00-1.23 (m, 64H), 0.85 (m, 33H). MS (+)–ES [M+H]$^+$1409 m/z.

(S)-Methyl 2-(4-((6-amino-2-(butylamino)-8-hydroxy-9H-purin-9-yl)methyl)benzamido)-6-(benzyloxycarbonylamino)hexanoate: To a solution of intermediate 4 (1.02 g, 2.87 mmol) in dry DMF (10 mL) was added L-Lys(Z)OMe 39 (1.29 g, 3.16 mmol), HATU (1.20 g, 3.16 mmol), and DIEA (2.50 mL, 14.4 mmol). The mixture was stirred at RT overnight. The solvent was then removed in vacuo and the residue was dissolved in EtOAc (30 mL) and washed with saturated NaHCO$_3$ solution water and brine. The organic layer was dried over MgSO$_4$, filtered and concentrated in vacuo. The crude compound was purified on column of silica gel (4% MeOH/DCM) to give the subject compound (0.685 g, yield 38%). Intermediate 50 was characterized by the following spectroscopic data: $^1$H NMR (DMSO-d6, 300 MHz) δ (ppm) 9.67 (s, 1H), 8.65 (d, 1H), 7.81 (d, 2H), 7.32-7.29 (m, 8H), 6.20 (t, 2H), 6.02 (sl, 1H), 4.98 (s, 2H), 4.86 (s, 2H), 4.37 (m, 1H), 3.62 (s, 3H), 3.14 (m, 2H), 2.97 (m, 2H), 1.78 (m, 2H), 1.43-1.26 (m, 8H), 0.88 (t, 3H).

Intermediate 51

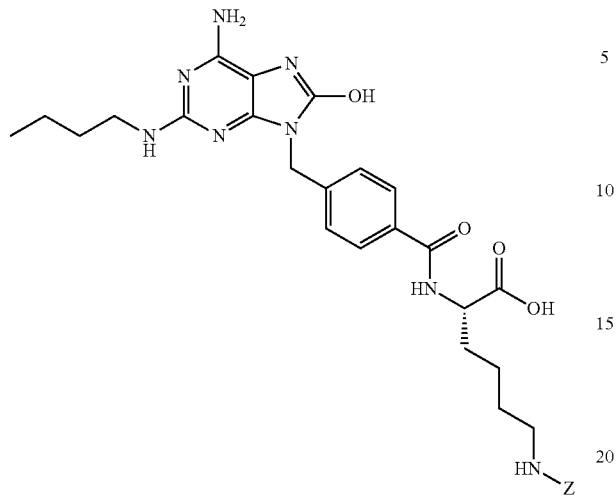

(S)-2-(4-((6-amino-2-(butylamino)-8-hydroxy-9H-purin-9-yl)methyl)benzamido)-6-(benzyloxycarbonylamino) hexanoic acid: To a solution of intermediate 50 (685 mg, 1.08 mmol) in dioxane (10 mL) was added 1N LiOH solution until pH 10. The mixture was stirred at RT overnight. The mixture was neutralized with 1M HCl solution (pH 6). The precipitate was filtered off, washed with water, EtOH and Et$_2$O to give the subject compound (668 mg, yield 99%), which was used for the next step without any further purification.

Intermediate 52

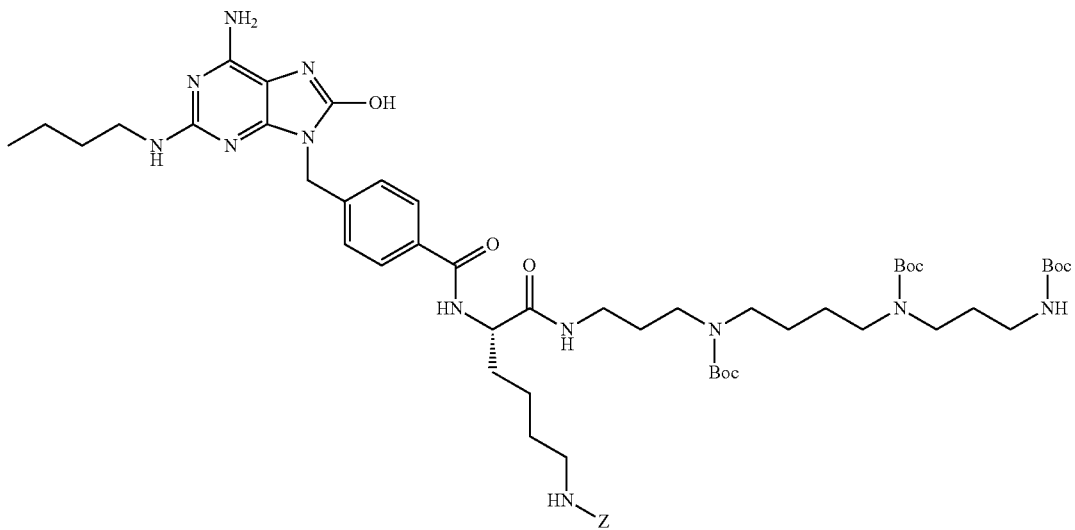

N1,N5,N10-triBoc-spermine (S)-2-(4-(6-amino-2-(butylamino)-8-hydroxy-9H-purin-9-yl) methyl)benzamido)acetamido)-6-(benzyloxycarbonylamino)hexanamide: To a solution of intermediate 51 (668 mg, 1.08 mmol) in dry DMF (20 mL) was added intermediate 5 (598 mg, 1.19 mmol), HATU (452 mg, 1.19 mmol), and DIEA (941 µL, 5.4 mmol). The mixture was stirred at RT overnight. The solvent was then removed in vacuo and the residue was dissolved in EtOAc (30 mL) and washed with saturated NaHCO$_3$ solution water and brine. The organic layer was dried over MgSO$_4$, filtered and concentrated in vacuo. The crude compound was purified on column of silica gel (3% MeOH/DCM) to give the subject compound (1.06 g, yield 89%). Intermediate 52 was characterized by the following spectroscopic data: $^1$H NMR (DMSO-d6, 300 MHz) δ (ppm) 9.66 (s, 1H), 8.33 (m, 1H), 7.91 (m, 1H), 7.83 (d, 2H), 7.36-7.32 (m, 7H), 6.76 (t, 1H), 6.19 (t, 1H), 6.01 (sl, 2H), 4.91 (s, 2H), 4.84 (s, 2H), 4.0.4 (m, 1H), 3.25-2.88 (m, 28H), 1.69-1.55 (m, 6H), 1.48-1.20 (m, 37H), 0.87 (t, 3H).

Intermediate 53

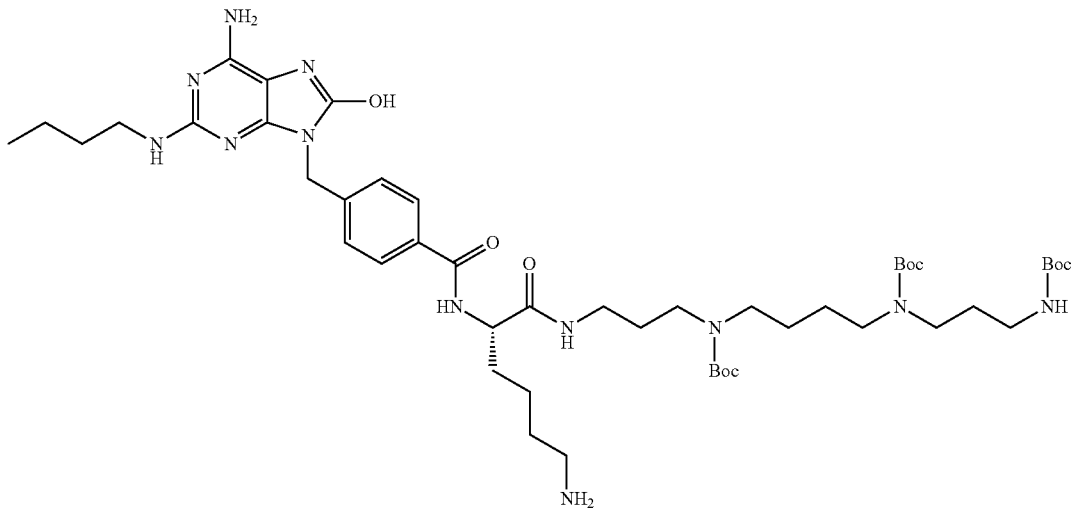

N1,N5,N10-triBoc-spermine (S)-2-(4-(6-amino-2-(butylamino)-8-hydroxy-9H-purin-9-yl) methyl)benzamido)acetamido)-6-amino)hexanamide: To a solution of intermediate 52 (1.06 g, 0.96 mmol) in a mixture of THF/MeOH (1/1) (30 mL) was added palladium on activated carbon 10% (0.05 eq). hydrogen gas was introduced via a balloon; the reaction mixture was stirred overnight at RT. The mixture was filtered through Celite and was washed with MeOH, the filtrate was concentrated in vacuo. The resulting solid was used for the next step without any further purification.

(13 mg, 0.12 mmol) and intermediate 21 (67 mg, 1.03 mmol). The mixture was stirred under reflux for 24H00. The solvent was then removed in vacuo, the residue was dissolved with DCM (20 mL) and was washed with water and brine. The organic layer was dried over $MgSO_4$ and concentrated in vacuo. The crude material was purified on column of silica gel (2% MeOH/DCM) to give the subject compound (140 mg, yield 88%). Intermediate 54 was characterized by the following spectroscopic data: $^1$H NMR Intermediate 54

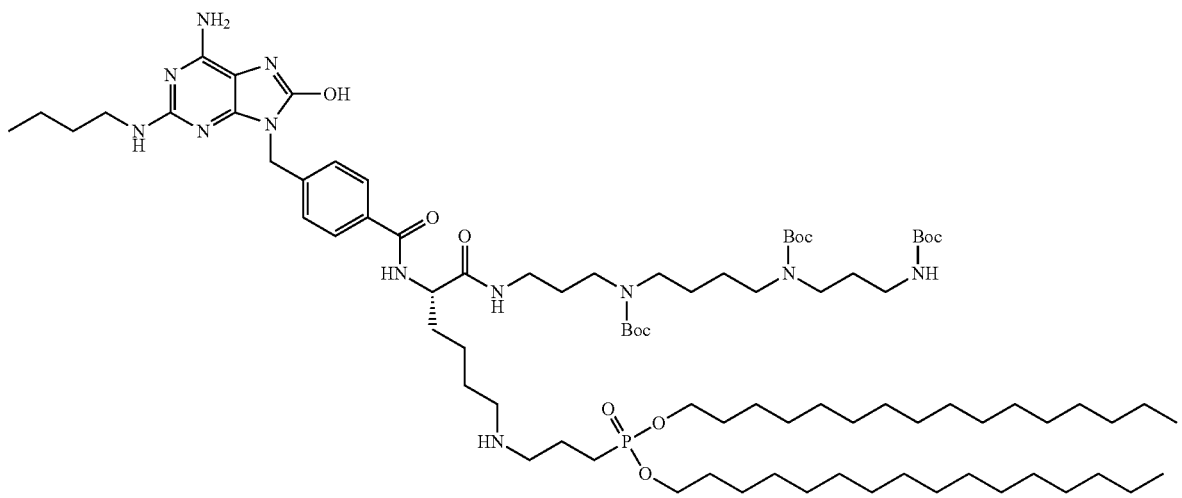

N1,N5,N10-triBoc-spermine (S)-2-(4-(6-amino-2-(butylamino)-8-hydroxy-9,1-purin-9-yl)methyl)benzamido)acetamido)-6-(1-aminopropyl-3-dihexadecylphosphonate) hexanamide: To a solution of intermediate 53 (100 mg, 0.103 mmol) in absolute EtOH (10 mL) was added $Na_2CO_3$ (DMSO-d6, 300 MHz) δ (ppm) 10.09 (s, 1H), 8.45 (m, 1H), 7.95 (m, 1H), 7.85 (d, 2H), 7.34 (d, 2H), 6.76 (m, 1H), 6.20 (sl, 2H), 4.84 (s, 2H), 4.33 (m, 1H), 3.89 (m, 2H), 3.08 (m, 16H), 2.88 (m, 6H), 1.72-1.55 (m, 12H), 1.35 (m, 51H), 1.23 (m, 42H), 0.85 (m, 9H).

Compound 55

CL488

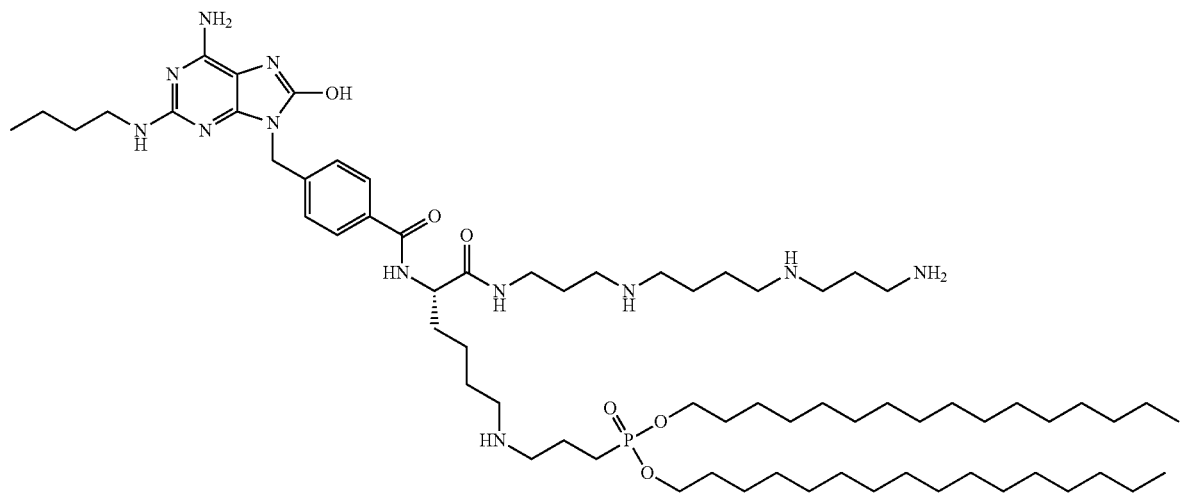

(S)-dihexadecyl 1-amino-15-(4-((6-amino-2-(butylamino)-8-hydroxy-9H-purin-9-yl) methyl)benzamido)-14-oxo-4,9,13,20-tetraazatricosan-23-ylphosphonate: To a solution of intermediate 54 (140 mg, 0.090 mmol) in dioxane (5 mL) was added 4N HCl solution in dioxane (15 mL). The mixture was stirred at RT overnight. Then the solvent were removed in vacuo, the residue was coevaporated 3 times with toluene. The residue was purified by flash chromatography on an ARMEN® system with C18 column eluting with a gradient of 0-10% MeCN in NH$_4$OAc (10 mM) solution (pH=9) to give the subject compound (100 mg, yield 73%). Compound 55 was characterized by the following spectroscopic data: $^1$H NMR (DMSO-d6, 300 MHz) δ (ppm) 10.40 (s, 1H), 9.25 (m, 1H), 9.24 (m, 1H), 9.05 (m, 2H), 8.89 (m, 1H), 8.21 (m, 1H), 8.04 (m, 1H), 7.90 (d, 2H), 7.34 (d, 2H), 6.44 (m, 2H), 6.17 (m, 1H), 4.85 (s, 2H), 4.50 (m, 1H), 4.33 (m, 2H), 4.15 (m, 2H), 3.96 (m, 2H), 3.80 (m, 6H), 3.70 (m, 2H), 3.62 (m, 2H), 3.16 (m, 2H), 3.04 (m, 6H), 2.91 (14H), 2.08 (m, 6H), 1.85-1.65 (m, 6H), 1.57 (m, 6H), 1.42 (m, 6H), 1.22 (m, 38H), 0.85 (m, 9H). MS (+)–ES [M+H]$^+$ 1239 m/z.

Example 12

Molecule CL494

Intermediate 56

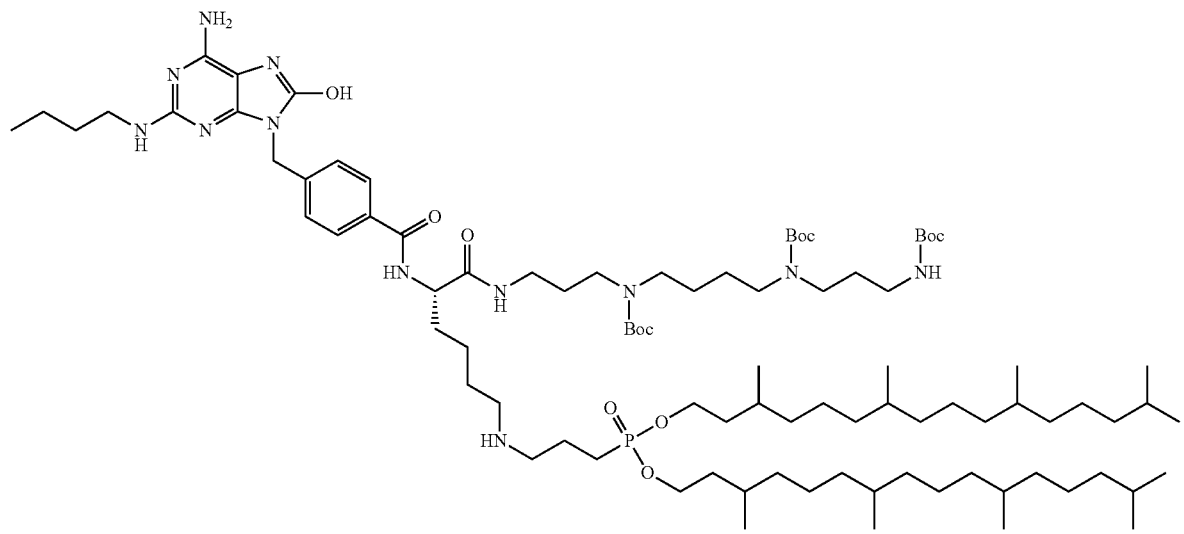

N1,N5,N10-triBoc-spermine (S)-2-(4-(6-amino-2-(butylamino)-8-hydroxy-9,1-purin-9-yl)methyl)benzamido)acetamido)-6-(1-aminopropyl bis(3,7,11,15-tetramethylhexadecyl) 3-phosphonate)hexanamide: To a solution of intermediate 53 (100 mg, 0.103 mmol) in absolute EtOH (10 mL) was added Na$_2$CO$_3$ (13 mg, 0.12 mmol) and intermediate 9 (79 mg, 0.103 mmol). The mixture was stirred under reflux for 18H00. The solvent was then removed in vacuo, the residue was dissolved with DCM (20 mL) and was washed with water and brine. The organic layer was dried over MgSO$_4$ and concentrated in vacuo. The crude material was purified on column of silica gel (2% MeOH/DCM) to give the subject compound (160 mg, yield 94%). Intermediate 56 was characterized by the following spectroscopic data: $^1$H NMR (DMSO-d6, 300 MHz) δ (ppm) 8.35 (s, 1H), 7.92 (m, 1H), 7.83 (d, 2H), 7.36 (d, 2H), 6.75 (m, 1H), 6.18 (m, 1H), 6.02 (sl, 2H), 4.85 (s, 2H), 4.33 (m, 1H), 3.92 (m, 4H), 3.16-3.10 (m, 16H), 2.88 (m, 6H), 1.94 (m, 10H), 1.65-1.05 (m, 86H), 0.78 (m, 33H).

Example 13

Molecule CL528

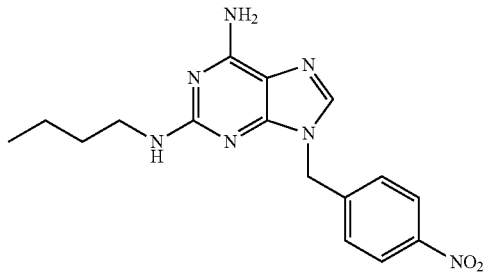

Intermediate 58

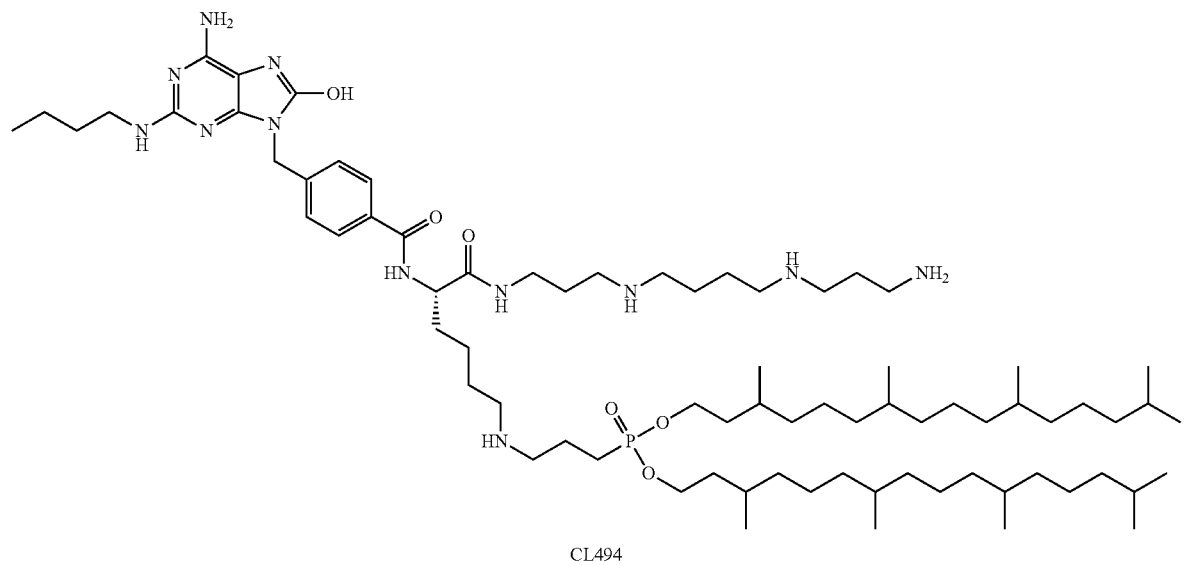

Compound 57

CL494

(S)-bis(3,7,11,15-tetramethylhexadecyl) 1-amino-15-(4-((6-amino-2-(butylamino)-8-hydroxy-9H-purin-9-yl)methyl)benzamido)-14-oxo-4,9,13,20-tetraazatricosan-23-ylphosphonate: To a solution of intermediate 56 (160 mg, 0.097 mmol) in dioxane (5 mL) was added 4N HCl solution in dioxane (15 mL). The mixture was stirred at RT overnight. Then the solvent were removed in vacuo, the residue was coevaporated 3 times with toluene. The residue was purified by flash chromatography on an ARMEN® system with C18 column eluting with a gradient of 0-10% MeCN in NH$_4$OAc (10 mM) solution (pH 9) to give the subject compound (111 mg, yield 78%). Compound 57 was characterized by the following spectroscopic data: $^1$H NMR (DMSO-d6, 300 MHz) δ (ppm) 10.32 (s, 1H), 9.41 (m, 2H), 9.27 (m, 2H), 8.54 (m, 4H), 8.28-8.19 (m, 4H), 7.98 (m, 2H), 7.89 (d, 2H), 7.34 (d, 2H), 4.87 (s, 2H), 4.33 (m, 1H), 3.96 (m, 2H), 3.73 (m, 4H), 3.67 (m, 2H), 3.14 (m, 6H), 3.06 (m, 2H), 2.55 (m, 10H), 2.00 (m, 4H), 1.98-1.23 (m, 64H), 0.84 (m, 33H). MS (+)–ES [M+H]$^+$1353 m/z.

N2-butyl-9-(4-nitrobenzyl)-9H-purine-2,6-diamine: 6-amino-2-butylamino-9H-purine (9.93 g, 48.2 mmol) and Cs$_2$CO$_3$ (15.69 g, 48.2 mmol) were suspended in DMF (200 ml). 4-nitrobenzyl bromide (12.48 mg, 57.8 mmol) was added thereto and the mixture was stirred at room temperature for 18 hours. After condensing the suspension in vacuo, to the residue was added brine and the mixture was extracted with ethyl acetate. The organic layer was washed the mixture was with brine, dried on MgSO$_4$, filtered and the solvent was evaporated in vacuo. The residue was purified on column of silica gel (5% MeOH/DCM) to give the subject compound (11.51 g, yield 70%). Intermediate 58 was characterized by the following spectroscopic data: $^1$H NMR (DMSO-d6, 300 MHz) δ (ppm) 8.19 (d, 2H), 7.83 (s, 1H), 7.49 (d, 2H), 6.69 (sl, 2H), 6.25 (t, 1H), 5.34 (s, 2H), 3.17 (m, 2H), 1.41 (m, 2H), 1.25 (q, 2H), 0.83 (t, 3H).

Intermediate 59

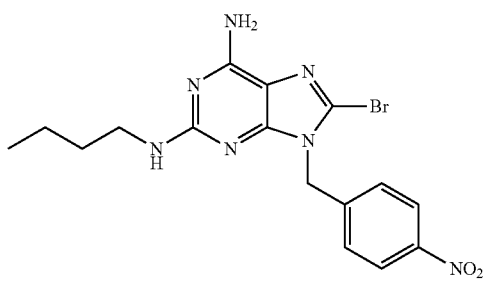

8-bromo-N2-butyl-9-(4-nitrobenzyl)-9H-purine-2,6-diamine: N2-butyl-9-(4-nitrobenzyl)-9H-purine-2,6-diamine (11.50 g, 33.7 mmol) and bromine (12.93 mL, 80.92 mmol) were dissolved in 200 ml of CHCl₃ and the solution was stirred at room temperature for 18 hours. Aqueous Na₂S₂O₃ was added to the reaction mixture. The precipitate obtained was filtered off and washed with water and DCM. The solid was purified on column of silica gel (3% MeOH/DCM) to give the subject compound (14.17 g, yield 100%). Intermediate 59 was characterized by the following spectroscopic data: ¹H NMR (DMSO-d6, 300 MHz) δ (ppm) 8.21 (d, 2H), 7.51 (d, 2H), 5.39 (s, 2H), 3.15 (m, 2H), 1.44 (m, 2H), 1.27 (q, 2H), 0.82 (t, 3H).

Intermediate 60

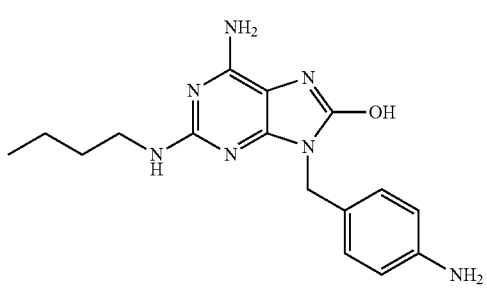

6-amino-2-(butylamino)-9-(4-nitrobenzyl)-9H-purin-8-ol: To 8-bromo-N2-butyl-9-(4-nitrobenzyl)-9H-purine-2,6-diamine (14.17 g, 33.72 mmol) in 150 ml of dioxane was added 100 mL of HCl 37% solution. The mixture was refluxed on heating under stirring for 18 hours. The mixture was concentrated in vacuo and the pH was adjusted to 5 with 2N aqueous NaOH to precipitate a solid. The solid was filtered, washed with water and dried in vacuo in presence of P₂O₅ to give the subject compound (11.05 g, yield 90%). Intermediate 60 was characterized by the following spectroscopic data: ¹H NMR (DMSO-d6, 300 MHz) δ (ppm) 10.35 (sl, 1H), 8.19 (d, 2H), 7.53 (d, 2H), 7.23 (sl, 2H), 4.98 (s, 2H), 3.19 (m, 2H), 1.41 (m, 2H), 1.24 (q, 2H), 0.80 (t, 3H).

Intermediate 61

6-amino-9-(4-aminobenzyl)-2-(butylamino)-9H-purin-8-ol: To a solution of 6-amino-2-(butylamino)-9-(4-nitrobenzyl)-9H-purin-8-ol (11.05 g, 30.9 mmol) in a mixture of THF/MeOH (1/1) (200 mL) was added Pd/C (1.79 g, 1.6 mmol), the reaction mixture was stirred at RT under hydrogen atmosphere for 18 hours. Then the mixture was filtered off over Celite, washed with MeOH. The filtrate was concentrated in vacuo and the residue was purified on column of silica gel with DCM/MeOH (0-7%) as eluent to give the subject compound (7.52 g, yield 74%). Intermediate 61 was characterized by the following spectroscopic data: ¹H NMR (DMSO-d6, 300 MHz) δ (ppm) 10.02 (sl, 1H), 7.07 (d, 2H), 6.87 (sl, 2H), 6.77 (sl, 2H), 6.58 (d, 2H), 4.65 (s, 2H), 3.23 (m, 2H), 1.49 (m, 2H), 1.33 (q, 2H), 0.92 (t, 3H).

Intermediate 62

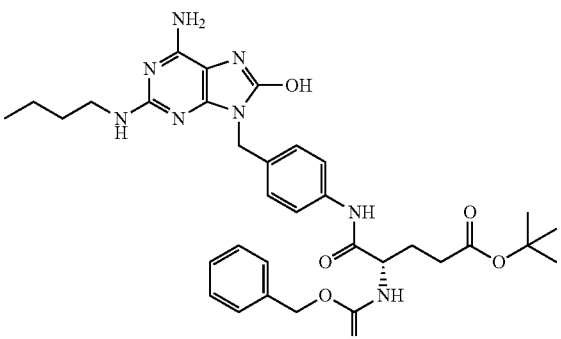

(S)-tert-butyl 5-(4-((6-amino-2-(butylamino)-8-hydroxy-9H-purin-9-yl)methyl)phenyl amino)-4-(benzyloxycarbonylamino)-5-oxopentanoate To a solution of Z-L-Glu(OtBu)OH (2.06 g, 6.1 mmol) in dry DMF (50 mL) was added intermediate 61 (2.0 g, 6.1 mmol), HATU (2.55 g, 6.72 mmol), and DIEA (5.23 mL, 30.5 mmol). The mixture was stirred at RT overnight. The solvent was then removed in vacuo and the residue was dissolved in EtOAc (50 mL) and washed with saturated NaHCO₃ solution water and brine. The organic layer was dried over MgSO₄, filtered and concentrated in vacuo. The crude compound was purified on column of silica gel (3% MeOH/DCM) to give the subject compound (3.12 g, yield 79%). Intermediate 62 was characterized by the following spectroscopic data: ¹H NMR (DMSO-d6, 300 MHz) δ (ppm) 9.62 (sl, 1H), 8.76 (d, 1H), 8.53 (d, 1H), 7.52 (d, 2H), 7.34 (s, 5H), 7.23 (d, 2H), 6.22 (t, 1H), 6.01 (sl, 2H), 5.02 (s, 2H), 4.74 (s, 2H), 4.12 (m, 1H), 3.15 (m, 2H), 2.26 (m, 2H), 2.08-1.79 (m, 2H), 1.44 (m, 2H), 1.42 (s, 9H), 1.35 (m, 2H), 0.89 (t, 3H).

Intermediate 63

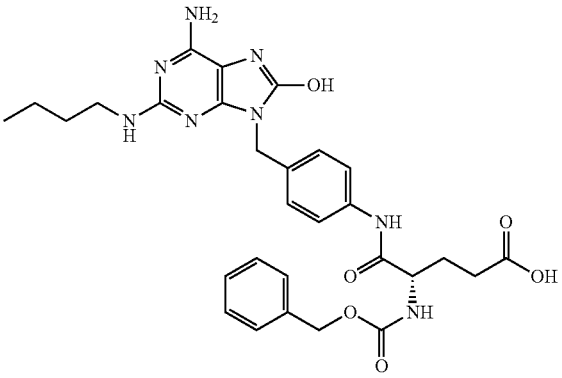

(S)-5-(4-((6-amino-2-(butylamino)-8-hydroxy-9H-purin-9-yl)methyl)phenylamino)-4-(benzyloxycarbonylamino)-5-oxopentanoic acid: To a solution of intermediate 62 (3.12 g, 2.13 mmol) in DMF (40 mL) was added 40 mL of TFA. The mixture was stirred at RT overnight. Then the solvent were removed in vacuo, the residue was coevaporated 3 times with toluene. The residue was precipitated in diethyl ether to give the subject compound (2.33 g, yield 82%). Intermediate 63 was characterized by the following spectroscopic data: $^1$H NMR (DMSO-d6, 300 MHz) δ (ppm) 10.62 (sl, 1H), 10.10 (sl, 1H), 7.82 (sl, 2H), 7.64 (d, 1H), 7.54 (d, 2H), 7.36 (s, 5H), 7.27 (m, 3H), 5.02 (s, 2H), 4.79 (s, 2H), 4.12 (m, 1H), 3.29 (m, 2H), 2.26 (m, 2H), 1.93-1.79 (m, 2H), 1.50 (m, 2H), 1.32 (m, 2H), 0.85 (t, 3H).

Intermediate 64

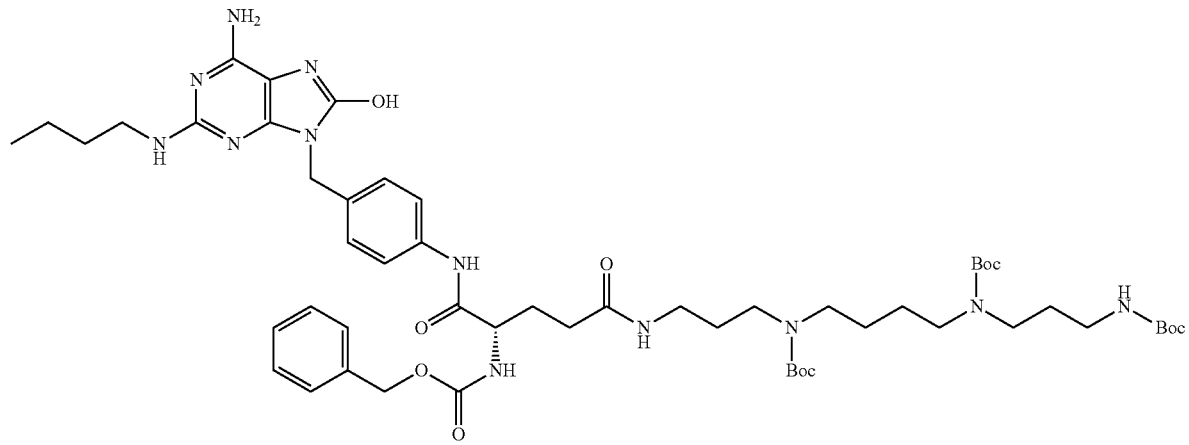

N1,N5,N10-triBoc-spermine (S)-5-(4-((6-amino-2-(butylamino)-8-hydroxy-9H-purin-9-yl)methyl)phenylamino)-4-(benzyloxycarbonylamino)-5-oxopentanamide:

To a solution of intermediate 63 (2.33 g, 3.9 mmol) in dry DMF (50 mL) was added intermediate 5 (1.93 g, 3.9 mmol), HATU (1.65 g, 4.3 mmol), and DIEA (3.44 mL, 19.7 mmol). The mixture was stirred at RT overnight. The solvent was then removed in vacuo and the residue was dissolved in EtOAc (100 mL) and washed with saturated NaHCO$_3$ solution water and brine. The organic layer was dried over MgSO$_4$, filtered and concentrated in vacuo. The crude compound was purified on column of silica gel (2% MeOH/DCM) to give the subject compound (3.74 g, yield 88%). Intermediate 64 was characterized by the following spectroscopic data: $^1$H NMR (DMSO-d6, 300 MHz) δ (ppm) 10.32 (s, 1H), 9.61 (m, 1H), 7.79 (m, 1H), 7.56 (m, 1H), 7.52 (d, 2H), 7.34 (m, 5H), 7.25 (d, 2H), 6.76 (m, 1H), 6.23 (t, 1H), 6.02 (sl, 2H), 5.01m, 2H), 4.74 (s, 2H), 4.10 (s, 2H), 3.34-3.07 (m, 14H), 2.89 (m, 2H), 1.56 (m, 4H), 1.48-1.20 (m, 33H), 0.83 (t, 3H).

Intermediate 65

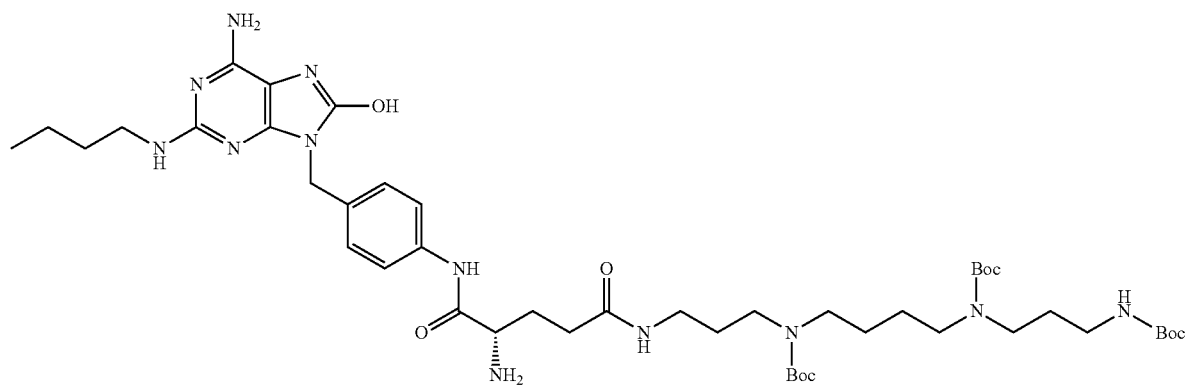

N1,N5,N10-triBoc-spermine (S)-5-(4-((6-amino-2-(butylamino)-8-hydroxy-9H-purin-9-yl)methyl)phenylamino)-4-amino-5-oxopentanamide: To a solution of intermediate 64 (3.74 g, 3.5 mmol) in a mixture of THF/MeOH (1/1) (40 mL) was added palladium on activated carbon 10% (0.05 eq). hydrogen gas was introduced via a balloon; the reaction mixture was stirred overnight at RT. The mixture was filtered through Celite and was washed with MeOH, the filtrate was concentrated in vacuo. The resulting solid was used for the next step without any further purification.

Intermediate 66

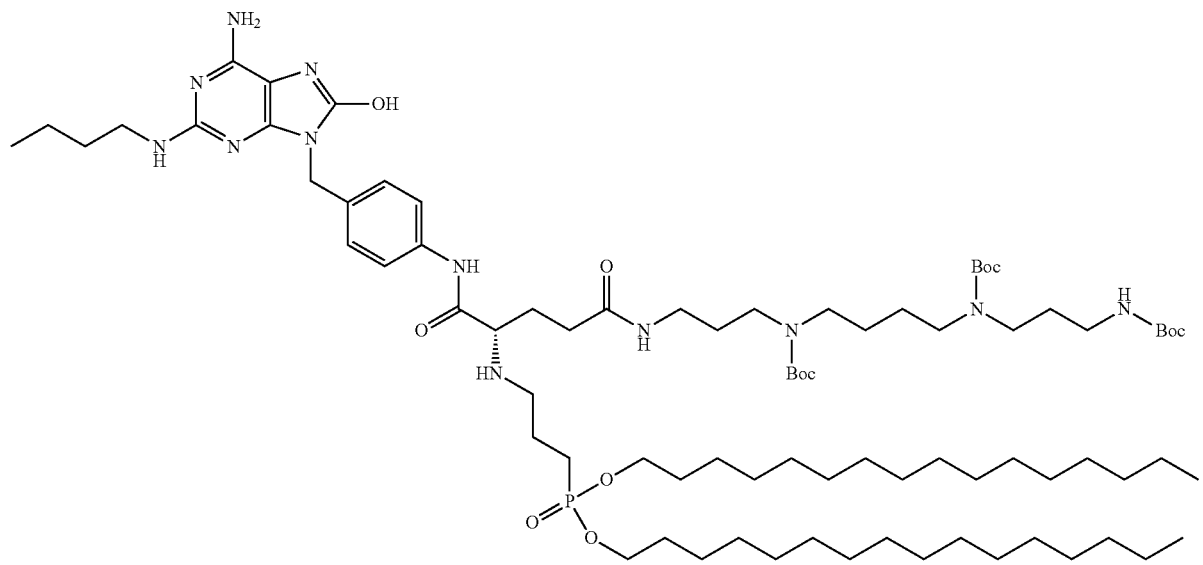

N1,N5,N10-triBoc-spermine (S)-5-(4-((6-amino-2-(butylamino)-8-hydroxy-9H-purin-9-yl)methyl)phenylamino)-4-(1-aminopropyl-3-dihexadecylphosphonate)-5-oxo-pentanamide:

To a solution of intermediate 65 (118 mg, 0.125 mmol) in dry DMF (7 mL) was added $Cs_2CO_3$ (28 mg, 0.087 mmol) and intermediate 21 (82 mg, 0.125 mmol). The mixture was stirred at 50° C. for 24H00. The solvent was then removed in vacuo; the residue was dissolved with EtOAc (20 mL) and was washed with water and brine. The organic layer was dried over $MgSO_4$ and concentrated in vacuo. The crude material was purified on column of silica gel (2% MeOH/DCM) to give the subject compound (56 mg, yield 30%). Intermediate 66 was characterized by the following spectroscopic data: $^1$H NMR (DMSO-d6, 300 MHz) δ (ppm) 8.82 (s, 1H), 8.13 (d, 1H), 7.83 (m, 1H), 7.54 (d, 2H), 7.24 (d, 2H), 6.77 (m, 1H), 6.25 (t, 1H), 6.15 (sl, 2H), 4.78 (s, 2H), 3.85 (m, 5H), 3.16-2.88 (m, 16H), 2.86 (m, 4H), 1.65-1.55 (m, 4H), 1.36 (m, 50H), 1.23 (m, 44H), 0.85 (m, 9H).

Compound 67

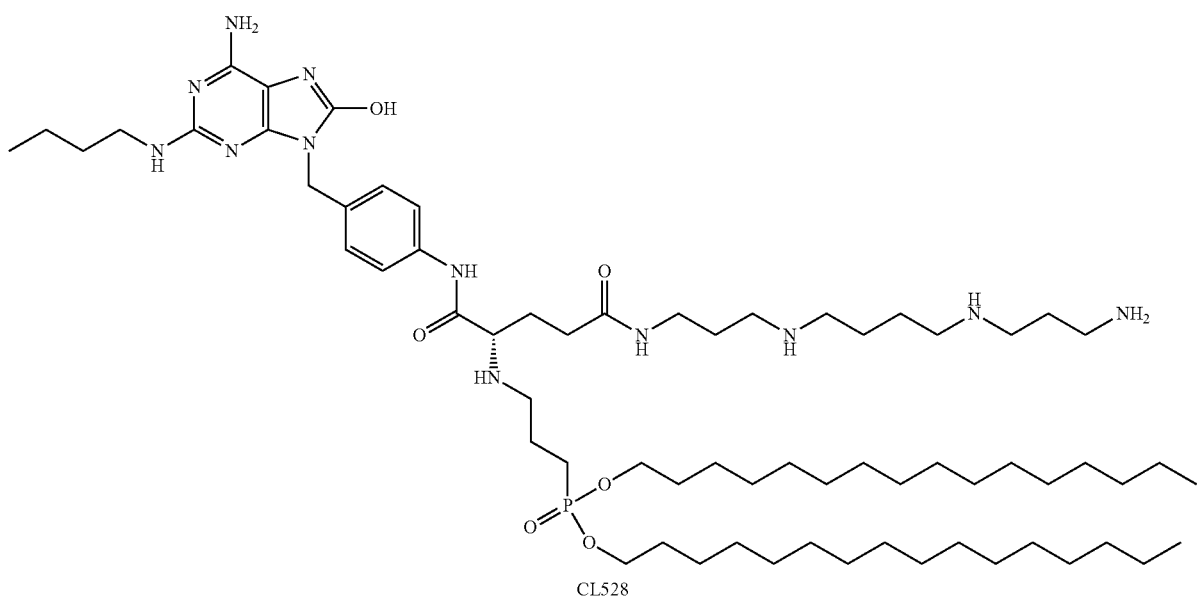

CL528

(S)-dihexadecyl 21-amino-5-(4-((6-amino-2-(butylamino)-8-hydroxy-9H-purin-9-yl) methyl)phenylcarbamoyl)-8-oxo-4,9,13,18-tetraazahenicosylphosphonate: To a solution of intermediate 66 (56 mg, 0.037 mmol) in dioxane (5 mL) was added 4N HCl solution in dioxane (15 mL). The mixture was stirred at RT overnight. Then the solvent were removed in vacuo, the residue was coevaporated 3 times with toluene. The residue was purified by flash chromatography on an ARMEN® system with C18 column eluting with a gradient of 0-10% MeCN in NH$_4$OAc (10 mM) solution (pH 9) to give the subject compound (49 mg, yield 99%). Compound 67 was characterized by the following spectroscopic data: $^1$H NMR (DMSO-d6, 300 MHz) δ (ppm) 10.93 (s, 1H), 9.18 (m, 1H), 8.95 (m, 1H), 8.44 (m, 4H), 8.08 (m, 2H), 7.60 (d, 2H), 7.29 (d, 2H), 4.84 (s, 2H), 3.88 (m, 8H), 3.18 (m, 2H), 2.88 (m, 14H), 2.08 (m, 2H), 1.98 (m, 4H), 1.75 (m, 10H), 1.54 (m, 6H), 1.43-1.22 (m, 53H), 0.85 (m, 9H). MS (+)–ES [M+H]$^+$1297 m/z.

Example 14

Molecule CL529

Intermediate 68

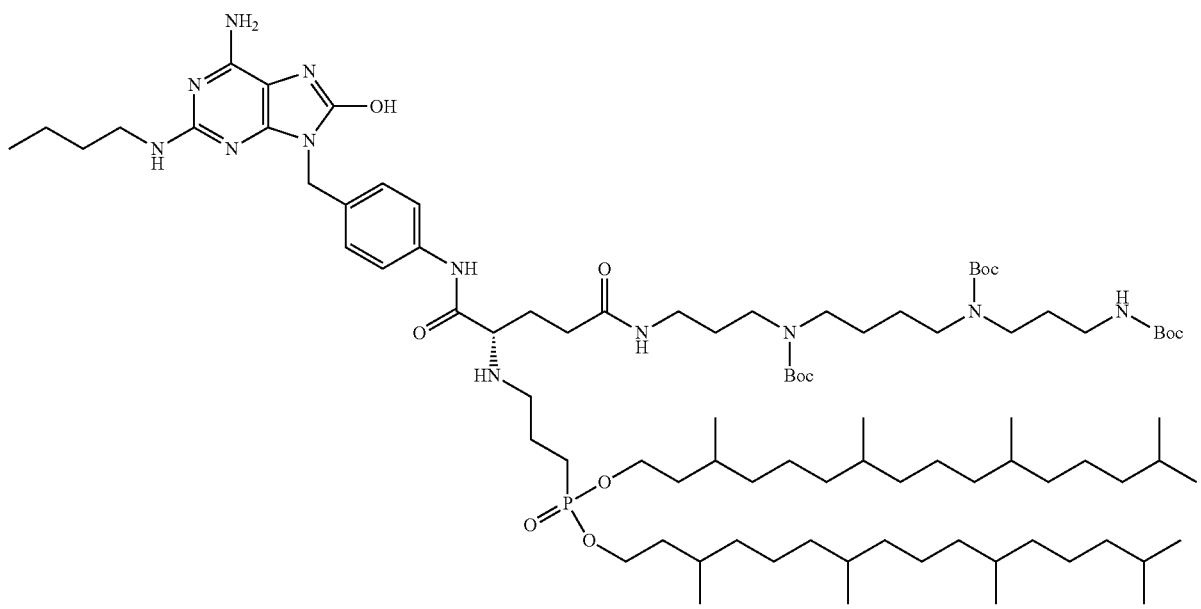

N1,N5,N10-triBoc-spermine (S)-5-(4-((6-amino-2-(butylamino)-8-hydroxy-9H-purin-9-yl)methyl)phenylamino)-4-(1-aminopropyl bis(3,7,11,15-tetramethylhexadecyl) 3-phosphonate)-5-oxo-pentanamide: To a solution of intermediate 65 (140 mg, 0.149 mmol) in dry DMF (5 mL) was added Cs₂CO₃ (34 mg, 0.104 mmol) and intermediate 9 (114 mg, 0.149 mmol). The mixture was stirred at 50° C. for 36H00. The solvent was then removed in vacuo; the residue was dissolved with EtOAc (20 mL) and was washed with water and brine. The organic layer was dried over MgSO₄ and concentrated in vacuo. The crude material was purified on column of silica gel (2% MeOH/DCM) to give the subject compound (49 mg, yield 20%). Intermediate 68 was characterized by the following spectroscopic data: ¹H NMR (DMSO-d6, 300 MHz) δ (ppm) 7.82 (m, 1H), 7.55 (d, 2H), 7.22 (d, 2H), 6.75 (m, 1H), 6.23 (m, 1H), 6.14 (sl, 2H), 4.78 (s, 2H), 3.90 (m, 6H), 3.18-2.88 (m, 14H), 2.86 (m, 3H), 1.70 (m, 6H), 1.53 (m, 13H), 1.35 (m, 43H), 1.23-1.02 (m, 32H), 0.82 (m, 33H).

Example 15

Molecule CL397

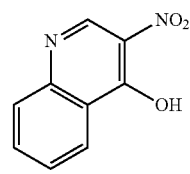

Intermediate 70

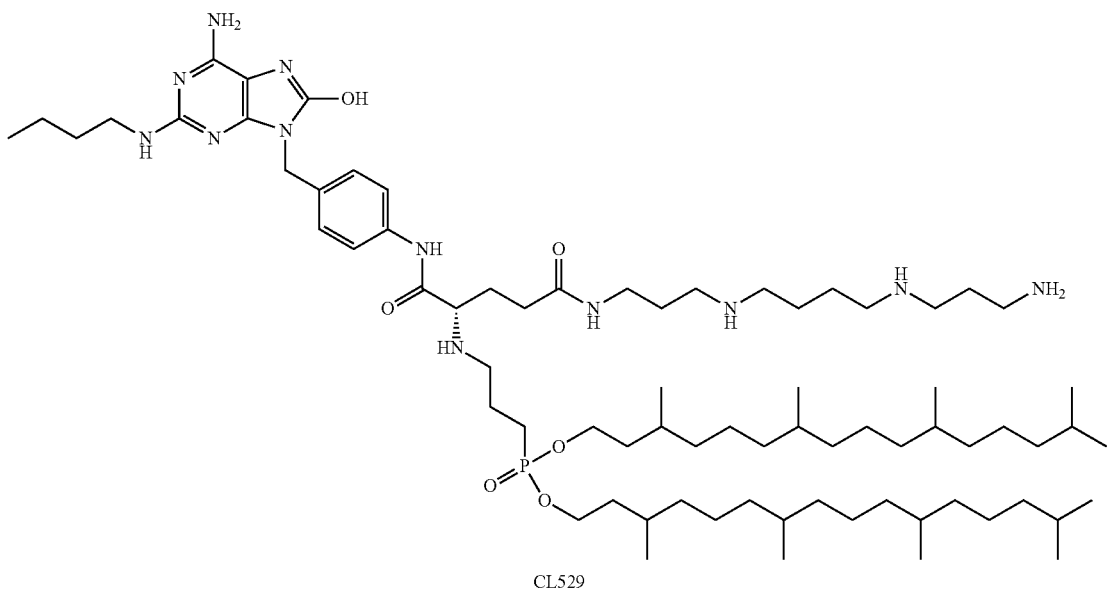

Compound 69

CL529 bis(3,7,11,15-tetramethylhexadecyl)-(S)-21-amino-5-(4-((6-amino-2-(butylamino)-8-hydroxy-9H-purin-9-yl)methyl)phenylcarbamoyl)-8-oxo-4,9,13,18-tetraazahenicosyl phosphonate: To a solution of intermediate 68 (49 mg, 0.097 mmol) in dioxane (5 mL) was added 4N HCl solution in dioxane (15 mL). The mixture was stirred at RT overnight. Then the solvent were removed in vacuo, the residue was coevaporated 3 times with toluene. The residue was purified by flash chromatography on an ARMEN® system with C18 column eluting with a gradient of 0-10% MeCN in NH₄OAc (10 mM) solution (pH 9) to give the subject compound (42 mg, yield 100%). Compound 69 was characterized by the following spectroscopic data: ¹H NMR (DMSO-d6, 300 MHz) δ (ppm) 10.94 (s, 1H), 9.18 (m, 2H), 8.95 (m, 2H), 8.44 (m, 2H), 8.25 (m, 2H), 8.08 (m, 2H), 7.61 (d, 2H), 7.29 (d, 2H), 4.84 (s, 2H), 4.84 (m, 2H), 3.94 (m, 8H), 3.09 (m, 2H), 2.88 (m, 12H), 2.26 (m, 4H), 2.08-1.13 (m, 64H), 0.85 (m, 33H). MS (+)–ES [M+H]⁺1324 m/z.

3-nitroquinolin-4-ol: 4-Hydroxyquinoline (20.0 g, 138 mmol) was added to propionic acid (150 mL) and the solution was heated to about 125° C. Nitric acid (6.85 mL, 165 mmol) was added dropwise with stirring. When the addition was complete, the mixture was stirred at about 125° C. overnight. Then the mixture was cooled to room temperature and was poured on ice. The precipitated solid was filtered, washed sequentially with water, EtOH and Et₂O, and dried to afford 3-nitro-4-hydroxyquinoline (18.7 g, yield 71%) as a light yellow powder.

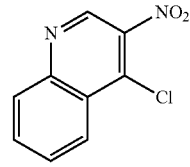

Compound 71

4-chloro-3-nitroquinoline: The Intermediate 3-nitro-4-hydroxyquinoline 70 (18.7 g, 98.4 mmol) was suspended in dichloromethane (150 mL). Thionyl chloride (17.2 mL, 236 mmol) and N,N-dimethylformamide (9.2 mL, 118 mmol)

were added. The reaction mixture was then heated at reflux overnight. The reaction mixture was then poured in ice. The layers were separated and the organic layer was washed with NaHCO₃ solution, water and brine. The organic layer was dried over Na₂SO₄, filtered and concentrated in vacuo. The residue (20.52 g, yield 93%) was used for the next step without any further purification.

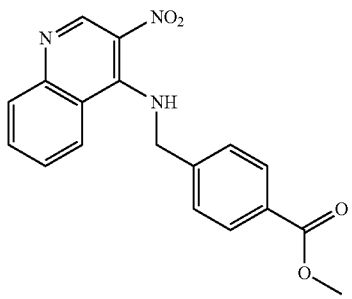

Intermediate 72

Methyl 4-((3-nitroquinolin-4-ylamino)methyl)benzoate: To a solution of intermediate 71 (5.94 g, 28.48 mmol) in dry DCM (50 mL) was added a solution of methyl 4-(aminomethyl)benzoate (5.05 g, 29.91 mmol), and triethylamine (19.9 mL, 142 mmol) in dichloromethane (50 mL) at 0° C. During the addition the temperature of the reaction mixture rose to 20° C. The resulting solution was heated at reflux overnight. Then the reaction mixture was cooled to RT and the solvent was removed at reduced pressure to afford a yellow solid product. The product was slurried in water, filtered, washed with water, and dried partially. The partially dried product was then slurried in ethanol (75 mL), filtered, washed successively with a small amount of ethanol and a small amount of diethyl ether, and dried at reduced pressure to afford the subject compound (8.31 g, yield 86%). Intermediate 72 was characterized by the following spectroscopic data: ¹H NMR (DMSO-d6, 300 MHz) δ (ppm) 9.51 (t, 1H), 9.01 (s, 1H), 8.47 (d, 1H), 7.92 (m, 3H), 7.85 (m, 1H), 7.56 (m, 1H), 7.49 (d, 2H), 4.96 (s, 2H), 3.84 (s, 3H).

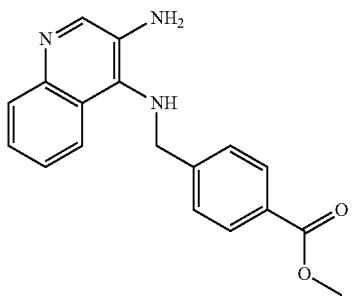

Intermediate 73

Methyl 4-((3-aminoquinolin-4-ylamino)methyl)benzoate: To a solution of intermediate 72 (8.31 g, 24.6 mmol) in a mixture of THF/MeOH (1/1) (140 mL) was added palladium on activated carbon 10% (0.05 eq). The reaction mixture was stirred under hydrogen (1 atm) overnight. The palladium was filtered off the filtrate was concentrated in vacuo. The crude mixture was purified on column of silica gel (5% MeOH/DCM) to give the subject compound (3.89 g, yield 52%). Intermediate 73 was characterized by the following spectroscopic data: ¹H NMR (DMSO-d6, 300 MHz) δ (ppm) 8.38 (s, 1H), 7.95 (m, 1H), 7.86 (d, 2H), 7.71 (m, 1H), 7.51 (d, 2H), 7.31 (m, 2H), 5.55 (t, 1H), 5.07 (s, 2H), 4.45 (s, 2H), 3.83 (s, 3H).

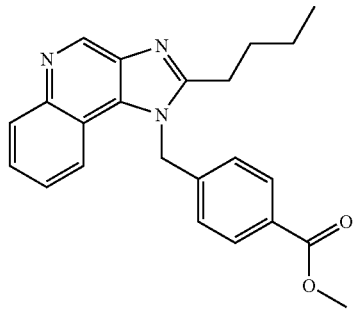

Intermediate 74

Methyl 4-((2-butyl-1H-imidazo[4,5-c]quinolin-1-yl) methyl)benzoate: The intermediate 73 (3.89 g, 12.7 mmol) and valeric acid (15 ml, 13.6 mmol) were stirred at 130° C. under argon atmosphere overnight. The mixture was cooled and was diluted with water and NH₄OH solution (50 mL). The solution was extracted 3 times with EtOAc. The organic layer was washed with NaHCO3 solution water and brine, dried over MgSO4, filtered and concentrated in vacuo. The crude material was purified on column of silica gel (4% MeOH/DCM) to give the subject compound (3.99 g, yield 84%). Intermediate 74 was characterized by the following spectroscopic data: ¹H NMR (DMSO-d6, 300 MHz) δ (ppm) 9.24 (s, 1H), 8.21 (d, 1H), 8.14 (d, 1H), 7.93 (d, 2H), 7.65 (m, 1H), 7.51 (m, 1H), 7.19 (d, 2H), 6.10 (s, 2H), 3.82 (s, 3H), 2.99 (t, 2H), 1.76 (m, 2H), 1.44 (m, 2H), 0.93 (t, 3H).

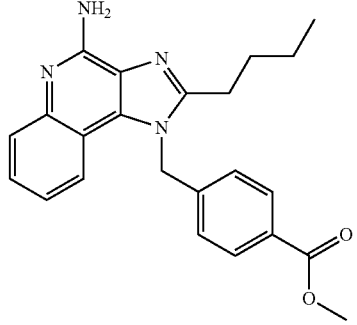

Intermediate 75

Methyl 4-((4-amino-2-butyl-1H-imidazo[4,5-c]quinolin-1-yl)methyl)benzoate: The intermediate 74 (3.99 g, 10.7 mmol) was dissolved in chloroform (100 mL). meta-chloroperoxybenzoic acid (mCPBA) (3.95 g, 16.03 mmol) was added and the solution was heated at reflux overnight. The solution was then cooled and the solvents were removed at reduced pressure. The residue was then dissolved in dichloromethane (10 mL) and NH4OH 20% solution (10 mL) was added to the stirred solution. The reaction mixture was refluxed overnight. A crystalline solid formed and was filtered from the mixture, washed with dichloromethane and hexane and dried to give the subject compound (2.83 g, yield 68%). Intermediate 75 was characterized by the following spectroscopic data: ¹H NMR (DMSO-d6, 300 MHz) δ (ppm) 7.91 (d, 2H), 7.71 (d, 1H), 7.57 (d, 1H), 7.32 (m, 1H), 7.15 (d, 2H), 7.00 (m, 1H), 6.52 (sl, 2H), 5.94 (s, 2H), 3.81 (s, 3H), 2.89 (t, 2H), 1.67 (m, 2H), 1.36 (m, 2H), 0.88 (t, 3H).

Intermediate 76

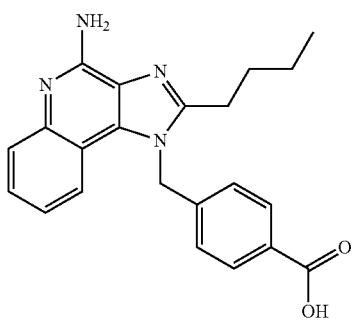

4-((4-amino-2-butyl-1H-imidazo[4,5-c]quinolin-1-yl)methyl)benzoic acid: To a solution of intermediate 75 (2.83 g, 7.29 mmol) in dioxane (30 mL) was added 1N LiOH solution until pH=10. The mixture was stirred at RT overnight. The mixture was neutralized with 1M HCl solution (pH 6). The precipitate was filtered off, washed with water, EtOH and Et$_2$O to give the subject compound (2.0 g, yield 73%), which was used for the next step without any further purification.

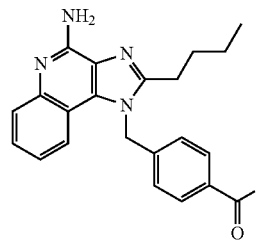

CL397

Bis(3,7,11,15-tetramethylhexadecyl) 1-(4-((4-amino-2-butyl-1H-imidazo[4,5-c]quinolin-1-yl)methyl)phenyl)-1-oxo-2,6,11,15-tetraazaoctadecan-18-ylphosphonate: To a solution of intermediate 76 (50 mg, 0.13 mmol) in dry DMF (5 mL) was added HATU (55 mg, 0.15 mmol), intermediate 11 (179 mg, 0.13 mmol) and NMM (146 µL, 1.33 mmol). The mixture was stirred at RT overnight. The solvent was removed in vacuo and the residue was directly applied to a column of silica gel (iPrOH/NH$_4$OH/H$_2$O 85/10/5) to give the subject compound (55 mg, yield 33%). Compound 77 was characterized by the following spectroscopic data: $^1$H NMR (DMSO-d6, 300 MHz) δ (ppm) 7.89 (d, 2H), 7.67 (m, 3H), 7.15 (d, 2H), 7.00 (m, 1H), 5.94 (s, 2H), 3.97 (m, 4H), 3.16-2.83 (m, 12H), 2.27 (m, 2H), 2.08 (m, 2H), 1.86 (m, 6H), 1.73 (m, 5H), 1.57 (m, 6H), 1.38-1.04 (m, 50H), 0.85 (m, 33H). MS (+)–ES [M+H]$^+$1243 m/z.

Example 16
Molecule CL545

Intermediate 78

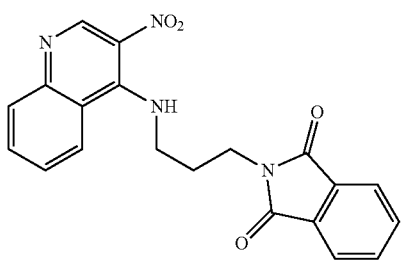

2-(3-(3-nitroquinolin-4-ylamino)propyl)isoindoline-1,3-dione: To a solution of intermediate 71 (2.00 g, 10 mmol) in dry DCM (25 mL) was added a solution of 3-phthalimido propylamine (2.44 g, 12 mmol), and triethylamine (6.69 mL, 47.9 mmol) in dichloromethane (25 mL) at 0° C. The resulting solution was heated at reflux overnight. Then the reaction mixture was cooled to RT and the solvent was removed at reduced pressure to afford a yellow solid product. The product was slurried in water, filtered, washed with water, and dried partially. The partially dried product was then slurried in ethanol (75 mL), filtered, washed successively with a small amount of ethanol and a small amount of diethyl ether, and dried at reduced pressure to afford the subject compound (3.55 g, yield 98%). Intermediate 78 was characterized by the following spectroscopic data: $^1$H NMR (DMSO-d6, 300 MHz) δ (ppm) 8.99 (s, 1H), 8.85 (t, 1H), 8.45 (d, 1H), 7.92 (d, 1H), 7.77 (m, 5H), 7.55 (m, 1H), 3.65 (m, 4H), 2.09 (t, 2H).

Compound 77

Intermediate 79

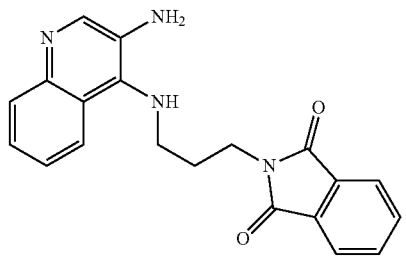

2-(3-(3-aminoquinolin-4-ylamino)propyl)isoindoline-1,3-dione: To a solution of intermediate 78 (3.55 g, 9.43 mmol) in a mixture of THF/MeOH (1/1) (100 mL) was added palladium on activated carbon 10% (0.05 eq). The reaction mixture was stirred under hydrogen (1 atm) overnight. The palladium was filtered off the filtrate was concentrated in vacuo. The crude mixture was purified on column of silica gel (5% MeOH/DCM) to give the subject compound (2.00 g, yield 61%). Intermediate 79 was characterized by the following spectroscopic data: $^1$H NMR (DMSO-d6, 300 MHz) δ (ppm) 8.42 (s, 1H), 8.05 (m, 1H), 7.85 (m, 4H), 7.73 (m, 1H), 7.32 (m, 2H), 5.02 (sl, 2H), 3.66 (m, 4H), 1.86 (m, 2H).

Intermediate 80

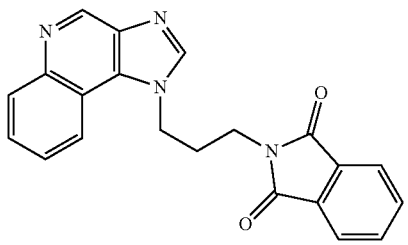

2-(3-(1H-imidazo[4,5-c]quinolin-1-yl)propyl)isoindoline-1,3-dione: The intermediate 79 (510 mg, 1.44 mole) was dissolved in triethyl orthoformate (15 mL). The solution was heated at 140° C. for 20 hours. The reaction mixture was allowed to cool to ambient temperature then the reaction mixture was concentrated under vacuum. The residue was directly applied to a column of silica gel (6% MeOH/DCM) to give the subject compound (455 mg, yield 88%). Intermediate 80 was characterized by the following spectroscopic data: $^1$H NMR (DMSO-d6, 300 MHz) δ (ppm) 8.81 (s, 1H), 8.22 (m, 1H), 7.98 (m, 1H), 7.92 (s, 1H), 7.88 (m, 4H), 7.78 (m, 1H), 7.60 (m, 1H), 4.55 (m, 2H), 4.05 (m, 2H), 2.65 (m, 2H).

Intermediate 81

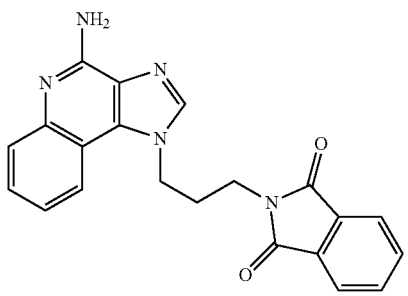

2-(3-(4-amino-1H-imidazo[4,5-c]quinolin-1-yl)propyl)isoindoline-1,3-dione: The intermediate 79 (455 mg, 1.27 mmol) was dissolved in chloroform (5 mL). meta-chloroperoxybenzoic acid (mCPBA) (327 mg, 1.91 mmol) was added and the solution was heated at reflux overnight. The solution was then cooled and the solvents were removed at reduced pressure. The residue was then dissolved in dichloromethane (10 mL) and NH4OH 20% solution (10 mL) was added to the stirred solution. The reaction mixture was refluxed overnight. A crystalline solid formed and was filtered from the mixture, washed with dichloromethane and hexane and dried to give the subject compound (419 mg, yield 89%). Intermediate 81 was characterized by the following spectroscopic data: $^1$H NMR (DMSO-d6, 300 MHz) δ (ppm) 8.10 (m, 1H), 7.95 (s, 1H), 7.86 (m, 4H), 7.75 (m, 1H), 7.69 (m, 1H), 7.37 (m, 1H), 6.96 (sl, 2H), 4.58 (m, 2H), 4.08 (m, 2H), 2.63 (m, 2H).

Intermediate 82

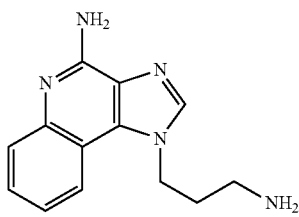

1-(3-aminopropyl)-1H-imidazo[4,5-c]quinolin-4-amine: To a solution of intermediate 81 (419 mg, 1.13 mmol) in absolute EtOH (10 mL) was added hydrazine monohydrate (109 µL, 2.26 mmol). The reaction mixture was warmed to 90° C. and was stirred at this temperature overnight. Then, the solution was cooled to 0° C. and a solution of HCl 37% (200 µL) was added dropwise and the mixture was stirred for 2H00 at 90° C. Then the mixture was cooled to RT, the solvents were removed in vacuo and the crude mixture was purified on column of silica gel (15% MeOH/DCM) to give the subject compound (212 mg, yield 78%). Intermediate 82 was characterized by the following spectroscopic data: $^1$H NMR (DMSO-d6, 300 MHz) δ (ppm) 8.12 (m, 1H), 7.92 (s, 1H), 7.66 (d, 1H), 7.55 (m, 1H), 7.28 (m, 1H), 6.66 (sl, 2H), 4.68 (m, 2H), 2.92 (m, 2H), 2.16 (m, 2H).

Intermediate 83

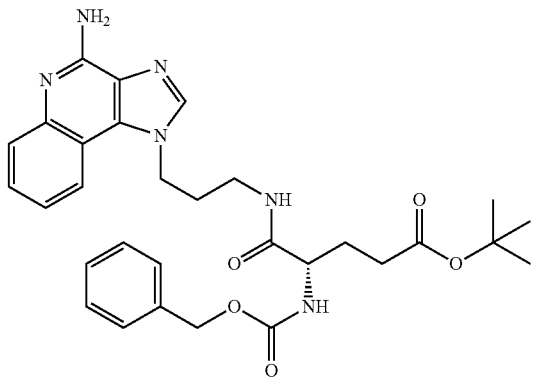

(S)-tert-butyl 5-(3-(4-amino-1H-imidazo[4,5-c]quinolin-1-yl)propylamino)-4-(benzyloxy carbonylamino)-5-oxopentanoate: To a solution of Z-L-Glu(OtBu)OH (300 mg, 0.89 mmol) in dry DMF (5 mL) was added intermediate 82 (212 mg, 0.88 mmol), HATU (340 g, 0.89 mmol), and DIEA (130 µL, 0.90 mmol). The mixture was stirred at RT overnight. The solvent was then removed in vacuo and the residue was dissolved in EtOAc (20 mL) and washed with saturated NaHCO3 solution water and brine. The organic layer was dried over MgSO4, filtered and concentrated in vacuo. The crude compound was purified on column of silica gel (3% MeOH/DCM) to give the subject compound (453 mg, yield 92%). Intermediate 83 was characterized by the following spectroscopic data: $^1$H NMR (DMSO-d6, 300 MHz) δ (ppm) 8.10 (m, 1H), 7.95 (s, 1H), 7.62 (m, 2H), 7.36 (m, 5H), 7.23 (m, 1H), 6.76 (sl, 2H), 5.04 (s, 2H), 4.12 (m, 2H), 3.20 (m, 2H), 2.28 (m, 2H), 2.08-1.79 (m, 2H), 1.42 (s, 9H).

Intermediate 84

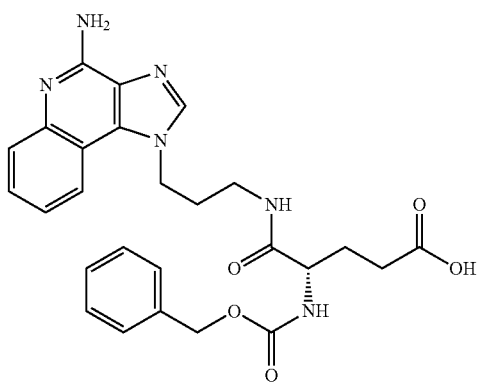

(S)-5-(3-(4-amino-1H-imidazo[4,5-c]quinolin-1-yl)propylamino)-4-(benzyloxycarbonyl amino)-5-oxopentanoic acid: To a solution of intermediate 83 (453 mg, 0.81 mmol) in DCM (10 mL) was added 10 mL of TFA. The mixture was stirred at RT overnight. Then the solvent were removed in vacuo, the residue was coevaporated 3 times with toluene. The residue was precipitated in diethyl ether to give the subject compound (375 mg, yield 92%). Intermediate 84 was characterized by the following spectroscopic data: $^1$H NMR (DMSO-d6, 300 MHz) δ (ppm) 10.62 (sl, 1H), 8.10 (m, 1H), 7.64 (m, 1H), 7.54 (m, 2H), 7.36 (s, 5H), 7.27 (m, 1H), 6.80 (sl, 2H), 4.79 (s, 2H), 4.12 (m, 2H), 3.29 (m, 2H), 2.26 (m, 2H), 1.93-1.79 (m, 2H).

Intermediate 85

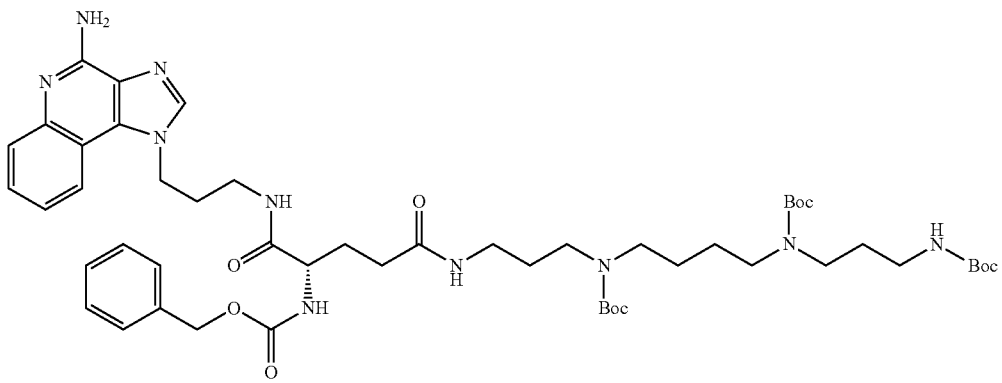

N1,N5,N10-triBoc-spermine-(S)-5-(3-(4-amino-1H-imidazo[4,5-c]quinolin-1-yl)propyl amino)-4-(benzyloxycarbonyl amino)-5-oxopentanamide: To a solution of intermediate 84 (375 mg, 0.74 mmol) in dry DMF (10 mL) was added intermediate 5 (450 mg, 0.89 mmol), HATU (340 mg, 0.89 mmol), and DIEA (180 µL, 1.11 mmol). The mixture was stirred at RT overnight. The solvent was then removed in vacuo and the residue was dissolved in EtOAc (20 mL) and washed with saturated NaHCO$_3$ solution water and brine. The organic layer was dried over MgSO$_4$, filtered and concentrated in vacuo. The crude compound was purified on column of silica gel (2% MeOH/DCM) to give the subject compound (658 mg, yield 90%). Intermediate 85 was characterized by the following spectroscopic data: $^1$H NMR (DMSO-d6, 300 MHz) δ (ppm) 8.10 (m, 1H), 7.76 (s, 1H), 7.65 (m, 1H), 7.54 (m, 2H), 7.34 (s, 5H), 6.76 (m, 1H), 6.02 (sl, 2H), 5.01 (m, 1H), 4.74 (s, 2H), 4.12 (m, 2H), 3.34-3.07 (m, 16H), 2.89 (m, 2H), 2.26 (m, 2H), 1.56 (m, 4H), 1.48-1.20 (m, 33H).

Intermediate 86

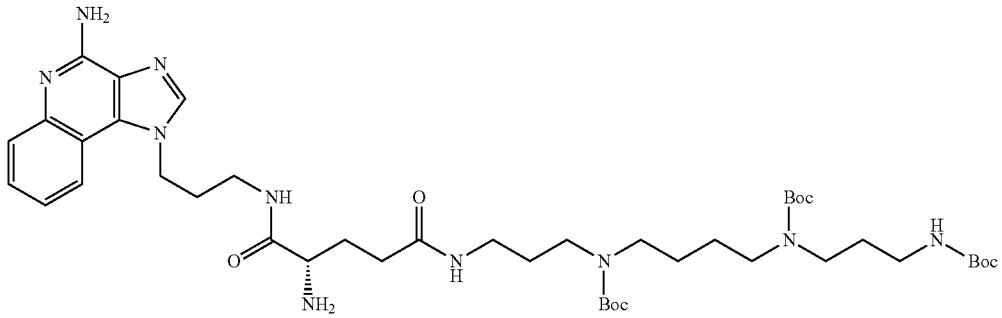

N1,N5,N10-triBoc-spermine-(S)-5-(3-(4-amino-1H-imidazo[4,5-c]quinolin-1-yl)propyl amino)-4-amine-5-oxopentanamide: To a solution of intermediate 85 (658 mg, 0.66 mmol) in a mixture of THF/MeOH (1/1) (20 mL) was added palladium on activated carbon 10% (0.05 eq). hydrogen gas was introduced via a balloon; the reaction mixture was stirred overnight at RT. The mixture was filtered through Celite and was washed with MeOH, the filtrate was concentrated in vacuo. The resulting solid was used for the next step without any further purification.

Intermediate 87

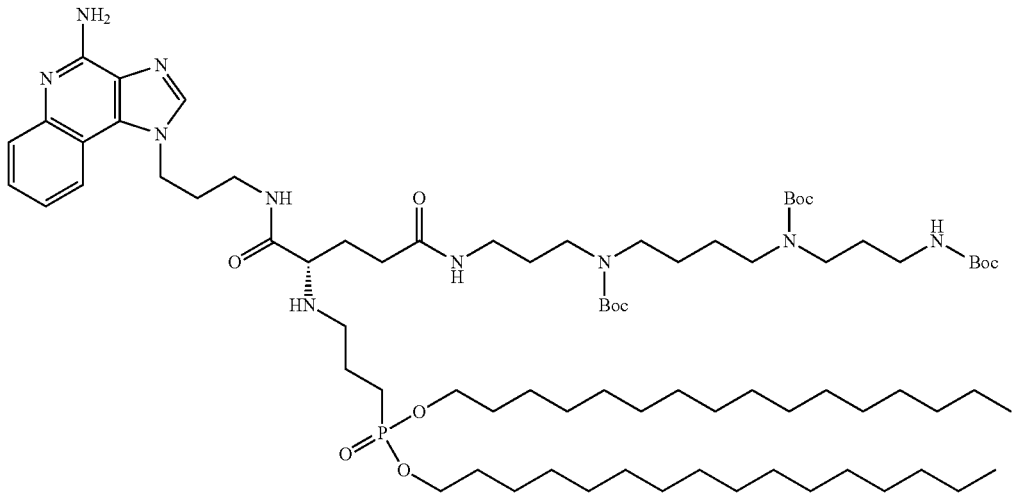

N1,N5,N10-triBoc-spermine-(S)-5-(3-(4-amino-1H-imidazo[4,5-c]quinolin-1-yl)propyl amino)-4-(1-aminopropyl-3-dihexadecylphosphonate)-5-oxopentanamide: To a solution of intermediate 86 (150 mg, 0.17 mmol) in dry DMF (7 mL) was added $Cs_2CO_3$ (38 mg, 0.119 mmol) and intermediate 21 (133 mg, 0.20 mmol). The mixture was stirred at 50° C. for 24H00. The solvent was then removed in vacuo; the residue was dissolved with EtOAc (30 mL) and was washed with water and brine. The organic layer was dried over $MgSO_4$ and concentrated in vacuo. The crude material was purified on column of silica gel (2% MeOH/DCM) to give the subject compound (60 mg, yield 25%). Intermediate 87 was characterized by the following spectroscopic data: $^1$H NMR (DMSO-d6, 300 MHz) δ (ppm) 8.13 (m, 1H), 7.83 (m, 1H), 7.79 (s, 1H), 7.65 (m, 1H), 7.54 (m, 2H), 7.24 (m, 1H), 6.15 (sl, 2H), 3.85 (m, 5H), 3.16-2.88 (m, 16H), 2.86 (m, 4H), 1.65-1.55 (m, 4H), 1.36 (m, 50H), 1.23 (m, 44H), 0.85 (m, 6H).

Compound 88

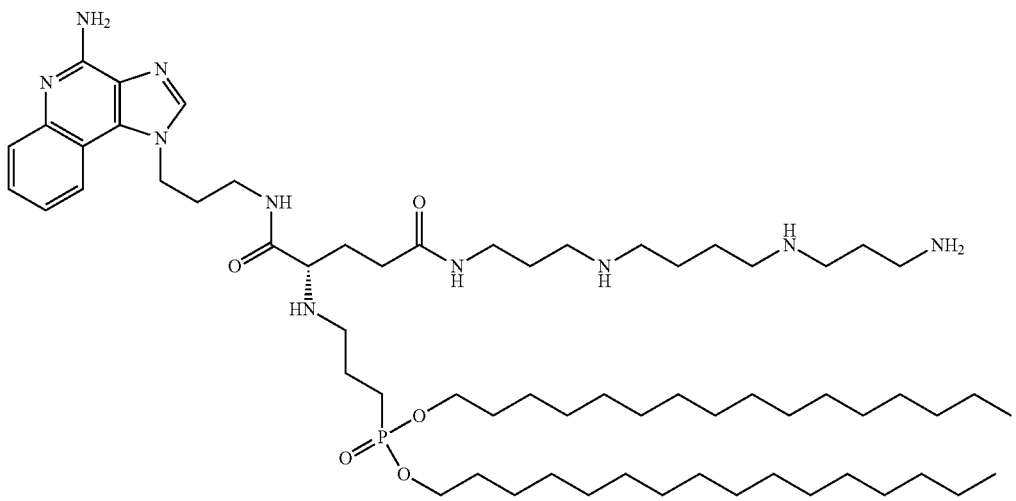

CL545

(S)-dihexadecyl 21-amino-5-(3-(4-amino-1H-imidazo[4,5-c]quinolin-1-yl)propylcarbamoyl)-8-oxo-4,9,13,18-tetraazahenicosylphosphonate: To a solution of intermediate 87 (60 mg, 0.042 mmol) in dioxane (5 mL) was added 4N HCl solution in dioxane (15 mL). The mixture was stirred at RT overnight. Then the solvent were removed in vacuo, the residue was coevaporated 3 times with toluene. The residue was purified by flash chromatography on an ARMEN® system with C18 column eluting with a gradient of 0-10% MeCN in NH₄OAc (10 mM) solution (pH=9) to give the subject compound (40 mg, yield 85%). Compound 88 was characterized by the following spectroscopic data: ¹H NMR (DMSO-d6, 300 MHz) δ (ppm) 8.12 (m, 1H), 7.85 (m, 1H), 7.80 (s, 1H), 7.66 (m, 1H), 7.57 (m, 2H), 7.27 (m, 1H), 6.05 (sl, 2H), 3.88 (m, 8H), 3.18 (m, 2H), 2.88 (m, 14H), 2.08 (m, 2H), 1.98 (m, 4H), 1.75 (m, 10H), 1.54 (m, 6H), 1.43-1.22 (m, 53H), 0.85 (m, 6H). MS (+)-ES [M+H]⁺1126 m/z.

Example 17

Molecule CL546

Intermediate 89

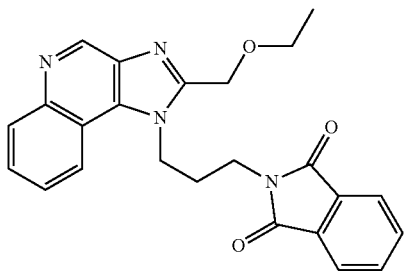

2-(3-(4-amino-2-(ethoxymethyl)-1H-imidazo[4,5-c]quinolin-1-yl)propyl)isoindoline-1,3-dione: The intermediate 79 (550 mg, 1.60 mole) was dissolved in ethoxyacetic acid (15 mL). The solution was heated at 120° C. for 20 hours. The reaction mixture was allowed to cool to ambient temperature then the mixture was diluted with water and NH₄OH solution. The mixture was extracted 3 times with EtOAc. The organic layer was dried over MgSO4, filtered and concentrated under vacuum. The residue was purified on a column of silica gel (6% MeOH/DCM) to give the subject compound (622 mg, yield 94%). Intermediate 89 was characterized by the following spectroscopic data: ¹H NMR (DMSO-d6, 300 MHz) δ (ppm) 9.16 (s, 1H), 8.31 (d, 1H), 8.15 (d, 1H), 7.90 (m, 4H), 7.86 (m, 1H), 7.55 (m, 1H), 4.80 (s, 2H), 4.73 (m, 2H), 3.87 (m, 2H), 3.50 (m, 2H), 2.26 (m, 2H), 1.09 (t, 3H).

Intermediate 90

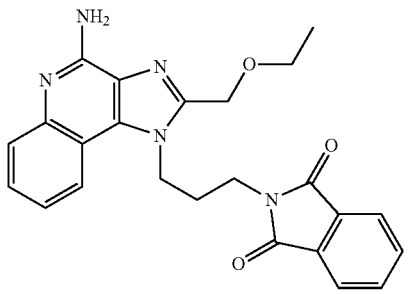

2-(3-(4-amino-2-(ethoxymethyl)-1H-imidazo[4,5-c]quinolin-1-yl)propyl)isoindoline-1,3-dione: The intermediate 89 (622 mg, 1.50 mmol) was dissolved in chloroform (5 mL). meta-chloroperoxybenzoic acid (mCPBA) (387 mg, 2.25 mmol) was added and the solution was heated at reflux overnight. The solution was then cooled and the solvents were removed at reduced pressure. The residue was then dissolved in dichloromethane (10 mL) and NH₄OH 20% solution (10 mL) was added to the stirred solution. The reaction mixture was refluxed overnight. A crystalline solid formed and was filtered from the mixture, washed with dichloromethane and hexane and dried to give the subject compound (341 mg, yield 53%). Intermediate 90 was characterized by the following spectroscopic data: ¹H NMR (DMSO-d6, 300 MHz) δ (ppm) 7.92 (m, 5H), 7.62 (d, 1H), 7.43 (m, 1H), 7.15 (m, 1H), 6.60 (sl, 2H), 4.73 (s, 2H), 4.65 (m, 2H), 3.87 (m, 2H), 3.49 (q, 2H), 2.23 (m, 2H), 1.10 (t, 3H).

Intermediate 91

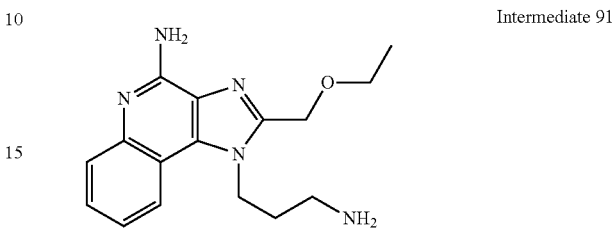

1-(3-aminopropyl)-2-(ethoxymethyl)-1H-imidazo[4,5-c]quinolin-4-amine: To a solution of intermediate 90 (341 mg, 0.79 mmol) in absolute EtOH (10 mL) was added hydrazine monohydrate (77 µL, 1.58 mmol). The reaction mixture was warmed to 90° C. and was stirred at this temperature overnight. Then, the solution was cooled to 0° C. and a solution of HCl 37% (100 µL) was added dropwise and the mixture was stirred for 2H00 at 90° C. Then the mixture was cooled to RT, the solvents were removed in vacuo and the crude mixture was purified on column of silica gel (15% MeOH/DCM) to give the subject compound (200 mg, yield 85%). Intermediate 91 was characterized by the following spectroscopic data: ¹H NMR (DMSO-d6, 300 MHz) δ (ppm) 8.14 (d, 1H), 7.62 (d, 1H), 7.46 (m, 1H), 7.26 (m, 1H), 6.66 (sl, 2H), 4.78 (s, 2H), 4.68 (m, 2H), 3.59 (m, 2H), 2.95 (q, 2H), 2.16 (m, 2H), 1.19 (t, 3H).

Intermediate 92

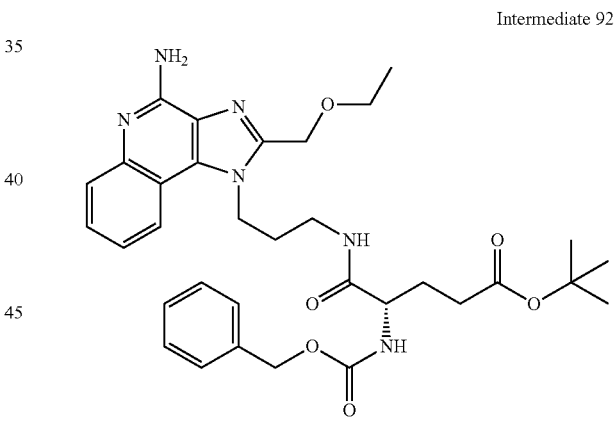

(S)-tert-butyl-5-(3-(4-amino-2-(ethoxymethyl)-1H-imidazo[4,5-c]quinolin-1-yl)propyl amino)-4-(benzyloxycarbonylamino)-5-oxopentanoate: To a solution of Z-L-Glu (OtBu)OH (250 mg, 0.73 mmol) in dry DMF (5 mL) was added intermediate 91 (200 mg, 0.67 mmol), HATU (280 g, 0.73 mmol), and DIEA (164 µL, 1.05 mmol). The mixture was stirred at RT overnight. The solvent was then removed in vacuo and the residue was dissolved in EtOAc (20 mL) and washed with saturated NaHCO₃ solution water and brine. The organic layer was dried over MgSO₄, filtered and concentrated in vacuo. The crude compound was purified on column of silica gel (3% MeOH/DCM) to give the subject compound (360 mg, yield 87%). Intermediate 92 was characterized by the following spectroscopic data: ¹H NMR (DMSO-d6, 300 MHz) δ (ppm) 8.17 (m, 1H), 8.05 (d, 1H), 7.65 (d, 1H), 7.48 (m, 2H), 7.33 (s, 5H), 7.19 (m, 1H), 6.94 (sl, 2H), 5.02 (q, 2H), 4.76 (s, 2H), 4.56 (m, 2H), 4.00 (m, 1H), 3.54 (q, 2H), 3.17 (m, 2H), 2.25 (m, 2H), 2.01 (m, 3H), 1.76 (m, 1H), 1.36 (s, 9H), 1.15 (t, 3H).

Intermediate 93

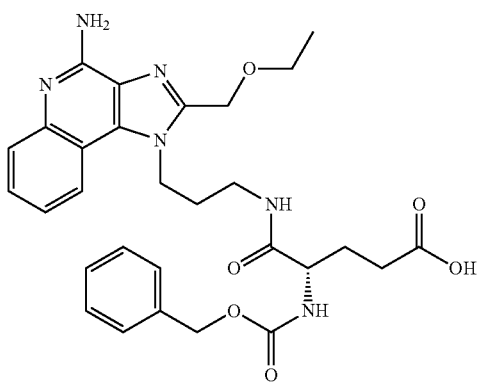

(S)-5-(3-(4-amino-2-(ethoxymethyl)-1H-imidazo[4,5-c]quinolin-1-yl)propylamino)-4-(benzyloxycarbonylamino)-5-oxopentanoic acid: To a solution of intermediate 92 (360 mg, 0.58 mmol) in DCM (10 mL) was added 10 mL of TFA. The mixture was stirred at RT overnight. Then the solvent were removed in vacuo, the residue was coevaporated 3 times with toluene. The residue was precipitated in diethyl ether to give the subject compound (319 mg, yield 98%). Intermediate 93 was characterized by the following spectroscopic data: $^1$H NMR (DMSO-d6, 300 MHz) δ (ppm) 14.01 (sl, 1H), 8.20 (d, 1H), 7.82 (m, 2H), 7.74 (m, 2H), 7.62 (m, 1H), 7.25 (m, 5H), 5.00 (m, 2H), 4.81 (s, 2H), 4.58 (m, 2H), 4.00 (m, 1H), 3.58 (q, 2H), 3.31 (m, 2H), 2.30 (m, 2H), 1.95 (m, 3H), 1.78 (m, 1H), 1.17 (t, 3H).

Intermediate 94

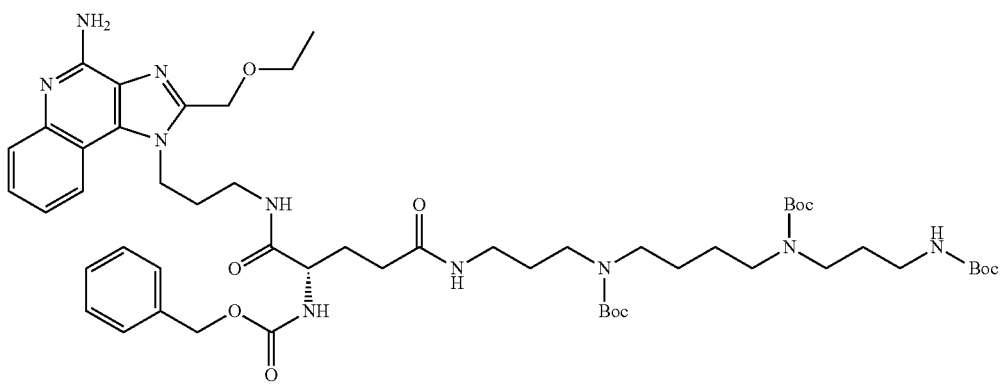

N1,N5,N10-triBoc-spermine-(S)-5-(3-(4-amino-2-(ethoxymethyl)-1H-imidazo[4,5-c]quinolin-1-yl)propylamino)-4-(benzyloxycarbonylamino)-5-oxopentanamide:
To a solution of intermediate 93 (319 mg, 0.57 mmol) in dry DMF (7 mL) was added intermediate 5 (315 mg, 0.62 mmol), HATU (235 mg, 0.62 mmol), and DIEA (140 µL, 0.85 mmol). The mixture was stirred at RT overnight. The solvent was then removed in vacuo and the residue was dissolved in EtOAc (20 mL) and washed with saturated NaHCO$_3$ solution water and brine. The organic layer was dried over MgSO$_4$, filtered and concentrated in vacuo. The crude compound was purified on column of silica gel (2% MeOH/DCM) to give the subject compound (531 mg, yield 89%). Intermediate 94 was characterized by the following spectroscopic data: $^1$H NMR (DMSO-d6, 300 MHz) δ (ppm) 8.20 (m, 1H), 8.03 (d, 1H), 7.78 (m, 2H), 7.62 (m, 1H), 7.48 (m, 2H), 7.32 (m, 5H), 6.77 (m, 1H), 6.68 (sl, 2H), 5.00 (m, 2H), 4.75 (s, 2H), 4.54 (m, 2H), 3.99 (m, 1H), 3.55 (q, 2H), 3.27 (m, 2H), 3.08 (m, 8H), 2.97 (m, 2H), 2.88 (m, 2H), 2.13 (m, 2H), 2.09 (m, 3H), 1.78 (m, 1H), 1.54 (m, 4H), 1.45 (m, 31H), 1.17 (t, 3H).

Intermediate 95

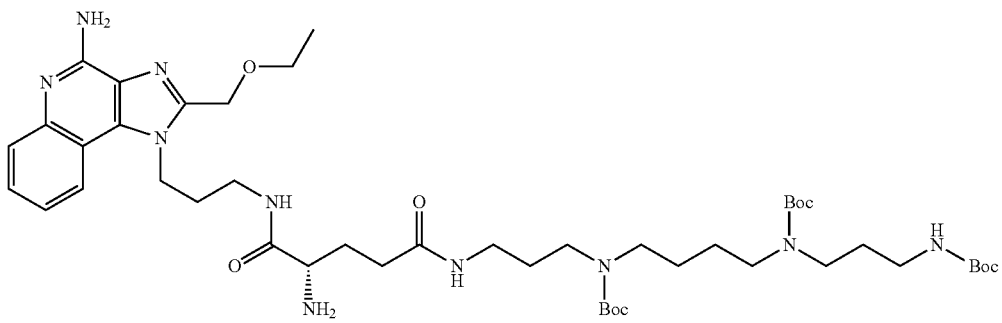

N1,N5,N10-triBoc-spermine-(S)-5-(3-(4-amino-2-(ethoxymethyl)-1H-imidazo[4,5-c]quinolin-1-yl)propylamino)-4-amino-5-oxopentanamide: To a solution of intermediate 94 (531 mg, 0.51 mmol) in a mixture of THF/MeOH (1/1) (20 mL) was added palladium on activated carbon 10% (0.05 eq). hydrogen gas was introduced via a balloon; the reaction mixture was stirred overnight at RT. The mixture was filtered through Celite and was washed with MeOH, the filtrate was concentrated in vacuo. The resulting solid was used for the next step without any further purification.

intermediate 95 (150 mg, 0.16 mmol) in dry DMF (7 mL) was added $Cs_2CO_3$ (37 mg, 0.115 mmol) and intermediate 9 (135 mg, 0.17 mmol). The mixture was stirred at 50° C. for 24H00. The solvent was then removed in vacuo; the residue was dissolved with EtOAc (30 mL) and was washed with water and brine. The organic layer was dried over $MgSO_4$ and concentrated in vacuo. The crude material was purified on column of silica gel (2% MeOH/DCM) to give the subject compound (81 mg, yield 32%). Intermediate 96 was characterized by the following spectroscopic data: $^1$H NMR (DMSO-d6, 300 MHz) δ (ppm) 8.15 (m, 1H), 7.86 (m, 2H), Intermediate 96

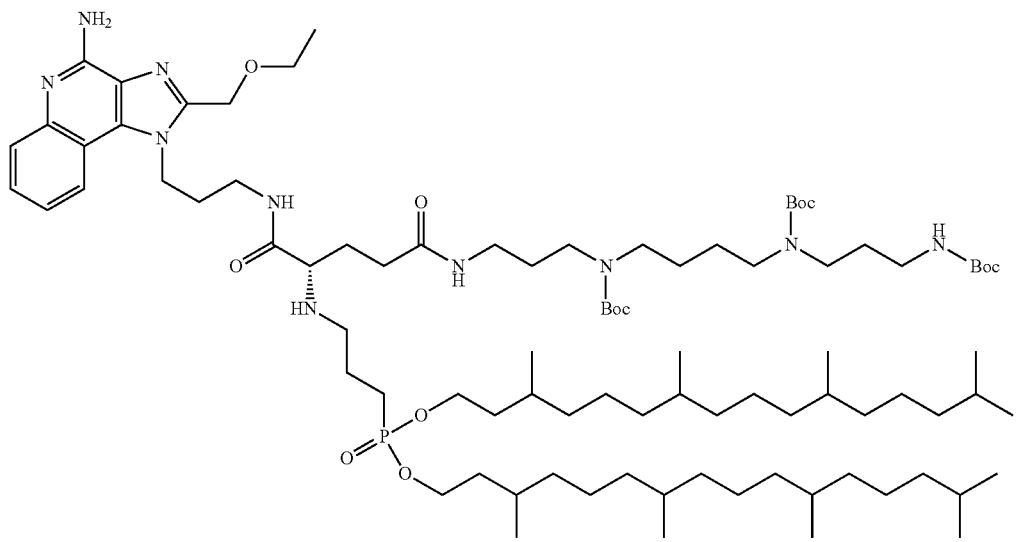

N1,N5,N10-triBoc-spermine-(S)-5-(3-(4-amino-2-(ethoxymethyl)-1H-imidazo[4,5-c]quinolin-1-yl)propylamino)-4-(1-aminopropyl-bis(3,7,11,15-tetramethylhexadecyl)-3-phosphonate)-5-oxopentanamide: To a solution of 7.67 (m, 1H), 7.55 (m, 1H), 7.15 (m, 1H), 6.88 (sl, 2H), 5.15 (m, 2H), 4.76 (s, 2H), 4.68 (m, 2H), 4.16 (m, 1H), 3.62 (m, 2H), 3.31-3.08 (m, 16H), 2.27 (m, 2H), 2.00 (m, 3H), 1.76-1.54 (m, 39H), 1.44 (m, 54H), 1.15 (m, 33H).

Compound 97

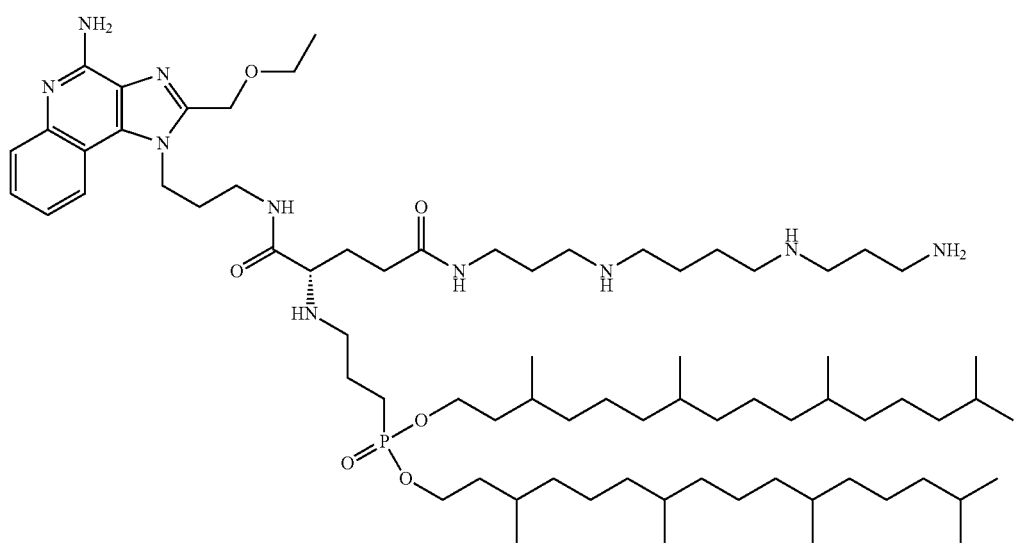

CL546 bis(3,7,11,15-tetramethylhexadecyl) (S)-21-amino-5-(3-(4-amino-2-(ethoxymethyl)-1H-imidazo[4,5-c]quinolin-1-yl)propylcarbamoyl)-8-oxo-4,9,13,18-tetraazahenicosyl phosphonate: To a solution of intermediate 96 (81 mg, 0.051 mmol) in dioxane (5 mL) was added 4N HCl solution in dioxane (15 mL). The mixture was stirred at RT overnight. Then the solvent were removed in vacuo, the residue was coevaporated 3 times with toluene. The residue was purified by flash chromatography on an ARMEN® system with C18 column eluting with a gradient of 0-10% MeCN in NH₄OAc (10 mM) solution (pH 9) to give the subject compound (57 mg, yield 82%). Compound 97 was characterized by the following spectroscopic data: ¹H NMR (DMSO-d6, 300 MHz) δ (ppm) 8.12 (d, 1H), 7.86 (m, 3H), 7.67 (m, 2H), 7.61 (m, 1H), 7.58 (m, 1H), 7.13 (m, 1H), 6.88 (sl, 2H), 5.14 (m, 2H), 4.75 (s, 2H), 4.56 (m, 2H), 4.20 (m, 1H), 3.55 (m, 2H), 3.34-3.08 (m, 16H), 2.25 (m, 2H), 2.00 (m, 5H), 1.74-1.56 (m, 7H), 1.43 (m, 54H), 1.15 (m, 33H). MS (+)–ES [M+H]⁺ 1297 m/z.

Example 18

Molecule CL547

Intermediate 98

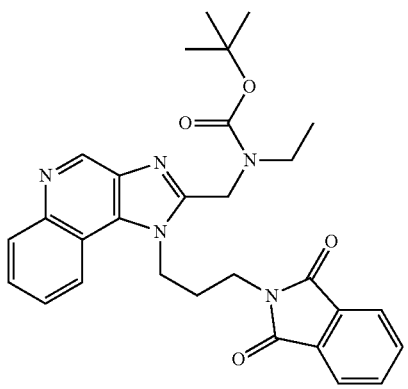

Tert-butyl-(1-(3-(1,3-dioxoisoindolin-2-yl)propyl)-1H-imidazo[4,5-c]quinolin-2-yl)methyl (ethyl)carbamate: The intermediate 79 (550 mg, 1.60 mole) was dissolved in N-Boc-N-Ethyl glycine (490 mg, 2.4 mmol). The solution was heated at 130° C. for 20 hours. The reaction mixture was allowed to cool to ambient temperature then the mixture was diluted with water and NH₄OH solution. The mixture was extracted 3 times with EtOAc. The organic layer was dried over MgSO4, filtered and concentrated under vacuum. The residue was purified on a column of silica gel (6% MeOH/DCM) to give the subject compound (607 mg, yield 74%). Intermediate 98 was characterized by the following spectroscopic data: ¹H NMR (DMSO-d6, 300 MHz) δ (ppm) 8.81 (s, 1H), 8.22 (d, 1H), 7.98 (d, 1H), 7.88 (m, 4H), 7.78 (m, 1H), 7.60 (m, 1H), 4.22 (s, 2H), 4.55 (m, 2H), 3.75 (q, 2H), 3.60 (m, 2H), 2.28 (m, 2H), 1.38 (s, 9H), 1.09 (t, 3H)

Intermediate 99

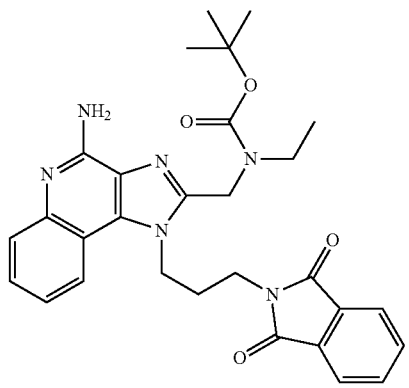

Tert-butyl-(4-amino-1-(3-(1,3-dioxoisoindolin-2-yl)propyl)-1H-imidazo[4,5-c]quinolin-2-yl)methyl(ethyl)carbamate: The intermediate 98 (607 mg, 1.18 mmol) was dissolved in chloroform (5 mL). meta-chloroperoxybenzoic acid (mCPBA) (304 mg, 1.77 mmol) was added and the solution was heated at reflux overnight. The solution was then cooled and the solvents were removed at reduced pressure. The residue was then dissolved in dichloromethane (10 mL) and NH₄OH 20% solution (10 mL) was added to the stirred solution. The reaction mixture was refluxed overnight. A crystalline solid formed and was filtered from the mixture, washed with dichloromethane and hexane and dried to give the subject compound (286 mg, yield 46%). Intermediate 99 was characterized by the following spectroscopic data: ¹H NMR (DMSO-d6, 300 MHz) δ (ppm) 8.10 (d, 1H), 7.92 (m, 4H), 7.65 (d, 1H), 7.44 (m, 1H), 7.16 (m, 1H), 6.86 (sl, 2H), 4.73 (m, 2H), 4.65 (s, 2H), 3.87 (m, 2H), 3.49 (q, 2H), 2.23 (m, 2H), 1.42 (s, 9H), 1.10 (t, 3H).

Intermediate 100

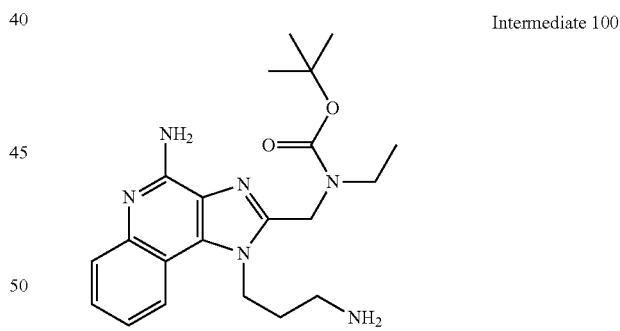

Tert-butyl-(4-amino-1-(3-aminopropyl)-1H-imidazo[4,5-c]quinolin-2-yl)methyl(ethyl) carbamate: To a solution of intermediate 99 (286 mg, 0.54 mmol) in absolute EtOH (10 mL) was added hydrazine monohydrate (55 µL, 1.08 mmol). The reaction mixture was warmed to 90° C. and was stirred at this temperature overnight. Then, the solution was cooled to 0° C. and a solution of HCl 37% (75 µL) was added dropwise and the mixture was stirred for 2H00 at 90° C. Then the mixture was cooled to RT, the solvents were removed in vacuo and the crude mixture was purified on column of silica gel (15% MeOH/DCM) to give the subject compound (203 mg, yield 95%). Intermediate 100 was characterized by the following spectroscopic data: ¹H NMR (DMSO-d6, 300 MHz) δ (ppm) 8.14 (d, 1H), 7.62 (d, 1H), 7.46 (m, 1H), 7.20 (m, 1H), 6.66 (sl, 2H), 4.73 (s, 2H), 4.65 (m, 2H), 3.67 (m, 2H), 3.55 (q, 2H), 2.25 (m, 2H), 1.42 (s, 9H), 1.10 (t, 3H).

Intermediate 101

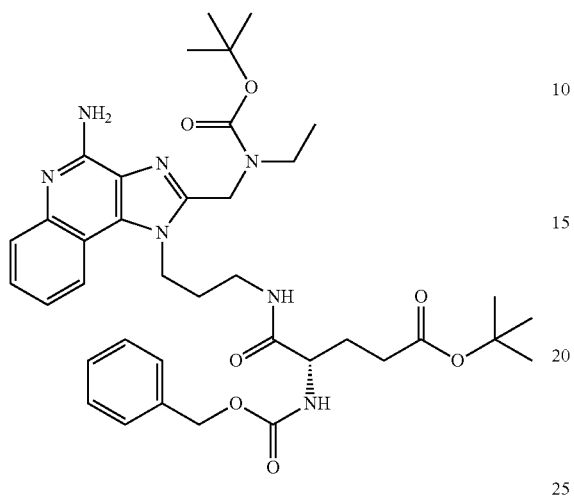

(S)-tert-butyl-5-(3-(4-amino-2-((tert-butoxycarbonyl (ethyl)amino)methyl)-1H-imidazo[4,5-c]quinolin-1-yl)propylamino)-4-(benzyloxycarbonylamino)-5-oxopentanoate: To a solution of Z-L-Glu(OtBu)OH (190 mg, 0.56 mmol) in dry DMF (5 mL) was added intermediate 100 (203 mg, 0.51 mmol), HATU (215 mg, 0.56 mmol), and DIEA (125 μL, 0.76 mmol). The mixture was stirred at RT overnight. The solvent was then removed in vacuo and the residue was dissolved in EtOAc (20 mL) and washed with saturated NaHCO₃ solution water and brine. The organic layer was dried over MgSO₄, filtered and concentrated in vacuo. The crude compound was purified on column of silica gel (3% MeOH/DCM) to give the subject compound (322 mg, yield 88%). Intermediate 101 was characterized by the following spectroscopic data: ¹H NMR (DMSO-d6', 300 MHz) δ (ppm) 8.15 (m, 1H), 8.06 (d, 1H), 7.67 (d, 1H), 7.50 (m, 2H), 7.30 (s, 5H), 7.18 (m, 1H), 6.95 (sl, 2H), 5.00 (q, 2H), 4.74 (s, 2H), 4.58 (m, 2H), 4.06 (m, 1H), 3.58 (q, 2H), 3.18 (m, 2H), 2.24 (m, 2H), 1.98 (m, 3H), 1.74 (m, 1H), 1.42 (s, 18H), 1.12 (t, 3H).

Intermediate 102

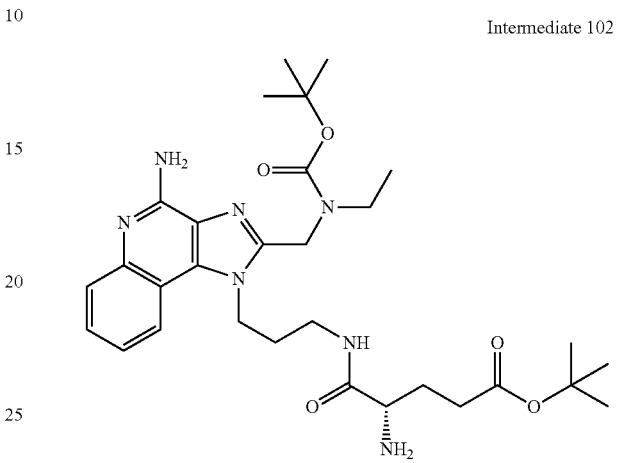

(S)-tert-butyl 4-amino-5-(3-(4-amino-2-((tert-butoxycarbonyl(ethyl)amino)methyl)-1H-imidazo[4,5-c]quinolin-1-yl)propylamino)-5-oxopentanoate: To a solution of intermediate 101 (322 mg, 0.45 mmol) in a mixture of THF/MeOH (1/1) (20 mL) was added palladium on activated carbon 10% (0.05 eq). hydrogen gas was introduced via a balloon; the reaction mixture was stirred overnight at RT. The mixture was filtered through Celite and was washed with MeOH, the filtrate was concentrated in vacuo. The resulting solid was used for the next step without any further purification.

Intermediate 103

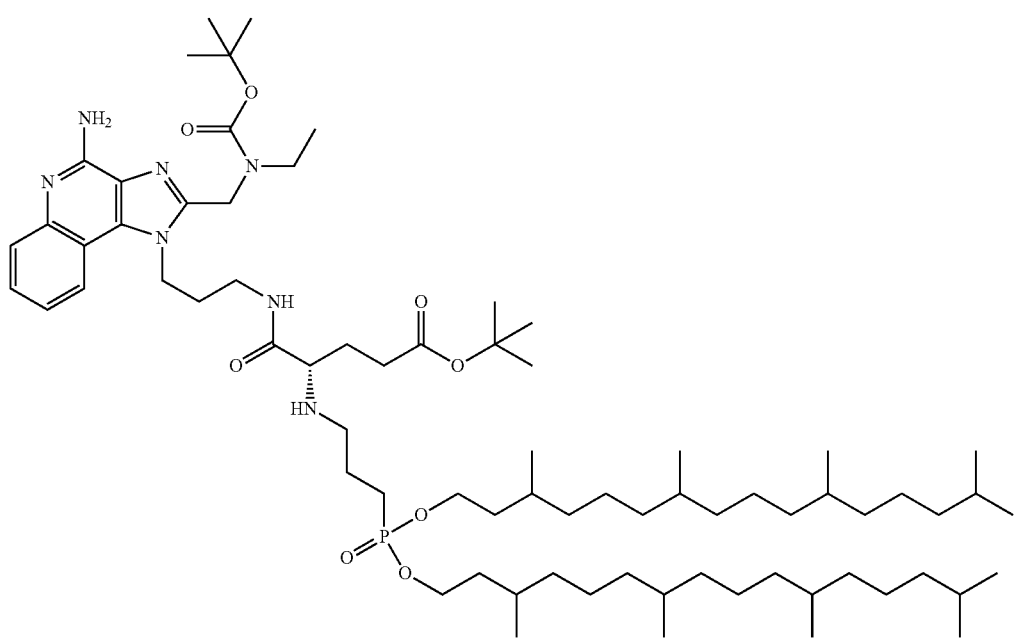

(4S)-tert-butyl-5-(3-(4-amino-2-((tert-butoxycarbonyl (ethyl)amino)methyl)-1H-imidazo[4,5-c]quinolin-1-yl)propylamino)-4-(3-(bis(3,7,11,15-tetramethylhexadecyloxy) phosphoryl)propylamino)-5-oxopentanoate: To a solution of intermediate 102 (100 mg, 0.17 mmol) in dry DMF (7 mL) was added $Cs_2CO_3$ (38 mg, 0.12 mmol) and intermediate 9 (140 mg, 0.18 mmol). The mixture was stirred at 50° C. for 24H00. The solvent was then removed in vacuo; the residue was dissolved with EtOAc (30 mL) and was washed with water and brine. The organic layer was dried over $MgSO_4$ and concentrated in vacuo. The crude material was purified on column of silica gel (2% MeOH/DCM) to give the subject compound (86 mg, yield 40%). Intermediate 103 was characterized by the following spectroscopic data: $^1$H NMR (DMSO-d6, 300 MHz) δ (ppm) 8.15 (m, 1H), 8.00 (d, 1H), 7.68 (m, 1H), 7.50 (m, 2H), 7.28 (m, 1H), 6.85 (sl, 2H), 5.15 (m, 2H), 4.76 (s, 2H), 4.68 (m, 2H), 4.16 (m, 1H), 3.55 (q, 2H), 3.20 (m, 2H), 2.25 (m, 2H), 2.00 (m, 3H), 1.78-1.55 (m, 9H), 1.44 (m, 48H), 1.34 (s, 18H), 1.02 (m, 33H).

Intermediate 104

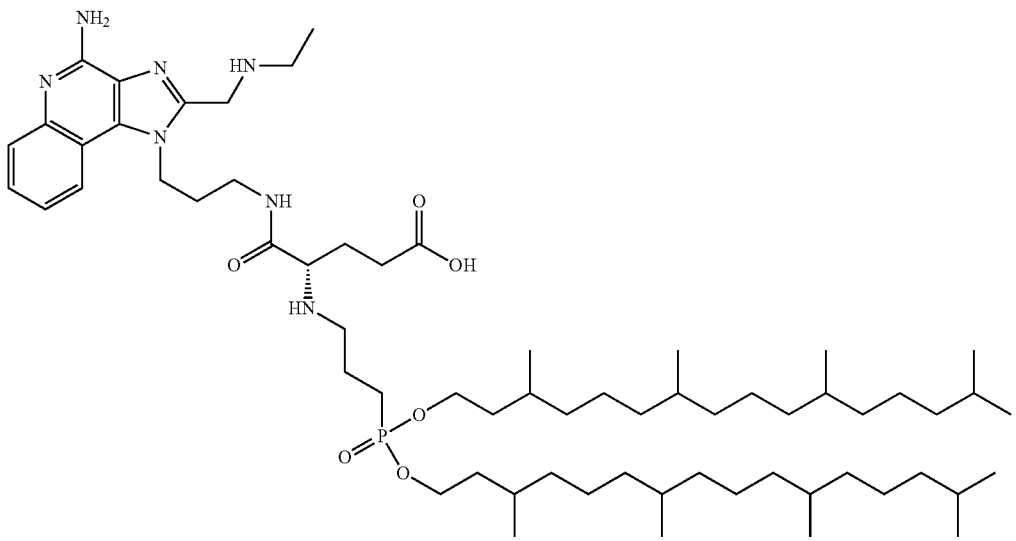

(4S)-5-(3-(4-amino-2-((ethylamino)methyl)-1H-imidazo [4,5-c]quinolin-1-yl)propyl amino)-4-(3-(bis(3,7,11,15-tetramethylhexadecyloxy)phosphoryl)propylamino)-5-oxo pentanoic acid: To a solution of intermediate 103 (86 mg, 0.07 mmol) in DCM (10 mL) was added 10 mL of TFA. The mixture was stirred at RT overnight. Then the solvent were removed in vacuo, the residue was coevaporated 3 times with toluene. The residue was precipitated in diethyl ether to give the subject compound (74 mg, yield 98%). Intermediate 104 was characterized by the following spectroscopic data: $^1$H NMR (DMSO-d6, 300 MHz) δ (ppm) 11.65 (sl, 1H), 8.01 (m, 1H), 7.80 (d, 1H), 7.68 (m, 1H), 7.55 (m, 2H), 7.13 (m, 1H), 6.88 (sl, 2H), 5.15 (m, 2H), 4.78 (s, 2H), 4.65 (m, 2H), 4.15 (m, 1H), 3.58 (q, 2H), 3.22 (m, 2H), 2.23 (m, 2H), 1.99 (m, 3H), 1.77-1.52 (m, 9H), 1.43 (m, 48H), 1.15 (m, 33H).

Intermediate 105

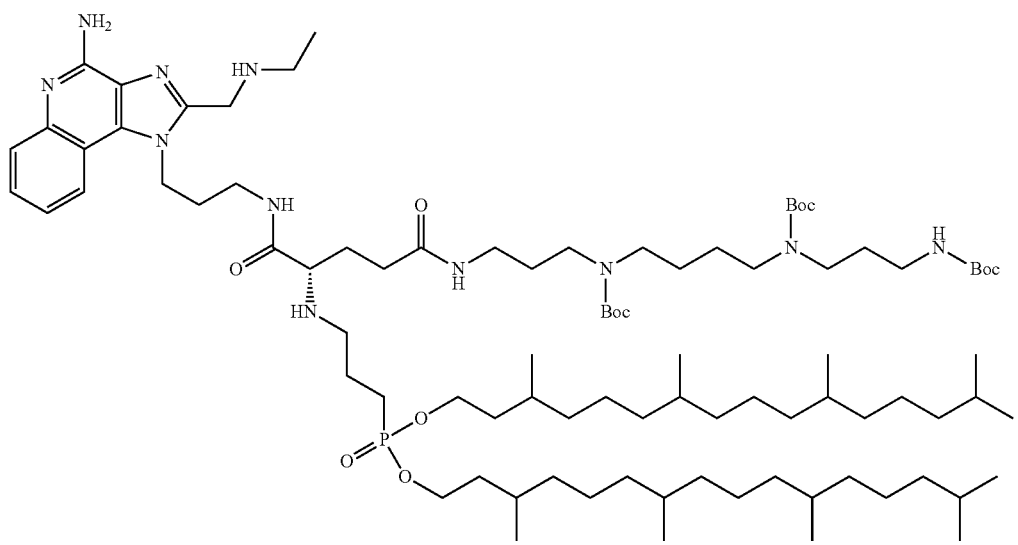

N1,N5,N10-triBoc-spermine-(4S)-5-(3-(4-amino-2-((ethylamino)methyl)-1H-imidazo[4,5-c]quinolin-1-yl)propylamino)-4-(3-(bis(3,7,11,15-tetramethylhexadecyloxy)phosphoryl) propylamino)-5-oxopentanamide: To a solution of intermediate 104 (74 mg, 0.07 mmol) in dry DMF (7 mL) was added intermediate 5 (38 mg, 0.08 mmol), HATU (30 mg, 0.08 mmol), and DIEA (20 μL, 0.12 mmol). The mixture was stirred at RT overnight. The solvent was then removed in vacuo and the residue was dissolved in EtOAc (10 mL) and washed with saturated NaHCO$_3$ solution water and brine. The organic layer was dried over MgSO$_4$, filtered and concentrated in vacuo. The crude compound was purified on column of silica gel (2% MeOH/DCM) to give the subject compound (75 mg, yield 59%). Intermediate 105 was characterized by the following spectroscopic data: $^1$H NMR (DMSO-d6, 300 MHz) δ (ppm) 8.15 (m, 1H), 7.85 (m, 2H), 7.66 (m, 1H), 7.54 (m, 1H), 7.15 (m, 1H), 6.88 (sl, 2H), 5.15 (m, 2H), 4.75 (s, 2H), 4.66 (m, 2H), 4.16 (m, 1H), 3.60 (m, 2H), 3.34-3.08 (m, 16H), 2.27 (m, 2H), 1.99 (m, 3H), 1.77-1.52 (m, 39H), 1.43 (m, 54H), 1.15 (m, 33H).

bis(3,7,11,15-tetramethylhexadecyl) (S)-21-amino-5-(3-(4-amino-2-((ethylamino)methyl)-1H-imidazo[4,5-c]quinolin-1-yl)propylcarbamoyl)-8-oxo-4,9,13,18-tetraazahenicosyl phosphonate: To a solution of intermediate 105 (75 mg, 0.047 mmol) in dioxane (5 mL) was added 4N HCl solution in dioxane (10 mL). The mixture was stirred at RT overnight. Then the solvent were removed in vacuo, the residue was coevaporated 3 times with toluene. The residue was purified by flash chromatography on an ARMEN® system with C18 column eluting with a gradient of 0-10% MeCN in NH$_4$OAc (10 mM) solution (pH 9) to give the subject compound (45 mg, yield 75%). Compound 97 was characterized by the following spectroscopic data: $^1$H NMR (DMSO-d6, 300 MHz) δ (ppm) 8.10 (d, 1H), 7.85 (m, 3H), 7.66 (m, 2H), 7.60 (m, 1H), 7.56 (m, 1H), 7.13 (m, 1H), 6.88 (sl, 2H), 5.13 (m, 2H), 4.75 (s, 2H), 4.56 (m, 2H), 4.20 (m, 1H), 3.55 (m, 2H), 3.34-3.08 (m, 16H), 2.25 (m, 2H), 2.00 (m, 5H), 1.77-1.52 (m, 7H), 1.43 (m, 54H), 1.15 (m, 33H). MS (+)–ES [M+H]$^+$1296 m/z.

Compound 106

CL547

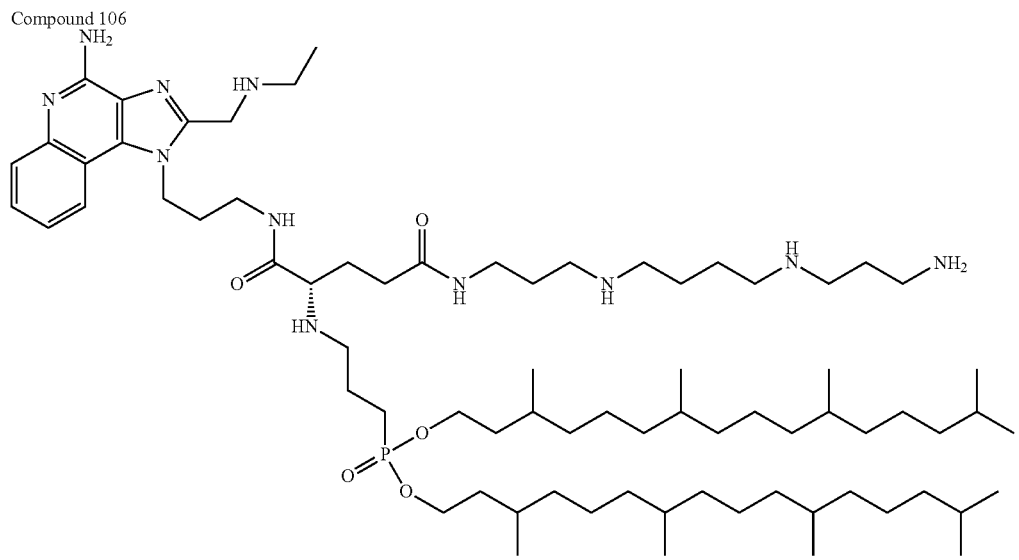

Example 19

Molecule CL543

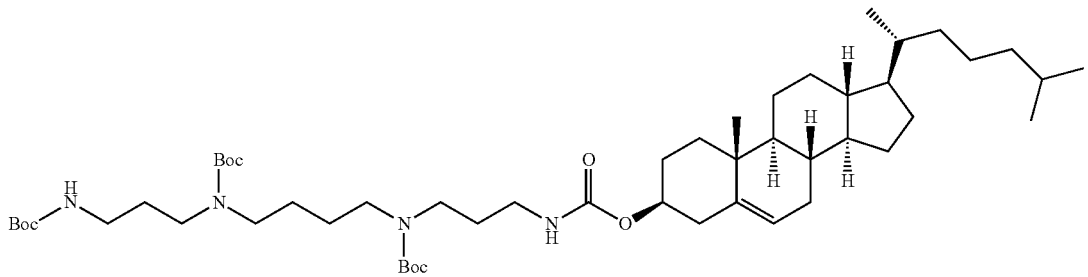

Intermediate 107

N1-N5-N10-triBoc-N14-((3S,8S,9S,10R,13R,14S,17R)-10,13-dimethyl-17-((R)-6-methyl heptan-2-yl)-2,3,4,7,8,9,10,11,12,13,14,15,16,17-tetradecahydro-1,1-cyclopenta[a]phenanthren-3-yl carbamate)spermine: To a solution of N1,N5,N10-triBoc-spermine (0.500 g, 0.99 mmol) in dry DCM (10 mL) was added DIEA (340 μL, 1.98 mmol) and a solution of cholesteryl chloroformate (0.447 g, 0.99 mmol) in dry DCM (2 mL). The mixture was stirred at RT for 18H00. The mixture was then diluted with DCM (20 mL) and was washed with 0.1 N HCl solution, water and brine. The organic layer was dried over MgSO$_4$ and concentrated in vacuo. The crude material was purified on column of silica gel (5% MeOH/DCM) to give the subject compound (0.899 g, yield 98%). Intermediate 107 was characterized by the following spectroscopic data: $^1$H NMR (DMSO-d6, 300 MHz) δ (ppm) 7.04 (m, 1H), 6.77 (m, 1H), 5.33 (m, 1H), 4.3 (m, 1H), 3.09 (m, 12H), 2.91 (m, 6H), 2.26 (m, 2H), 1.94-1.80 (m, 9H), 1.54-1.50 (m, 5H), 1.48 (m, 40H), 1.10-0.91 (m, 7H), 0.88 (d, 6H), 0.68 (s, 3H).

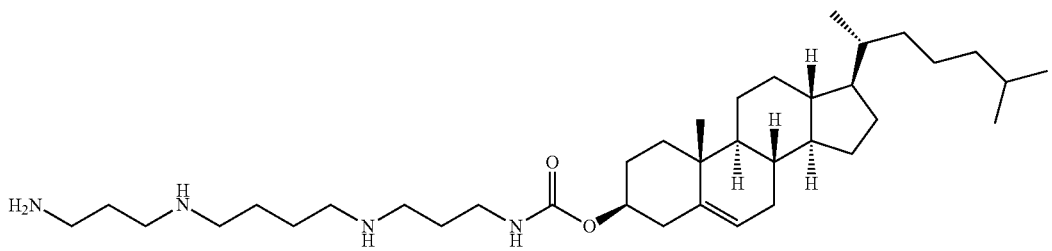

Intermediate 108

N1-((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl carbamate)spermine: To a solution of intermediate 107 (899 mg, 0.98 mmol) in dioxane (15 mL) was added 15 mL of 4M HCl in dioxane. The mixture was stirred at RT for 1H00. Then the solvent were removed in vacuo and the residue was precipitated in diethyl ether to give the subject compound (671 mg, yield 96%) which was used for the next step without any further purification.

Compound 109

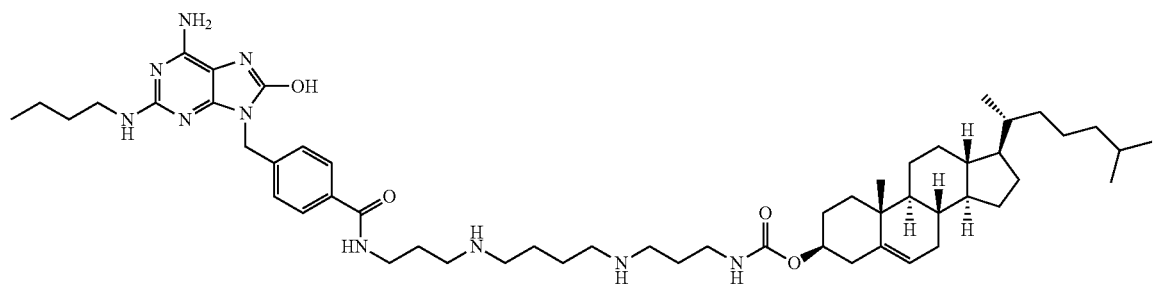

CL543

(3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(4-(3-(4-((6-amino-2-(butylamino)-8-hydroxy-9H-purin-9-yl)methyl)benzamido)propylamino)butyl-amino)propylcarbamate: To a solution of intermediate 4 (100 mg, 0.28 mmol) in dry DMF (5 mL) were added N-hydroxysuccinimide (35 mg, 0.30 mmol), EDCI (64 mg, 0.33 mmol) and DMAP (40 mg, 0.33 mmol). The mixture was stirred at RT overnight. Then the solvent was removed in vacuo and the residue was triturated with water. The precipitate was filtered, washed with water EtOH and Et$_2$O and dried. The resulting solid was dissolved in dry DMF (3 mL) and were added intermediate 108 (202 mg, 0.28 mmol) and DIEA (575 µL, 3.3 mmol). The mixture was stirred at RT overnight. The solvent was removed in vacuo and the residue was directly applied to a column of silica gel (iPrOH/NH$_4$OH/H$_2$O 85/10/5) to give the subject compound (138 mg, yield 52%). Compound 109 was characterized by the following spectroscopic data: $^1$H NMR (DMSO-d6, 300 MHz) δ (ppm) 8.52 (m, 1H), 7.77 (d, 2H), 7.33 (d, 2H), 6.16 (t, 1H), 6.04 (sl, 2H), 5.32 (m, 1H), 4.84 (s, 2H), 4.29 (m, 1H), 3.28 (m, 6H), 3.15 (m, 3H), 2.99 (m, 3H), 2.69 (m, 4H), 2.00-1.75 (m, 9H), 1.69-1.25 (m, 26H), 1.15-0.95 (m, 15H), 0.88 (d, 6H), 0.65 (s, 3H). MS (+)–ES [M+H]$^+$954 m/z.

Biological Testing of the TLR7-Cationic Lipid Molecules of the Invention

Example 19

In Vitro Testing of Molecules

Activation of the TLR7 Receptor in Cells in Culture

In order to test the molecules for their ability to activate TLR7 signaling, in vitro cell based assays were carried out using TLR7 reporter cell lines, HEK-Blue™ TLR7 Cells, generated at InvivoGen. These cells are engineered HEK293 cells, a human embryonic kidney cell line (ATCC, CRL-1573) that stably co-express either a human or murine TLR7 gene, and an NF-κB-inducible secreted embryonic alkaline phosphatase (SEAP) reporter gene. The SEAP reporter gene is placed under the control of the NF-κB and AP-inducible promoter. Stimulation with a TLR7 ligand activates NF-κB and AP-1, which induces the production of SEAP. Real-time detection of SEAP is measured following culturing cells in HEK-Blue™ Detection (InvivoGen). HEK-Blue™ Detection is a cell culture media that contains a SEAP substrate, which upon hydrolysis by SEAP produces a colorimetric change allowing detection of SEAP as the reporter protein is secreted by cells. The cationic molecules of the invention were assayed for their ability to activate TLR7 to demonstrate their function as TLR7 agonists. Similarly, HEK-Blue™ TLR8 Cells (InvivoGen) were used to test molecules for their ability to activate TLR8. Assays were also performed using the molecules in complex with DNA to ensure that TLR7 and/or TLR8 activity is retained. These assays were carried out using RAW-Blue™ Cells (InvivoGen), derived from RAW 264.7 mouse leukaemic monocyte macrophage cell line (ATCC, CRL 2278) stably overexpressing a NF-κB/AP-1 inducible SEAP reporter construct.

To perform the assay, cells were seeded on 96 well microtiter plates at 50,000 or 100,000 cells per well for HEK-Blue™ TLR7 Cells and RAW-Blue™ Cells respectively, and cultured at 37° C. in the presence of the TLR7 (or TLR7/8)-cationic lipid molecules of the invention alone or complexed with plasmid DNA (pDNA). The TLR7-cationic lipid molecules were prepared as follows: First, stock solutions of the cationic lipid molecules of the invention were prepared in ethanol or water to a concentration of 5 mg/ml. The control used in these experiments was a cationic lipid molecule PPCL/DiPPE (LyoVec™, InvivoGen) prepared in a similar manner. A working dilution of the cationic lipid molecules alone was made up in water or PBS and added to cells at a final concentration of 1 or 10 µg/ml. For pDNA/cationic lipid complexes, a ratio of pDNA/cationic lipid molecule ratio 3:24 (w:w) was prepared in serum-free culture medium or in 5% glucose. The cationic lipid molecule of interest was prediluted in serum-free culture medium or in 5% glucose and incubated for 5 minutes at room temperature, prior to the addition of an endotoxin-free, salt-free preparation of pDNA. In these experiments, the pBsr2 pCpGLacZh plasmid was used in the pDNA/cationic lipid molecule complexes. The pDNA/cationic lipid molecule mixtures were incubated at room temperature for 30 minutes to allow the formation of the complex. The working dilutions of the molecules alone or the pDNA/cationic lipid molecule complexes were directly added to the TLR7 reporter cell lines and incubated at 37° C. for 24 hours. After 24 hours of incubation, the effect of the cationic lipid molecules of the invention alone or in complex with DNA on reporter gene activity was determined by reading the OD at 655 nm using iMark™ Microplate Reader (BIO-RAD).

All the 18 molecules synthesized were tested alone for their ability to specifically activate TLR7, alongside the known TLR7 activators R848 and CL264 (InvivoGen) used as positive controls and a TLR2 agonist Pam3CSK4 (InvivoGen) used as a negative control. Of the 18 molecules, the molecules: CL346, CL347, CL349, CL481, CL493, CL528, CL529 showed strong and specific TLR7 activity. Specific TLR7 activity was determined by use of reporter cell lines to assess activity towards all the other TLRs (data not shown). FIG. 1A demonstrates the molecules of the invention alone that best activate TLR7. The results demonstrate that conjugation of a cationic lipid moiety to a TLR7 agonist does not abrogate TLR7 activity. The molecules showed a tendency to activate both mouse and human TLR7. Among the selected molecules displayed in FIG. 1A are both linear (CL346, CL347, CL349) and branched (CL481, CL493, CL528, CL529) variants of molecules synthesized, indicating that the position of conjugation of the cationic lipid moiety to the TLR7 agonist moiety does not appear to affect the activity towards TLR7. Furthermore, compared to the small molecule TLR7 activators R848 and CL264 that induce maximal activation at 1 g/ml, the molecules of the invention induced maximal activity at 10 g/ml, which can be in part due to their higher molecular weight. The molecules of the invention being TLR7-cationic lipids are able to complex pDNA. To determine that complex formation with pDNA did not affect TLR7 activity of the molecules of the invention, various dilutions of complex volumes were tested for their ability to stimulate TLR7 activity. FIG. 1B shows the effect of the molecules of the invention when complexed with pDNA on inducing NF-κB activity in RAW-Blue™ Cells. Molecules of the invention complexed with pDNA retains TLR7 activating potential.

Gel Shift Assay and Determination of Nanoparticle Size

To demonstrate that the cationic lipid molecules effectively bind to plasmid DNA (pDNA), we performed an in vitro mobility shift assay. To perform this assay, pDNA/cationic lipid molecule complexes were prepared as previously described. Then, 10 µl of pDNA/cationic lipid molecule complexes and 2 µl of charge buffer were mixed and loaded into wells of a 0.8% agarose gel. Samples were migrated through the gel in TAE buffer under 135 voltage for 21 mins and the migration of the pDNA was visualized following ethidium bromide staining under UV light. The ability of cationic lipid molecules to complex/associate with the pDNA was identified by partial or complete retardation of the pDNA migration toward the anode in the gel compared to pDNA alone. In order to confirm that TLR7 cationic lipid molecules complex DNA, lipoplex size was determined. The physical characterization of complex was achieved by dynamic light scattering using the analytical equipment for laser diffraction Zetasizer Nano-ZS (Malvern). pDNA/cationic lipid molecule complexes were prepared as described above. Subsequently, 50 µl of pDNA/cationic lipid complexes were placed into a disposable sizing cuvette and measurements were made under conditions defined according to manufacturer's instructions. The measurements were made at 25° C. in triplicate and a size distribution report was obtained (data not shown).

A panel of TLR7-catonic lipid molecules complexed with pDNA were tested. FIG. 2A demonstrates that out of 12 TLR7-catonic lipid molecules exemplified, 7 formed nanoparticle complexes with pDNA no greater than 250 nm in diameter, thus they showed conformity. The gel shift assay shows that pDNA was unable to migrate through the agarose gel when compared to the control of pDNA alone. In some cases ethidium bromide intercalation of pDNA was visualized as a smear in the wells of the gel and other cases no ethidium bromide was visualized. In the latter situation, despite observing migration of the dye front, the lack of ethidium bromide visualization is likely due to compact complex formation that prevents ethidium bromide intercalation. The sizes of the TLR7-cationic lipid molecules complexed with pDNA generally ranged between 130 and 250 nm in diameter as measured by the particle sizer. Size measurements are displayed in the table in FIG. 2B. These data suggest that the molecules of the invention are able to form nanoparticle complexes with pDNA. Furthermore, TLR7-cationic lipid molecules complexed with pDNA were observed for their conformity into uniform nanoparticles. The table describes the conformity or non-conformity of the complexes tested.

Cell Transfection

To determine if the TLR7-cationic lipid molecules are capable of transporting double stranded DNA into cells by virtue of the cationic lipid moiety, the molecules complexed with plasmid DNA (pDNA) were tested for their ability to transfect cells. The pVitro14 LGFP SEAP plasmid (Invivo-Gen) was complexed to TLR7-cationic lipid molecules and to the control cationic lipid transfection agent, LyoVec™ (InvivoGen). The human HEK293 (ATCC, CRL-1573) and mouse B16 melanoma (ATCC, CRL-6323) cell lines were seeded at a density of 50 000 cells/well and 20 000 cells/well respectively, in the absence or presence of different volumes of the plasmid encoding for the SEAP protein in complex with different volumes of TLR7-cationic lipid molecules for 48 hours at 37° C. and 10% $CO_2$. Transfection efficiency was assessed by measuring SEAP reporter gene expression: 20 µl of supernatant was sampled and mixed with 180 µl of QUANTI-Blue™ Detection (InvivoGen). In the presence of alkaline phosphatase SEAP, the color of QUANTI-Blue™ changes from pink to purple/blue. The intensity of the blue hue reflects the activity of SEAP. The levels of SEAP secretion were determined quantitatively by reading the OD at 620-655 nm using a spectrophotometer, iMark™ Microplate Reader (BIO-RAD).

Examples of TLR7-cationic lipid molecules showing their ability to transfect two different cell lines with the complexed pDNA is demonstrated in FIG. 3. Complexes that showed conformity, ability to form uniform nanoparticles (FIG. 2B), were able to transfect the two cell lines comparable to the control LyoVec™ cationic lipid complex. Molecule CL481 complexed with pDNA was used as a negative control due to its non-conformity, thus inability to transfect cells.

IFN Response Assay

The effect of the pDNA/cationic lipid molecule complexes on inducing an interferon response was examined. pDNA/cationic lipid molecule mixtures (pDNA/cationic lipid ratio 3:24, w:w) in serum-free medium or 5% glucose were prepared as described above and added to IFN reporter cells. Luciferase reporter cell lines were used to assay interferon response. A plasmid containing an interferon-inducible luciferase reporter gene was introduced into mouse RAW 264.7 macrophages and mouse B16 melanoma cells, giving rise to the RAW-ISG54-Luc and B16-ISG54-Luc reporter cell lines respectively. Expression of the luciferase reporter gene by the plasmid is under the control of an interferon-inducible promoter (1-ISG54) comprising five interferon-stimulated response elements (ISRE) and the minimal promoter of the human ISG-54K (Interferon Stimulation of a Gene encoding a 54 kDa protein) gene. The ISG-54K gene is induced by interferon regulatory factor 3 (IRF3), which has a key involvement in anti-inflammatory responses (Grandvaux et al. 2002) and the minimal promoter of the human ISG-54K gene contains two ISRE sites and fully inducible by type I interferons (IFN-α and IFN-β) and interferon regulatory factors (IRFs) (Wathelet et al. 1988; Grandvaux et al. 2002).

The RAW-ISG54-Luc and B16-ISG54-Luc reporter cell lines were seeded onto 96 well microtiter plates at 100,000 cells per well and 75,000 cells per well respectively. Cells were cultured in DMEM supplemented with 10% (v/v) heat inactivated fetal bovine serum (30 min at 56° C.), 4.5 g/l glucose, 2 mM L-glutamine, 50 U/ml penicillin, 50 µg/ml streptomycin, 100 µg/ml Normocin™ (InvivoGen) together with pDNA/cationic lipid molecules at 37° C. overnight. pDNA/cationic lipid molecule complexes were prepared as described above prior to adding to the IFN reporter cells. The induced luciferase expression was assessed in the reporter cell lines. Secreted luciferase activity was determined by bioluminescence quantification of the cell culture media using a microplate luminometer (FLUOstar OPTIMA from BMG Labtech).

FIG. 4 exemplifies TLR7-cationic lipid molecules with the ability to induce ISG54 promoter activity. Molecules that do not form complexes with pDNA, or molecules that do not form uniform nanoparticles of 250 nm and less (non-conformity of complexes) induce robust promoter activity. In RAW cells however, molecule complexes may be taken up by phagocytosis, triggering a cytosolic sensors of DNA and thus an interferon response. In general, molecule complexes that conformed as nanoparticles and demonstrated ability to transfect cells, correlated with the induction of ISG54 promoter activity by the production of type 1 interferons, interferons α and β.

Example 20

In Vivo Testing of Molecules

In Vivo Evaluation of pDNA/CL347 Cationic Lipid Molecules Formulation on a Mouse B16 Tumor Model To investigate whether administering in vivo a therapeutically effective amount of a composition concerned by the invention into a tumor environment affects tumor growth, C57BL/6 mice (Janvier S.A.S.) were shaved (on their backs) and were injected subcutaneously with approximately 50 µl ($5 \times 10^5$) of viable B16-F1 cells (ATCC, CRL-6323) under anesthesia, using 7 mice per group. Once the tumor volume reached about 5 mm in diameter, around day 7 after tumor cells were grafted, the mice were divided into 4 groups. A first group (control) received intra-tumoral injections of vehicle (Hydros 5% Pluronic PF68 2% that is often used to facilitate drug solubilization and so enhance delivery), for a total of 3 injections. All animal work was carried out at the animal facility at the Institut de Pharmacologie et de Biologie Structurale (IPBS) in Toulouse, in accordance with institutional guidelines. The second and third groups received intra-tumoral injections of pDNA/CL347 lipid cationic complexes at ratio pDNA/lipid of 3:24 or 10:40 (w:w), for a total of 3 injections. A fourth group received intra-tumoral injections of a CL347 lipid cationic molecule solution alone (40 μg in 100 μl Bionolyte G5 Pluronic® F-68 2%) for a total of 3 injections. By day 45 following tumor cell graft, 50% of mice in the pDNA/CL347 TLR7 cationic lipid complex treated group were still alive. In contrast, by day 28, there was no survival of mice from the control groups of vehicle treated or in mice treated with CL347 alone. Tumor growth was monitored and measured with calipers after day 5 of grafting tumor cells into mice and then every 2 days after. Measurements were performed under gas anesthesia. Tumor volume in mm$^3$ was determined according to the formula $V=W^2 \times L/2$, where L=length (mm) and W=width (mm)

FIG. 5A shows the significant reduction in tumor volume and FIG. 5B shows the increased rate of survival in mice treated with pDNA/CL347 TLR7-cationic lipid molecule complexes compared to CL347 alone and vehicle control. Altogether these data demonstrate that the molecules of the invention when complexed with pDNA are TLR7 agonists and transfection agents delivering pDNA to cells that induce an effective interferon response to suppress tumor growth.

Thus, these examples illustrate that the molecules of the invention are TIR7 and/or TLR8 agonists conjugated to cationic lipid molecules that can be complexed with DNA, and when introduced into cells, trigger a strong interferon response. Furthermore an example of one of the molecules of the invention is demonstrated in vivo for its anti-tumor ability using a mouse tumor model. Accordingly, the novel cationic lipid molecules according to the invention can be used as transfection agents to deliver coding or non-coding DNA of interest into cells while concomitantly activating multiple sensors of the innate immune system, namely TLR7, TLR7/8 and cytosolic nucleic acid sensors. As indicated by the results of the in vivo mouse tumor model, one application of the molecules can be useful in the treatment of cancer. Other applications include the use of the molecules and compositions of for the treatment of immune disorders and for use as vaccine adjuvants.

REFERENCES

Throughout this application, various references describe the state of the art to which this invention pertains. The disclosures of these references are hereby incorporated by reference into the present disclosure.

Ambach A, Bonnekoh B, Nguyen M, Schon M P, Gollnick H. 2004. Imiquimod, a Toll-like receptor-7 agonist, induces perforin in cytotoxic T lymphocytes in vitro. Molecular immunology 40: 1307-1314.

Barber G N. 2011a. Innate immune DNA sensing pathways: STING, AIMII and the regulation of interferon production and inflammatory responses. Current opinion in immunology 23: 10-20.

Barber G N. 2011b. STING-dependent signaling. Nature immunology 12: 929-930.

Beutler B A. 2009. TLRs and innate immunity. Blood 113: 1399-1407.

Burdette D L, Monroe K M, Sotelo-Troha K, Iwig J S, Eckert B, Hyodo M, Hayakawa Y, Vance R E. 2011. STING is a direct innate immune sensor of cyclic di-GMP. Nature 478: 515-518.

Caviar T, Ablasser A, Hornung V. 2012. Induction of type I IFNs by intracellular DNA-sensing pathways. Immunology and cell biology.

Chiu Y H, Macmillan J B, Chen Z J. 2009. RNA polymerase III detects cytosolic DNA and induces type I interferons through the RIG-I pathway. Cell 138: 576-591.

Garland S M. 2003. Imiquimod. Current opinion in infectious diseases 16: 85-89.

Grandvaux N, Servant M J, tenOever B, Sen G C, Balachandran S, Barber G N, Lin R, Hiscott J. 2002. Transcriptional profiling of interferon regulatory factor 3 target genes: direct involvement in the regulation of interferon-stimulated genes. Journal of virology 76: 5532-5539.

Hemmi H, Kaisho T, Takeuchi O, Sato S, Sanjo H, Hoshino K, Horiuchi T, Tomizawa H, Takeda K, Akira S. 2002. Small anti-viral compounds activate immune cells via the TLR7 MyD88-dependent signaling pathway. Nature immunology 3: 196-200.

Janeway C A, Jr., Medzhitov R. 2002. Innate immune recognition. Annual review of immunology 20: 197-216.

Kawai T, Akira S. 2011. Toll-like receptors and their cross-talk with other innate receptors in infection and immunity. Immunity 34: 637-650.

Keating S E, Baran M, Bowie A G. 2011. Cytosolic DNA sensors regulating type I interferon induction. Trends in immunology 32: 574-581.

Kurimoto A, Ogino T, Ichii S, Isobe Y, Tobe M, Ogita H, Takaku H, Sajiki H, Hirota K, Kawakami H. 2004. Synthesis and evaluation of 2-substituted 8-hydroxyadenines as potent interferon inducers with improved oral bioavailabilities. Bioorganic & medicinal chemistry 12: 1091-1099.

Lee J, Chuang T H, Redecke V, She L, Pitha P M, Carson D A, Raz E, Cottam H B. 2003. Molecular basis for the immunostimulatory activity of guanine nucleoside analogs: activation of Toll-like receptor 7. Proceedings of the National Academy of Sciences of the United States of America 100: 6646-6651.

Muruve D A, Petrilli V, Zaiss A K, White L R, Clark S A, Ross P J, Parks R J, Tschopp J. 2008. The inflammasome recognizes cytosolic microbial and host DNA and triggers an innate immune response. Nature 452: 103-107.

Satoh T, Kato H, Kumagai Y, Yoneyama M, Sato S, Matsushita K, Tsujimura T, Fujita T, Akira S, Takeuchi O. 2010. LGP2 is a positive regulator of RIG-1- and MDA5-mediated antiviral responses. Proceedings of the National Academy of Sciences of the United States of America 107: 1512-1517.

Sun L, Wu J, Du F, Chen X, Chen Z J. 2013. Cyclic GMP-AMP Synthase is a cytosolic DNA sensor that activates the type I interferon pathway. Science. 15: 786-91.

Takaoka A, Wang Z, Choi M K, Yanai H, Negishi H, Ban T, Lu Y, Miyagishi M, Kodama T, Honda K et al. 2007. DAI (DLM-1/ZBP1) is a cytosolic DNA sensor and an activator of innate immune response. Nature 448: 501-505.

Takeshita F, Ishii K J. 2008. Intracellular DNA sensors in immunity. Current opinion in immunology 20: 383-388.

Takeuchi O Akira S. 2009. Innate immunity to virus infection Immunological reviews 227: 75-86.

Wang Z, Choi M K, Ban T, Yanai H, Negishi H, Lu Y, Tamura T, Takaoka A, Nishikura K, Taniguchi T. 2008. Regulation of innate immune responses by DAI (DLM-1/ZBP1) and other DNA-sensing molecules. Proceedings of the National Academy of Sciences of the United States of America 105: 5477-5482.

Wathelet M G, Clauss I M, Content J, Huez G A. 1988. Regulation of two interferon-inducible human genes by interferon, poly(rI).poly(rC) and viruses. European journal of biochemistry/FEBS 174: 323-329.

Wu J, Sun L, Chen X, Du F, Shi H, Chen C, Chen Z J. 2013. Cyclic GMP-AMP is an endogenous second messenger in innate immune signaling by cytosolic DNA. Science 15: 826-30.

Yang P, An H, Liu X, Wen M, Zheng Y, Rui Y, Cao X. 2010. The cytosolic nucleic acid sensor LRRFIP1 mediates the production of type I interferon via a beta-catenin-dependent pathway. Nature immunology 11: 487-494.

Biggadike et al., US 2011/0229500 A1 (Glaxo). Sep. 22, 2011. Purine derivatives for use in the treatment of allergic, inflammatory and infectious diseases.

Carson et al., US 2010/0210598 A1. Aug. 19, 2010. Toll-like modulators and treatment of diseases.

Cook et al., US 2010/0240623 (AstraZeneca). Sep. 23, 2010. 8-oxoadenine derivatives acting as modulator of TLR7.

Fink et al., U.S. Pat. No. 7,485,432 B2 (3M). Feb. 3, 2009. Selective Modulation of TLR-mediated biological Activity.

Gorden et al., US 2011/0070575 A1 (Coley). Mar. 24, 2011 Immunomodualtory compositions, combinations and Methods (TLR7).

Isobe et al., US 2011/8044056 B2 (Sumitomo). Oct. 25, 2011. Adenine Compound.

Jackson et al., US 2010/0310595 A1. Dec. 9, 2010. Methods of Transfection and compositions therefor.

Johnson et al., US 2011/0282061 A1. (Glaxo). Nov. 17, 2011. Lipidated imidazoquinoline derviatives.

Jones et al. WO Pat. No. 2007/093901 (Pfizer). Aug. 23, 2007. 3-Deazapurine derivatives as TLR7 modulators.

Wu et al., US 2011/0053893 A1 (Novartis). Mar. 3, 2011. Compounds and compositions as TLR activity modulators.

The invention claimed is:

1. A conjugated compound containing a purine derivative agonist of TRL7 and/or TRL8, said conjugated compound being chosen among compounds of formula (I'):

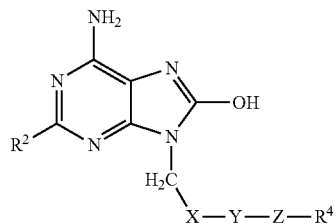

a tautomer thereof or a pharmaceutically acceptable salt of said compound or tautomer, wherein:
  $R^2$ is $C_1$-$C_{10}$alkylamino;
  X is a phenylene;
  Y is NH or —C(O)—; and
  Z—$R^4$ is selected from the group consisting of:

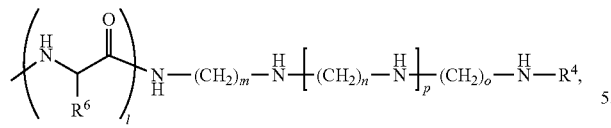

Formula II

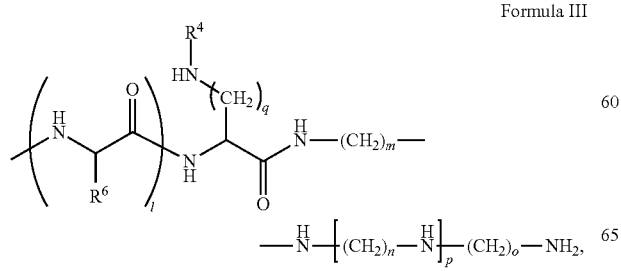

Formula III

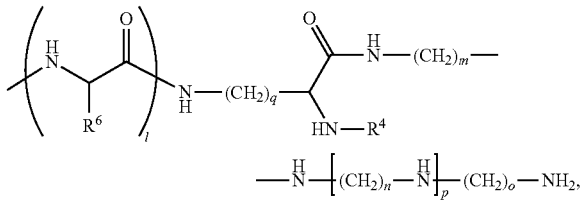

Formula IV

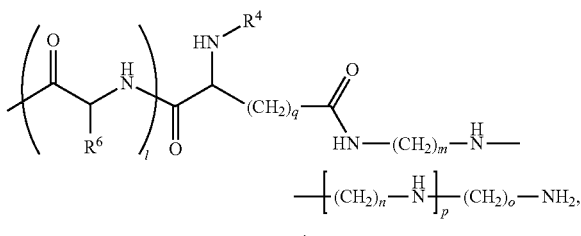

Formula V

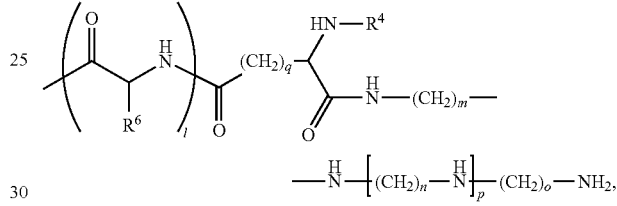

Formula VI wherein:
  $R^6$ is the specific side chain of an amino acid selected from the group consisting of L or D isomers of alanine, valine, leucine, isoleucine, phenylalanine, tryptophan, methionine, glycine, serine, threonine, cysteine, tyrosine, asparagine, glutamine, aspartic acid, glutamic acid, lysine, arginine, proline and histidine;
  l is 0 or 1;
  p is integer from 0 to 6;
  m, n, o, and q, identical or different, are integers from 1 to 4; and
  $R^4$ is a lipid of formula VII or VIII:

Formula VII

Formula VIII wherein:
R[7] and R[8] independently of each other are a linear or branched hydrocarbon chain comprising from 10 to 24 carbon atoms, and which optionally contains from 2 to 4 double or triple bonds,
G[1] is a single bond, —NH— or —O—,
G[2] is a single bond or (—CH$_2$—)r, and
r is an integer from 1 to 6.
2. The conjugated compound according to claim 1, wherein —Z— is selected from the group consisting of:
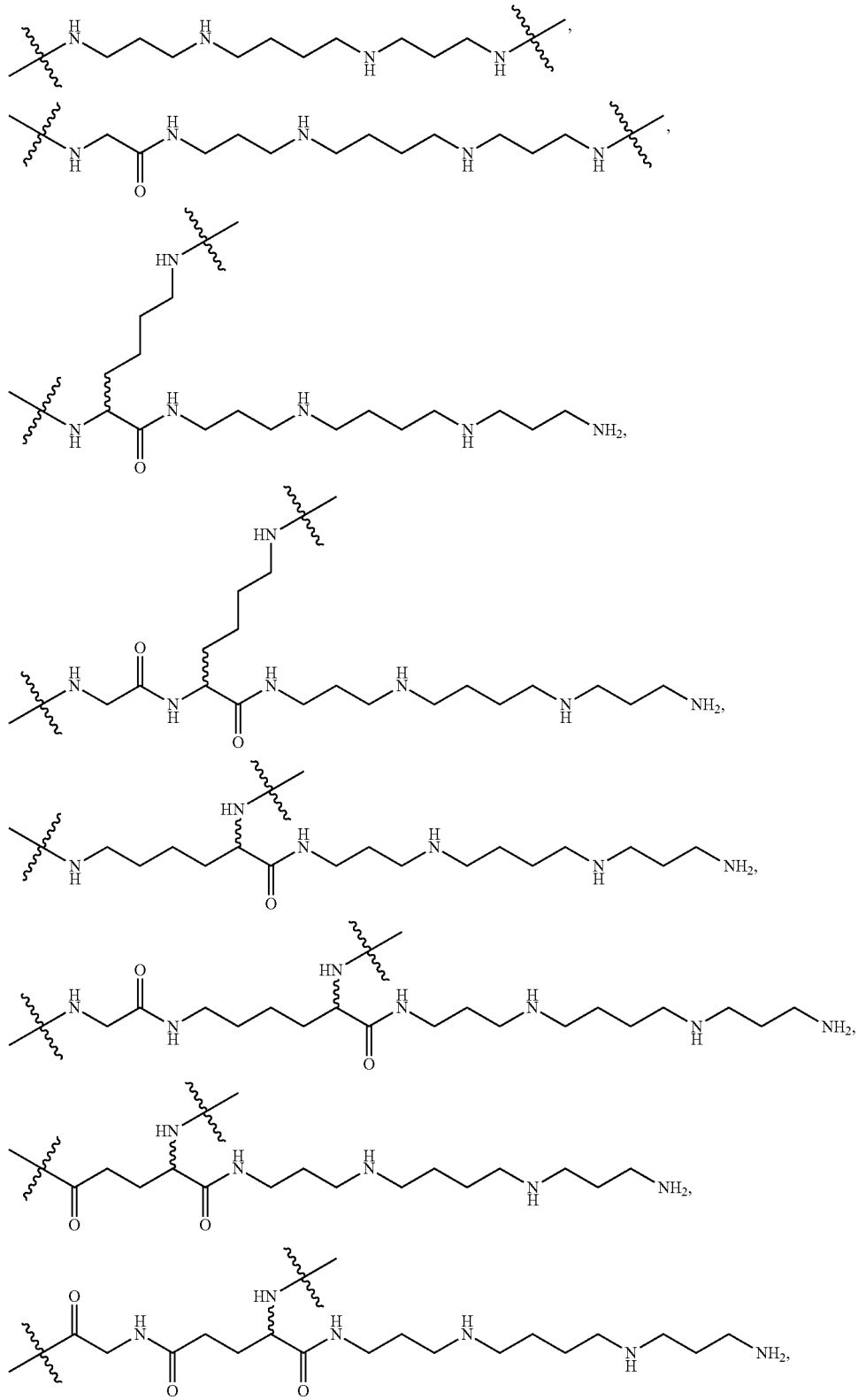

-continued

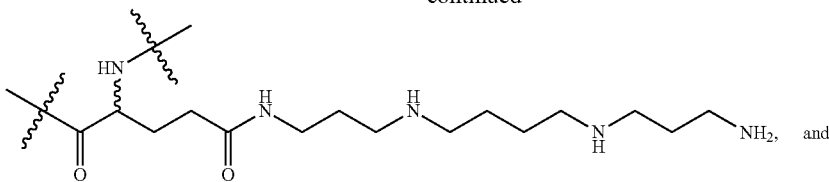

and

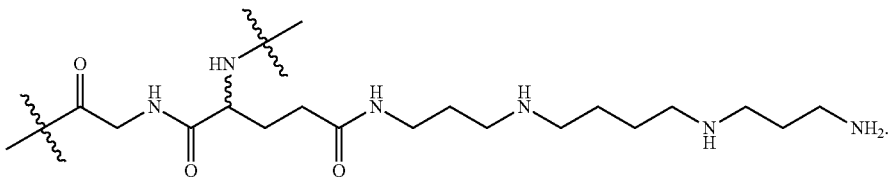

3. The conjugated compound according to claim 1, wherein R⁴ is of formula (VII):

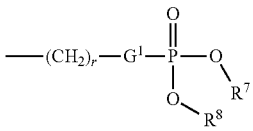

(VII)

wherein:
r is an integer from 1 to 4,
G¹ is a single bond,
R⁷ and R⁸, identical or different, are selected from the group consisting of tetradecyl, hexadecyl, octadecyl, oleyl, phytanyl, C18:2 alkenyl, C18:3 alkenyl and C18:1 alkenyl.

4. The conjugated compound according to claim 1, wherein R⁴ is of formula (VIII):

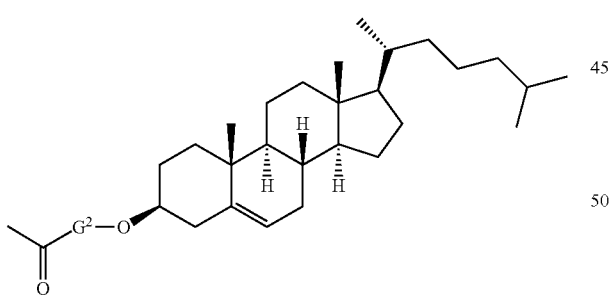

(VIII)

wherein G² is a single bond or (—CH₂—)r, wherein r is an integer from 1 to 6.

5. The conjugated compound according to claim 1, wherein said conjugated compound is selected from the group consisting of:
bis(3,7,11,15-tetramethylhexadecyl) 1-(4-((6-amino-2-(butylamino)-9H-purin-9-yl)methyl)phenyl)-1-oxo-2,6,11,15-tetraazaoctadecan-18-ylphosphonate,
bis(3,7,11,15-tetramethylhexadecyl) 1-(4-((6-amino-2-(butylamino)-9H-purin-9-yl)methyl)phenyl)-1,4-dioxo-2,5,9,14,18-pentaazahenicosan-21-ylphosphonate,
di(Z)-octadec-9-enyl 1-(4-((6-amino-2-(butylamino)-8-hydroxy-9H-purin-9-yl)methyl)phenyl)-1-oxo-2,6,11,15-tetraazaoctadecan-18-ylphosphonate,
di(Z)-octadec-9-enyl 1-(4-((6-amino-2-(butylamino)-8-hydroxy-9H-purin-9-yl)methyl)phenyl)-1,4-dioxo-2,5,9,14,18-pentaazahenicosan-21-ylphosphonate,
dihexadecyl 1-(4-((6-amino-2-(butylamino)-8-hydroxy-9H-purin-9-yl)methyl)phenyl)-1-oxo-2,6,11,15-tetraazaoctadecan-18-ylphosphonate,
dihexadecyl 1-(4-((6-amino-2-(butylamino)-8-hydroxy-9H-purin-9-yl)methyl)phenyl)-1,4-dioxo-2,5,9,14,18-pentaazahenicosan-21-ylphosphonate,
(S)-dihexadecyl 19-amino-5-(4-(2-(4-((6-amino-2-(butylamino)-8-hydroxy-9H-purin-9-yl)methyl)benzamido)acetamido)butyl)-6-oxo-4,7,11,16-tetraazanonadecylphosphonate,
(S)-bis(3,7,11,15-tetramethylhexadecyl)-19-amino-5-(4-(2-(4-((6-amino-2-(butylamino)-8-hydroxy-9H-purin9-yl)methyl)benzamido)acetamido)butyl)-6-oxo-4,7,11,16-tetraazanonadecylphosphonate,
(S)-Dihexadecyl-1-amino-15-(2-(4-((6-amino-2-(butylamino)-8-hydroxy-9H-purin-9-yl)methyl)benzamido)acetamido)-14-oxo-4,9,13,20-tetraazatricosan-23-ylphosphonate,
(S)-bis(3,7,11,15-tetramethylhexadecyl)-1-amino-15-(2-(4-((6-amino-2-(butylamino)-8-hydroxy-9H-purin-9-yl)methyl)benzamido)acetamido)-14-oxo-4,9,13,20-tetraazatricosan-23-ylphosphonate,
(S)-Dihexadecyl-1-amino-15-(4-((6-amino-2-(butylamino)-8-hydroxy-9H-purin-9-yl)methyl)benzamido)-14-oxo-4,9,13,20-tetraazatricosan-23-ylphosphonate,
(S)-bis(3,7,11,15-tetramethylhexadecyl)-1-amino-15-(4-((6-amino-2-(butylamino)-8-hydroxy-9H-purin-9-yl)methyl)benzamido)-14-oxo-4,9,13,20-tetraazatricosan-23-ylphosphonate,
(S)-dihexadecyl-21-amino-5-(4-((6-amino-2-(butylamino)-8-hydroxy-9H-purin-9-yl)methyl)phenylcarbamoyl)-8-oxo-4,9,13,18-tetraazahenicosylphosphonate,
bis(3,7,11,15-tetramethylhexadecyl)-(S)-21-amino-5-(4-((6-amino-2-(butylamino)-8-hydroxy-9H-purin-9-yl)methyl)phenylcarbamoyl)-8-oxo-4,9,13,18-tetraazahenicosylphosphonate, and
(3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(4-(3-(4-((6-amino-2-(butylamino)-8-hydroxy-9H-purin-9yl)methyl)benzamido)propylamino)butylamino)propylcarbamate, a tautomer thereof or a pharmaceutically acceptable salt of said compound or tautomer.

6. A pharmaceutical composition comprising the conjugated compound according to claim 1 and a pharmaceutically acceptable excipient or carrier.

7. A vaccine comprising the conjugated compound according to claim 1.

* * * * *